US011560391B2

(12) United States Patent
Stafford et al.

(10) Patent No.: US 11,560,391 B2
(45) Date of Patent: Jan. 24, 2023

(54) SULFONYLUREA COMPOUNDS AS INHIBITORS OF INTERLEUKIN-1 ACTIVITY

(71) Applicant: Genentech, Inc., South San Francisco, CA (US)

(72) Inventors: Jeffrey A. Stafford, South San Francisco, CA (US); James M. Veal, South San Francisco, CA (US); Lynnie Lin Trzoss, South San Francisco, CA (US); Christopher McBride, South San Francisco, CA (US); Richard M. Pastor, South San Francisco, CA (US); Steven Thomas Staben, South San Francisco, CA (US); Craig Stivala, South San Francisco, CA (US); Matthew Volgraf, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 17/150,380

(22) Filed: Jan. 15, 2021

(65) Prior Publication Data

US 2021/0261568 A1    Aug. 26, 2021

Related U.S. Application Data

(63) Continuation of application No. PCT/US2019/042703, filed on Jul. 19, 2019.

(60) Provisional application No. 62/701,358, filed on Jul. 20, 2018.

(51) Int. Cl.
*C07D 498/04* (2006.01)

(52) U.S. Cl.
CPC ................. *C07D 498/04* (2013.01)

(58) Field of Classification Search
None
See application file for complete search history.

(56) References Cited

U.S. PATENT DOCUMENTS

| | | | |
|---|---|---|---|
| 6,147,115 | A | 11/2000 | Crowell et al. |
| 10,538,487 | B2 | 1/2020 | O'Neill et al. |
| 11,040,985 | B2 | 6/2021 | Stafford et al. |
| 2014/0221340 | A1 | 8/2014 | Yamamoto et al. |
| 2019/0119203 | A1 | 4/2019 | Glick et al. |
| 2019/0119224 | A1 | 4/2019 | Glick et al. |
| 2019/0119241 | A1 | 4/2019 | Glick et al. |
| 2019/0337965 | A1 | 11/2019 | Stafford et al. |
| 2021/0253596 | A1 | 8/2021 | McBride. et al. |
| 2021/0395268 | A1 | 12/2021 | Stafford et al. |

FOREIGN PATENT DOCUMENTS

| | | |
|---|---|---|
| WO | 98/032733 A1 | 7/1998 |
| WO | 01/019390 A1 | 3/2001 |
| WO | 2003/045400 A1 | 6/2003 |
| WO | 2011/102149 A1 | 8/2011 |
| WO | 2013/031931 A1 | 3/2013 |
| WO | 2016/131098 A1 | 8/2016 |
| WO | WO 2016/131098 * | 8/2016 ........... C07D 231/08 |
| WO | 2017/140778 A1 | 8/2017 |
| WO | 2017/184604 A1 | 10/2017 |
| WO | 2017/184623 A1 | 10/2017 |
| WO | 2017/184624 A1 | 10/2017 |
| WO | 2018/136890 A1 | 7/2018 |
| WO | 2018/215818 A1 | 11/2018 |
| WO | 2019/008025 A1 | 1/2019 |
| WO | 2019/008029 A1 | 1/2019 |
| WO | 2019/034686 A1 | 2/2019 |
| WO | 2019/034688 A1 | 2/2019 |
| WO | 2019/034690 A1 | 2/2019 |
| WO | 2019/034692 A1 | 2/2019 |
| WO | 2019/034693 A1 | 2/2019 |
| WO | 2019/034696 A1 | 2/2019 |
| WO | 2019/034697 A1 | 2/2019 |
| WO | 2019/043610 A1 | 3/2019 |
| WO | 2019/092170 A1 | 5/2019 |
| WO | 2019/092171 A1 | 5/2019 |
| WO | 2019/092172 A1 | 5/2019 |
| WO | 2019/121691 A1 | 6/2019 |
| WO | 2019/166619 A1 | 9/2019 |
| WO | 2019/166621 A1 | 9/2019 |
| WO | 2019/166623 A1 | 9/2019 |
| WO | 2019/206871 A1 | 10/2019 |
| WO | 2020/010118 A1 | 1/2020 |
| WO | 2020/010143 A1 | 1/2020 |
| WO | 2020/016452 | 1/2020 |
| WO | 2020/018975 A1 | 1/2020 |

(Continued)

OTHER PUBLICATIONS

Asano, T., et al., "Identification, synthesis, and biological evaluation of 6-[(6R)-2-(4-fluorophenyl)-6-(hydroxymehyl)-4,5,6,7-tetrahydropyrazolo[1,5-a]pyrimidin-3-yl]-2-(2-methylphenyl)pyridazin-3(2H)-one (AS1940477), a potent p38 MAP kinase inhibitor" J Med Chem 55(17):7772-7785 (Sep. 13, 2012).

Cable News Network, "FDA mulls drug to slow late-stage Alzheimer's" CNN News:1-2 (Sep. 24, 2003).

Damasio, A., "Alzheimer's Disease and Related Dementias" Cecil Textbook of Medicine 20(2):1992-1996 (Jan. 1, 1996).

Golub, T.R., et al., "Molecular Classification of Cancer: Class Discovery and Class Prediction of Gene Expression" Science 286(5439):531-537 (Oct. 15, 1999).

Lala, P.K., et al., "Role of nitric oxide in tumor progression: Lessons from experimental tumors" Cancer Metast Rev 17(1):91-106 (Mar. 1, 1998).

(Continued)

*Primary Examiner* — Craig D Ricci
(74) *Attorney, Agent, or Firm* — Katherine J. Mackenzie

(57) ABSTRACT

The present disclosure relates to novel sulfonylurea compounds and related compounds useful in treating a disorder responsive to modulation of cytokines such as IL-1β and IL-18, modulation of NLRP3 or inhibition of the activation of NLRP3 or related components of the inflammatory process.

21 Claims, No Drawings

(56) References Cited

FOREIGN PATENT DOCUMENTS

| WO | 2020/035464 A1 | 2/2020 |
| WO | 2020/035465 A1 | 2/2020 |
| WO | 2020/035466 A1 | 2/2020 |
| WO | 2020/079207 A1 | 4/2020 |
| WO | 2020/086732 A1 | 4/2020 |
| WO | 2020/104657 A1 | 5/2020 |
| WO | 2020/154321 A1 | 7/2020 |
| WO | 2021/002887 A1 | 1/2021 |

OTHER PUBLICATIONS

Layzer, R., "Section Five: Degenerative Disease of the Nervous System" Cecil Textbook of Medicine 20(2):2050-2057 (Jan. 1, 1996).

USPTO,"U.S. Appl. No. 17/686,183, filed Mar. 3, 2022".

Baldwin, A.G., et al., "Inhibiting the Inflammasome: A Chemical Perspective" J Med Chem 59(5):1691-1710 (Mar. 10, 2016).

Hill, J., et al., "Sulfonylureas as Concomitant Insulin Secretagogues and NLRP3 Inflammasome Inhibitors" Chem Med Chem 12(17):1449-1457 (Sep. 7, 2017).

Howbert, J.J., et al., "Novel agents effective against solid tumors: The Diarylsulfonylureas. Synthesis, Activities, and Analysis of Quantitative Structure-Activity Relationships" J Med Chem 33(9):2393-2407 (Sep. 1, 1990).

"International Preliminary Report on Patentability—PCT/US2018/014728" (dated Jul. 23, 2019, Chapter I),: pp. 1-7 (Aug. 1, 2019).

"International Preliminary Report on Patentability—PCT/US2019/042703" (dated Jan. 26, 2021, Chapter I),: pp. 1-8) (Feb. 4, 2021).

"International Search Report—PCT/US2018/014728":pp. 1-5 (Mar. 20, 2018).

"International Search Report—PCT/US2019/042703":pp. 1-12 (Sep. 25, 2019).

Shah, F., et al., "Analysis of Pfizer Compounds in EPA's ToxCast Chemicals—Assay Space" Chem Res Toxicol 27(1):86-98 (Jan. 21, 2014).

USPTO, "U.S. Appl. No. 17/150,349, filed Jan. 15, 2021".

USPTO, "U.S. Appl. No. 17/157,749, filed Jan. 25, 2021".

* cited by examiner

SULFONYLUREA COMPOUNDS AS INHIBITORS OF INTERLEUKIN-1 ACTIVITY

CROSS REFERENCE TO RELATED APPLICATIONS

This application is a continuation of International Application No. PCT/US2019/042703, filed Jul. 19, 2019, which claims the benefit of U.S. Provisional Application No. 62/701,358, filed Jul. 20, 2018, which are incorporated herein by reference in their entireties.

FIELD OF DISCLOSURE

The present disclosure relates to novel sulfonylurea compounds and related compounds useful in treating a disorder responsive to modulation of cytokines such as IL-1β and IL-18, modulation of NLRP3, or inhibition of the activation of NLRP3 or related components of the inflammatory process.

BACKGROUND

The NOD-like receptor (NLR) family, pyrin domain-containing protein 3 (NLRP3) inflammasome is a component of the inflammatory process, and its aberrant activation is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular receptor protein that senses certain inflammatory signals. Upon activation, NLRP3 binds to apoptosis-associated speck-like protein containing a caspase activation and recruitment domain (ASC). The NLRP3-ASC complex then polymerizes to form a large aggregate known as an ASC speck. Polymerized NLRP3-ASC in turn interacts with the cysteine protease caspase-1 to form a complex termed the inflammasome. This results in the activation of caspase-1, which cleaves the proinflammatory cytokines IL-1β and IL-18 to their active forms and mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the proinflammatory cytokines IL-6 and TNF. IL-1β and IL-18 synergize with IL-23 to induce IL-17 production by memory CD4 Th17 cells and by γδ T cells in the absence of T cell receptor engagement. IL-18 and IL-12 also synergize to induce IFN-γ production from memory T cells and NK cell driving a Th1 response.

Other intracellular pattern recognition receptors (PRRs) are also capable of forming inflammasomes. These include other NLR family members such as NLRP1 and NLRC4, as well as non-NLR PRRs such as the double-stranded DNA (dsDNA) sensors absent in melanoma 2 (AIM2) and interferon, gamma inducible protein 16 (IFI16). NLRP3-dependent IL-1β processing can also be activated by an indirect, non-canonical pathway downstream of caspase-11.

The inherited CAPS disease Muckle-Wells syndrome (MWS), familial cold autoinflammatory syndrome and neonatal-onset multisystem inflammatory disease are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using mice with constitutive NLRP3 activation, but there have also been insights into the specific activation of NLRP3 in these diseases. In type 2 diabetes, the deposition of islet amyloid polypeptide in the pancreas activates NLRP3 and IL-1β signaling, resulting in cell death and inflammation.

There is a need to provide compounds and pharmaceutical compositions with improved pharmacological and/or physiological and/or physicochemical properties and/or those that provide a useful alternative to known compounds and pharmaceutical compositions.

SUMMARY

The present disclosure provides compounds and pharmaceutical compositions that may be useful for inhibiting an inflammasome, such as the NLRP3 inflammasome. The compounds and pharmaceutical compositions are also useful in modulating interleukins. The disclosed compounds have desirable molecular weights, physico-chemical properties, and lipophilicity, which are features that help with achieving therapeutic efficacy and decreasing unintended liabilities.

The present disclosure provides a compound having the structure of Formula (I),

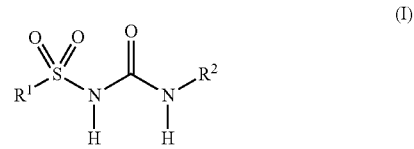

or a pharmaceutically acceptable salt, solvate, isomer, prodrug, or tautomer thereof, wherein:

$R^1$ is

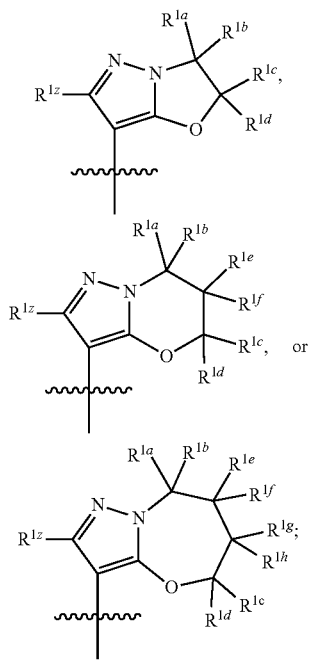

$R^{1z}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_3$-C$_{10}$cycloalkyl, C$_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a C$_3$-C$_{10}$cycloalkyl or a 3-7-membered heterocyclyl; wherein the C$_3$-C$_{10}$cycloalkyl and 3-7-membered heterocyclyl are independently unsubstituted or substituted with one or more substituents selected from the group consisting of D, —CN, halogen, C$_1$-C$_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups $R^{1a}$ and $R^{1b}$; $R^{1c}$ and $R^{1d}$; $R^{1e}$ and $R^{1f}$; or $R^{1g}$ and $R^{1h}$, when present, can form an oxo group;

$R^2$ is selected from the group consisting of C$_1$-C$_6$alkyl, C$_3$-C$_{10}$cycloalkyl, 5-7-membered heterocyclyl, 5-membered heteroaryl, 6-membered heteroaryl containing 6-11 annular atoms, or —NR$^{2g}$R$^{2h}$; wherein the C$_1$-C$_6$alkyl, C$_3$-C$_{10}$cycloalkyl, 5-7-membered heterocyclyl, 5-membered heteroaryl, and 6-membered heteroaryl containing 6-11 annular atoms are independently unsubstituted or substituted with one or more substituents, or optionally two of the substituents when present, together with the atoms to which they are attached can form a ring;

each $R^{2g}$ and $R^{2h}$ is independently H, D, C$_1$-C$_6$alkyl, C$_3$-C$_{10}$cycloalkyl, C$_6$aryl, 3-7 membered heterocyclyl, or 5-6 membered heteroaryl, wherein the C$_1$-C$_6$alkyl, C$_3$-C$_{10}$cycloalkyl, C$_6$aryl, 3-7 membered heterocyclyl, and 5-6 membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7 membered heterocyclyl, and 5-6-membered heteroaryl;

$R^{7a}$, $R^{8a}$, $R^{11a}$, $R^{12a}$, $R^{13a}$, $R^{14a}$, $R^{21a}$, and $R^{22a}$ are independently, at each occurrence, H, D, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7 membered heterocyclyl, or 5-6-membered heteroaryl; wherein the C$_1$-C$_6$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7 membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7 membered heterocyclyl, and 5-6 membered heteroaryl; and $R^{7b}$, $R^{8b}$, $R^{11b}$, $R^{12b}$, $R^{13b}$, $R^{14b}$, $R^{21b}$, and $R^{22b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

In one aspect, provided is a compound of formula (I), and pharmaceutically acceptable salts, solvates, isomers, prodrugs, and tautomers thereof, wherein:

$R^1$ is

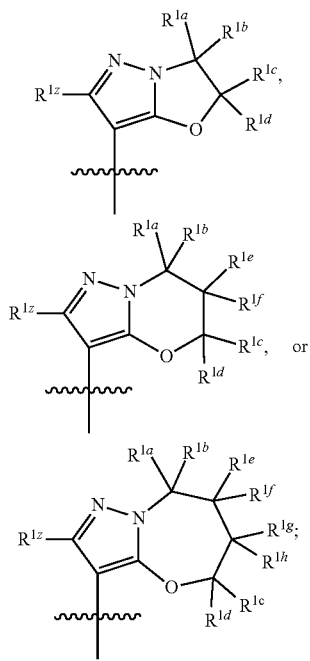

$R^{1z}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7-membered heterocyclyl, and 5-6 membered heteroaryl;

each R$^{1a}$, R$^{1b}$, R$^{1c}$, R$^{1d}$, R$^{1e}$, R$^{1f}$, R$^{1g}$, and R$^{1h}$ is independently selected from H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_3$-C$_{10}$cycloalkyl, C$_6$aryl, 3-7-membered heterocyclyl, and 5-6 membered heteroaryl; or two of the following groups, R$^{1a}$, R$^{1b}$, R$^{1c}$, R$^{1d}$, R$^{1e}$, R$^{1f}$, R$^{1g}$, and R$^{1h}$, when present, together with the atoms to which they are attached can form a C$_3$-C$_{10}$cycloalkyl or a 3-7-membered heterocyclyl; wherein the C$_3$-C$_{10}$cycloalkyl and 3-7-membered heterocyclyl are independently unsubstituted or substituted with one or more substituents selected from the group consisting of D, —CN, halogen, C$_1$-C$_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups R$^{1a}$ and R$^{1b}$; R$^{1c}$ and R$^{1d}$; R$^{1e}$ and R$^{1f}$; or R$^{1g}$ and R$^{1h}$, when present, can form an oxo group;

R$^2$ is selected from the group consisting of C$_1$-C$_6$alkyl, C$_3$-C$_{10}$cycloalkyl, 5-7-membered heterocyclyl, 5-membered heteroaryl, 6-membered heteroaryl containing 6-11 annular atoms, or —NR$^{2g}$R$^{2h}$, wherein the C$_1$-C$_6$alkyl, C$_3$-C$_{10}$cycloalkyl, 5-7-membered heterocyclyl, 5-membered heteroaryl, and 6-membered heteroaryl containing 6-11 annular atoms are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

each R$^{2g}$ and R$^{2h}$ is independently H, D, C$_1$-C$_6$alkyl, C$_3$-C$_{10}$cycloalkyl, C$_6$aryl, 3-7 membered heterocyclyl, or 5-6 membered heteroaryl, wherein the C$_1$-C$_6$alkyl, C$_3$-C$_{10}$cycloalkyl, C$_6$aryl, 3-7 membered heterocyclyl, and 5-6 membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

R$^{7a}$, R$^{8a}$, R$^{11a}$, R$^{12a}$, R$^{13a}$, R$^{14a}$, R$^{21a}$, R$^{22a}$, R$^{23a}$, and R$^{24a}$ are independently, at each occurrence, H, D, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl; and R$^{7b}$, R$^{8b}$, R$^{11b}$, R$^{12b}$, R$^{13b}$, R$^{14b}$, R$^{21b}$, R$^{22b}$, R$^{23b}$, and R$^{24b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

In some embodiments of the compound of formula (I), or a pharmaceutically acceptable salt, solvate, isomer, prodrug, or tautomer thereof, wherein R$^2$ is C$_1$-C$_6$alkyl, which is unsubstituted or substituted with one or more C$_6$aryl. In some of these embodiments, $R^2$ is $C_3$-$C_{10}$cycloalkyl, which is unsubstituted or substituted with one or more substituents selected from the group consisting of $C_1$-$C_6$alkyl and $C_6$aryl. In some of these embodiments, $R^2$ is $C_5$cycloalkyl, $C_6$cycloalkyl, or $C_7$cycloalkyl, each of which is independently unsubstituted or substituted with one or more substituents selected from the group consisting of $C_1$-$C_6$alkyl and $C_6$aryl. In some of these embodiments, the $C_3$-$C_{10}$cycloalkyl of $R^2$ is cyclohexyl, cycloheptyl, 2-adamantyl, 2,3-dihydro-1H-inden-2-yl, or 9-fluorenyl, each of which is independently unsubstituted or substituted with one or more substituents selected from the group consisting of $C_1$-$C_6$alkyl and $C_6$aryl. In some of these embodiments, the $C_3$-$C_{10}$cycloalkyl of $R^2$ is selected from the group consisting of

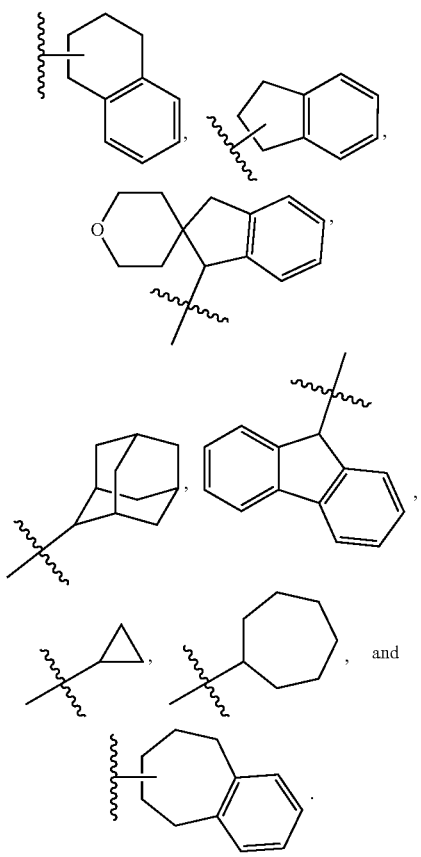

In some embodiments of the compound of formula (I), or a pharmaceutically acceptable salt, solvate, isomer, or tautomer thereof, wherein $R^2$ is 5-7-membered heterocyclyl, which is unsubstituted or substituted with one or more $C_1$-$C_6$alkyl. In some of these embodiments, the 5-7-membered heterocyclyl of $R^2$ is selected from the group consisting of

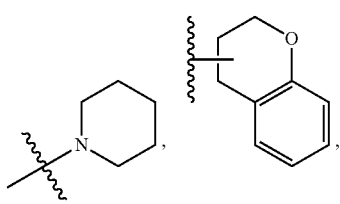

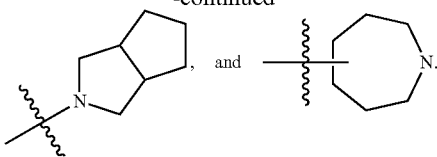

In some embodiments of the compound of formula (I), or a pharmaceutically acceptable salt, solvate, isomer, or tautomer thereof, wherein $R^2$ is 5-membered heteroaryl, which is unsubstituted or substituted with one or more substituents selected from the group consisting of $C_1$-$C_6$alkyl, $C_6$aryl, oxo, and —$(CH_2)_{1-4}C_3$-$C_{10}$cycloalkyl. In some of these embodiments, the 5-membered heteroaryl contains 2 nitrogens. In some of these embodiments, the 5-membered heteroaryl of $R^2$ is selected from the group consisting of

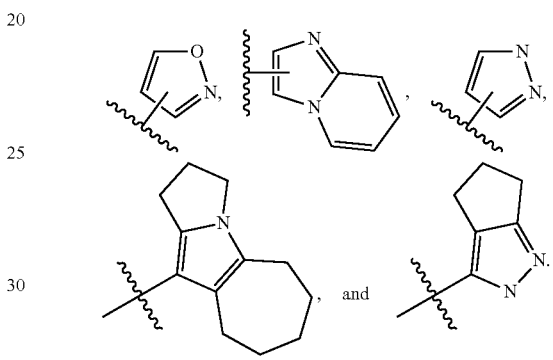

In some embodiments of the compound of formula (I), or a pharmaceutically acceptable salt, solvate, isomer, or tautomer thereof, wherein $R^2$ is 6-membered heteroaryl containing 6-11 annular atoms, which is unsubstituted or substituted with one or more substituents selected from the group consisting of halogen, $C_1$-$C_6$alkyl, $C_1$-$C_6$haloalkyl, $C_6$aryl, —$OR^{23a}$, $C_3$-$C_{10}$cycloalkyl, $C_2$-$C_6$alkenyl, —CN, and —$NR^{23a}R^{24a}$. In some of these embodiments, $R^2$ is the 6-membered heteroaryl containing 6-11 annular atoms contains 2 nitrogens. In some of these embodiments, the 6-membered heteroaryl of $R^2$ is selected from the group consisting of

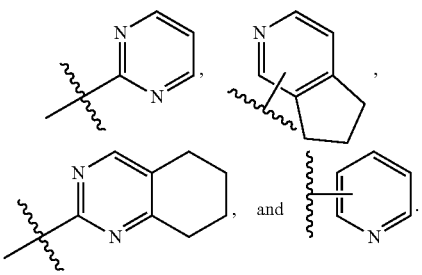

The present disclosure provides pharmaceutical compositions comprising one or more compounds of the present disclosure, e.g., a compound of Formula (I) or any variations detailed herein or one or more of Compound Nos. 1-82 in Table 1, and pharmaceutically acceptable salts, solvates (e.g., hydrates), isomers, prodrugs, and tautomers thereof, and a pharmaceutically acceptable carrier.

The present disclosure provides methods of treating disorders including the step of administering an effective amount of one or more compounds of the present disclosure, e.g., a compound of Formula (I) or any variations detailed herein or one or more of Compound Nos. 1-82 in Table 1, and pharmaceutically acceptable salts, solvates (e.g., hydrates), isomers, prodrugs, and tautomers thereof, to thereby treat the disorder in a subject in need thereof.

The present disclosure provides a methods of treating disorders including the step of administering an effective amount of one or more pharmaceutical compositions of the present disclosure to thereby treat the disorder in a subject in need thereof.

The present disclosure provides one or more compounds of the present disclosure, e.g., a compound of Formula (I) or any variations detailed herein or one or more of Compound Nos. 1-82 in Table 1, and pharmaceutically acceptable salts, solvates (e.g., hydrates), isomers, prodrugs, and tautomers thereof, or one or more pharmaceutical compositions of the present disclosure for use in the treatment of a disorder in a subject in need thereof.

The present disclosure provides for the use of one or more compounds of the present disclosure, e.g., a compound of Formula (I) or any variations detailed herein or one or more of Compound Nos. 1-82 in Table 1, and pharmaceutically acceptable salts, solvates (e.g., hydrates), isomers, prodrugs, and tautomers thereof, for the treatment of a disorder in a subject in need thereof.

The present disclosure provides for the use of one or more pharmaceutical compositions of the present disclosure for the treatment of a disorder in a subject in need thereof.

The present disclosure provides for the use of one or more compounds of the present disclosure, e.g., a compound of Formula (I) or any variations detailed herein or one or more of Compound Nos. 1-82 in Table 1, and pharmaceutically acceptable salts, solvates (e.g., hydrates), isomers, prodrugs, and tautomers thereof, in the manufacture of a medicament for the treatment of a disorder.

The present disclosure provides for the use of one or more pharmaceutical compositions of the present disclosure in the manufacture of a medicament for the treatment of a disorder.

In some embodiments, the disorder is responsive to inflammasome inhibition.

In some embodiments, the disorder is responsive to inhibition of activation of the NLRP3 inflammasome.

In some embodiments, the disorder is a disorder of the immune system, the liver, the lung, the skin, the cardiovascular system, the renal system, the gastrointestinal tract, the respiratory system, the endocrine system, the central nervous system, or is a cancer or other malignancy, or is caused by or associated with a pathogen.

The present disclosure provides methods of modulating the activity of a biological target comprising the step of exposing the biological target to one or more compounds of the present disclosure, e.g., a compound of Formula (I) or any variations detailed herein or one or more of Compound Nos. 1-82 in Table 1, and pharmaceutically acceptable salts, solvates (e.g., hydrates), isomers, prodrugs, and tautomers thereof.

The present disclosure provides methods of modulating the activity of a biological target comprising the step of exposing the biological target to one or more pharmaceutical compositions of the present disclosure.

The biological target may be selected from a group consisting of the NLRP3 inflammasome, IL-6, IL-1β, IL-17, IL-18, IL-1α, IL-37, IL-22, IL-33 and Th17 cells.

DETAILED DESCRIPTION

Definitions

As used throughout this disclosure, the following terms, unless otherwise indicated, shall be understood to have the following meanings. If a term is missing, the conventional term as known to one skilled in the art controls.

It should also be noted that any carbon as well as any heteroatom with unsatisfied valences in the text, schemes, examples and Tables herein is assumed to have the sufficient number of hydrogen atom(s) to satisfy the valences.

As described herein, compounds of the present disclosure may optionally be substituted with one or more substituents, such as those illustrated generally herein, or as exemplified by particular classes, subclasses, and species of the present disclosure. In general, the term "substituted" refers to the replacement of a hydrogen atom in a given structure with a specified substituent. Combinations of substituents envisioned by the present disclosure are typically those that result in the formation of stable or chemically feasible compounds.

As used herein, the terms "including," "containing," and "comprising" are used in their open, non-limiting sense.

The articles "a" and "an" as used in this disclosure may refer to one or more than one (i.e., to at least one) of the grammatical object of the article. By way of example, "an element" may mean one element or more than one element.

The term "and/or" as used in this disclosure may mean either "and" or "or" unless indicated otherwise.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

A "patient" or "subject" may encompass both mammals and non-mammals. Examples of mammals may include, but are not limited to, any member of the class Mammalia: humans; non-human primates such as chimpanzees, monkeys, baboons, or rhesus monkeys, as well as other apes and monkey species; farm animals such as cattle, horses, sheep, goats, and swine; companion animals such as rabbits, dogs, and cats; laboratory animals including rodents, such as rats, mice and guinea pigs; and the like. Examples of non-mammals include, but are not limited to, birds, fish, and the like. "Patient" or "subject" may include both human and animals. In some embodiments, the patient or subject is a human.

The term "inhibitor" may refer to a molecule such as a compound, a drug, enzyme, or a hormone that blocks or otherwise interferes with a particular biologic activity.

The terms "effective amount" or "therapeutically effective amount" when used in connection with one or more compounds or pharmaceutical compositions may refer to a sufficient amount of the one or more compounds or pharmaceutical compositions to provide the desired biological result. That result can be reduction and/or alleviation of the signs, symptoms, or causes of a disorder, or any other desired alteration of a biological system. For example, an "effective amount" for therapeutic use may be the amount of the pharmaceutical composition comprising one or more compounds, or pharmaceutically acceptable salts, prodrugs, solvates, hydrates, isomers, prodrugs, and tautomers thereof, as disclosed herein required to provide a clinically significant decrease in a disorder. An appropriate "effective amount" in any individual case may be determined by one of ordinary skill in the art using routine experimentation. Thus, the expression "effective amount" may generally refer to the quantity for which the active substance has therapeutic effects. In the present case the active substance may be an inhibitor of the inflammasome.

As used herein, the terms "treat" or "treatment" are meant to indicate a postponement of development of disorders; preventing the development of disorders; and/or reducing severity of such symptoms that will or are expected to develop. Thus, these terms may include ameliorating existing disorder symptoms; preventing additional symptoms; ameliorating or preventing the underlying causes of symptoms; inhibiting the disorder, e.g., arresting the development of the disorder; relieving the disorder; causing regression of the disorder; relieving a symptom caused by the disorder; or stopping or alleviating the symptoms of the disorder.

The terms "pharmaceutically acceptable" or "pharmacologically acceptable" may refer to a material which is not biologically, or otherwise, undesirable—the material may be administered to an individual without causing any substantially undesirable biological effects or interacting in a deleterious manner with any of the components of the composition in which it is contained.

The term "carrier," as used in this disclosure, may encompass carriers, excipients, and diluents and may mean a material, composition or vehicle, such as a liquid or solid filler, diluent, excipient, solvent or encapsulating material, involved in carrying or transporting a pharmaceutical agent, such as one or more compounds, or pharmaceutically acceptable salts, prodrugs, solvates, hydrates, isomers, prodrugs, and tautomers thereof, of the disclosure, from one organ, or portion of the body, to another organ, or portion of the body of a subject. Carriers should be selected on the basis of compatibility and the release profile properties of the desired dosage form. Exemplary carrier materials may include, e.g., binders, suspending agents, disintegration agents, filling agents, surfactants, solubilizers, stabilizers, lubricants, wetting agents, diluents, spray-dried dispersions, and the like. See, e.g., Hoover, John E., Remington's Pharmaceutical Sciences, Mack Publishing Co., Easton, Pa. 1975.

The term "$IC_{50}$", as used herein, may refer to concentrations at which a measurable activity, phenotype or response, for example growth or proliferation of cells such as tumor cells, is inhibited by 50%. $IC_{50}$ values can be estimated from an appropriate dose-response curve, for example by eye or by using appropriate curve fitting or statistical software. More accurately, $IC_{50}$ values may be determined using non-linear regression analysis.

The terms "administered," "administration," or "administering" as used in this disclosure may refer to either directly administering one or more compounds, and pharmaceutically acceptable salts, solvates (e.g., hydrates), isomers, prodrugs, and tautomers thereof, or pharmaceutical compositions of the disclosure to a subject.

As used herein, "alkyl" may mean a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight or branched. As used herein, "lower alkyl" means an alkyl having from 1 to 6 carbon atoms.

As used herein, an "alkenyl" may include an unbranched or branched hydrocarbon chain containing 2-12 carbon atoms. The "alkenyl" group contains at least one double bond. The double bond of an alkenyl group can be unconjugated or conjugated to another unsaturated group. Examples of alkenyl groups may include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted. Alkenyl, as defined herein, may also be branched or straight.

As used herein, "alkynyl" may include an unbranched or branched unsaturated hydrocarbon chain containing 2-12 carbon atoms. The "alkynyl" group contains at least one triple bond. The triple bond of an alkynyl group can be unconjugated or conjugated to another unsaturated group. Examples of alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "halo" or "halogen" refers to fluorine, chlorine, bromine, or iodine.

The term "haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

The term "annular atoms" used in conjunction with terms relating to ring systems described herein (e.g., cycloalkyl, cycloalkenyl, aryl, heterocyclyl, and heteroaryl) refers to the total number of ring atoms present in the system. "Annular atoms" therefore does not include the atoms present in a substituent attached to the ring. Thus, the number of "annular atoms" includes all atoms present in a fused ring. For example, an 2-indolyl ring,

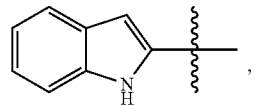 [SMILES: *c1cc2ccccc2[nH]1]

is considered a 5-membered heteroaryl, but is also a heteroaryl containing 9 annular atoms. In another example, pyridine is considered a 6-membered heteroaryl, and is a heteroaryl containing 6 annular atoms.

"Cycloalkyl" refers to a single saturated all carbon ring having 3 to 20 annular carbon atoms (i.e., $C_3$-$C_{20}$ cycloalkyl), for example from 3 to 15 annular atoms, for example, from 3 to 12 annular atoms. In certain embodiments, the cycloalkyl group is either monocyclic ("monocyclic cycloalkyl") or contains a fused, bridged or spiro ring system such as a bicyclic system ("bicyclic cycloalkyl") and can be saturated. "Cycloalkyl" includes ring systems where the cycloalkyl ring, as defined above, is fused with one or more cycloalkyl, cycloalkenyl, heterocyclyl, aryl or heteroaryl groups, wherein the point of attachment is on a cycloalkyl ring, and, in such instances, the number of carbon atoms recited continues to designate the number of carbons in the cycloalkyl ring containing the point of attachment. Examples of cycloalkyl groups include cyclohexyl, cycloheptyl, 2-adamantyl

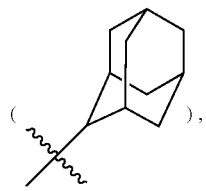 [SMILES: *C1C2CC3CC(C2)CC1C3]

2-(2,3-dihydro-1H-indene)

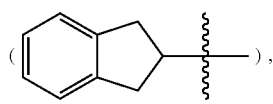

and 9-fluorenyl

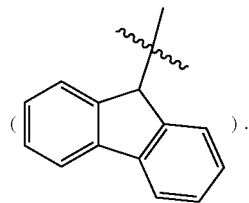 [SMILES: *C1c2ccccc2-c2ccccc21]

As noted above, cycloalkyl rings can be further characterized by the number of annular atoms. For example, a cyclohexyl ring is a $C_6$ cycloalkyl ring with 6 annular atoms, while 2-(2,3-dihydro-1H-indene) is a $C_5$ cycloalkyl ring with 9 annular atoms. Also, for example, 9-fluorenyl is a $C_5$ cycloalkyl ring with 13 annular atoms and 2-adamantyl is a $C_6$ cycloalkyl with 10 annular atoms.

In certain embodiments, a $C_3$-$C_{10}$ cycloalkyl has 3-14 annular atoms. In certain embodiments, a $C_3$-$C_{10}$ cycloalkyl has 3-10 annular atoms. In certain embodiments, a $C_3$-$C_{10}$ cycloalkyl has 3-12 annular atoms. In certain embodiments, a $C_3$-$C_7$ cycloalkyl has 3-7 annular atoms. In certain embodiments, a $C_3$-$C_9$ cycloalkyl has 3-14 annular atoms. In certain embodiments, a $C_3$-$C_9$ cycloalkyl has 3-10 annular atoms. In certain embodiments, a $C_3$-$C_9$ cycloalkyl has 3-9 annular atoms. In certain embodiments, a $C_3$-$C_8$ cycloalkyl has 3-8 annular atoms. In certain embodiments, a $C_3$-$C_8$ cycloalkyl has 3-14 annular atoms. In certain embodiments, a $C_3$-$C_7$ cycloalkyl has 3-14 annular atoms. In certain embodiments, a $C_3$-$C_7$ cycloalkyl has 3-10 annular atoms. In certain embodiments, a $C_3$-$C_7$ cycloalkyl has 3-7 annular atoms.

As used herein, the term "cycloalkenyl" may refer to a partially saturated, monocyclic, fused or spiro polycyclic, all carbon ring having from 3 to 18 carbon atoms per ring and contains at least one double bond. "Cycloalkenyl" includes ring systems where the cycloalkenyl ring, as defined above, is fused with one or more cycloalkyl, cycloalkenyl, heterocyclyl, aryl or heteroaryl groups, wherein the point of attachment is on a cycloalkenyl ring, and, in such instances, the number of carbon atoms recited continues to designate the number of carbons in the cycloalkenyl ring containing the point of attachment. Cycloalkenyl rings can be further characterized by the number of annular atoms. Examples of cycloalkenyl include 1-cyclohex-1-enyl and cyclopent-1-enyl.

In certain embodiments, the cycloalkenyl has 3-14 annular atoms. In certain embodiments, the cycloalkenyl has 3-10 annular atoms. In certain embodiments, the cycloalkenyl has 3-9 annular atoms. In certain embodiments, the cycloalkenyl has 3-7 annular atoms. In certain embodiments, a $C_3$-$C_{10}$ cycloalkenyl has 3-14 annular atoms. In certain embodiments, a $C_3$-$C_{10}$ cycloalkenyl has 3-10 annular atoms. In certain embodiments, a $C_3$-$C_9$ cycloalkenyl has 3-9 annular atoms. In certain embodiments, a $C_3$-$C_8$ cycloalkenyl has 3-8 annular atoms. In certain embodiments, a $C_3$-$C_8$ cycloalkenyl has 3-14 annular atoms. In certain embodiments, a $C_3$-$C_7$ cycloalkenyl has 3-14 annular atoms. In certain embodiments, a $C_3$-$C_7$ cycloalkenyl has 3-10 annular atoms. In certain embodiments, a $C_3$-$C_7$ cycloalkenyl has 3-7 annular atoms.

The term "aryl" as used herein refers to a single all carbon aromatic ring or a multiple condensed all carbon ring system wherein at least one of the rings is aromatic. For example, in certain embodiments, an aryl group has 5 to 20 annular carbon atoms, 5 to 14 annular carbon atoms, or 5 to 12 annular carbon atoms. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., cycloalkyl). "Aryl" includes ring systems where the aryl ring, as defined above, is fused with one or more cycloalkyl, cycloalkenyl, heterocyclyl, aryl or heteroaryl groups, and wherein the point of attachment is on an aryl ring, and, in such instances, the number of carbon atoms recited continues to designate the number of carbon atoms in the aryl ring containing the point of attachment. Examples of aryl groups include phenyl and 5-(2,3-dihydro-1H-indene)

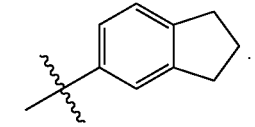 [SMILES: *c1ccc2c(c1)CCC2]

As noted above, aryl rings can be further characterized by the number of annular atoms. For example, phenyl is a $C_6$ aryl with 6 annular atoms, while 5-(2,3-dihydro-1H-indene) is a $C_6$ aryl with 9 annular atoms.

In certain embodiments the aryl ring is a $C_6$-aryl with 6-14 annular atoms. In certain embodiments the aryl ring is a $C_6$ aryl with 6-10 annular atoms. In certain embodiments the aryl ring is a $C_6$ aryl with 6-12 annular atoms.

"Heterocyclyl" as used herein refers to a single saturated or partially unsaturated non-aromatic ring or a non-aromatic multiple ring system that has at least one heteroatom in the ring (at least one annular heteroatom selected from oxygen, nitrogen, and sulfur). Unless otherwise specified, a heterocyclyl group has from 5 to about 20 annular atoms, for example from 5 to 15 annular atoms, for example from 5 to 10 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The term also includes single saturated or partially unsaturated rings (e.g., 5, 6, 7, 8, 9, or 10-membered rings) having from about 4 to 9 annular carbon atoms and from about 1 to 3 annular heteroatoms selected from the group consisting of oxygen, nitrogen and sulfur in the ring. "Heterocyclyl" includes ring systems where the heterocyclyl ring, as defined above, is fused with one or more cycloalkyl, cycloalkenyl, heterocyclyl, aryl or heteroaryl groups, wherein the point of attachment is on a heterocyclic ring, and, in such instances, the number of ring members recited continues to designate the number of annular atoms in the heterocyclic ring containing the point of attachment. Heterocyclic rings can be further characterized by the number of annular atoms. Examples of heterocyclic groups include piperidinyl (6-membered heterocycle with 6 annular atoms), azepanyl (7-membered heterocycle with 7 annular atoms), and 3-chromanyl (6-membered heterocycle with 10 annular atoms)

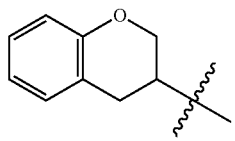

In certain embodiments, a 3-7 membered heteocyclyl has 3-7 annular atoms. In certain embodiments, a 3-6 membered heteocyclyl has 3-6 annular atoms. In certain embodiments, a 3-5 membered heteocyclyl has 3-5 annular atoms. In certain embodiments, a 3-5 membered heteocyclyl has 3-9 annular atoms. In certain embodiments, a 3-7 membered heteocyclyl has 3-14 annular atoms. In certain embodiments, a 3-7 membered heteocyclyl has 3-12 annular atoms. In certain embodiments, a 3-7 membered heteocyclyl has 3-10 annular atoms.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring. Thus, the term includes single heteroaryl rings of from about 1 to 6 annular carbon atoms and about 1-4 annular heteroatoms selected from the group consisting of oxygen, nitrogen and sulfur in the rings. The sulfur and nitrogen atoms may also be present in an oxidized form provided the ring is aromatic. "Heteroaryl" includes ring systems where the heteroaryl ring, as defined above, is fused with one or more cycloalkyl, cycloalkenyl, heterocyclyl, aryl or heteroaryl groups, wherein the point of attachment is on a heteroaryl ring, and, in such instances, the number of ring members continues to designate the number of ring members in the heteroaryl ring containing the point of attachment. Heteroaryl rings can be further characterized by the number of annular atoms. For example, pyridine is a 6-membered heteroaryl having 6 annular atoms.

In certain embodiments the heteroaryl ring is a 5-6 membered heteroaryl with 5-15 annular atoms. In certain embodiments the heteroaryl ring is a 5-6 membered heteroaryl with 5-10 annular atoms. In certain embodiments the heteroaryl ring is a 5-6 membered heteroaryl with 5-6 annular atoms. In certain embodiments the heteroaryl ring is a 5-6 membered heteroaryl with 5-12 annular atoms. In certain embodiments the heteroaryl ring is a 5-membered heteroaryl with 5-15 annular atoms. In certain embodiments, the 5-membered heteroaryl has 5 annular atoms. In certain embodiments, the 5-membered heteroaryl has 5-8 annular atoms. In certain embodiments, the 5-membered heteroaryl has 5-9 annular atoms. In certain embodiments, the 5-membered heteroaryl has 5-10 annular atoms. In certain embodiments, the 5-membered heteroaryl has 5-12 annular atoms. In certain embodiments the heteroaryl ring is a 6-membered heteroaryl with 6-15 annular atoms. In certain embodiments the heteroaryl ring is a 6-membered heteroaryl with 6-10 annular atoms. In certain embodiments the heteroaryl ring is a 6 membered heteroaryl with 6-14 annular atoms. In certain embodiments, the 6-membered heteroaryl has 6-13 annular atoms. In certain embodiments, the 6-membered heteroaryl has 6 annular atoms. In certain embodiments, the 6-membered heteroaryl has 6-9 annular atoms. In certain embodiments, the 6-membered heteroaryl has 6-10 annular atoms. In certain embodiments, the 6-membered heteroaryl has 6-12 annular atoms.

Numerical ranges, as used herein, may include sequential integers. For example, a range expressed as "from 0 to 5" would include 0, 1, 2, 3, 4 and 5.

As used herein, the term "unsubstituted" may mean that the specified group bears no substituents beyond the moiety recited (e.g., where valency satisfied by hydrogen).

The term "oxo" as used herein refers to an "=O" group. It can also be abbreviated herein as C(O) or as C=O.

The present disclosure is directed to compounds as described herein and pharmaceutically acceptable salts, solvates (e.g., hydrates), isomers, prodrugs, and tautomers thereof, and pharmaceutical compositions comprising one or more compounds as described herein, and pharmaceutically acceptable salts, solvates (e.g., hydrates), isomers, prodrugs, and tautomers thereof.

The disclosure is directed to compounds as described herein and pharmaceutically acceptable salts, enantiomers, hydrates, solvates, prodrugs, isomers, prodrugs, or tautomers thereof. The use of the terms "salt," "hydrate," "solvate," "prodrug," "ester," and the like, is intended to equally apply to the salt, hydrate, solvate, prodrug, or ester of enantiomers, isomers, prodrugs, rotamers, tautomers, positional isomers, or racemates of the disclosed compounds.

It should be understood that all isomeric forms are included within the present disclosure, including mixtures thereof. The term "isomer" may refer to compounds that have the same composition and molecular weight but differ in physical and/or chemical properties. The structural difference may be in constitution (geometric or positional isomers) or in the ability to rotate the plane of polarized light (stereoisomers). With regard to stereoisomers, the compounds of the disclosure may have one or more asymmetric carbon atom and may occur as racemates, racemic mixtures and as individual enantiomers or diastereomers. Individual isomers of the compounds of the disclosure may, for example, be substantially free of other isomers, or may be admixed, for example, as racemates or with all other, or other selected, isomers. If the compound contains a double bond, the substituent may be in the E or Z configuration or cis or trans configuration or mixtures of any of the foregoing. Disclosed assay results may reflect the data collected for the racemic form, the enantiomerically pure form, or any other form in terms of stereochemistry or constitution (e.g., geometric or positional isomers).

The compounds of the disclosure may contain asymmetric or chiral centers, and, therefore, exist in different stereoisomeric forms. The term "stereoisomers" may refer to the set of compounds which have the same number and type of atoms and share the same bond connectivity between those atoms, but differ in three dimensional structure. The term "stereoisomer" may refer to any member of this set of compounds. For instance, a stereoisomer may be an enantiomer or a diastereomer. It is intended that all stereoisomeric forms of the compounds of the disclosure as well as mixtures thereof, including racemic mixtures, form part of the present disclosure.

The term "enantiomers" may refer to a pair of stereoisomers which are non-superimposable mirror images of one another. The term "enantiomer" may refer to a single member of this pair of stereoisomers. The term "racemic" may refer to a 1:1 mixture of a pair of enantiomers. Each compound herein disclosed may include all the enantiomers (which may exist even in the absence of asymmetric carbons) that conform to the general structure of the compound, unless the stereochemistry is specifically indicated. The compounds may be in a racemic or enantiomerically pure form, or any other form in terms of stereochemistry. The chiral centers of the present disclosure may have the S or R configuration as defined by the IUPAC 1974 Recommendations. In some examples presented, the synthetic route may produce a single enantiomer or a mixture of enantiomers. In some embodiments of the disclosure, the compounds of the disclosure are enantiomers. In some embodiments, the compounds of the disclosure are the (S)-enantiomer. In some embodiments, the compounds of the disclosure are the (R)-enantiomer. In some embodiments, the compounds of the disclosure may be (+) or (−) enantiomers.

The term "diastereomers" may refer to the set of stereoisomers which cannot be made superimposable by rotation around single bonds. For example, cis- and trans-double bonds, endo- and exo-substitution on bicyclic ring systems, and compounds containing multiple stereogenic centers with different relative configurations may be considered to be diastereomers. The term "diastereomer" may refer to any member of this set of compounds. In some examples presented, the synthetic route may produce a single diastereomer or a mixture of diastereomers. The disclosure may include diastereomers of the compounds described herein.

In some embodiments, pharmaceutical compositions of the disclosure may be enriched to provide predominantly one enantiomer of a compound described herein. An enantiomerically enriched mixture may comprise, for example, at least 60 mol percent of one enantiomer, or more preferably at least 75, at least 80, at least 85, at least 90, at least 95, at least 96, at least 97, at least 98, at least 99, at least 99.5 or even 100 mol percent. In some embodiments, the compositions described herein enriched in one enantiomer may be substantially free of the other enantiomer, wherein substantially free may mean that the substance in question makes up less than 10%, or less than 5%, or less than 4%, or less than 3%, or less than 2%, or less than 1% as compared to the amount of the other enantiomer, e.g., in the pharmaceutical composition or compound mixture. For example, if a pharmaceutical composition or compound mixture contains 98 grams of a first enantiomer and 2 grams of a second enantiomer, it would be said to contain 98 mol percent of the first enantiomer and only 2 mol percent of the second enantiomer.

In some embodiments, the pharmaceutical compositions of the disclosure may be enriched to provide predominantly one diastereomer of a compound disclosed herein. A diastereomerically enriched mixture may comprise, for example, at least 60 mol percent of one diastereomer, or more preferably at least 75, at least 80, at least 85, at least 90, at least 95, at least 96, at least 97, at least 98, at least 99, at least 99.5, or even 100 mol percent. In some embodiments, the compositions described herein enriched in one diastereomer may be substantially free of other diastereomers, wherein substantially free may mean that the substance in question makes up less than 10%, or less than 5%, or less than 4%, or less than 3%, or less than 2%, or less than 1% as compared to the amount of other disastereomers, e.g., in the pharmaceutical composition or compound mixture.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column. Also, some of the compounds of the disclosure may be atropisomers or rotameric forms and are considered as part of this disclosure.

Compounds of the disclosure may exist in their tautomeric form (for example, as an amide or imino ether). All such tautomeric forms are contemplated herein as part of the present disclosure. Also, for example, all keto-enol and imine-enamine forms of the compounds are included in the present disclosure. Also, it should be noted that the sulfonimidamidyl ureas described here have tautomeric forms. The structures have been graphically represented as one form throughout this document, but it is noted that the tautomers can exist in an equilibrium. All tautomeric forms for each compound are embraced although only one tautomeric form may be represented for each compound, which may be a major tautomeric form or a minor tautomeric form.

The disclosure may include pharmaceutically acceptable salts of the compounds disclosed herein. A "pharmaceutically acceptable salt" may be acceptable for use in humans or domestic animals and may refer to those salts that retain the biological effectiveness and properties of the free forms, which are not biologically or otherwise undesirable. Representative "pharmaceutically acceptable salts" may include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

Pharmaceutically acceptable salts may also include both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethyl amine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

The disclosure may include zwitterions of the compounds disclosed herein. A "zwitterion" may refer to a molecule that has both positively-charged and negatively-charged groups but has no overall charge, i.e., the + and − charges are balanced within the molecule. For examples, the compounds of the disclosure may include protonated amino groups and deprotonated sulfate groups.

Compounds of the disclosure may exist as solvates. The term "solvate" may refer to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates may include compositions containing stoichiometric amounts of water, as well as compositions containing variable amounts of water.

The compounds described herein further include all pharmaceutically acceptable isotopically labeled compounds. An "isotopically" or "radio-labeled" compound may be a compound where one or more atoms are replaced or substituted by an atom having an atomic mass or mass number different from the atomic mass or mass number typically found in nature (i.e., naturally occurring). For example, in some embodiments, in the compounds described herein hydrogen atoms are replaced or substituted by one or more deuterium or tritium. Certain isotopically labeled compounds of this disclosure, for example, those incorporating a radioactive isotope, may be useful in drug and/or substrate tissue distribution studies. The radioactive isotopes tritium, i.e., $^3H$, and carbon 14, i.e., $^{14}C$, may be particularly useful for this purpose in view of their ease of incorporation and ready means of detection. Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. In some embodiments, the compound comprises at least one deuterium atom. For example, one or more hydrogen atoms in a compound of the present disclosure can be replaced or substituted by deuterium. In some embodiments, the compound comprises two or more deuterium atoms. In some embodiments, the compound comprises 1, 2, 3, 4, 5, 6, 7, 8, 9, 10, 11 or 12 deuterium atoms. Suitable isotopes that may be incorporated in compounds described herein include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. Substitution with positron emitting isotopes, such as $^{11}C$, $^{18}F$, $^{15}O$, and $^{13}N$, can be useful in Positron Emission Topography (PET) studies.

Isotopically labelled compounds of the compounds disclosed herein can generally be prepared by following procedures analogous to those disclosed in the Schemes and/or in the Examples herein, by substituting an appropriate isotopically labelled reagent for a non-isotopically labelled reagent.

Compounds

The present disclosure provides a compound having the structure of Formula (I),

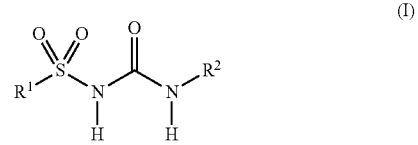

(I)

or a pharmaceutically acceptable salt, solvate, isomer, prodrug, or tautomer thereof, wherein:

$R^1$ is

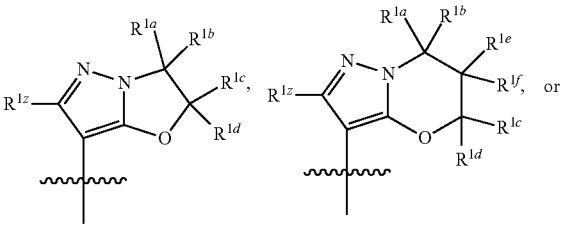

-continued

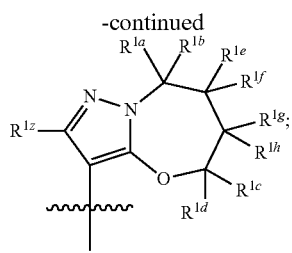

$R^{1z}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_3$-C$_{10}$cycloalkyl, C$_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a C$_3$-C$_{10}$cycloalkyl or a 3-7-membered heterocyclyl; wherein the C$_3$-C$_{10}$cycloalkyl and 3-7-membered heterocyclyl are independently unsubstituted or substituted with one or more substituents selected from the group consisting of D, —CN, halogen, C$_1$-C$_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups $R^{1a}$ and $R^{1b}$; $R^{1c}$ and $R^{1d}$; $R^{1e}$ and $R^{1f}$; or $R^{1g}$ and $R^{1h}$, when present, can form an oxo group;

$R^2$ is selected from the group consisting of C$_1$-C$_6$alkyl, C$_3$-C$_{10}$cycloalkyl, 5-7-membered heterocyclyl, 5-membered heteroaryl, 6-membered heteroaryl containing 6-11 annular atoms, or —NR$^{2g}$R$^{2h}$; wherein the C$_1$-C$_6$alkyl, C$_3$-C$_{10}$cycloalkyl, 5-7-membered heterocyclyl, 5-membered heteroaryl, and 6-membered heteroaryl containing 6-11 annular atoms are independently unsubstituted or substituted with one or more substituents, or optionally two of the substituents when present, together with the atoms to which they are attached can form a ring;

each $R^{2g}$ and $R^{2h}$ is independently H, D, C$_1$-C$_6$alkyl, C$_3$-C$_{10}$cycloalkyl, C$_6$aryl, 3-7 membered heterocyclyl, or 5-6 membered heteroaryl, wherein the C$_1$-C$_6$alkyl, C$_3$-C$_{10}$cycloalkyl, C$_6$aryl, 3-7 membered heterocyclyl, and 5-6 membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

$R^{7a}$, $R^{8a}$, $R^{11a}$, $R^{12a}$, $R^{13a}$, $R^{14a}$, $R^{21a}$, and $R^{22a}$ are independently, at each occurrence, H, D, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl; and $R^{7b}$, $R^{8b}$, $R^{11b}$, $R^{12b}$, $R^{13b}$, $R^{14b}$, $R^{21b}$, and $R^{22b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

In some embodiments, provided is a compound having the structure of Formula (I),

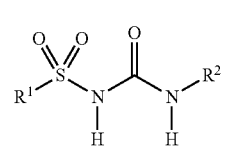

(I)

and pharmaceutically acceptable salts, solvates, isomers, prodrugs, and tautomers thereof, wherein:

$R^1$ is

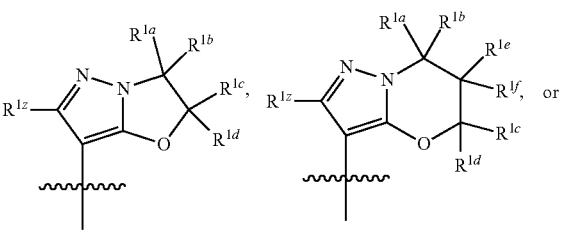

-continued

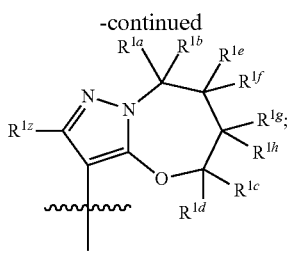

$R^{1z}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_7$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_3$-C$_{10}$cycloalkyl, C$_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a C$_3$-C$_{10}$cycloalkyl or a 3-7-membered heterocyclyl; wherein the C$_3$-C$_{10}$cycloalkyl and 3-7-membered heterocyclyl are independently unsubstituted or substituted with one or more substituents selected from the group consisting of D, —CN, halogen, C$_1$-C$_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups $R^{1a}$ and $R^{1b}$; $R^{1c}$ and $R^{1d}$; $R^{1e}$ and $R^{1f}$; or $R^{1g}$ and $R^{1h}$, when present, can form an oxo group;

$R^2$ is selected from the group consisting of C$_1$-C$_6$alkyl, C$_3$-C$_{10}$cycloalkyl, 5-7-membered heterocyclyl, 5-membered heteroaryl, 6-membered heteroaryl containing 6-11 annular atoms, or —NR$^{2g}$R$^{2h}$, wherein the C$_1$-C$_6$alkyl, C$_3$-C$_{10}$cycloalkyl, 5-7-membered heterocyclyl, 5-membered heteroaryl, and 6-membered heteroaryl containing 6-11 annular atoms are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

each $R^{2g}$ and $R^{2h}$ is independently H, D, C$_1$-C$_6$alkyl, C$_3$-C$_{10}$cycloalkyl, C$_6$aryl, 3-7 membered heterocyclyl, or 5-6 membered heteroaryl, wherein the C$_1$-C$_6$alkyl, C$_3$-C$_{10}$cycloalkyl, C$_6$aryl, 3-7 membered heterocyclyl, and 5-6 membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

$R^{7a}$, $R^{8a}$, $R^{11a}$, $R^{12a}$, $R^{13a}$, $R^{14a}$, $R^{21a}$, $R^{22a}$, $R^{23a}$, and $R^{24a}$ are independently, at each occurrence, H, D, C$_1$-C$_6$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_6$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl; and $R^{7b}$, $R^{8b}$, $R^{11b}$, $R^{12b}$, $R^{13b}$, $R^{14b}$, $R^{21b}$, $R^{22b}$, $R^{23b}$, and $R^{24b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_1$-C$_8$cycloalkyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

As described above, $R^2$ is selected from the group consisting of C$_1$-C$_6$alkyl, C$_3$-C$_{10}$cycloalkyl, 5-7-membered heterocyclyl, 5-membered heteroaryl, 6-membered heteroaryl containing 6-11 annular atoms, or —NR$^{2g}$R$^{2h}$.

In certain embodiments, $R^2$ is C$_1$-C$_6$alkyl. In certain embodiments, $R^2$ is C$_1$alkyl. C$_2$alkyl, C$_3$alkyl, C$_4$alkyl, C$_5$alkyl, or C$_6$alkyl. In certain embodiments, $R^2$ is C$_1$-C$_6$alkyl substituted with one or more C$_6$aryl.

In certain embodiments, $R^2$ is a C$_3$-C$_{10}$cycloalkyl. In certain embodiments, the C$_3$-C$_{10}$cycloalkyl has 3-14 annular atoms. In certain embodiments, the C$_3$-C$_{10}$cycloalkyl has 3-12 annular atoms. In certain embodiments, the C$_3$-C$_{10}$cycloalkyl has 3-10 annular atoms. In certain embodiments, $R_2$ is a C$_3$-C$_9$cycloalkyl with 3-9 annular atoms. In certain embodiments, $R^2$ is a C$_3$-C$_9$cycloalkyl with 3-14 annular atoms. In certain embodiments, $R_2$ is a C$_3$-C$_9$cycloalkyl with 3-10 annular atoms. In certain embodiments, $R_2$ is a C$_3$-C$_8$cycloalkyl with 3-8 annular atoms. In certain embodiments, $R_2$ is a C$_3$-C$_8$cycloalkyl with 3-14 annular atoms. In certain embodiments, $R_2$ is a C$_3$-C$_7$cycloalkyl with 3-14 annular atoms. In certain embodiments, $R_2$ is a $C_3$-$C_7$cycloalkyl with 3-10 annular atoms. In certain embodiments, $R_2$ is a $C_3$-$C_7$cycloalkyl with 3-7 annular atoms.

In certain embodiments, $R^2$ is $C_5$cycloalkyl, $C_6$cycloalkyl, or $C_7$cycloalkyl.

Examples of cycloalkyl groups include cyclohexyl, cycloheptyl, 2-adamantyl

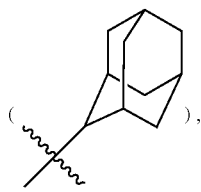 [SMILES: *C1C2CC3CC(C2)CC1C3]

2-(2,3-dihydro-1H-indene)

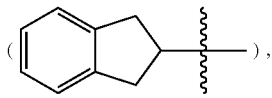

and 9-fluorenyl

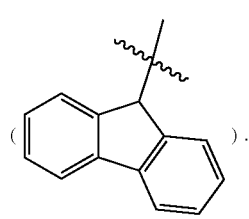 [SMILES: *C1c2ccccc2-c2ccccc21]

As noted above, cycloalkyl rings can be further characterized by the number of annular atoms. For example, a cyclohexyl ring is a $C_6$cycloalkyl ring with 6 annular atoms, while 2-(2,3-dihydro-1H-indene) is a $C_5$cycloalkyl ring with 9 annular atoms. Also, for example, 9-fluorenyl is a $C_5$cycloalkyl ring with 13 annular atoms and 2-adamantyl is a $C_6$cycloalkyl ring with 10 annular atoms.

In certain embodiments, $R^2$ is an unsubstituted or substituted $C_3$-$C_{10}$cycloalkyl, where the $C_3$-$C_{10}$cycloalkyl is selected from the group consisting of

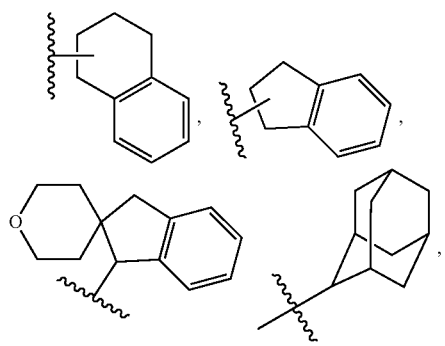

-continued

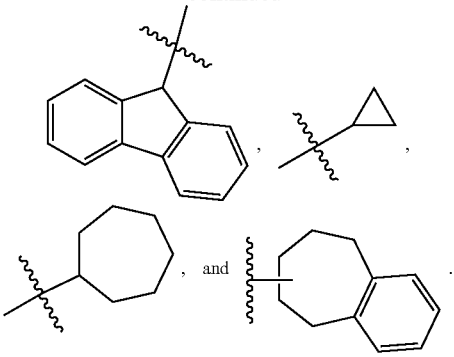

In certain embodiments, $R^2$ is $C_3$-$C_{10}$cycloalkyl substituted with one or more substituents selected from the group consisting of $C_1$-$C_6$alkyl and $C_6$aryl.

In certain embodiments, $R^2$ is a 5-7 membered heteocyclyl. In certain embodiments, the 5-7 membered heteocyclyl has 5-7 annular atoms. In certain embodiments, the 5-7 membered heteocyclyl has 5-9 annular atoms. In certain embodiments, the 5-7 membered heteocyclyl has 5-14 annular atoms. In certain embodiments, the 5-7 membered heteocyclyl has 5-12 annular atoms. In certain embodiments, the 5-7 membered heteocyclyl has 5-10 annular atoms.

In certain embodiments, $R^2$ is an unsubstituted or substituted 5-7 membered heterocyclyl, where the 5-7 membered heterocyclyl is selected from the group consisting of

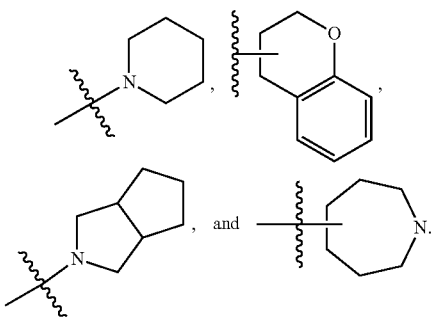

In certain embodiments, $R^2$ is 5-7 membered heterocyclyl substituted with one or more $C_1$-$C_6$alkyl.

In certain embodiments, $R^2$ is a 5-membered heteroaryl. In certain embodiments, the 5-membered heteroaryl has 5 annular atoms. In certain embodiments, the 5-membered heteroaryl has 5-8 annular atoms. In certain embodiments, the 5-membered heteroaryl has 5-9 annular atoms. In certain embodiments, the 5-membered heteroaryl has 5-10 annular atoms. In certain embodiments, the 5-membered heteroaryl has 5-12 annular atoms.

In certain embodiments, $R^2$ is a 5-membered heteroaryl containing 1 or 2 nitrogens. In certain embodiments, $R^2$ is a 5-membered heteroaryl containing 1 nitrogen. In certain embodiments, $R^2$ is a 5-membered heteroaryl containing 2 nitrogens.

In certain embodiments, $R^2$ is an unsubstituted or substituted 5-membered heteroaryl, where the 5-membered heteroaryl is selected from the group consisting of

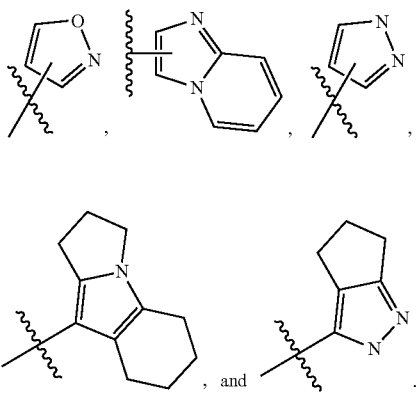

In certain embodiments, $R^2$ is 5-membered heteroaryl substituted with one or more substituents selected from the group consisting of $C_1$-$C_6$alkyl, $C_6$aryl, oxo, and —(CH$_2$)$_{1-4}$$C_3$-$C_{10}$cycloalkyl.

In certain embodiments, $R^2$ is a 6-membered heteroaryl containing 6-11 annular atoms. In certain embodiments, the 6-membered heteroaryl containing 6-11 annular atoms has 6 annular atoms. In certain embodiments, the 6-membered heteroaryl containing 6-11 annular atoms has 6-8 annular atoms. In certain embodiments, the 6-membered heteroaryl containing 6-11 annular atoms has 6-9 annular atoms. In certain embodiments, the 6-membered heteroaryl containing 6-11 annular atoms has 6-10 annular atoms. In certain embodiments, the 6-membered heteroaryl containing 6-11 annular atoms has 6-11 annular atoms.

In certain embodiments, $R^2$ is a 6-membered heteroaryl containing 6-11 annular atoms containing 1 or 2 nitrogens. In certain embodiments, $R^2$ is a 6-membered heteroaryl containing 6-11 annular atoms containing 1 nitrogen. In certain embodiments, $R^2$ is a 6-membered heteroaryl containing 6-11 annular atoms containing 2 nitrogens.

In certain embodiments, $R^2$ is an unsubstituted or substituted 6-membered heteroaryl containing 6-11 annular atoms, where the 6-membered heteroaryl containing 6-11 annular atoms is selected from the group consisting of

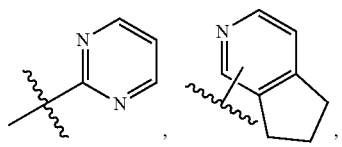

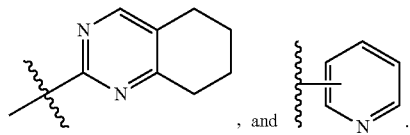

In certain embodiments, $R^2$ is 6-membered heteroaryl containing 6-11 annular atoms substituted with one or more substituents selected from the group consisting of halogen, $C_1$-$C_6$alkyl, $C_1$-$C_6$haloalkyl, $C_6$aryl, —OR$^{23a}$, $C_3$-$C_{10}$cycloalkyl, $C_2$-$C_6$alkenyl, —CN, and —NR$^{23a}$R$^{24a}$.

In certain embodiments, $R^2$ is —NR$^{2g}$R$^{2h}$. As described above, each $R^{2g}$ and $R^{2h}$ is independently H, D, $C_1$-$C_6$alkyl, $C_3$-$C_{10}$cycloalkyl, $C_6$aryl, 3-7 membered heterocyclyl, or 5-6 membered heteroaryl, wherein the $C_1$-$C_6$alkyl, $C_3$-$C_{10}$cycloalkyl, $C_6$aryl, 3-7 membered heterocyclyl, and 5-6 membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$$C_3$-$C_{10}$cycloalkyl, $C_3$-$C_{10}$cycloalkyl, $C_6$aryl, 3-7-membered heterocyclyl, and 5-6-membered heteroaryl. In certain embodiments, $R^{2g}$ is H and $R^{2h}$ is D, $C_1$-$C_6$alkyl, $C_3$-$C_{10}$cycloalkyl, $C_6$aryl, 3-7 membered heterocyclyl, or 5-6 membered heteroaryl.

As described above, in certain embodiments, $R^1$ is selected from the group consisting of

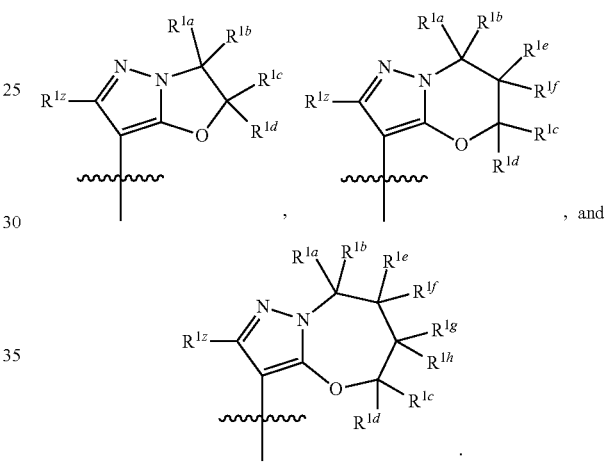

In certain embodiments, $R^1$ is

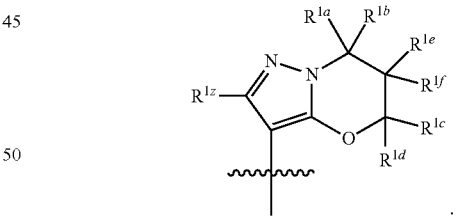

In certain embodiments, $R^1$ is

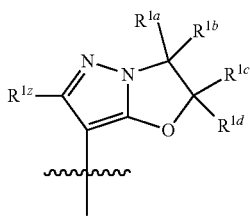

In certain embodiments, R¹ is

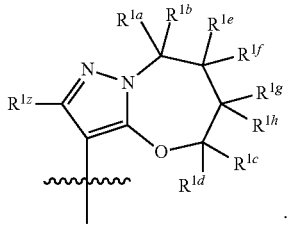

In certain embodiments, R$^{1z}$ is H.
In certain embodiments, R¹ is

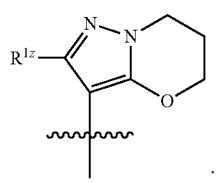

In certain embodiments, R¹ is

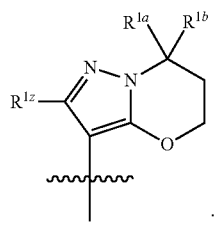

In certain embodiments, R¹ is

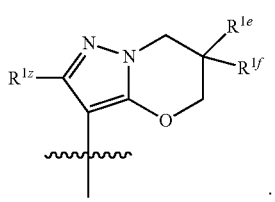

In certain embodiments, R¹ is

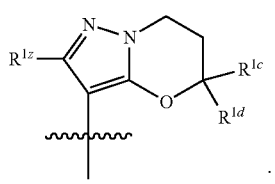

In certain embodiments, R¹ is selected from the group consisting of

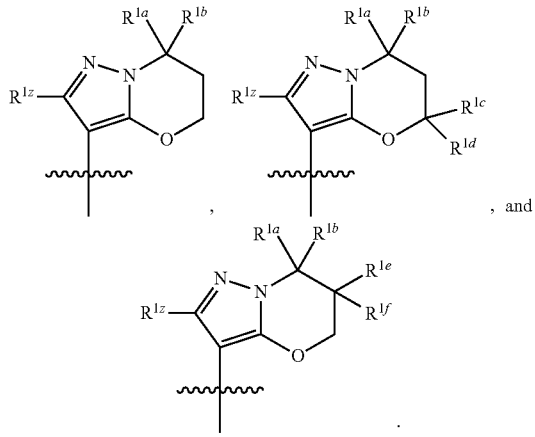

In certain embodiments, R¹ is selected from the group consisting of

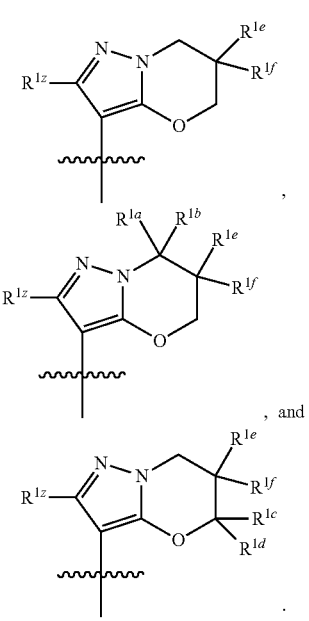

In certain embodiments, R¹ is selected from the group consisting of

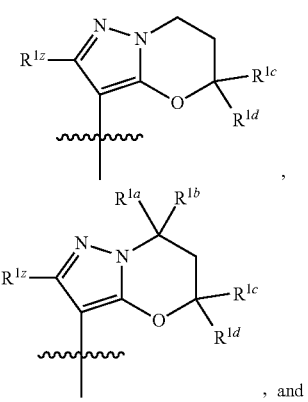

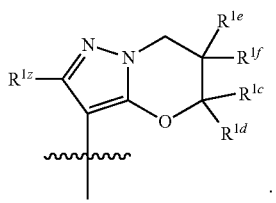
In certain embodiments, $R^1$ is
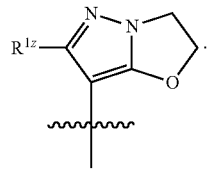
In certain embodiments, $R^1$ is
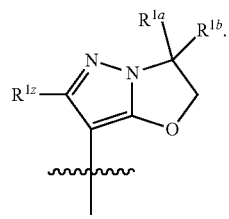
In certain embodiments, $R^1$ is
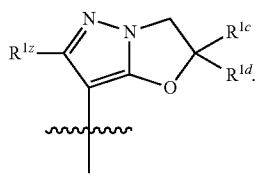
In certain embodiments, $R^1$ is
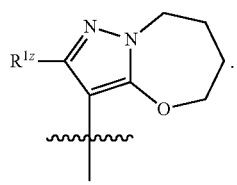
In certain embodiments, $R^1$ is
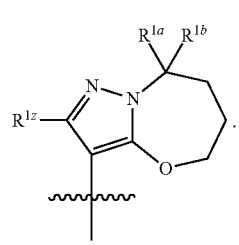
In certain embodiments, $R^1$ is
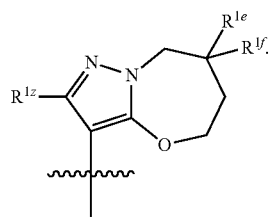
In certain embodiments, $R^1$ is
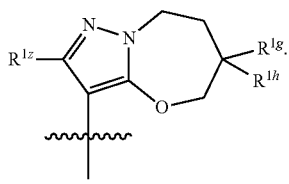
In certain embodiments, $R^1$ is
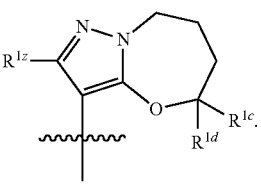
In certain embodiments, $R^1$ is selected from the group consisting of
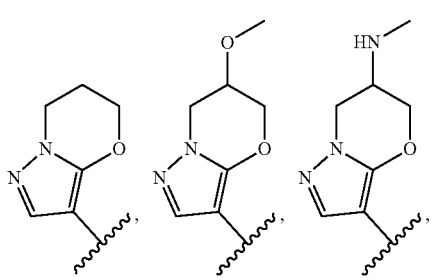
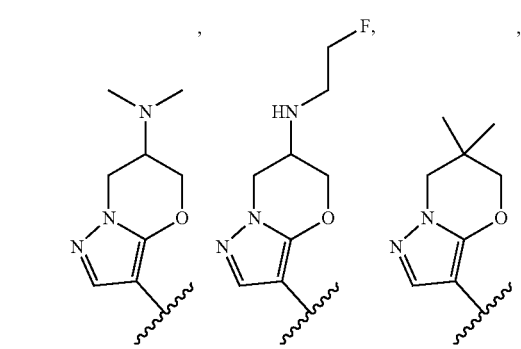

-continued
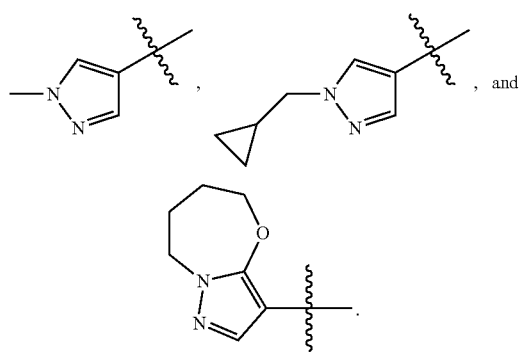
In certain embodiments, $R^1$ is selected from the group consisting of
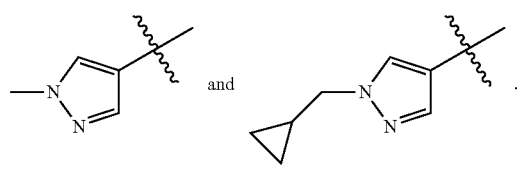
In certain embodiments, $R^1$ is selected from the group consisting of
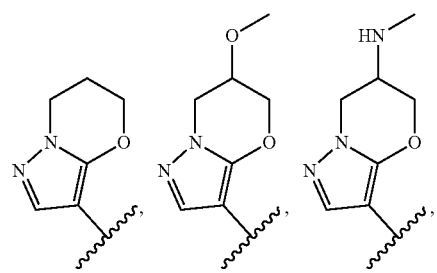
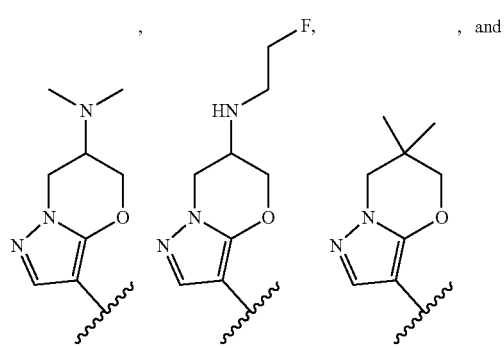
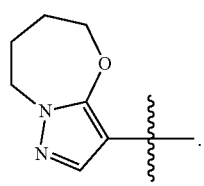
In certain embodiments, $R^1$ is selected from the group consisting of
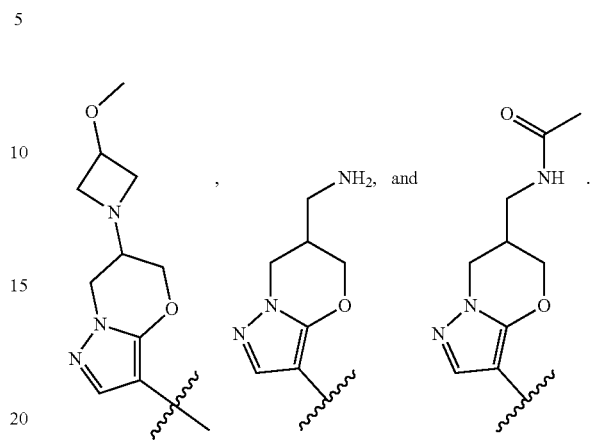
In certain embodiments, $R^1$ is selected from the group consisting of
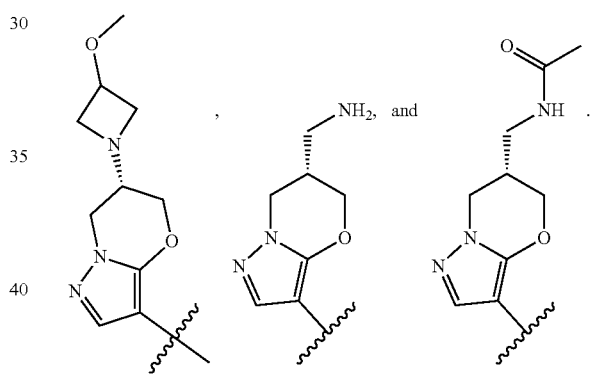
In certain embodiments, $R^1$ is selected from the group consisting of
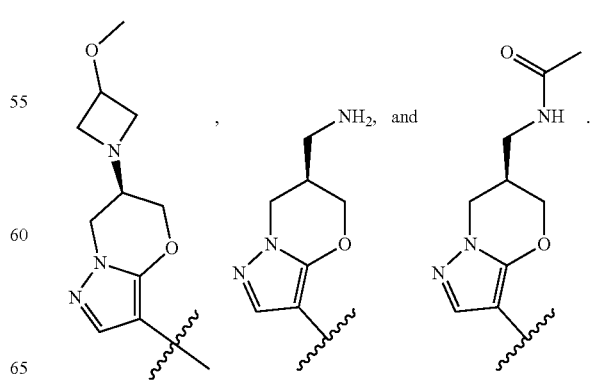

In certain embodiments, $R^1$ is selected from the group consisting of

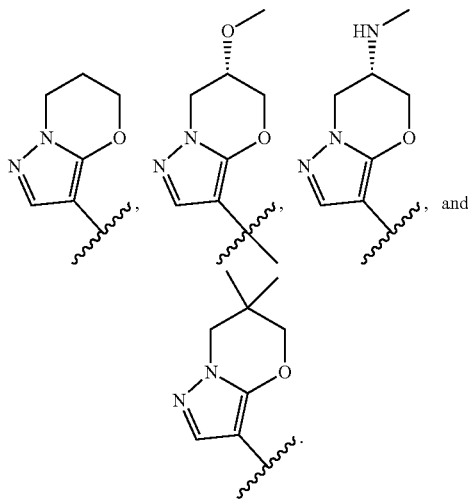

In certain embodiments, $R^1$ is selected from the group consisting of

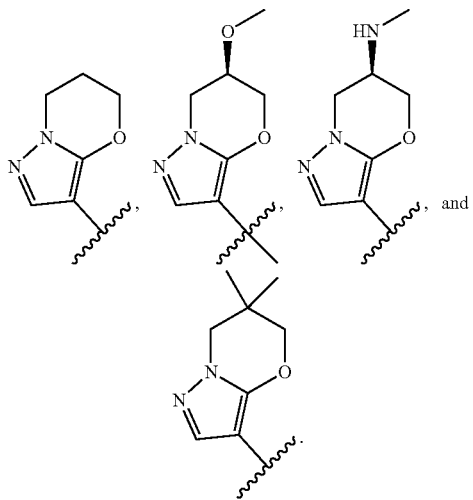

In certain embodiments, $R^{1a}$ and $R^{1b}$ are independently H, halogen, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_3$-C$_8$cycloalkyl, C$_6$aryl, 3-7-membered heterocyclyl, or 5-6-membered heteroaryl. In certain embodiments, at least one of $R^{1a}$ and $R^{1b}$ is other than H. In certain embodiments one of $R^{1a}$ and $R^{1b}$ is other than H. In certain embodiments, both $R^{1a}$ and $R^{1b}$ are other than H. In certain embodiments, $R^{1a}$ and $R^{1b}$ are H.

In certain embodiments, $R^{1c}$ and $R^{1d}$ are independently H, halogen, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_3$-C$_8$cycloalkyl, C$_6$aryl, 3-7-membered heterocyclyl, or 5-6-membered heteroaryl. In certain embodiments, at least one of $R^{1c}$ and $R^{1d}$ is other than H. In certain embodiments one of $R^{1c}$ and $R^{1d}$ is other than H. In certain embodiments, both $R^{1c}$ and $R^{1d}$ are other than H. In certain embodiments, $R^{1c}$ and $R^{1d}$ are H.

In certain embodiments, $R^{1e}$ and $R^{1f}$ are independently H, halogen, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_3$-C$_8$cycloalkyl, C$_6$aryl, 3-7-membered heterocyclyl, or 5-6-membered heteroaryl. In certain embodiments, at least one of $R^{1e}$ and $R^{1f}$ is other than H. In certain embodiments one of $R^{1e}$ and $R^{1f}$ is other than H. In certain embodiments, both $R^{1e}$ and $R^{1f}$ are other than H. In certain embodiments, $R^{1e}$ and $R^{1f}$ are H.

In certain embodiments, $R^{1g}$ and $R^{1h}$ are independently H, halogen, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_3$-C$_8$cycloalkyl, C$_6$aryl, 3-7-membered heterocyclyl, or 5-6-membered heteroaryl. In certain embodiments, at least one of $R^{1g}$ and $R^{1h}$ is other than H. In certain embodiments one of $R^{1g}$ and $R^{1h}$ is other than H. In certain embodiments, both $R^{1g}$ and $R^{1h}$ are other than H. In certain embodiments, $R^{1g}$ and $R^{1h}$ are H.

Compounds of the present disclosure can contain a basic amino group. Incorporation of a basic amino group to a compound of the present disclosure, which can also bear an acidic moiety, would be expected to exist as a zwitterion, having a net zero charge. Zwitterionic compounds can have different physicochemical properties than weak organic acids. Notably, there may be increased volumes of distribution in vivo as well as lowered plasma protein binding.

In certain embodiments, at least one of $R^{1a}$, $R^{1b}$, $R^{1c}$, $R^{1d}$, $R^{1e}$, $R^{1f}$, $R^{1g}$, and $R^{1h}$ is —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or 3-7-membered heterocyclyl; wherein the C$_1$-C$_6$alkyl is substituted with one or more substituents selected from the group consisting of —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$; and wherein the 3-7-membered heterocyclyl is unsubstituted or substituted with one or more substituents selected from the group consisting of —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$. In certain embodiments, the 3-7-membered heterocyclyl contains a nitrogen.

In certain embodiments, at least one of $R^{1a}$, $R^{1b}$, $R^{1c}$, $R^{1d}$, $R^{1e}$, $R^{1f}$, $R^{1g}$, and $R^{1h}$ is —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or 3-7-membered heterocyclyl; wherein the C$_1$-C$_6$alkyl is substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$; and wherein the 3-7-membered heterocyclyl is unsubstituted or substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$. In certain embodiments, the 3-7-membered heterocyclyl contains a nitrogen.

In certain embodiments, $R^{1a}$ and $R^{1b}$ are independently H, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or 3-7-membered heterocyclyl; wherein the C$_1$-C$_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, $R^{1a}$ is H and $R^{1b}$ is —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, the 3-7-membered heterocyclyl contains a nitrogen. In certain embodiments, at least one of $R^{1a}$ and $R^{1b}$ is other than H. In certain embodiments one of $R^{1a}$ and $R^{1b}$ is other than H. In certain embodiments, both $R^{1a}$ and $R^{1b}$ are other than H.

In certain embodiments, $R^{1a}$ and $R^{1b}$ are independently H, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, $R^{1a}$ is H and $R^{1b}$ is —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, the 3-7-membered heterocyclyl contains a nitrogen. In certain embodiments, at least one of $R^{1a}$ and $R^{1b}$ is other than H. In certain embodiments one of $R^{1a}$ and $R^{1b}$ is other than H. In certain embodiments, both $R^{1a}$ and $R^{1b}$ are other than H. In certain embodiments, $R^{1a}$ and $R^{1b}$ are H.

In certain embodiments, $R^{1c}$ and $R^{1d}$ are independently H, —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, $R^{1c}$ is H and $R^{1d}$ is —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$ In certain embodiments, the 3-7-membered heterocyclyl contains a nitrogen. In certain embodiments, at least one of $R^{1c}$ and $R^{1d}$ is other than H. In certain embodiments one of $R^{1c}$ and $R^{1d}$ is other than H. In certain embodiments, both $R^{1c}$ and $R^{1d}$ are other than H.

In certain embodiments, $R^{1c}$ and $R^{1d}$ are independently H, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, $R^{1c}$ is H and $R^{1d}$ is —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, the 3-7-membered heterocyclyl contains a nitrogen. In certain embodiments, at least one of $R^{1c}$ and $R^{1d}$ is other than H. In certain embodiments one of $R^{1c}$ and $R^{1d}$ is other than H. In certain embodiments, both $R^{1c}$ and $R^{1d}$ are other than H.

In certain embodiments, $R^{1e}$ and $R^{1f}$ are independently H, —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, $R^{1e}$ is H and $R^{1f}$ is —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$ In certain embodiments, the 3-7-membered heterocyclyl contains a nitrogen. In certain embodiments, at least one of $R^{1e}$ and $R^{1f}$ is other than H. In certain embodiments one of $R^{1e}$ and $R^{1f}$ is other than H. In certain embodiments, both $R^{1e}$ and $R^{1f}$ are other than H.

In certain embodiments, $R^{1e}$ and $R^{1f}$ are independently H, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, $R^{1e}$ is H and $R^{1f}$ is —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, the 3-7-membered heterocyclyl contains a nitrogen. In certain embodiments, at least one of $R^{1e}$ and $R^{1f}$ is other than H. In certain embodiments one of $R^{1e}$ and $R^{1f}$ is other than H. In certain embodiments, both $R^{1e}$ and $R^{1f}$ are other than H.

In certain embodiments, $R^{1g}$ and $R^{1h}$ are independently H, —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, $R^{1g}$ is H and $R^{1h}$ is —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, the 3-7-membered heterocyclyl contains a nitrogen. In certain embodiments, at least one of $R^{1g}$ and $R^{1h}$ is other than H. In certain embodiments one of $R^{1g}$ and $R^{1h}$ is other than H. In certain embodiments, both $R^{1g}$ and $R^{1h}$ are other than H.

In certain embodiments, $R^{1g}$ and $R^{1h}$ are independently H, —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, $R^{1g}$ is H and $R^{1h}$ is —N$R^{11a}R^{12a}$, —N$R^{11a}$C(O)$R^{12a}$, —N$R^{11a}$C(O)O$R^{12a}$, —N$R^{11a}$C(O)N$R^{12a}$, —N$R^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$; and wherein the 3-7-membered heterocyclyl is unsubstituted or substituted with one or more substituents selected from the group consisting of —N$R^{11a}R^{12a}$, —N$R^{11a}$C(O)$R^{12a}$, —N$R^{11a}$C(O)O$R^{12a}$, —N$R^{11a}$C(O)N$R^{12a}$, and —N$R^{11a}$S(O)$_2R^{12a}$. In certain embodiments, the 3-7-membered heterocyclyl contains a nitrogen. In certain embodiments, at least one of $R^{1g}$ and $R^{1h}$ is other than H. In certain embodiments one of $R^{1g}$ and $R^{1h}$ is other than H. In certain embodiments, both $R^{1g}$ and $R^{1h}$ are other than H.

In certain embodiments, the present disclosure provides a compound, and pharmaceutically acceptable salts, solvates (e.g., hydrates), prodrugs, and isomers thereof, that is selected from the group consisting of

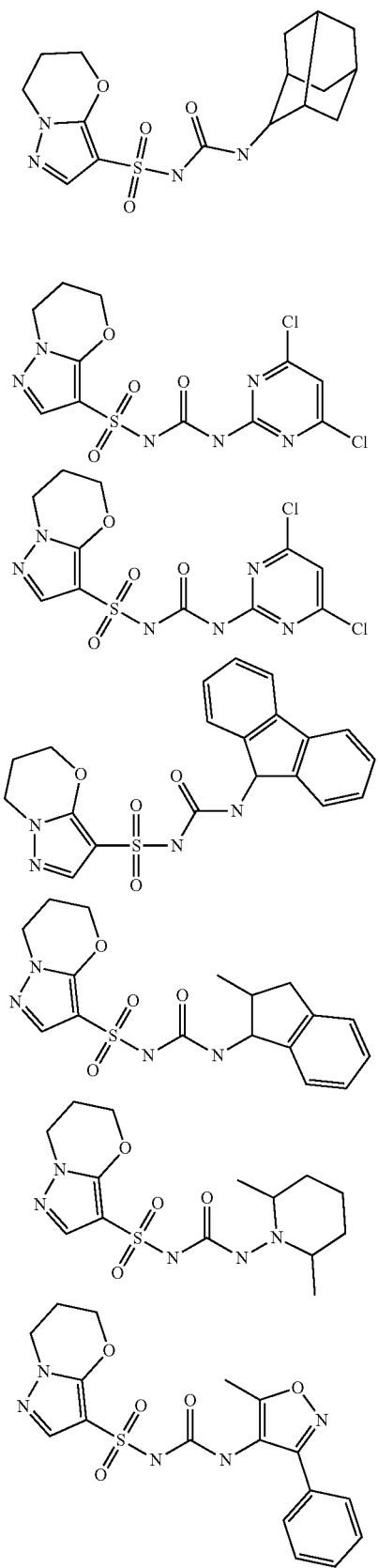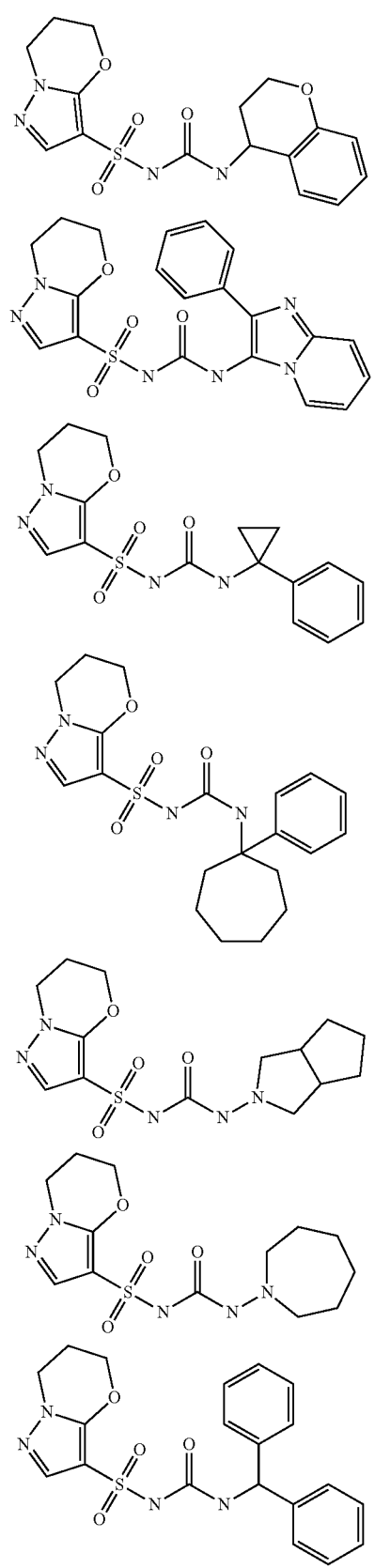

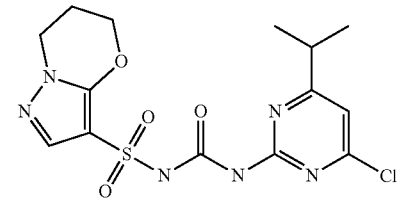
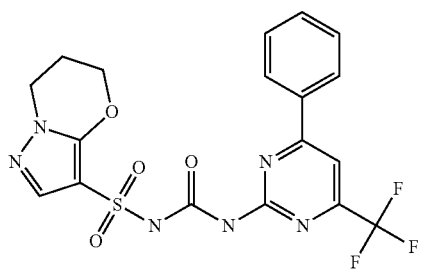
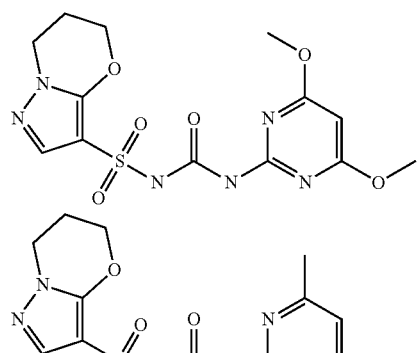
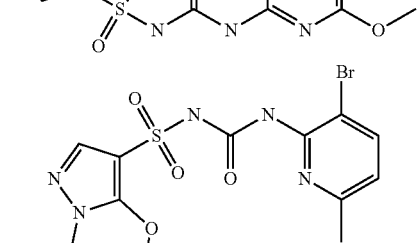
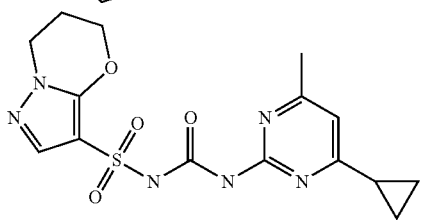
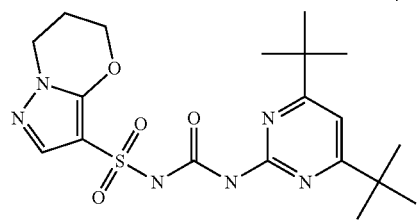
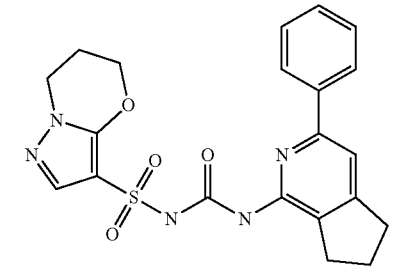
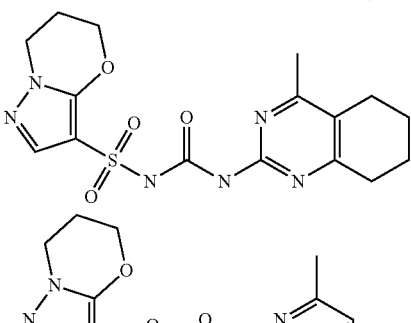
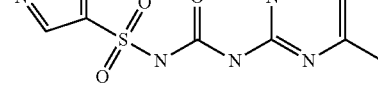
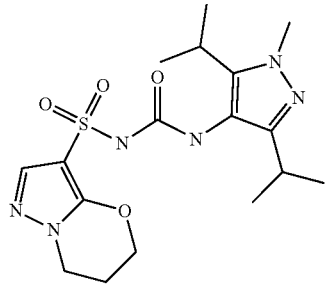
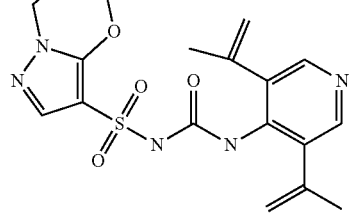
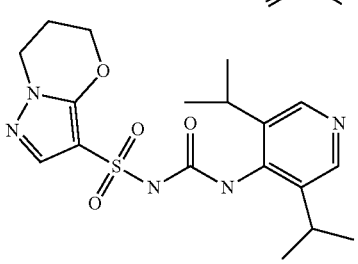
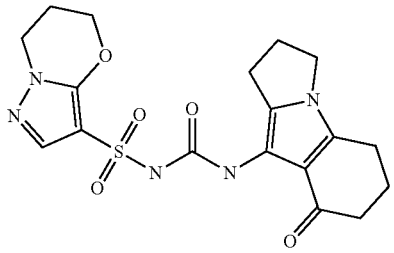

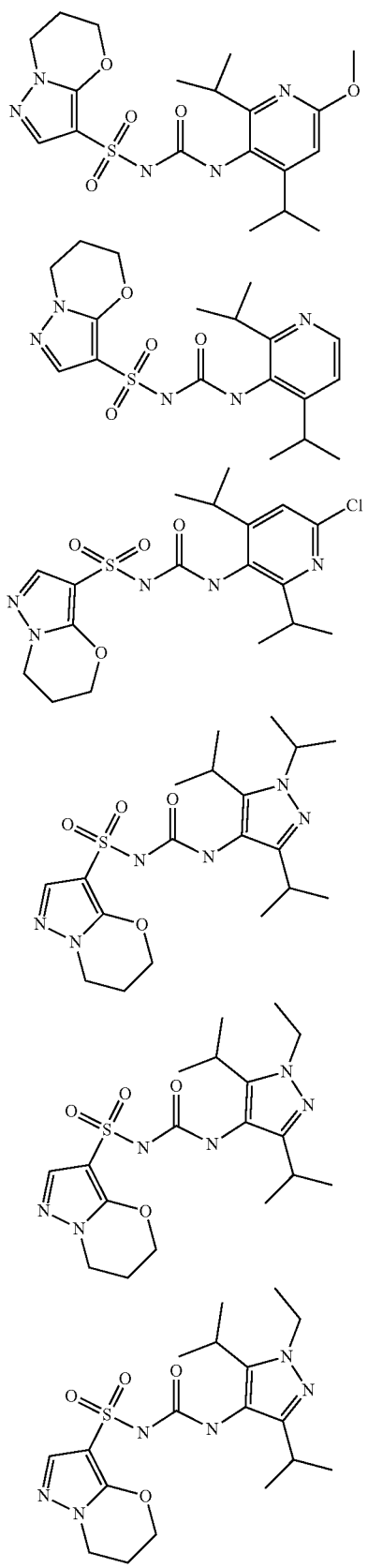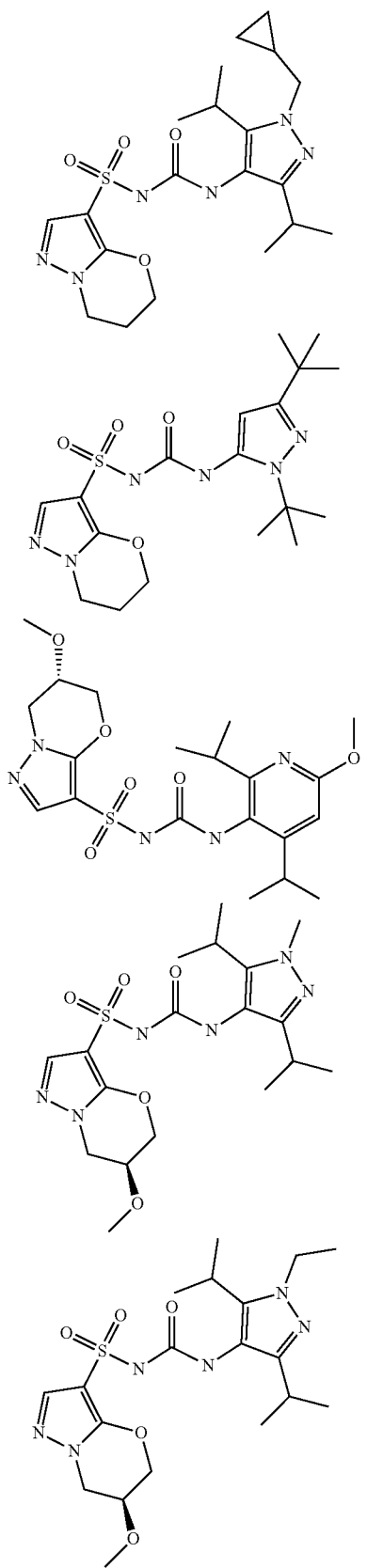

47
-continued
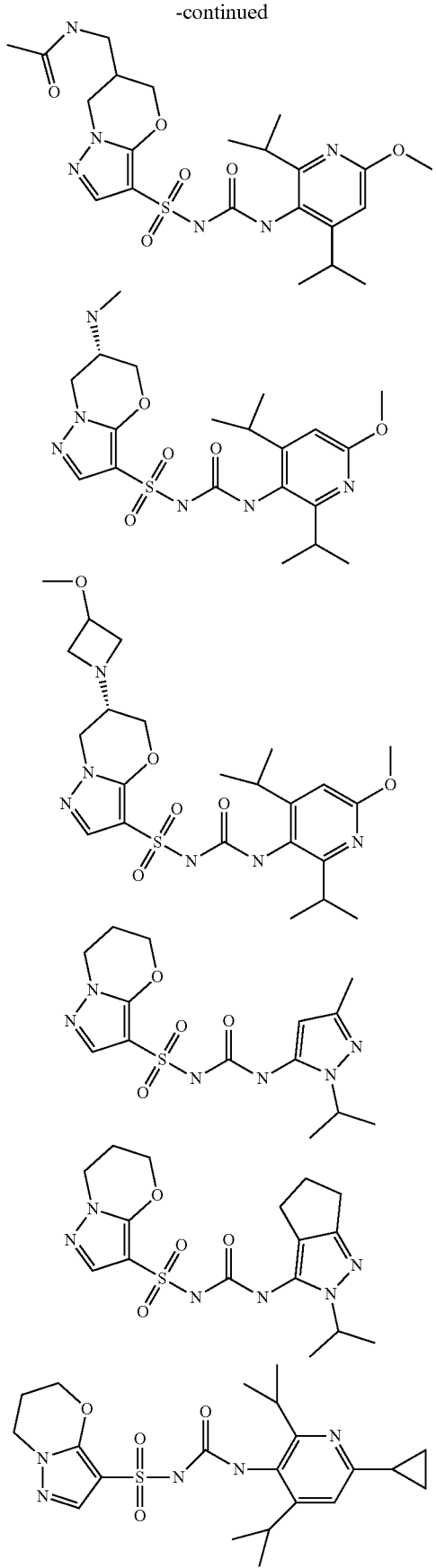
48
-continued
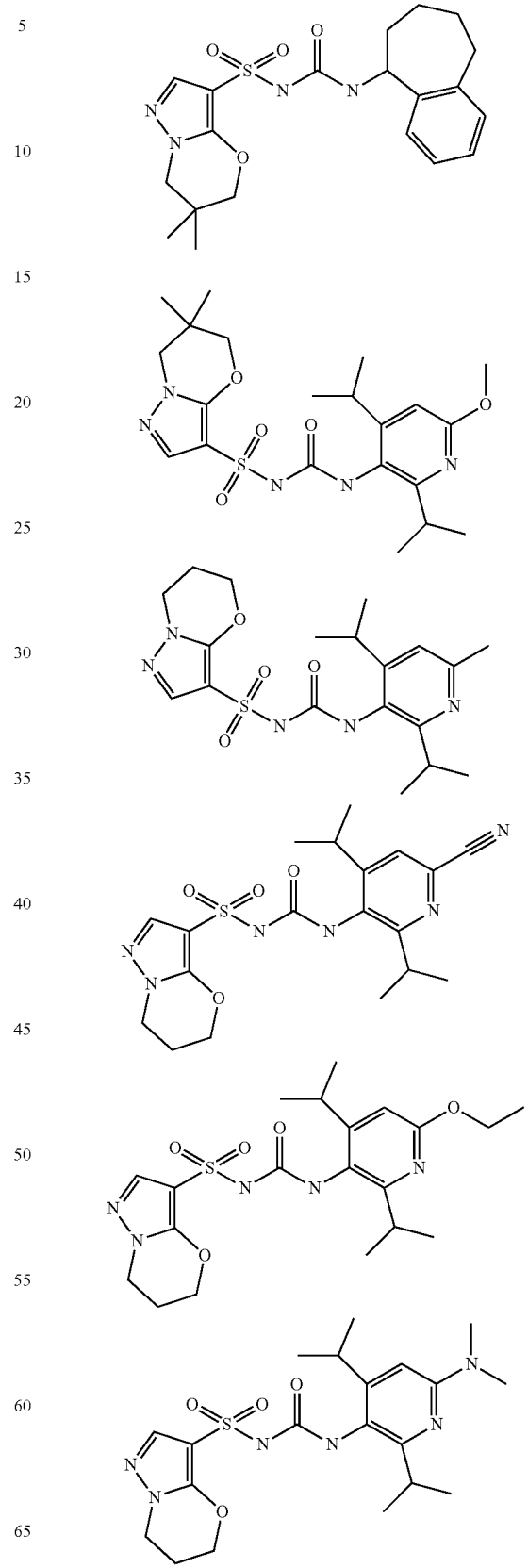

49
-continued

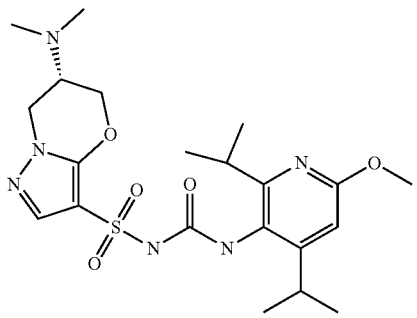

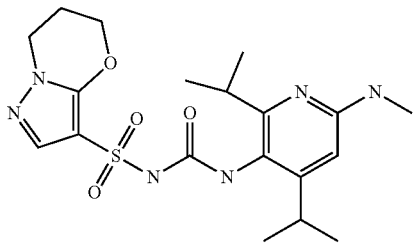

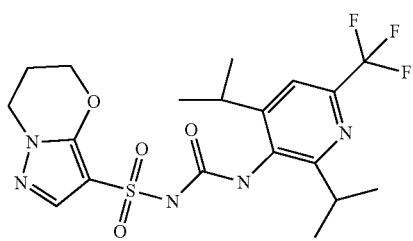

50
-continued

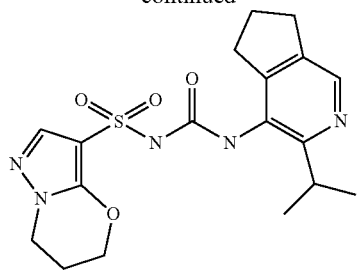

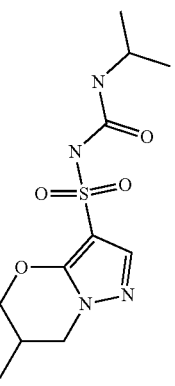

In certain embodiments, the present disclosure provides above compounds of Formula I, where the stereochemistry is not determined.

Representative compounds are listed in Table 1. It is understood that individual enantiomers and diastereomers are included in the table below by Compound No. and Compound Name, and their corresponding structures can be readily determined therefrom. In some instances, the enantiomers or diastereomers are identified by their respective perperties, for example, retention times on a chiral HPLC or its biological activities, and the absolute stereo configurations of the chiral centers are arbitrarily assigned.

TABLE 1

| Ex. No. | Compound Structure | Name |
|---|---|---|
| 1 | | N-((2,2-dimethyl-1,2,3,4-tetrahydronaphthalen-1-yl)carbamoyl)-6,7-dihydro-5H-pyrazolo[5,1-b][1,3]oxazine-3-sulfonamide |
| 1a | | N-(((1R)-2,2-dimethyl-1,2,3,4-tetrahydronaphthalen-1-yl)carbamoyl)-6,7-dihydro-5H-pyrazolo[5,1-b][1,3]oxazine-3-sulfonamide |
| 1b | | N-(((1S)-2,2-dimethyl-1,2,3,4-tetrahydronaphthalen-1-yl)carbamoyl)-6,7-dihydro-5H-pyrazolo[5,1-b][1,3]oxazine-3-sulfonamide |

TABLE 1-continued

| Ex. No. | Compound Structure | Name |
|---|---|---|
| 2 | 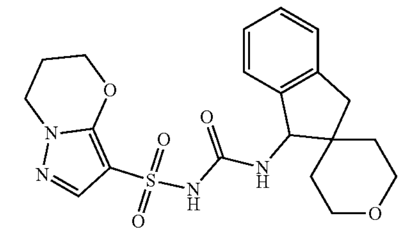 [SMILES: O=C(NC1c2ccccc2CC12CCOCC2)NS(=O)(=O)c1cnn2c1OCCC2] | N-((1,2',3,3',5',6'-hexahydrospiro[indene-2,4'-pyran]-1-yl)carbamoyl)-6,7-dihydro-5H-pyrazolo[5,1-b][1,3]oxazine-3-sulfonamide |
| 2a 2b | | N-(((1R)-1,2',3,3',5',6'-hexahydrospiro[indene-2,4'-pyran]-1-yl)carbamoyl)-6,7-dihydro-5H-pyrazolo[5,1-b][1,3]oxazine-3-sulfonamide<br>N-(((1S)-1,2',3,3',5',6'-hexahydrospiro[indene-2,4'-pyran]-1-yl)carbamoyl)-6,7-dihydro-5H-pyrazolo[5,1-b][1,3]oxazine-3-sulfonamide |
| 3 | 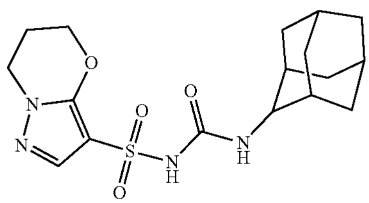 [SMILES: O=C(NC1C2CC3CC(C2)CC1C3)NS(=O)(=O)c1cnn2c1OCCC2] | N-((adamantan-2-yl)carbamoyl)-6,7-dihydro-5H-pyrazolo[5,1-b][1,3]oxazine-3-sulfonamide |
| 4 | 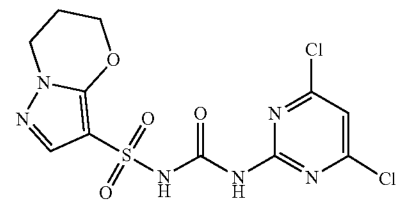 [SMILES: O=C(Nc1nc(Cl)cc(Cl)n1)NS(=O)(=O)c1cnn2c1OCCC2] | N-((4,6-dichloropyrimidin-2-yl)carbamoyl)-6,7-dihydro-5H-pyrazolo[5,1-b][1,3]oxazine-3-sulfonamide |
| 5 | 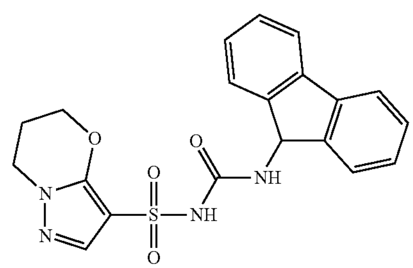 [SMILES: O=C(NC1c2ccccc2-c2ccccc21)NS(=O)(=O)c1cnn2c1OCCC2] | N-((9H-fluoren-9-yl)carbamoyl)-6,7-dihydro-5H-pyrazolo[5,1-b][1,3]oxazine-3-sulfonamide |
| 6 | 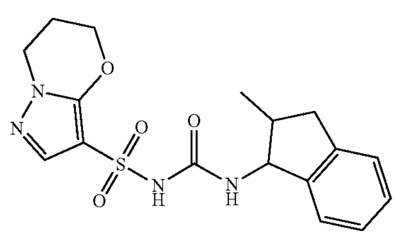 [SMILES: CC1Cc2ccccc2C1NC(=O)NS(=O)(=O)c1cnn2c1OCCC2] | N-((2-methyl-2,3-dihydro-1H-inden-1-yl)carbamoyl)-6,7-dihydro-5H-pyrazolo[5,1-b][1,3]oxazine-3-sulfonamide |
| 6a 6b 6c 6d | | N-(((1R,2S)-2-methyl-2,3-dihydro-1H-inden-1-yl)carbamoyl)-6,7-dihydro-5H-pyrazolo[5,1-b][1,3]oxazine-3-sulfonamide<br>N-(((1R,2R)-2-methyl-2,3-dihydro-1H-inden-1-yl)carbamoyl)-6,7-dihydro-5H-pyrazolo[5,1-b][1,3]oxazine-3-sulfonamide<br>N-(((1S,2S)-2-methyl-2,3-dihydro-1H-inden-1-yl)carbamoyl)-6,7-dihydro-5H-pyrazolo[5,1-b][1,3]oxazine-3-sulfonamide<br>N-(((1S,2R)-2-methyl-2,3-dihydro-1H-inden-1-yl)carbamoyl)-6,7-dihydro-5H-pyrazolo[5,1-b][1,3]oxazine-3-sulfonamide |

TABLE 1-continued

| Ex. No. | Compound Structure | Name |
|---|---|---|
| 7 | 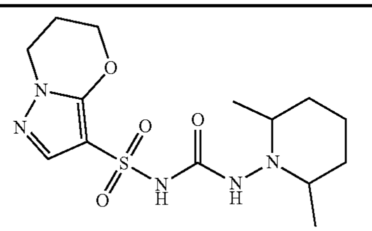 | N-((2,6-dimethylpiperidin-1-yl)carbamoyl)-6,7-dihydro-5H-pyrazolo[5,1-b][1,3]oxazine-3-sulfonamide |
| 7a 7b 7c | | N-(((2R,6S)-2,6-dimethylpiperidin-1-yl)carbamoyl)-6,7-dihydro-5H-pyrazolo[5,1-b][1,3]oxazine-3-sulfonamide N-(((2S,6S)-2,6-dimethylpiperidin-1-yl)carbamoyl)-6,7-dihydro-5H-pyrazolo[5,1-b][1,3]oxazine-3-sulfonamide N-(((2R,6R)-2,6-dimethylpiperidin-1-yl)carbamoyl)-6,7-dihydro-5H-pyrazolo[5,1-b][1,3]oxazine-3-sulfonamide |
| 8 | 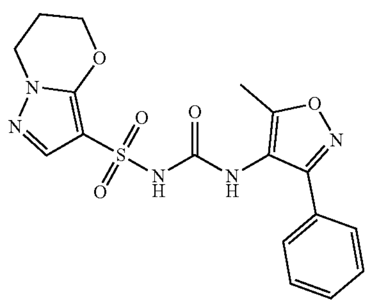 [SMILES: Cc1onc(-c2ccccc2)c1NC(=O)NS(=O)(=O)c1cnn2c1OCCC2] | N-((5-methyl-3-phenylisoxazol-4-yl)carbamoyl)-6,7-dihydro-5H-pyrazolo[5,1-b][1,3]oxazine-3-sulfonamide |
| 9 | 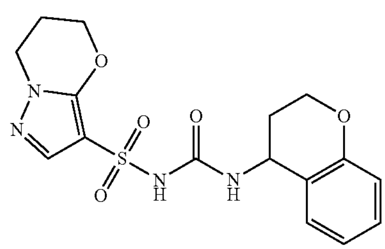 [SMILES: O=C(NC1CCOc2ccccc21)NS(=O)(=O)c1cnn2c1OCCC2] | N-(chroman-4-ylcarbamoyl)-6,7-dihydro-5H-pyrazolo[5,1-b][1,3]oxazine-3-sulfonamide |
| 9a 9b | | N-((R)-chroman-4-ylcarbamoyl)-6,7-dihydro-5H-pyrazolo[5,1-b][1,3]oxazine-3-sulfonamide N-((S)-chroman-4-ylcarbamoyl)-6,7-dihydro-5H-pyrazolo[5,1-b][1,3]oxazine-3-sulfonamide |
| 10 | 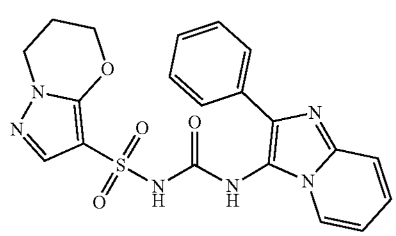 [SMILES: O=C(Nc1c(-c2ccccc2)nc2ccccn12)NS(=O)(=O)c1cnn2c1OCCC2] | N-((2-phenylimidazo[1,2-a]pyridin-3-yl)carbamoyl)-6,7-dihydro-5H-pyrazolo[5,1-b][1,3]oxazine-3-sulfonamide |
| 11 | 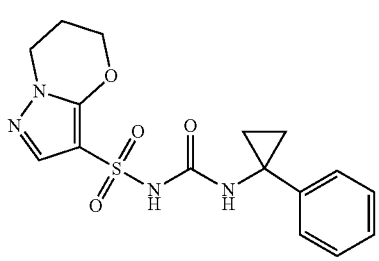 [SMILES: O=C(NC1(c2ccccc2)CC1)NS(=O)(=O)c1cnn2c1OCCC2] | N-((1-phenylcyclopropyl)carbamoyl)-6,7-dihydro-5H-pyrazolo[5,1-b][1,3]oxazine-3-sulfonamide |

TABLE 1-continued

| Ex. No. | Compound Structure | Name |
|---|---|---|
| 12 | 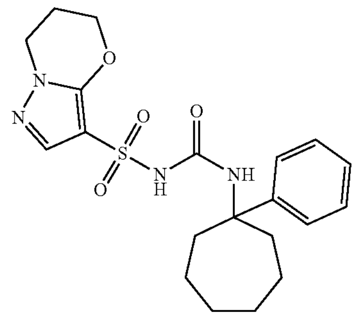 [SMILES: O=C(NC1(c2ccccc2)CCCCCC1)NS(=O)(=O)c1cnn2c1OCCC2] | N-((1-phenylcycloheptyl)carbamoyl)-6,7-dihydro-5H-pyrazolo[5,1-b][1,3]oxazine-3-sulfonamide |
| 13 | 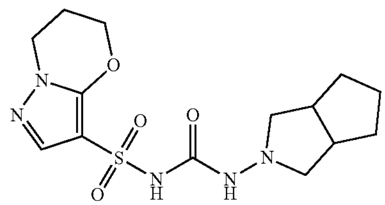 [SMILES: O=C(NN1CC2CCCC2C1)NS(=O)(=O)c1cnn2c1OCCC2] | N-((hexahydrocyclopenta[c]pyrrol-2(1H)-yl)carbamoyl)-6,7-dihydro-5H-pyrazolo[5,1-b][1,3]oxazine-3-sulfonamide |
| 13a 13b 13c | | N-(((3aR,6aS)-hexahydrocyclopenta[c]pyrrol-2(1H)-yl)carbamoyl)-6,7-dihydro-5H-pyrazolo[5,1-b][1,3]oxazine-3-sulfonamide N-(((3aS,6aS)-hexahydrocyclopenta[c]pyrrol-2(1H)-yl)carbamoyl)-6,7-dihydro-5H-pyrazolo[5,1-b][1,3]oxazine-3-sulfonamide N-(((3aR,6aR)-hexahydrocyclopenta[c]pyrrol-2(1H)-yl)carbamoyl)-6,7-dihydro-5H-pyrazolo[5,1-b][1,3]oxazine-3-sulfonamide |
| 14 | 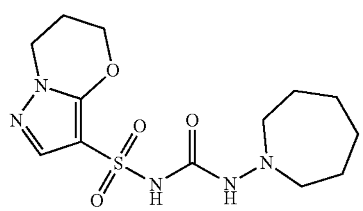 [SMILES: O=C(NN1CCCCCC1)NS(=O)(=O)c1cnn2c1OCCC2] | N-(azepan-1-ylcarbamoyl)-6,7-dihydro-5H-pyrazolo[5,1-b][1,3]oxazine-3-sulfonamide |
| 15 | 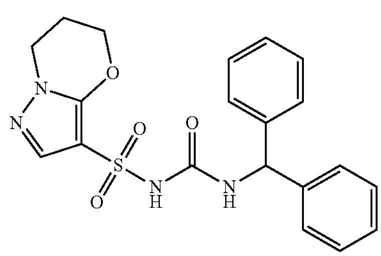 [SMILES: O=C(NC(c1ccccc1)c1ccccc1)NS(=O)(=O)c1cnn2c1OCCC2] | N-(benzhydrylcarbamoyl)-6,7-dihydro-5H-pyrazolo[5,1-b][1,3]oxazine-3-sulfonamide |
| 16 | 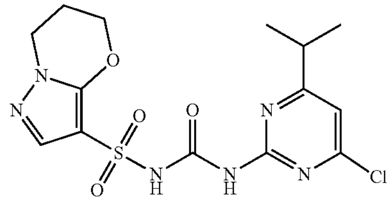 [SMILES: CC(C)c1cc(Cl)nc(NC(=O)NS(=O)(=O)c2cnn3c2OCCC3)n1] | N-((4-chloro-6-isopropylpyrimidin-2-yl)carbamoyl)-6,7-dihydro-5H-pyrazolo[5,1-b][1,3]oxazine-3-sulfonamide |

TABLE 1-continued

| Ex. No. | Compound Structure | Name |
|---|---|---|
| 17 | 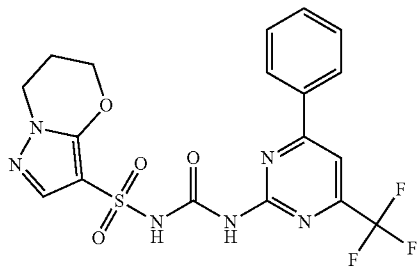 [SMILES: O=C(Nc1nc(-c2ccccc2)cc(C(F)(F)F)n1)NS(=O)(=O)c1cnn2c1OCCC2] | N-((4-phenyl-6-(trifluoromethyl)pyrimidin-2-yl)carbamoyl)-6,7-dihydro-5H-pyrazolo[5,1-b][1,3]oxazine-3-sulfonamide |
| 18 | 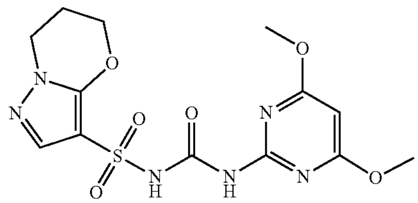 [SMILES: COc1cc(OC)nc(NC(=O)NS(=O)(=O)c2cnn3c2OCCC3)n1] | N-((4,6-dimethoxypyrimidin-2-yl)carbamoyl)-6,7-dihydro-5H-pyrazolo[5,1-b][1,3]oxazine-3-sulfonamide |
| 19 | 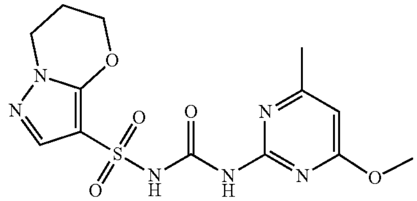 [SMILES: COc1cc(C)nc(NC(=O)NS(=O)(=O)c2cnn3c2OCCC3)n1] | N-((4-methoxy-6-methylpyrimidin-2-yl)carbamoyl)-6,7-dihydro-5H-pyrazolo[5,1-b][1,3]oxazine-3-sulfonamide |
| 20 | 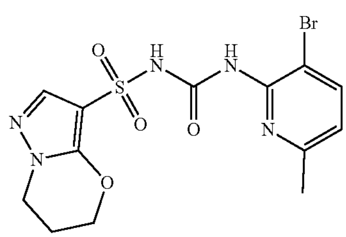 [SMILES: Cc1ccc(Br)c(NC(=O)NS(=O)(=O)c2cnn3c2OCCC3)n1] | N-((3-bromo-6-methylpyridin-2-yl)carbamoyl)-6,7-dihydro-5H-pyrazolo[5,1-b][1,3]oxazine-3-sulfonamide |
| 21 | 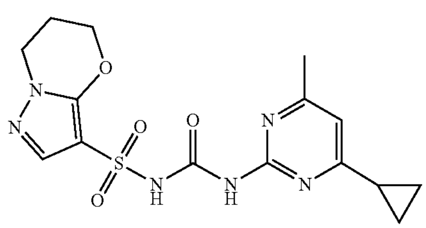 [SMILES: Cc1cc(C2CC2)nc(NC(=O)NS(=O)(=O)c2cnn3c2OCCC3)n1] | N-((4-cyclopropyl-6-methylpyrimidin-2-yl)carbamoyl)-6,7-dihydro-5H-pyrazolo[5,1-b][1,3]oxazine-3-sulfonamide |
| 22 | 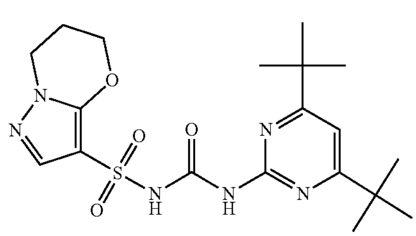 [SMILES: CC(C)(C)c1cc(C(C)(C)C)nc(NC(=O)NS(=O)(=O)c2cnn3c2OCCC3)n1] | N-((4,6-di-tert-butylpyrimidin-2-yl)carbamoyl)-6,7-dihydro-5H-pyrazolo[5,1-b1[1,3]oxazine-3-sulfonamide |

TABLE 1-continued

| Ex. No. | Compound Structure | Name |
|---|---|---|
| 23 | 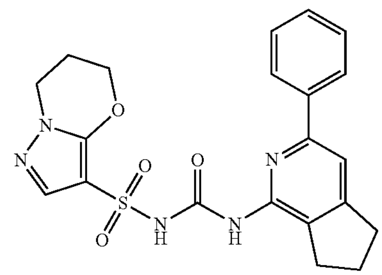 [SMILES: O=C(Nc1nc(-c2ccccc2)cc2c1CCC2)NS(=O)(=O)c1cnn2c1OCCC2] | N-((3-phenyl-6,7-dihydro-5H-cyclopenta[c]pyridin-1-yl)carbamoyl)-6,7-dihydro-5H-pyrazolo[5,1-b][1,3]oxazine-3-sulfonamide |
| 24 | 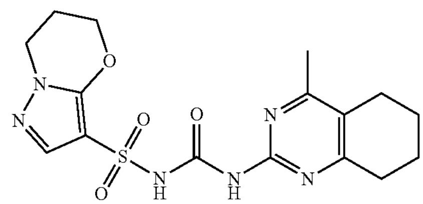 [SMILES: Cc1nc(NC(=O)NS(=O)(=O)c2cnn3c2OCCC3)nc2c1CCCC2] | N-((4-methyl-5,6,7,8-tetrahydroquinazolin-2-yl)carbamoyl)-6,7-dihydro-5H-pyrazolo[5,1-b][1,3]oxazine-3-sulfonamide |
| 25 | 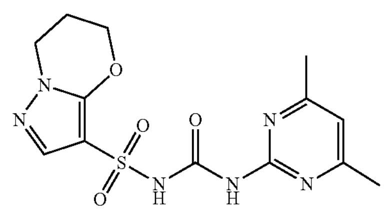 [SMILES: Cc1cc(C)nc(NC(=O)NS(=O)(=O)c2cnn3c2OCCC3)n1] | N-((4,6-dimethylpyrimidin-2-yl)carbamoyl)-6,7-dihydro-5H-pyrazolo[5,1-b][1,3]oxazine-3-sulfonamide |
| 26 | 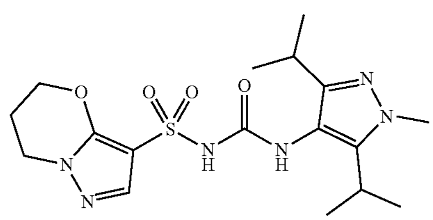 [SMILES: CC(C)c1nn(C)c(C(C)C)c1NC(=O)NS(=O)(=O)c1cnn2c1OCCC2] | N-((3,5-diisopropyl-1-methyl-1H-pyrazol-4-yl)carbamoyl)-6,7-dihydro-5H-pyrazolo[5,1-b][1,3]oxazine-3-sulfonamide |
| 27 | 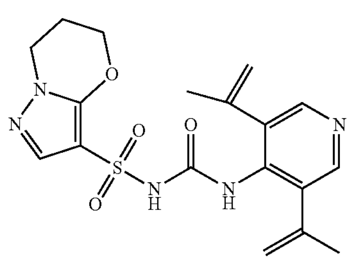 [SMILES: C=C(C)c1cncc(C(=C)C)c1NC(=O)NS(=O)(=O)c1cnn2c1OCCC2] | N-((3,5-di(prop-1-en-2-yl)pyridin-4-yl)carbamoyl)-6,7-dihydro-5H-pyrazolo[5,1-b][1,3]oxazine-3-sulfonamide |
| 28 | 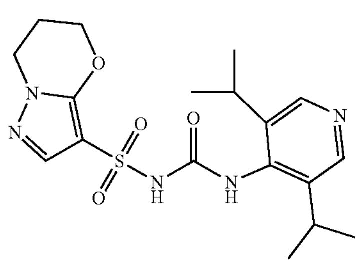 [SMILES: CC(C)c1cncc(C(C)C)c1NC(=O)NS(=O)(=O)c1cnn2c1OCCC2] | N-((3,5-diisopropylpyridin-4-yl)carbamoyl)-6,7-dihydro-5H-pyrazolo[5,1-b][1,3]oxazine-3-sulfonamide |

| Ex. No. | Compound Structure | Name |
|---|---|---|
| 29 | 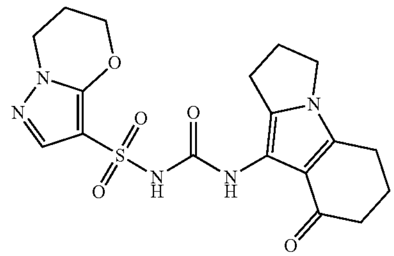 [SMILES: O=C(Nc1c2c(n3c1CCC3)CCCC2=O)NS(=O)(=O)c1cnn2c1OCCC2] | N-((8-oxo-2,3,5,6,7,8-hexahydro-1H-pyrrolo[1,2-a]indol-9-yl)carbamoyl)-6,7-dihydro-5H-pyrazolo[5,1-b][1,3]oxazine-3-sulfonamide |
| 30 | 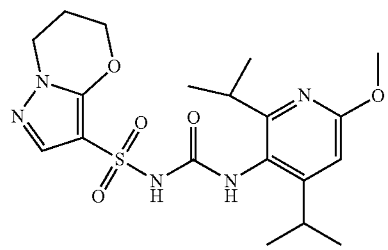 [SMILES: COc1cc(C(C)C)c(NC(=O)NS(=O)(=O)c2cnn3c2OCCC3)c(C(C)C)n1] | N-((2,4-diisopropyl-6-methoxypyridin-3-yl)carbamoyl)-6,7-dihydro-5H-pyrazolo[5,1-b][1,3]oxazine-3-sulfonamide |
| 31 | 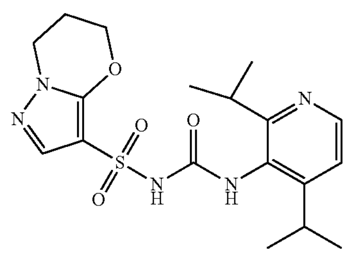 [SMILES: CC(C)c1ccnc(C(C)C)c1NC(=O)NS(=O)(=O)c1cnn2c1OCCC2] | N-((2,4-diisopropylpyridin-3-yl)carbamoyl)-6,7-dihydro-5H-pyrazolo[5,1-b][1,3]oxazine-3-sulfonamide |
| 32 | 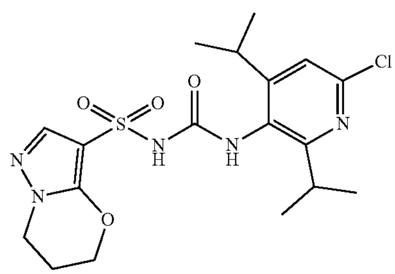 [SMILES: CC(C)c1cc(Cl)nc(C(C)C)c1NC(=O)NS(=O)(=O)c1cnn2c1OCCC2] | N-((6-chloro-2,4-diisopropylpyridin-3-yl)carbamoyl)-6,7-dihydro-5H-pyrazolo[5,1-b][1,3]oxazine-3-sulfonamide |
| 33 | 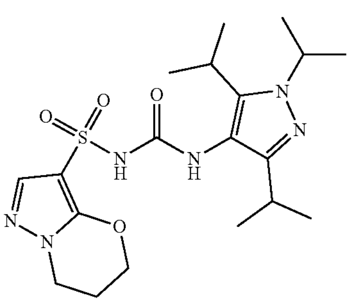 [SMILES: CC(C)c1nn(C(C)C)c(C(C)C)c1NC(=O)NS(=O)(=O)c1cnn2c1OCCC2] | N-((1,3,5-triisopropyl-1H-pyrazol-4-yl)carbamoyl)-6,7-dihydro-5H-pyrazolo[5,1-b][1,3]oxazine-3-sulfonamide |
| 34 | 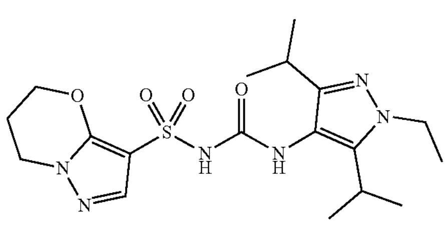 [SMILES: CCn1nc(C(C)C)c(NC(=O)NS(=O)(=O)c2cnn3c2OCCC3)c1C(C)C] | N-((1-ethyl-3,5-diisopropyl-1H-pyrazol-4-yl)carbamoyl)-6,7-dihydro-5H-pyrazolo[5,1-b][1,3]oxazine-3-sulfonamide |

TABLE 1-continued

| Ex. No. | Compound Structure | Name |
|---|---|---|
| 35 | 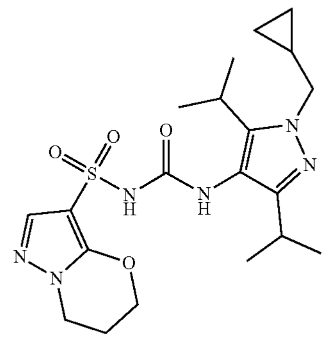 [SMILES: CC(C)c1nn(CC2CC2)c(C(C)C)c1NC(=O)NS(=O)(=O)c1cnn2c1OCCC2] | N-((1-(cyclopropylmethyl)-3,5-diisopropyl-1H-pyrazol-4-yl)carbamoyl)-6,7-dihydro-5H-pyrazolo[5,1-b][1,3]oxazine-3-sulfonamide |
| 36 | 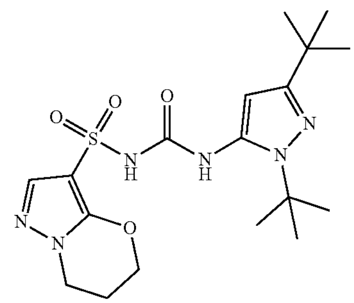 [SMILES: CC(C)(C)c1cc(NC(=O)NS(=O)(=O)c2cnn3c2OCCC3)n(C(C)(C)C)n1] | N-((1,3-di-tert-butyl-1H-pyrazol-5-yl)carbamoyl)-6,7-dihydro-5H-pyrazolo[5,1-b][1,3]oxazine-3-sulfonamide |
| 37 | 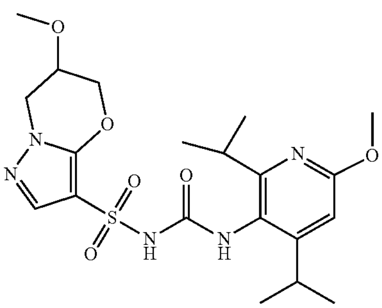 [SMILES: COc1cc(C(C)C)c(NC(=O)NS(=O)(=O)c2cnn3c2OCC(OC)C3)c(C(C)C)n1] | N-((2,4-diisopropyl-6-methoxypyridin-3-yl)carbamoyl)-6-methoxy-6,7-dihydro-5H-pyrazolo[5,1-b][1,3]oxazine-3-sulfonamide |
| 37a | | N-(((6S)-2,4-diisopropyl-6-methoxypyridin-3-yl)carbamoyl)-6-methoxy-6,7-dihydro-5H-pyrazolo[5,1-b][1,3]oxazine-3-sulfonamide |
| 37b | | N-(((6R)-2,4-diisopropyl-6-methoxypyridin-3-yl)carbamoyl)-6-methoxy-6,7-dihydro-5H-pyrazolo[5,1-b][1,3]oxazine-3-sulfonamide |
| 38 | 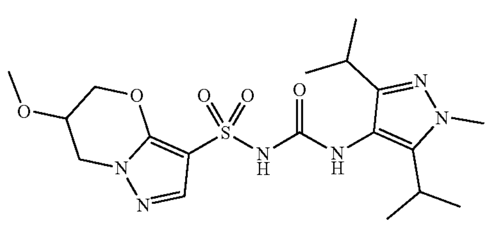 | N-((3,5-diisopropyl-1-methyl-1H-pyrazol-4-yl)carbamoyl)-6-methoxy-6,7-dihydro-5H-pyrazolo[5,1-b][1,3]oxazine-3-sulfonamide |
| 38a | | N-(((6S)-3,5-diisopropyl-1-methyl-1H-pyrazol-4-yl)carbamoyl)-6-methoxy-6,7-dihydro-5H-pyrazolo[5,1-b][1,3]oxazine-3-sulfonamide |
| 38b | | N-(((6R)-3,5-diisopropyl-1-methyl-1H-pyrazol-4-yl)carbamoyl)-6-methoxy-6,7-dihydro-5H-pyrazolo[5,1-b][1,3]oxazine-3-sulfonamide |

TABLE 1-continued

| Ex. No. | Compound Structure | Name |
|---|---|---|
| 39 | 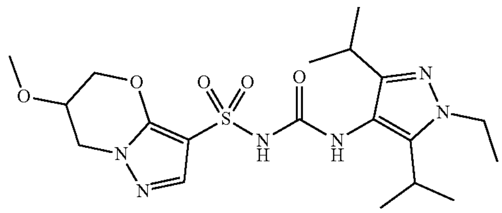 [SMILES: CCn1nc(C(C)C)c(NC(=O)NS(=O)(=O)c2cnn3c2OCC(OC)C3)c1C(C)C] | N-((1-ethyl-3,5-diisopropyl-1H-pyrazol-4-yl)carbamoyl)-6-methoxy-6,7-dihydro-5H-pyrazolo[5,1-b][1,3]oxazine-3-sulfonamide |
| 39a | | N-(((6S)-3-(N-((2,4-diisopropyl-6-methoxypyridin-3-yl)carbamoyl)sulfamoyl)-6,7-dihydro-5H-pyrazolo[5,1-b][1,3]oxazin-6-yl)methyl)acetamide |
| 39b | | N-(((6R)-3-(N-((2,4-diisopropyl-6-methoxypyridin-3-yl)carbamoyl)sulfamoyl)-6,7-dihydro-5H-pyrazolo[5,1-b][1,3]oxazin-6-yl)methyl)acetamide |
| 40 | 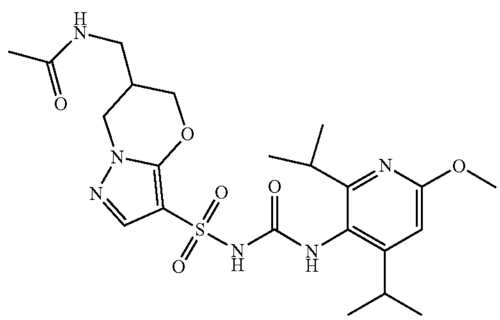 [SMILES: COc1cc(C(C)C)c(NC(=O)NS(=O)(=O)c2cnn3c2OCC(CNC(C)=O)C3)c(C(C)C)n1] | N-((3-(N-((2,4-diisopropyl-6-methoxypyridin-3-yl)carbamoyl)sulfamoyl)-6,7-dihydro-5H-pyrazolo[5,1-b][1,3]oxazin-6-yl)methyl)acetamide |
| 40a 40b | | N-(((6R)-3-(N-((2,4-diisopropyl-6-methoxypyridin-3-yl)carbamoyl)sulfamoyl)-6,7-dihydro-5H-pyrazolo[5,1-b][1,3]oxazin-6-yl)methyl)acetamide<br>N-(((6S)-3-(N-((2,4-diisopropyl-6-methoxypyridin-3-yl)carbamoyl)sulfamoyl)-6,7-dihydro-5H-pyrazolo[5,1-b][1,3]oxazin-6-yl)methyl)acetamide |
| 41 | 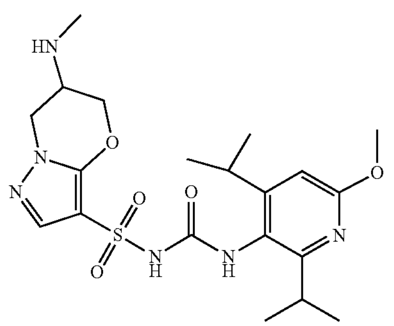 [SMILES: CNC1COc2c(S(=O)(=O)NC(=O)Nc3c(C(C)C)cc(OC)nc3C(C)C)cnn2C1] | N-((2,4-diisopropyl-6-methoxypyridin-3-yl)carbamoyl)-6-(methylamino)-6,7-dihydro-5H-pyrazolo[5,1-b][1,3]oxazine-3-sulfonamide |
| 41a 41b | | N-(((6S)-2,4-diisopropyl-6-methoxypyridin-3-yl)carbamoyl)-6-(methylamino)-6,7-dihydro-5H-pyrazolo[5,1-b][1,3]oxazine-3-sulfonamide<br>N-(((6R)-2,4-diisopropyl-6-methoxypyridin-3-yl)carbamoyl)-6-(methylamino)-6,7-dihydro-5H-pyrazolo[5,1-b][1,3]oxazine-3-sulfonamide |

TABLE 1-continued

| Ex. No. | Compound Structure | Name |
|---|---|---|
| 42 | 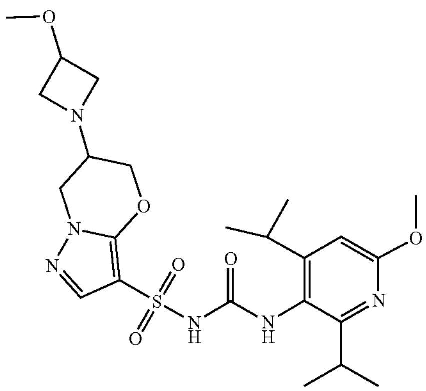 | N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide |
| 42a | | N-(((6S)-2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide |
| 42b | | N-(((6R)-2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide |
| 43 | 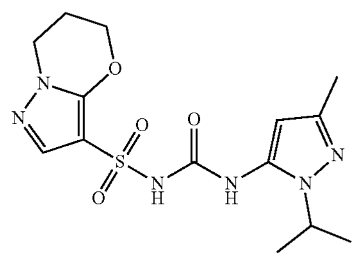 [SMILES: Cc1cc(NC(=O)NS(=O)(=O)c2cnn3c2OCCC3)n(C(C)C)n1] | N-((1-isopropyl-3-methyl-1H-pyrazol-5-yl)carbamoyl)-6,7-dihydro-5H-pyrazolo[5,1-b][1,3]oxazine-3-sulfonamide |
| 44 | 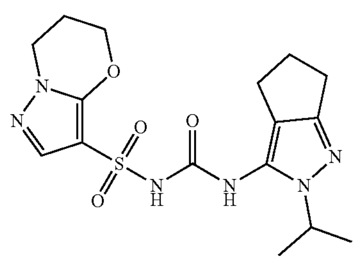 [SMILES: CC(C)n1nc2c(c1NC(=O)NS(=O)(=O)c1cnn3c1OCCC3)CCC2] | N-((2-isopropyl-2,4,5,6-tetrahydrocyclopenta[c]pyrazol-3-yl)carbamoyl)-6,7-dihydro-5H-pyrazolo[5,1-b][1,3]oxazine-3-sulfonamide |
| 45 | 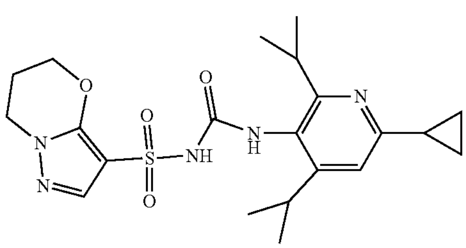 [SMILES: CC(C)c1cc(C2CC2)nc(C(C)C)c1NC(=O)NS(=O)(=O)c1cnn2c1OCCC2] | N-((6-cyclopropyl-2,4-diisopropylpyridin-3-yl)carbamoyl)-6,7-dihydro-5H-pyrazolo[5,1-b][1,3]oxazine-3-sulfonamide |

TABLE 1-continued

| Ex. No. | Compound Structure | Name |
|---|---|---|
| 46 | 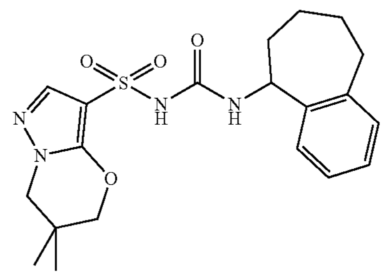 [SMILES: CC1(C)COc2c(S(=O)(=O)NC(=O)NC3CCCCc4ccccc43)cnn2C1] | 6,6-dimethyl-N-((6,7,8,9-tetrahydro-5H-benzo[7]annulen-5-yl)carbamoyl)-6,7-dihydro-5H-pyrazolo[5,1-b][1,3]oxazine-3-sulfonamide |
| 47 | 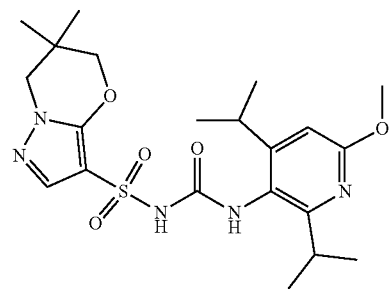 [SMILES: COc1cc(C(C)C)c(NC(=O)NS(=O)(=O)c2cnn3c2OCC(C)(C)C3)c(C(C)C)n1] | N-((2,4-diisopropyl-6-methoxypyridin-3-yl)carbamoyl)-6,6-dimethyl-6,7-dihydro-5H-pyrazolo[5,1-b][1,3]oxazine-3-sulfonamide |
| 48 | 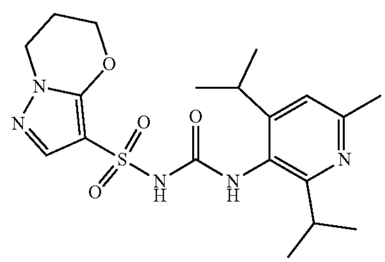 [SMILES: Cc1cc(C(C)C)c(NC(=O)NS(=O)(=O)c2cnn3c2OCCC3)c(C(C)C)n1] | N-((2,4-diisopropyl-6-methylpyridin-3-yl)carbamoyl)-6,7-dihydro-5H-pyrazolo[5,1-b][1,3]oxazine-3-sulfonamide |
| 49 | 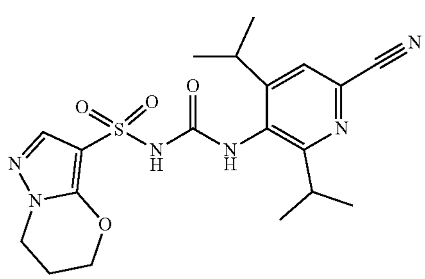 [SMILES: CC(C)c1cc(C#N)nc(C(C)C)c1NC(=O)NS(=O)(=O)c1cnn2c1OCCC2] | N-((6-cyano-2,4-diisopropylpyridin-3-yl)carbamoyl)-6,7-dihydro-5H-pyrazolo[5,1-b][1,3]oxazine-3-sulfonamide |
| 50 | 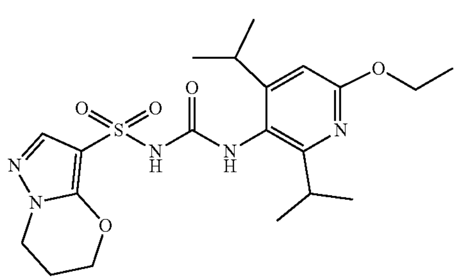 [SMILES: CCOc1cc(C(C)C)c(NC(=O)NS(=O)(=O)c2cnn3c2OCCC3)c(C(C)C)n1] | N-((6-ethoxy-2,4-diisopropylpyridin-3-yl)carbamoyl)-6,7-dihydro-5H-pyrazolo[5,1-b][1,3]oxazine-3-sulfonamide |

TABLE 1-continued

| Ex. No. | Compound Structure | Name |
|---|---|---|
| 51 | 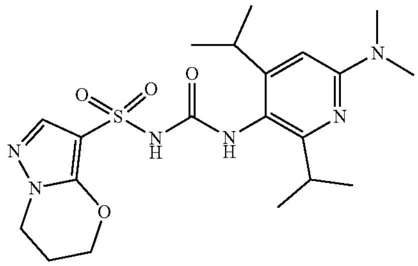 [SMILES: CC(C)c1cc(N(C)C)nc(C(C)C)c1NC(=O)NS(=O)(=O)c1cnn2c1OCCC2] | N-((6-(dimethylamino)-2,4-diisopropylpyridin-3-yl)carbamoyl)-6,7-dihydro-5H-pyrazolo[5,1-b][1,3]oxazine-3-sulfonamide |
| 52 | 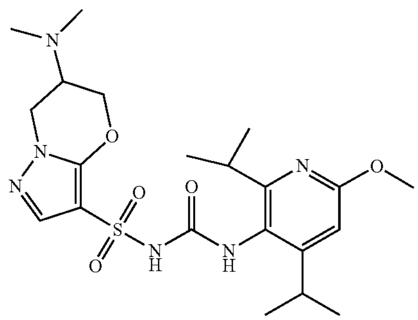 | N-((2,4-diisopropyl-6-methoxypyridin-3-yl)carbamoyl)-6-(dimethylamino)-6,7-dihydro-5H-pyrazolo[5,1-b][1,3]oxazine-3-sulfonamide |
| 52a | | N-(((6S)-2,4-diisopropyl-6-methoxypyridin-3-yl)carbamoyl)-6-(dimethylamino)-6,7-dihydro-5H-pyrazolo[5,1-b][1,3]oxazine-3-sulfonamide |
| 52b | | N-(((6R)-2,4-diisopropyl-6-methoxypyridin-3-yl)carbamoyl)-6-(dimethylamino)-6,7-dihydro-5H-pyrazolo[5,1-b][1,3]oxazine-3-sulfonamide |
| 53 | 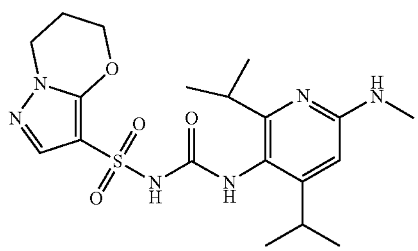 [SMILES: CNc1cc(C(C)C)c(NC(=O)NS(=O)(=O)c2cnn3c2OCCC3)c(C(C)C)n1] | N-((2,4-diisopropyl-6-(methylamino)pyridin-3-yl)carbamoyl)-6,7-dihydro-5H-pyrazolo[5,1-b][1,3]oxazine-3-sulfonamide |
| 54 | 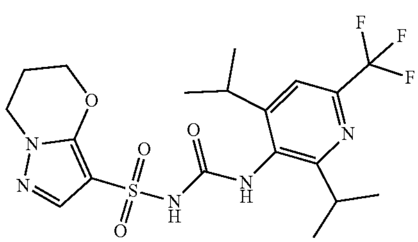 [SMILES: CC(C)c1cc(C(F)(F)F)nc(C(C)C)c1NC(=O)NS(=O)(=O)c1cnn2c1OCCC2] | N-((2,4-diisopropyl-6-(trifluoromethyl)pyridin-3-yl)carbamoyl)-6,7-dihydro-5H-pyrazolo[5,1-b][1,3]oxazine-3-sulfonamide |
| 55 | 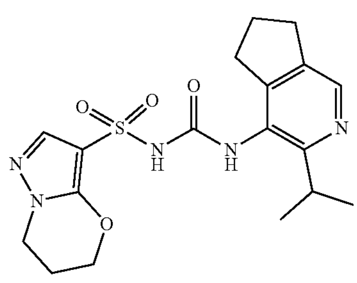 [SMILES: CC(C)c1ncc2c(c1NC(=O)NS(=O)(=O)c1cnn3c1OCCC3)CCC2] | N-((3-isopropyl-6,7-dihydro-5H-cyclopenta[c]pyridin-4-yl)carbamoyl)-6,7-dihydro-5H-pyrazolo[5,1-b][1,3]oxazine-3-sulfonamide |

TABLE 1-continued

| Ex. No. | Compound Structure | Name |
|---|---|---|
| 56 | 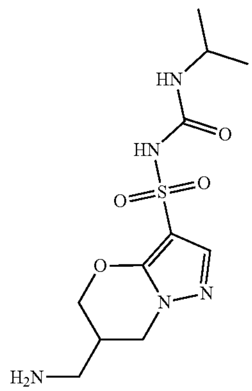 [SMILES: CC(C)NC(=O)NS(=O)(=O)c1cnn2c1OCC(CN)C2] | 6-(aminomethyl)-N-(isopropylcarbamoyl)-6,7-dihydro-5H-pyrazolo[5,1-b][1,3]oxazine-3-sulfonamide |
| 56a | | (R)-6-(aminomethyl)-N-(isopropylcarbamoyl)-6,7-dihydro-5H-pyrazolo[5,1-b][1,3]oxazine-3-sulfonamide |
| 56b | | 6S)-6-(aminomethyl)-N-(isopropylcarbamoyl)-6,7-dihydro-5H-pyrazolo[5,1-b][1,3]oxazine-3-sulfonamide |
| 57 | 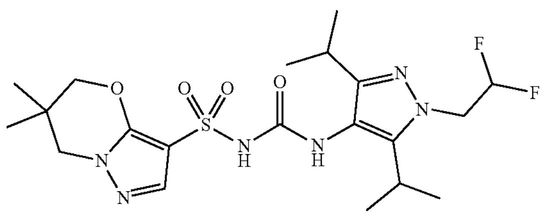 [SMILES: CC(C)c1nn(CC(F)F)c(C(C)C)c1NC(=O)NS(=O)(=O)c1cnn2c1OCC(C)(C)C2] | N-((1-(2,2-difluoroethyl)-3,5-diisopropyl-1H-pyrazol-4-yl)carbamoyl)-6,6-dimethyl-6,7-dihydro-5H-pyrazolo[5,1-b][1,3]oxazine-3-sulfonamide |
| 58 | 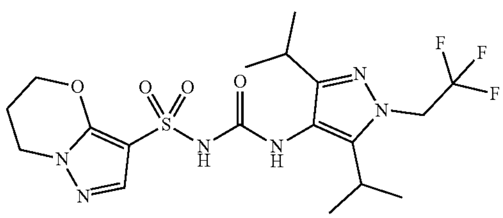 [SMILES: CC(C)c1nn(CC(F)(F)F)c(C(C)C)c1NC(=O)NS(=O)(=O)c1cnn2c1OCCC2] | N-((3,5-diisopropyl-1-(2,2,2-trifluoroethyl)-1H-pyrazol-4-yl)carbamoyl)-6,7-dihydro-5H-pyrazolo[5,1-b][1,3]oxazine-3-sulfonamide |
| 59 | 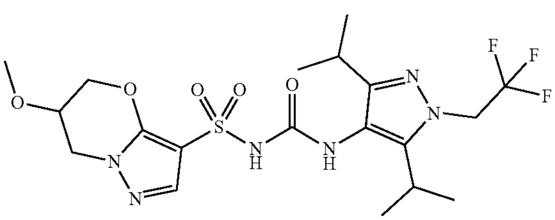 [SMILES: COC1COc2c(S(=O)(=O)NC(=O)Nc3c(C(C)C)nn(CC(F)(F)F)c3C(C)C)cnn2C1] | N-((3,5-diisopropyl-1-(2,2,2-trifluoroethyl)-1H-pyrazol-4-yl)carbamoyl)-6-methoxy-6,7-dihydro-5H-pyrazolo[5,1-b][1,3]oxazine-3-sulfonamide |
| 59a | | N-(((6S)-3,5-diisopropyl-1-(2,2,2-trifluoroethyl)-1H-pyrazol-4-yl)carbamoyl)-6-methoxy-6,7-dihydro-5H-pyrazolo[5,1-b][1,3]oxazine-3-sulfonamide |
| 59b | | N-(((6R)-3,5-diisopropyl-1-(2,2,2-trifluoroethyl)-1H-pyrazol-4-yl)carbamoyl)-6-methoxy-6,7-dihydro-5H-pyrazolo[5,1-b][1,3]oxazine-3-sulfonamide |

TABLE 1-continued

| Ex. No. | Compound Structure | Name |
|---|---|---|
| 60 | 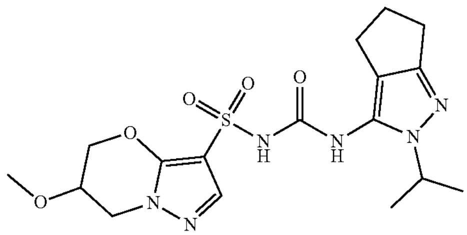 [SMILES: COC1COc2c(S(=O)(=O)NC(=O)Nc3c4c(nn3C(C)C)CCC4)cnn2C1] | N-((2-isopropyl-2,4,5,6-tetrahydrocyclopenta[c]pyrazol-3-yl)carbamoyl)-6-methoxy-6,7-dihydro-5H-pyrazolo[5,1-b][1,3]oxazine-3-sulfonamide |
| 60a | | N-(((6S)-2-isopropyl-2,4,5,6-tetrahydrocyclopenta[c]pyrazol-3-yl)carbamoyl)-6-methoxy-6,7-dihydro-5H-pyrazolo[5,1-b][1,3]oxazine-3-sulfonamide |
| 60b | | N-(((6R)-2-isopropyl-2,4,5,6-tetrahydrocyclopenta[c]pyrazol-3-yl)carbamoyl)-6-methoxy-6,7-dihydro-5H-pyrazolo[5,1-b][1,3]oxazine-3-sulfonamide |
| 61 | 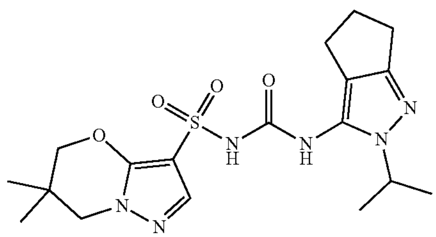 [SMILES: CC(C)n1nc2c(c1NC(=O)NS(=O)(=O)c1cnn3c1OCC(C)(C)C3)CCC2] | N-((2-isopropyl-2,4,5,6-tetrahydrocyclopenta[c]pyrazol-3-yl)carbamoyl)-6,6-dimethyl-6,7-dihydro-5H-pyrazolo[5,1-b][1,3]oxazine-3-sulfonamide |
| 62 | 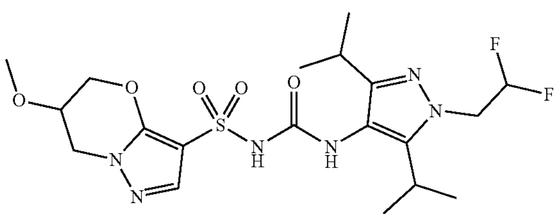 [SMILES: COC1COc2c(S(=O)(=O)NC(=O)Nc3c(C(C)C)nn(CC(F)F)c3C(C)C)cnn2C1] | N-((1-(2,2-difluoroethyl)-3,5-diisopropyl-1H-pyrazol-4-yl)carbamoyl)-6-methoxy-6,7-dihydro-5H-pyrazolo[5,1-b][1,3]oxazine-3-sulfonamide |
| 62a | | N-(((6S)-1-(2,2-difluoroethyl)-3,5-diisopropyl-1H-pyrazol-4-yl)carbamoyl)-6-methoxy-6,7-dihydro-5H-pyrazolo[5,1-b][1,3]oxazine-3-sulfonamide |
| 62b | | N-(((6R)-1-(2,2-difluoroethyl)-3,5-diisopropyl-1H-pyrazol-4-yl)carbamoyl)-6-methoxy-6,7-dihydro-5H-pyrazolo[5,1-b][1,3]oxazine-3-sulfonamide |
| 63 | 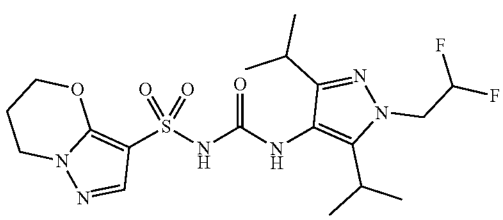 [SMILES: CC(C)c1nn(CC(F)F)c(C(C)C)c1NC(=O)NS(=O)(=O)c1cnn2c1OCCC2] | N-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonamide |
| 64 | 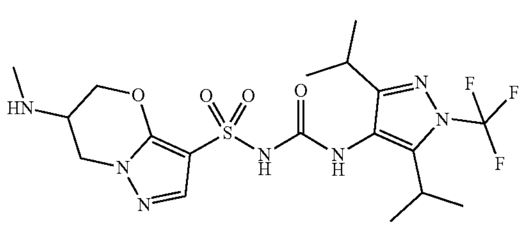 [SMILES: CNC1COc2c(S(=O)(=O)NC(=O)Nc3c(C(C)C)nn(C(F)(F)F)c3C(C)C)cnn2C1] | N-((3,5-diisopropyl-1-(trifluoromethyl)-1H-pyrazol-4-yl)carbamoyl)-6-(methylamino)-6,7-dihydro-5H-pyrazolo[5,1-b][1,3]oxazine-3-sulfonamide |

TABLE 1-continued

| Ex. No. | Compound Structure | Name |
| --- | --- | --- |
| 64a | | N-(((6S)-3,5-diisopropyl-1-(trifluoromethyl)-1H-pyrazol-4-yl)carbamoyl)-6-(methylamino)-6,7-dihydro-5H-pyrazolo[5,1-b][1,3]oxazine-3-sulfonamide |
| 64b | | N-(((6R)-3,5-diisopropyl-1-(trifluoromethyl)-1H-pyrazol-4-yl)carbamoyl)-6-(methylamino)-6,7-dihydro-5H-pyrazolo[5,1-b][1,3]oxazine-3-sulfonamide |
| 65 | 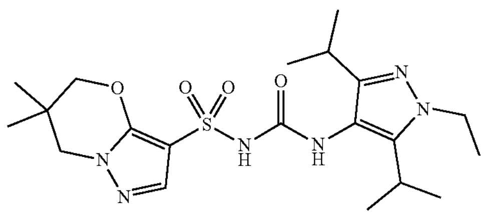 [SMILES: CCn1nc(C(C)C)c(NC(=O)NS(=O)(=O)c2cnn3c2OCC(C)(C)C3)c1C(C)C] | N-((1-ethyl-3,5-diisopropyl-1H-pyrazol-4-yl)carbamoyl)-6,6-dimethyl-6,7-dihydro-5H-pyrazolo[5,1-b][1,3]oxazine-3-sulfonamide |
| 66 | 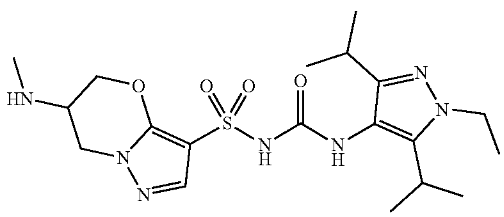 [SMILES: CCn1nc(C(C)C)c(NC(=O)NS(=O)(=O)c2cnn3c2OCC(NC)C3)c1C(C)C] | N-((1-ethyl-3,5-diisopropyl-1H-pyrazol-4-yl)carbamoyl)-6-(methylamino)-6,7-dihydro-5H-pyrazolo[5,1-b][1,3]oxazine-3-sulfonamide |
| 66a | | N-(((6S)-3,5-diisopropyl-1-(trifluoromethyl)-1H-pyrazol-4-yl)carbamoyl)-6,7-dihydro-5H-pyrazolo[5,1-b][1,3]oxazine-3-sulfonamide |
| 66b | | N-(((6R)-3,5-diisopropyl-1-(trifluoromethyl)-1H-pyrazol-4-yl)carbamoyl)-6,7-dihydro-5H-pyrazolo[5,1-b][1,3]oxazine-3-sulfonamide |
| 67 | 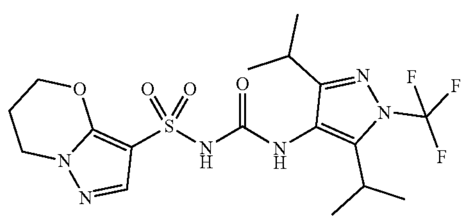 [SMILES: CC(C)c1nn(C(F)(F)F)c(C(C)C)c1NC(=O)NS(=O)(=O)c1cnn2c1OCCC2] | N-((3,5-diisopropyl-1-(trifluoromethyl)-1H-pyrazol-4-yl)carbamoyl)-6,7-dihydro-5H-pyrazolo[5,1-b][1,3]oxazine-3-sulfonamide |
| 68 | 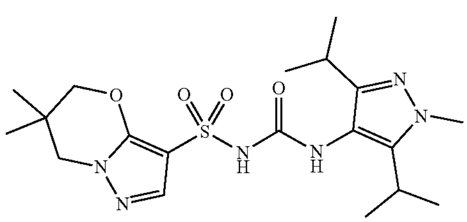 | N-((3,5-diisopropyl-1-methyl-1H-pyrazol-4-yl)carbamoyl)-6,6-dimethyl-6,7-dihydro-5H-pyrazolo[5,1-b][1,3]oxazine-3-sulfonamide |
| 69 | 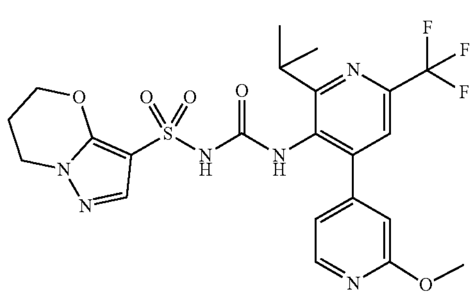 [SMILES: COc1cc(-c2cc(C(F)(F)F)nc(C(C)C)c2NC(=O)NS(=O)(=O)c2cnn3c2OCCC3)ccn1] | N-((2-isopropyl-2'-methoxy-6-(trifluoromethyl)-[4,4'-bipyridin]-3-yl)carbamoyl)-6,7-dihydro-5H-pyrazolo[5,1-b][1,3]oxazine-3-sulfonamide |

TABLE 1-continued

| Ex. No. | Compound Structure | Name |
|---|---|---|
| 70 | (structure) | N-((1-(2,2-difluoroethyl)-3,5-diisopropyl-1H-pyrazol-4-yl)carbamoyl)-6-(methylamino)-6,7-dihydro-5H-pyrazolo[5,1-b][1,3]oxazine-3-sulfonamide |
| 70a | | N-(((6S)-1-(2,2-difluoroethyl)-3,5-diisopropyl-1H-pyrazol-4-yl)carbamoyl)-6-(methylamino)-6,7-dihydro-5H-pyrazolo[5,1-b][1,3]oxazine-3-sulfonamide |
| 70b | | N-(((6R)-1-(2,2-difluoroethyl)-3,5-diisopropyl-1H-pyrazol-4-yl)carbamoyl)-6-(methylamino)-6,7-dihydro-5H-pyrazolo[5,1-b][1,3]oxazine-3-sulfonamide |
| 71 | (structure) | N-((2,4-diisopropyl-6-(trifluoromethoxy)pyridin-3-yl)carbamoyl)-6,7-dihydro-5H-pyrazolo[5,1-b][1,3]oxazine-3-sulfonamide |
| 72 | (structure) | N-((3,5-diisopropyl-1-(2,2,2-trifluoroethyl)-1H-pyrazol-4-yl)carbamoyl)-6-(methylamino)-6,7-dihydro-5H-pyrazolo[5,1-b][1,3]oxazine-3-sulfonamide |
| 72a | | N-(((6S)-3,5-diisopropyl-1-(2,2,2-trifluoroethyl)-1H-pyrazol-4-yl)carbamoyl)-6-(methylamino)-6,7-dihydro-5H-pyrazolo[5,1-b][1,3]oxazine-3-sulfonamide |
| 72b | | N-(((6R)-3,5-diisopropyl-1-(2,2,2-trifluoroethyl)-1H-pyrazol-4-yl)carbamoyl)-6-(methylamino)-6,7-dihydro-5H-pyrazolo[5,1-b][1,3]oxazine-3-sulfonamide |
| 73 | (structure) | N-((3,5-diisopropyl-1-methyl-1H-pyrazol-4-yl)carbamoyl)-6-(methylamino)-6,7-dihydro-5H-pyrazolo[5,1-b][1,3]oxazine-3-sulfonamide |
| 73a | | N-(((6S)-3,5-diisopropyl-1-methyl-1H-pyrazol-4-yl)carbamoyl)-6-(methylamino)-6,7-dihydro-5H-pyrazolo[5,1-b][1,3]oxazine-3-sulfonamide |
| 73b | | N-(((6R)-3,5-diisopropyl-1-methyl-1H-pyrazol-4-yl)carbamoyl)-6-(methylamino)-6,7-dihydro-5H-pyrazolo[5,1-b][1,3]oxazine-3-sulfonamide |

TABLE 1-continued

| Ex. No. | Compound Structure | Name |
|---|---|---|
| 74 | 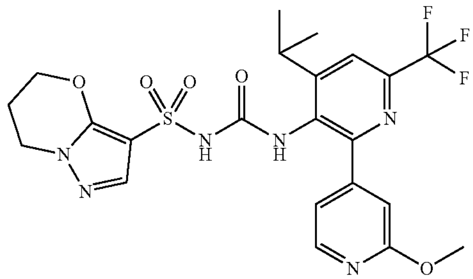 [SMILES: COc1cc(-c2nc(C(F)(F)F)cc(C(C)C)c2NC(=O)NS(=O)(=O)c2cnn3c2OCCC3)ccn1] | N-((4-isopropyl-2'-methoxy-6-(trifluoromethyl)-[2,4'-bipyridin]-3-yl)carbamoyl)-6,7-dihydro-5H-pyrazolo[5,1-b][1,3]oxazine-3-sulfonamide |
| 75 | 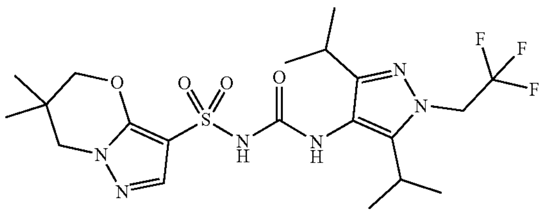 [SMILES: CC(C)c1nn(CC(F)(F)F)c(C(C)C)c1NC(=O)NS(=O)(=O)c1cnn2c1OCC(C)(C)C2] | N-((3,5-diisopropyl-1-(2,2,2-trifluoroethyl)-1H-pyrazol-4-yl)carbamoyl)-6,6-dimethyl-6,7-dihydro-5H-pyrazolo[5,1-b][1,3]oxazine-3-sulfonamide |
| 76 | 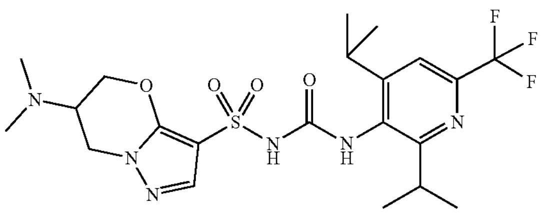 [SMILES: CC(C)c1cc(C(F)(F)F)nc(C(C)C)c1NC(=O)NS(=O)(=O)c1cnn2c1OCC(N(C)C)C2] | N-((2,4-diisopropyl-6-(trifluoromethyl)pyridin-3-yl)carbamoyl)-6-(dimethylamino)-6,7-dihydro-5H-pyrazolo[5,1-b][1,3]oxazine-3-sulfonamide |
| 76a | | N-(((6S)-2,4-diisopropyl-6-(trifluoromethyl)pyridin-3-yl)carbamoyl)-6-(dimethylamino)-6,7-dihydro-5H-pyrazolo[5,1-b][1,3]oxazine-3-sulfonamide |
| 76b | | N-(((6R)-2,4-diisopropyl-6-(trifluoromethyl)pyridin-3-yl)carbamoyl)-6-(dimethylamino)-6,7-dihydro-5H-pyrazolo[5,1-b][1,3]oxazine-3-sulfonamide |
| 77 | 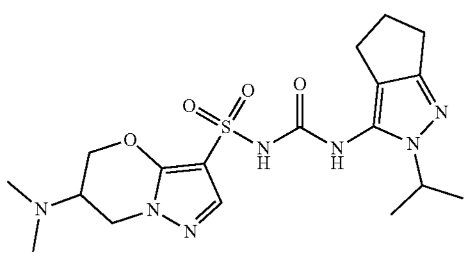 [SMILES: CC(C)n1nc2c(c1NC(=O)NS(=O)(=O)c1cnn3c1OCC(N(C)C)C3)CCC2] | 6-(dimethylamino)-N-((2-isopropyl-2,4,5,6-tetrahydrocyclopenta[c]pyrazol-3-yl)carbamoyl)-6,7-dihydro-5H-pyrazolo[5,1-b][1,3]oxazine-3-sulfonamide |
| 77a | | 6-(S)-(dimethylamino)-N-((2-isopropyl-2,4,5,6-tetrahydrocyclopenta[c]pyrazol-3-yl)carbamoyl)-6,7-dihydro-5H-pyrazolo[5,1-b][1,3]oxazine-3-sulfonamide |
| 77b | | 6-(R)-(dimethylamino)-N-((2-isopropyl-2,4,5,6-tetrahydrocyclopenta[c]pyrazol-3-yl)carbamoyl)-6,7-dihydro-5H-pyrazolo[5,1-b][1,3]oxazine-3-sulfonamide |
| 78 | 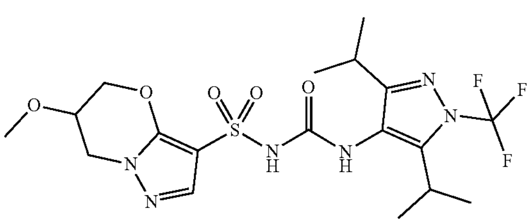 [SMILES: COC1COc2c(S(=O)(=O)NC(=O)Nc3c(C(C)C)nn(C(F)(F)F)c3C(C)C)cnn2C1] | N-((3,5-diisopropyl-1-(trifluoromethyl)-1H-pyrazol-4-yl)carbamoyl)-6-methoxy-6,7-dihydro-5H-pyrazolo[5,1-b][1,3]oxazine-3-sulfonamide |

TABLE 1-continued

| Ex. No. | Compound Structure | Name |
|---|---|---|
| 78a | | N-(((6S)-3,5-diisopropyl-1-(trifluoromethyl)-1H-pyrazol-4-yl)carbamoyl)-6-methoxy-6,7-dihydro-5H-pyrazolo[5,1-b][1,3]oxazine-3-sulfonamide |
| 78b | | N-(((6R)-3,5-diisopropyl-1-(trifluoromethyl)-1H-pyrazol-4-yl)carbamoyl)-6-methoxy-6,7-dihydro-5H-pyrazolo[5,1-b][1,3]oxazine-3-sulfonamide |
| 79 | (structure) | N-((3,5-diisopropyl-1-(trifluoromethyl)-1H-pyrazol-4-yl)carbamoyl)-6,6-dimethyl-6,7-dihydro-5H-pyrazolo[5,1-b][1,3]oxazine-3-sulfonamide |
| 80 | (structure) | N-((2,4-diisopropyl-6-(trifluoromethyl)pyridin-3-yl)carbamoyl)-6-methoxy-6,7-dihydro-5H-pyrazolo[5,1-b][1,3]oxazine-3-sulfonamide |
| 80a | | N-(((6S)-2,4-diisopropyl-6-(trifluoromethyl)pyridin-3-yl)carbamoyl)-6-methoxy-6,7-dihydro-5H-pyrazolo[5,1-b][1,3]oxazine-3-sulfonamide |
| 80b | | N-(((6R)-2,4-diisopropyl-6-(trifluoromethyl)pyridin-3-yl)carbamoyl)-6-methoxy-6,7-dihydro-5H-pyrazolo[5,1-b][1,3]oxazine-3-sulfonamide |
| 81 | (structure) | N-((6-cyclopropoxy-2,4-diisopropylpyridin-3-yl)carbamoyl)-6,7-dihydro-5H-pyrazolo[5,1-b][1,3]oxazine-3-sulfonamide |
| 82 | (structure) | N-((2,4-diisopropyl-6-(trifluoromethyl)pyridin-3-yl)carbamoyl)-6,6-dimethyl-6,7-dihydro-5H-pyrazolo[5,1-b][1,3]oxazine-3-sulfonamide |

In some embodiments, provided is a compound selected from Compound Nos. 1-82 in Table 1, or a salt (e.g., a pharmaceutically acceptable salt) thereof. In some embodiments, provided is a compound selected from Compound Nos. 1-56 in Table 1, or a salt (e.g., a pharmaceutically acceptable salt) thereof. In some embodiments, provided is a compound selected from Compound Nos. 57-82 in Table 1, or a salt (e.g., a pharmaceutically acceptable salt) thereof.

Methods of Synthesizing the Compounds

The compounds of the present disclosure may be made by a variety of methods, including standard chemistry. Suitable synthetic routes are depicted in the schemes given herein.

The compounds disclosed herein may be prepared by methods known in the art of organic synthesis as set forth in part by the synthetic schemes herein. In the schemes described herein, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of disclosed herein.

Those skilled in the art will recognize if a stereocenter exists in the compounds disclosed herein. In some embodiments, compounds of the disclosure can exist as enantiomeric or diastereomeric stereoisomers. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. For example, enantiomerically pure compounds of the disclosure can be prepared using enantiomerically pure chiral building blocks. Alternatively, racemic mixtures of the final compounds or a racemic mixture of an advanced intermediate can be subjected to chiral purification as described herein to deliver the desired enantiomerically pure intermediates or final compounds. In the instances where an advanced intermediate is purified into its individual enantiomers, each individual enantiomer can be carried on separately to deliver the final enantiomerically pure compounds of the disclosure. Resolution of the final product, an intermediate, or a starting material may be affected by any suitable method known in the art. See, for example, "Stereochemistry of Organic Compounds," by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

By way of example, compounds of the present disclosure can be synthesized by following the steps outlined in General Schemes 1 and 2 which comprise examples of sequence of assembling compounds of the disclosure. Starting materials are either commercially available or made by known procedures in the reported literature or as illustrated. Preferred methods include, but are not limited to, those methods described herein.

Compounds of the present disclosure can be prepared according to the general procedures outlined in General Scheme 1. In Method A-1, disclosed compounds are readily accessible from reaction of sulfonyl isocyanate or isothiocyanate (compound A-1) and an amine (compound A-2). In certain embodiments, compound A-2 is treated with a base in an appropriate solvent. Then, compound A-1 is added to compound A-2. The reaction is performed in a suitable solvent (e.g., tetrahydrofuran or dichloromethane) at room temperature to reflux.

With continued reference to General Scheme 1, in Method B-1, compounds of the present disclosure are readily accessible from reaction of an isocyanate or isothiocyanate (compound B-1) and a sulfonamide (compound B-2). In certain embodiments, compound B-2 is treated with a base in an appropriate solvent. Then, compound B-1 is added to compound B-2. The reaction is performed in a suitable solvent (e.g., tetrahydrofuran or dichloromethane) at room temperature to reflux.

General Scheme 1

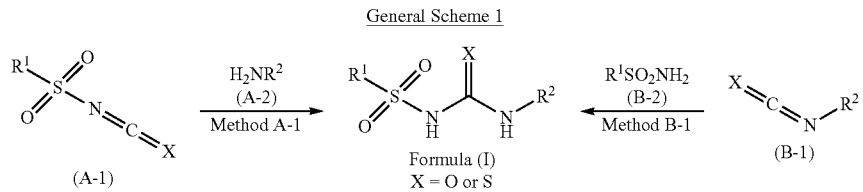

General Scheme 2 shows a representative synthesis of an $R^1$ moiety.

General Scheme 2

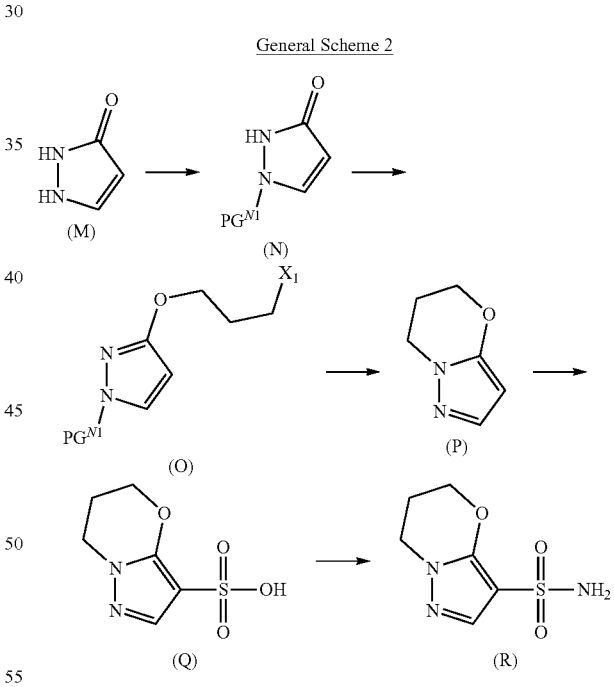

General Scheme 2 shows the preparation of a Compound (R), or a salt or solvate thereof. In General Scheme 2, $X^1$ is a halogen (e.g., chloro, bromo, iodo, or fluoro), sulfonate (e.g., nosylate, tosylate, or mesylate), nitrate, phosphate, or other suitable leaving group and $PG^{N1}$ is an amino protecting group.

Compound (M) is protected to yield compound (N). Compound (N) is then alkylated to form compound (O), for example with a Mitsonobu reaction. Compound (O) undergoes a deprotection and cyclization to form compound (P). Then, compound (P) is reacted with a sulfonating reagent to form compound (Q). Then, compound (Q) is activated (i.e. via chlorination) and then reacted with an ammonia source to form compound (R).

Pharmaceutical Compositions

The disclosed compounds, and pharmaceutically acceptable salts, solvates (e.g., hydrates), isomers, prodrugs, and tautomers thereof, may be used on their own but will generally be administered in the form of a pharmaceutical composition in which one or more disclosed compounds, and pharmaceutically acceptable salts, solvates (e.g., hydrates), isomers, prodrugs, and tautomers thereof (active ingredient), is in association with a pharmaceutically acceptable adjuvant or carrier. Conventional procedures for the selection and preparation of suitable pharmaceutical compositions are described in, for example, "Pharmaceuticals—The Science of Dosage Form Designs," M. E. Aulton, Churchill Livingstone, 1988, which is hereby incorporated by reference in its entirety. In certain embodiments, the compound, or pharmaceutically acceptable salts, isomers, prodrugs, and tautomers thereof, is in the form of a hydrate.

Depending on the mode of administration, the pharmaceutical composition will comprise from about 0.05 to about 99 wt % (percent by weight), more particularly from about 0.05 to about 80 wt %, still more particularly from about 0.10 to about 70 wt %, and even more particularly from about 0.10 to about 50 wt %, of one or more disclosed compounds, and pharmaceutically acceptable salts, solvates (e.g., hydrates), isomers, prodrugs, and tautomers thereof, all percentages by weight being based on total composition.

The present disclosure also provides a pharmaceutical composition comprising one or more disclosed compounds, and pharmaceutically acceptable salts, solvates (e.g., hydrates), isomers, prodrugs, and tautomers thereof, as hereinbefore defined, in association with a pharmaceutically acceptable carrier.

The present disclosure further provides a process for the preparation of a pharmaceutical composition of the present disclosure which comprises mixing one or more disclosed compounds, and pharmaceutically acceptable salts, solvates (e.g., hydrates), isomers, prodrugs, and tautomers thereof, as hereinbefore defined with a pharmaceutically acceptable adjuvant, diluent or carrier. Pharmaceutical compositions of the disclosure can also be prepared according to conventional mixing, granulating or coating methods.

Pharmaceutical compositions of the present disclosure may comprise a therapeutically effective amount of one or more disclosed compounds, and pharmaceutically acceptable salts, solvates (e.g., hydrates), isomers, prodrugs, and tautomers thereof, formulated together with one or more pharmaceutically acceptable carriers. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the pharmaceutical composition, according to the judgment of the formulator.

Depending on the intended mode of administration, the disclosed pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. These modes may include systemic or local administration such as oral, nasal, parenteral (as by intravenous (both bolus and infusion), intramuscular, or subcutaneous injection), transdermal, vaginal, buccal, rectal or topical (as by powders, ointments, or drops) administration modes. These modes may also include intracisternally, intraperitoneally, as an oral or nasal spray, or as a liquid aerosol or dry powder pharmaceutical composition for inhalation. In some embodiments, the pharmaceutical composition of disclosure comprising one or more disclosed compounds, and pharmaceutically acceptable salts, solvates (e.g., hydrates), isomers, prodrugs, and tautomers thereof, is for oral administration. In some embodiments, the pharmaceutical composition of disclosure comprising one or more disclosed compounds, and pharmaceutically acceptable salts, solvates (e.g., hydrates), isomers, prodrugs, and tautomers thereof, is for intravenous administration.

Solid dosage forms for oral administration may include capsules, tablets, pills, powders, and granules. In such solid dosage forms, one or more disclosed compounds, and pharmaceutically acceptable salts, solvates (e.g., hydrates), isomers, prodrugs, and tautomers thereof, may be mixed with at least one inert, pharmaceutically acceptable excipient or carrier such as a diluent, fillers or extenders, binders, humectants, disintegrating agents, solution retarding agents, absorption accelerators, wetting agents, absorbents, lubricants, an emulsifier or dispersing agent, and/or an agent that enhances absorption of the one or more disclosed compounds, and pharmaceutically acceptable salts, solvates (e.g., hydrates), isomers, prodrugs, and tautomers thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the one or more disclosed compounds, and pharmaceutically acceptable salts, solvates (e.g., hydrates), isomers, prodrugs, and tautomers thereof, only, or preferentially, in a certain part of the intestinal tract, optionally, in a delayed manner. Examples of embedding compositions that can be used include polymeric substances and waxes.

The one or more disclosed compounds, and pharmaceutically acceptable salts, solvates (e.g., hydrates), isomers, prodrugs, and tautomers thereof, can also be in micro-encapsulated form with one or more excipients as noted herein. The solid dosage forms of tablets, dragees, capsules, pills, and granules can be prepared with coatings and shells such as enteric coatings, release controlling coatings and other coatings well known in the pharmaceutical formulating art. In such solid dosage forms, one or more disclosed compounds, and pharmaceutically acceptable salts, solvates (e.g., hydrates), isomers, prodrugs, and tautomers thereof, may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the one or more disclosed compounds, and pharmaceutically acceptable salts, solvates (e.g., hydrates), isomers, prodrugs, and tautomers thereof, only, or preferentially, in a certain part of the intestinal tract, optionally, in a delayed manner. Examples of embedding compositions that can be used may include polymeric substances and waxes.

Liquid dosage forms for oral administration may include pharmaceutically acceptable emulsions, microemulsions, solutions, suspensions, syrups and elixirs. In addition to the one or more disclosed compounds, and pharmaceutically acceptable salts, solvates (e.g., hydrates), isomers, prodrugs, and tautomers thereof, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral pharmaceutical compositions can also include adjuvants such as wetting agents, emulsifying and suspending agents, sweetening, flavoring, and perfuming agents.

Injectable pharmaceutical compositions, for example, sterile injectable aqueous or oleaginous suspensions comprising one or more disclosed compounds, and pharmaceutically acceptable salts, solvates (e.g., hydrates), isomers, prodrugs, and tautomers thereof, may be formulated according to the known art using suitable dispersing or wetting agents and suspending agents. The sterile injectable pharmaceutical composition may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, 1% lidocaine, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the composition of injectables.

The injectable pharmaceutical compositions can be sterilized, for example, by filtration through a bacterial-retaining filter, or by incorporating sterilizing agents in the form of sterile solid pharmaceutical compositions that can be dissolved or dispersed in sterile water or other sterile injectable medium prior to use.

In order to prolong the effect of one or more disclosed compounds, and pharmaceutically acceptable salts, solvates (e.g., hydrates), isomers, prodrugs, and tautomers thereof, it may desirable to slow the absorption of the one or more disclosed compounds, and pharmaceutically acceptable salts, solvates (e.g., hydrates), isomers, prodrugs, and tautomers thereof, from subcutaneous or intramuscular injection. This may be accomplished by the use of a liquid suspension of crystalline or amorphous material with poor water solubility. The rate of absorption of the one or more disclosed compounds, and pharmaceutically acceptable salts, solvates (e.g., hydrates), isomers, prodrugs, and tautomers thereof, then depends upon its rate of dissolution that, in turn, may depend upon crystal size and crystalline form. Alternatively, delayed absorption of a parenterally administered one or more disclosed compounds, and pharmaceutically acceptable salts, solvates (e.g., hydrates), isomers, prodrugs, and tautomers thereof, may be accomplished by dissolving or suspending the one or more disclosed compounds, and pharmaceutically acceptable salts, solvates (e.g., hydrates), isomers, prodrugs, and tautomers thereof, in an oil vehicle. Injectable depot forms are made by forming microencapsule matrices of the one or more disclosed compounds, and pharmaceutically acceptable salts, solvates (e.g., hydrates), isomers, prodrugs, and tautomers thereof, in biodegradable polymers such as polylactide-polyglycolide. Depending upon the ratio of the one or more disclosed compounds, and pharmaceutically acceptable salts, solvates (e.g., hydrates), isomers, prodrugs, and tautomers thereof, to polymer and the nature of the particular polymer employed, the rate of release for the one or more disclosed compounds, and pharmaceutically acceptable salts, solvates (e.g., hydrates), isomers, prodrugs, and tautomers thereof, can be controlled. Examples of other biodegradable polymers include poly(orthoesters) and poly (anhydrides). Depot injectable pharmaceutical compositions may also be prepared by entrapping the one or more disclosed compounds, and pharmaceutically acceptable salts, solvates (e.g., hydrates), isomers, prodrugs, and tautomers thereof, in liposomes or microemulsions that are compatible with body tissues.

Pharmaceutical compositions for rectal or vaginal administration may be suppositories that can be prepared by mixing the one or more disclosed compounds, and pharmaceutically acceptable salts, solvates (e.g., hydrates), isomers, prodrugs, and tautomers thereof, with suitable non-irritating excipients or carriers such as cocoa butter, polyethylene glycol or a suppository wax which are solid at ambient temperature but liquid at body temperature and therefore melt in the rectum or vaginal cavity and release the one or more disclosed compounds, and pharmaceutically acceptable salts, solvates (e.g., hydrates), isomers, prodrugs, and tautomers thereof.

The one or more disclosed compounds, and pharmaceutically acceptable salts, solvates (e.g., hydrates), isomers, prodrugs, and tautomers thereof, can be also formulated as a suppository that can be prepared from fatty emulsions or suspensions; using polyalkylene glycols such as propylene glycol, as the carrier.

Dosage forms for topical or transdermal administration of one or more disclosed compounds, and pharmaceutically acceptable salts, solvates (e.g., hydrates), isomers, prodrugs, and tautomers thereof, include ointments, pastes, creams, lotions, gels, powders, solutions, sprays, inhalants or patches. The one or more disclosed compounds, and pharmaceutically acceptable salts, solvates (e.g., hydrates), isomers, prodrugs, and tautomers thereof, is admixed under sterile conditions with a pharmaceutically acceptable carrier and any needed preservatives or buffers as may be required. Ophthalmic pharmaceutical compositions, ear drops, and the like are also contemplated as being within the scope of this disclosure.

The ointments, pastes, creams and gels may contain, in addition to one or more disclosed compounds, and pharmaceutically acceptable salts, solvates (e.g., hydrates), isomers, prodrugs, and tautomers thereof, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

One or more disclosed compounds, and pharmaceutically acceptable salts, solvates (e.g., hydrates), isomers, prodrugs, and tautomers thereof, may also be formulated for use as topical powders and sprays that can contain, in addition to one or more disclosed compounds, and pharmaceutically acceptable salts, solvates (e.g., hydrates), isomers, prodrugs, and tautomers thereof, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of one or more disclosed compounds, and pharmaceutically acceptable salts, solvates (e.g., hydrates), isomers, prodrugs, and tautomers thereof, across the skin. The rate can be controlled by either providing a rate controlling membrane or by dispersing the one or more disclosed compounds, and pharmaceutically acceptable salts, solvates (e.g., hydrates), isomers, prodrugs, and tautomers thereof, in a polymer matrix or gel.

Pharmaceutical compositions of the disclosure may also be formulated for delivery as a liquid aerosol or inhalable dry powder. Liquid aerosol pharmaceutical compositions may be nebulized predominantly into particle sizes that can be delivered to the terminal and respiratory bronchioles. Liquid aerosol and inhalable dry powder pharmaceutical compositions may be delivered throughout the endobronchial tree to the terminal bronchioles and eventually to the parenchymal tissue.

Aerosolized pharmaceutical compositions of the disclosure may be delivered using an aerosol forming device, such as a jet, vibrating porous plate or ultrasonic nebulizer, selected to allow the formation of an aerosol particles having with a mass medium average diameter predominantly between 1 to 5 µm. Further, the pharmaceutical composition may have balanced osmolarity ionic strength and chloride concentration, and the smallest aerosolizable volume able to deliver effective dose of the one or more disclosed compounds, and pharmaceutically acceptable salts, solvates (e.g., hydrates), isomers, prodrugs, and tautomers thereof. Additionally, the aerosolized pharmaceutical composition may not impair negatively the functionality of the airways and does not cause undesirable side effects.

Aerosolization devices suitable for administration of aerosol pharmaceutical compositions of the disclosure include, for example, jet, vibrating porous plate, ultrasonic nebulizers and energized dry powder inhalers, that are able to nebulize the pharmaceutical composition of the disclosure into aerosol particle size predominantly in the size range from 1-5 µm. Predominantly in this application means that at least 70% but optionally more than 90% of all generated aerosol particles are 1 to 5 µm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb and AeroDose vibrating porous plate nebulizers (AeroGen, Inc., Sunnyvale, Calif.), Sidestream7 nebulizers (Medic-Aid Ltd., West Sussex, England), Pari LC7 and Pari LC Star7 jet nebulizers (Pari Respiratory Equipment, Inc., Richmond, Va.), and Aerosonic (DeVilbiss Medizinische Produkte (Deutschland) GmbH, Heiden, Germany) and µLtraAire7 (Omron Healthcare, Inc., Vernon Hills, Ill.) ultrasonic nebulizers.

Methods of Use

The disclosed compounds, and pharmaceutically acceptable salts, solvates (e.g., hydrates), isomers, prodrugs, and tautomers thereof, and compositions may be useful as pharmaceuticals, as discussed herein.

The present disclosure provides methods for treating a disorder including the step of administering an effective amount of one or more compounds of the present disclosure, and pharmaceutically acceptable salts, solvates (e.g., hydrates), isomers, prodrugs, and tautomers thereof, to thereby treat the disorder in a subject in need thereof.

The present disclosure provides methods for treating a disorder including the step of administering an effective amount of one or more pharmaceutical compositions of the present disclosure to thereby treat the disorder in a subject in need thereof.

The present disclosure provides one or more compounds of the present disclosure, and pharmaceutically acceptable salts, solvates (e.g., hydrates), isomers, prodrugs, and tautomers thereof, or one or more pharmaceutical compositions of the present disclosure for use in the treatment of a disorder in a subject in need thereof.

The present disclosure provides for use of one or more compounds of the present disclosure, and pharmaceutically acceptable salts, solvates (e.g., hydrates), isomers, prodrugs, and tautomers thereof, for the treatment of a disorder in a subject in need thereof. The present disclosure also provides for use of one or more compounds of the present disclosure, and pharmaceutically acceptable salts, solvates (e.g., hydrates), isomers, prodrugs, and tautomers thereof, for the treatment of a disorder in a subject in need thereof, wherein the disorder is responsive to inflammasome inhibition.

The present disclosure provides for use of one or more compositions of the present disclosure for the treatment of a disorder in a subject in need thereof. The present disclosure also provides for use of one or more compositions of the present disclosure for the treatment of a disorder in a subject in need thereof, wherein the disorder is responsive to inflammasome inhibition.

The present disclosure provides for use of one or more compounds of the present disclosure, and pharmaceutically acceptable salts, solvates (e.g., hydrates), isomers, prodrugs, and tautomers thereof, in the manufacture of a medicament for the treatment of a disorder. The present disclosure also provides for use of one or more compounds of the present disclosure, and pharmaceutically acceptable salts, solvates (e.g., hydrates), isomers, prodrugs, and tautomers thereof, in the manufacture of a medicament for the treatment of a disorder that is responsive to inflammasome inhibition.

The present disclosure provides for use of one or more compositions of the present disclosure in the manufacture of a medicament for the treatment of a disorder. The present disclosure also provides for use of one or more compositions of the present disclosure in the manufacture of a medicament for the treatment of a disorder that is responsive to inflammasome inhibition.

The present disclosure provides for use of one or more compounds of the present disclosure, and pharmaceutically acceptable salts, solvates (e.g., hydrates), isomers, prodrugs, and tautomers thereof, as a medicament for the treatment of a disorder.

The present disclosure provides for use of one or more compositions of the present disclosure as a medicament for the treatment of a disorder.

In some embodiments, the disorder is one which is responsive to inhibition of activation of an inflammasome. In some embodiments, the disorder is one which is responsive to inhibition of activation of the NLRP3 inflammasome.

According to some embodiments, one or more compounds, and pharmaceutically acceptable salts, solvates (e.g., hydrates), isomers, prodrugs, and tautomers thereof, or pharmaceutical compositions of the present disclosure is useful as a specific inhibitor of NLRP3.

In some embodiments, the disorder is responsive to modulation of one or more of IL-6, IL-1β, IL-17, IL-18, IL-1α, IL-37, IL-22, IL-33, and Th17 cells. In some embodiments, the disorder is responsive to modulation of one or more of IL-1β and IL-18.

In some embodiments, the modulation is inhibition of one or more of IL-6, IL-1β, IL-17, IL-18, IL-1α, IL-37, IL-22, and IL-33. In some embodiments, the modulation is inhibition of one or more of IL-1β and IL-18.

In some embodiments, the modulation of Th17 cells is by inhibition of production and/or secretion of IL-17.

In some embodiments, the disorder is a disorder of the immune system, the cardiovascular system, the endocrine system, the gastrointestinal tract, the renal system, the respiratory system, the central nervous system, is a cancer or other malignancy and/or is caused by or associated with a pathogen.

It will be appreciated that general embodiments defined according to broad categories of disorders are not mutually exclusive. In this regard any particular disorder may be categorized according to more than one of the general embodiments disclosed herein. A non-limiting example is Type I diabetes which is an autoimmune disease and a disease of the endocrine system.

In some embodiments, the disorder is of the immune system. In some embodiments, the disorder is an inflammatory disorder or an autoimmune disorder.

In some embodiments, the disorder is of the liver.
In some embodiments, the disorder is of the lung.
In some embodiments, the disorder is of the skin.
In some embodiments, the disorder is of the cardiovascular system.

In some embodiments, the disorder is a cancer, tumor or other malignancy. As used herein, cancers, tumors, and malignancies, refer to disorders, or to cells or tissues associated with the disorders, characterized by aberrant or abnormal cell proliferation, differentiation and/or migration often accompanied by an aberrant or abnormal molecular phenotype that includes one or more genetic mutations or other genetic changes associated with oncogenesis, expression of tumor markers, loss of tumor suppressor expression or activity and/or aberrant or abnormal cell surface marker expression. In some embodiments, cancers, tumors, and malignancies may include sarcomas, lymphomas, leukemias, solid tumors, blastomas, gliomas, carcinomas, melanomas and metastatic cancers, although without limitation thereto. A more comprehensive listing of cancers, tumors, and malignancies may be found at the National Cancer Institutes website http://www.cancer.gov/cancertopics/types/alphalist, which is hereby incorporated by reference in its entirety.

In some embodiments, the disorder is of the renal system.
In some embodiments, the disorder is of the gastrointestinal tract.
In some embodiments, the disorder is of the respiratory system.
In some embodiments, the disorder is of the endocrine system.
In some embodiments, the disorder is of the central nervous system (CNS).

In some embodiments, the disorder is caused by, or is associated with, a pathogen. The pathogen may be a virus, a bacterium, a protist, a worm or a fungus or any other organism capable of infecting a mammal, although without limitation thereto.

Non-limiting examples of viruses include influenza virus, cytomegalovirus, Epstein Barr Virus, human immunodeficiency virus (HIV), alphavirus such as Chikungunya and Ross River virus, flaviviruses such as Dengue virus, Zika virus and papillomavirus, although without limitation thereto.

Non-limiting examples of pathogenic bacteria include *Staphylococcus aureus, Helicobacter pylori, Bacillus anthracis, Bordatella pertussis, Corynebacterium diptheriae, Clostridium tetani, Clostridium botulinum, Streptococcus pneumoniae, Streptococcus pyogenes, Listeria monocytogenes, Hemophilus influenzae, Pasteureiia multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* and *Yersinia pestis*, although without limitation thereto.

Non-limiting examples of protists include *Plasmodium, Babesia, Giardia, Entamoeba, Leishmania* and *Trypanosomes*, although without limitation thereto.

Non-limiting examples of worms include helminths inclusive of schistisimes, roundworms, tapeworms and flukes, although without limitation thereto.

Non-limiting examples of fungi include *Candida* and *Aspergillus* species, although without limitation thereto.

In some embodiments, the disorder is selected from a group consisting of: constitutive inflammation including a cryopyrin-associated periodic syndrome (CAPS): Muckle-Wells syndrome (MWS), familial cold autoinflammatory syndrome (FCAS) and neonatal-onset multisystem inflammatory disease (NOMID); an autoinflammatory disease: familial Mediterranean fever (FMF), TNF receptor associated periodic syndrome (TRAPS), mevalonate kinase deficiency (MKD), hyperimmunoglobulinemia D and periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, and developmental delay (SIFD); Sweet's syndrome; chronic nonbacterial osteomyelitis (CNO); chronic recurrent multifocal osteomyelitis (CRMO) and synovitis; acne; pustulosis; hyperostosis; osteitis syndrome (SAPHO); an autoimmune disease including multiple sclerosis (MS), type-1 diabetes, psoriasis, rheumatoid arthritis, Behcet's disease, Sjogren's syndrome, and Schnitzler syndrome; a respiratory disease including idiopathic pulmonary fibrosis (IPF), chronic obstructive pulmonary disorder (COPD), steroid-resistant asthma, asbestosis, silicosis and cystic fibrosis; a central nervous system disease including Parkinson's disease, Alzheimer's disease, motor neuron disease, Huntington's disease, cerebral malaria and brain injury from pneumococcal meningitis; a metabolic disease including Type 2 diabetes, atherosclerosis, obesity, gout, and pseudo-gout; an ocular disease including those of the ocular epithelium, age-related macular degeneration (AMD), corneal infection, uveitis and dry eye; a kidney disease including chronic kidney disease, oxalate nephropathy, and diabetic nephropathy; a liver disease including non-alcoholic steatohepatitis and alcoholic liver disease; an inflammatory reaction in the skin including contact hypersensitivity, and sunburn; an inflammatory reaction in the joints including osteoarthritis, systemic juvenile idiopathic arthritis, adult-onset Still's disease, and relapsing polychondritis; a viral infection including alpha virus (Chikungunya, Ross River) and flavivirus (Dengue and Zika Virus), flu, and HIV; hidradenitis suppurativa (HS) and other cyst-causing skin diseases; cancer including lung cancer metastasis, pancreatic cancer, gastric cancer, myelodisplastic syndrome, and leukemia; polymyositis; stroke; myocardial infarction; Graft versus Host Disease; hypertension; colitis; helminth infection; bacterial infection; abdominal aortic aneurism; wound healing; depression, psychological stress; pericarditis including Dressier's syndrome; ischaemia reperfusion injury; and any disorder where an individual has been determined to carry a germline or somatic non-silent mutation in NLRP3.

In some embodiments, the disorder is a cryopyrin-associated periodic syndrome (CAPS).

In some embodiments, the disorder is atherosclerosis.

In one non-limiting example of those described, the disorder being treated is NASH. NLRP3 inflammasome activation is central to inflammatory recruitment in NASH, and inhibition of NLRP3 may both prevent and reverse liver fibrosis. One or more compounds, or pharmaceutically acceptable salts, prodrugs, solvates, hydrates, isomers, prodrugs, and tautomers thereof, or pharmaceutical compositions of the present disclosure, by interrupting the function of NLRP3 inflammasomes in liver tissue, can cause histological reductions in liver inflammation, decreased recruitment of macrophages and neutrophils, and suppression of NF-κB activation. Inhibition of the NLRP3 can reduce hepatic expression of pro-IL-1β and normalized hepatic and circulating IL-1β, IL-6 and MCP-1 levels thereby assisting in treatment of the disorder.

In a further non-limiting example of those described, the disorder being treated is severe steroid resistant (SSR) asthma. Respiratory infections induce an NLRP3 inflammasome/caspase-1/IL-1β signaling axis in the lungs that promotes SSR asthma. The NLRP3 inflammasome recruits, and activates, pro-caspase-1 to induce IL-1β responses. NLRP3 inflammasome-induced IL-β responses are therefore important in the control of infections, however, excessive activation results in aberrant inflammation and has been associated with the pathogenesis of SSR asthma and COPD. The administration of one or more compounds, or pharmaceutically acceptable salts, prodrugs, solvates, hydrates, isomers, prodrugs, and tautomers thereof, or pharmaceutical compositions of the present disclosure that target specific disease processes, are more therapeutically attractive than non-specifically inhibiting inflammatory responses with steroids or IL-1β. Targeting the NLRP3 inflammasome/caspase-1/IL-1β signaling axis with one or more compounds, or pharmaceutically acceptable salts, prodrugs, solvates, hydrates, isomers, prodrugs, and tautomers thereof, or pharmaceutical compositions of the present disclosure may therefore be useful in the treatment of SSR asthma and other steroid-resistant inflammatory conditions.

In one further non-limiting example of those described, the disorder being treated is Parkinson's disease. Parkinson's is the most common neurodegenerative movement disorder and is characterized by a selective loss of dopaminergic neurons, accompanied by the accumulation of misfolded a-synuclein (Syn) into Lewy bodies that are pathological hallmarks of the disease. Chronic microglial neuroinflammation is evident early in the disease, and has been proposed to drive pathology.

A central role for microglial NLRP3 is postulated in Parkinson's progression. The NLRP3 inflammasome is activated by fibrillar Syn via a Syk kinase dependent mechanism, and also occurs in the absence of Syn pathology at the early stages of dopaminergic degeneration, and drives neuronal loss. One or more compounds, or pharmaceutically acceptable salts, prodrugs, solvates, hydrates, isomers, prodrugs, and tautomers thereof, or pharmaceutical compositions of the present disclosure may block NLRP3 inflammasome activation by fibrillar Syn or mitochondrial dysfunction and thereby confer effective neuroprotection of the nigrostriatal dopaminergic system and assist with treatment of Parkinson's.

In some embodiments, the method treats a disorder, including, but not limited to, a bacterial infection, a viral infection, a fungal infection, inflammatory bowel disease, celiac disease, colitis, intestinal hyperplasia, cancer, metabolic syndrome, obesity, rheumatoid arthritis, liver disease, liver fibrosis, hepatic steatosis, fatty liver disease, gout, lupus, lupus nephritis, Crohn's disease, IBD (inflammatory bowel disease), myelodysplastic syndrome (MDS), myeloproliferative neoplasm (MPN), non-alcoholic fatty liver disease (NAFLD), and non-alcoholic steatohepatitis (NASH).

In some embodiments, the disorder is selected from a group consisting of: NASH (nonalcoholic steatohepatitis); myelodysplastic syndrome (MDS); myeloproliferative neoplasm (MPN); CAPS (Cryopyrin Associated Periodic Syndromes); IPF (Idiopathic pulmonary fibrosis); MI (R/I) (myocardial infarction and reperfusion injury); Gout; I/O (immuno-oncology); Asthma; IBD (inflammatory bowel disease); Renal fibrosis; adult onset Still's disease; systemic juvenile idiopathic arthritis; tumor necrosis factor receptor-associated periodic syndrome (TRAPS); colchicine-resistant familial Mediterranean fever (FMF); hyper IgD syndrome (HIDS)/Mevalonate Kinase Deficiency (MKD); traumatic brain injury; Parkinson's Disease; moderate to severe inflammatory acne; acute non-anterior non-infectious uveitis (NIU); AD (Alzheimer's disease); COPD (Chronic Obstructive Pulmonary Disease); Sepsis; MS (multiple sclerosis); Behcet's disease; Crohn's disease; RA (rheumatoid arthritis); erosive osteoarthritis; T1D (Type 1 diabetes); T2D (Type 2 diabetes); Obesity; osteoporosis; cystic fibrosis; alcoholic liver disease; aging; HCC (hepatocellular carcinoma); depression; endometriosis; pyoderma gangrenosum ("PG"), a rare ulcerative skin disease; Lupus, Lupus Nephritis; Epilepsy; ischemic stroke; deafness; sickle cell disease; SLE (Systemic Lupus Erythematosus); and Spinal cord injury.

In some embodiments, the disorder is selected from the group consisting of lupus, lupus nephritis, cryopyrin-associated periodic syndromes (CAPS), myelodysplastic syndromes (MDS), gout, myeloproliferative neoplasms (MPN), atherosclerosis, Crohn's disease, and inflammatory bowel disease (IBD).

In some embodiments, the disorder is gout.

In some embodiments, the disorder is lupus

In some embodiments, the disorder is lupus nephritis.

In some embodiments, the disorder is Crohn's disease.

In some embodiments, the disorder is IBD (inflammatory bowel disease).

In some embodiments, the disorder is MDS (myelodysplastic syndromes).

In some embodiments, the disorder is MPN (myeloproliferative neoplasms).

For the therapeutic uses mentioned herein, the dosage administered will, of course, vary with the one or more compounds, and pharmaceutically acceptable salts, solvates (e.g., hydrates), isomers, prodrugs, and tautomers thereof, or pharmaceutical compositions employed, the mode of administration, the treatment desired and the disorder indicated. For example, the daily dosage of the one or more compounds, and pharmaceutically acceptable salts, solvates (e.g., hydrates), isomers, prodrugs, and tautomers thereof, of the present disclosure, if inhaled, may be in the range from about 0.05 micrograms per kilogram body weight (µg/kg) to about 100 micrograms per kilogram body weight (µg/kg). Alternatively, if the one or more compounds, and pharmaceutically acceptable salts, solvates (e.g., hydrates), isomers, prodrugs, and tautomers thereof, is administered orally, then the daily dosage of the one or more compounds of the present disclosure may be in the range from about 0.01 micrograms per kilogram body weight (µg/kg) to about 100 milligrams per kilogram body weight (mg/kg).

It will be understood, however, that the total daily usage of the one or more compounds, and pharmaceutically acceptable salts, solvates (e.g., hydrates), isomers, prodrugs, and tautomers thereof, and pharmaceutical compositions of the present disclosure will be decided by the attending physician within the scope of sound medical judgment. The specific therapeutically effective dose level for any particular patient will depend upon a variety of factors including the disorder being treated and the severity of the disorder; the activity of the specific compound employed; the specific pharmaceutical composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. A physician or veterinarian of ordinary skill in the art can readily determine and prescribe the therapeutically effective amount of the one or more compounds, and pharmaceutically acceptable salts, solvates (e.g., hydrates), isomers, prodrugs, and tautomers thereof, or pharmaceutical compositions disclosed herein required to treat, counter, or arrest the progress of the disorder.

Combination Therapy

In some embodiments, one or more compounds, and pharmaceutically acceptable salts, solvates (e.g., hydrates), isomers, prodrugs, and tautomers thereof, or pharmaceutical compositions described herein may be used alone or together or conjointly administered, or used in combination, with a known therapeutic agent or pharmaceutical composition. Conjoint administration or used in combination may refer to any form of administration of two or more different compounds or pharmaceutical compositions such that the second compound or pharmaceutical composition is administered while the previously administered compound or pharmaceutical composition is still effective in the body. For example, the different compounds or pharmaceutical compositions can be administered either in the same formulation or in a separate formulation, either simultaneously, sequentially, or by separate dosing of the individual components of the treatment. In some embodiments, the different compounds or pharmaceutical compositions can be administered within one hour, 12 hours, 24 hours, 36 hours, 48 hours, 72 hours, or a week of one another. Thus, an individual who receives such treatment can benefit from a combined effect of different compounds or pharmaceutical compositions.

In some embodiments, one or more of the compounds, and pharmaceutically acceptable salts, solvates (e.g., hydrates), isomers, prodrugs, and tautomers thereof, or pharmaceutical compositions of the disclosure are used in combination with one or more other compounds, and pharmaceutically acceptable salts, solvates (e.g., hydrates), isomers, prodrugs, and tautomers thereof, or pharmaceutical compositions of the disclosure in the methods or uses of the disclosure. In certain such embodiments, the combination of one or more other compounds, and pharmaceutically acceptable salts, solvates (e.g., hydrates), isomers, prodrugs, and tautomers thereof, or pharmaceutical compositions of the disclosure is used in a method for treating one or more of the disorders listed herein.

In some embodiments, combinations of one or more compounds, and pharmaceutically acceptable salts, solvates (e.g., hydrates), isomers, prodrugs, and tautomers thereof, or pharmaceutical compositions provided herein, or combinations of other known agents or pharmaceutical compositions and one or more compounds, and pharmaceutically acceptable salts, solvates (e.g., hydrates), isomers, prodrugs, and tautomers thereof, or pharmaceutical compositions provided herein, are formulated into pharmaceutical compositions and medicaments that are useful in the methods and uses of the disclosure. The disclosure also provides for use of such combinations in treating one or more of the disorders listed herein.

In some embodiments of the disclosure, one or more compounds, and pharmaceutically acceptable salts, solvates (e.g., hydrates), isomers, prodrugs, and tautomers thereof, or pharmaceutical compositions of the disclosure are administered at a sub-therapeutic dose, wherein a subtherapeutic dose is a dose that would be insufficient to treat one of the disorders listed herein if administered alone.

EXEMPLARY EMBODIMENTS

Some embodiments of this disclosure are Embodiments I as follows.

Embodiment I-1. A compound having the structure of Formula (I),

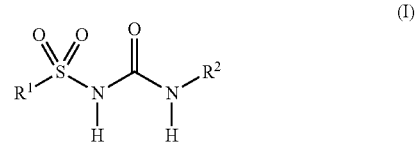

or a pharmaceutically acceptable salt, solvate, isomer, prodrug, or tautomer thereof, wherein:

$R^1$ is

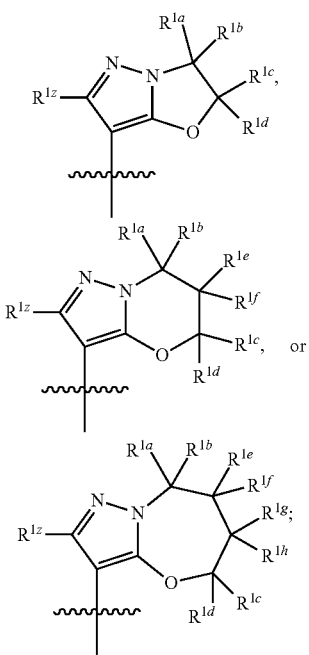

$R^{1z}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_7$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7 membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_7$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_3$-C$_{10}$cycloalkyl, C$_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a C$_3$-C$_{10}$cycloalkyl or a 3-7-membered heterocyclyl; wherein the C$_3$-C$_{10}$cycloalkyl and 3-7-membered heterocyclyl are independently unsubstituted or substituted with one or more substituents selected from the group consisting of D, —CN, halogen, C$_1$-C$_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups $R^{1a}$ and $R^{1b}$; $R^{1c}$ and $R^{1d}$; $R^{1e}$ and $R^{1f}$; or $R^{1g}$ and $R^{1h}$, when present, can form an oxo group;

$R^2$ is selected from the group consisting of C$_1$-C$_6$alkyl, C$_3$-C$_{10}$cycloalkyl, 5-7-membered heterocyclyl, 5-membered heteroaryl, 6-membered heteroaryl containing 6-11 annular atoms, or —NR$^{2g}$R$^{2h}$; wherein the C$_1$-C$_6$alkyl, C$_3$-C$_{10}$cycloalkyl, 5-7-membered heterocyclyl, 5-membered heteroaryl, and 6-membered heteroaryl containing 6-11 annular atoms are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

each $R^{2g}$ and $R^{2h}$ is independently H, D, C$_1$-C$_6$alkyl, C$_3$-C$_{10}$cycloalkyl, C$_6$aryl, 3-7 membered heterocyclyl, or 5-6 membered heteroaryl, wherein the C$_1$-C$_6$alkyl, C$_3$-C$_{10}$cycloalkyl, C$_6$aryl, 3-7 membered heterocyclyl, and 5-6 membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

$R^{7a}$, $R^{8a}$, $R^{11a}$, $R^{12a}$, $R^{13a}$, $R^{14a}$, $R^{21a}$, $R^{22a}$, $R^{23a}$, and $R^{24a}$ are independently, at each occurrence, H, D, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_6$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl; and $R^{7b}$, $R^{8b}$, $R^{11b}$, $R^{12b}$, $R^{13b}$, $R^{14b}$, $R^{21b}$, $R^{22b}$, $R^{23b}$, and $R^{24b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_6$alkyl, C$_2$-C$_8$alkenyl, C$_2$-C$_8$alkynyl, C$_3$-C$_{10}$cycloalkyl, C$_1$-C$_8$cycloalkyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

Embodiment I-2. The compound of Embodiment I-1, or a pharmaceutically acceptable salt, solvate, isomer, or tautomer thereof, wherein $R^2$ is C$_1$-C$_6$alkyl.

Embodiment I-3. The compound of Embodiment I-1, or a pharmaceutically acceptable salt, solvate, isomer, or tautomer thereof, wherein $R^2$ is $C_3$-$C_{10}$cycloalkyl.

Embodiment I-4. The compound of Embodiment I-3, or a pharmaceutically acceptable salt, solvate, isomer, or tautomer thereof, wherein $R^2$ is $C_5$cycloalkyl, $C_6$cycloalkyl, or $C_7$cycloalkyl.

Embodiment I-5. The compound of Embodiment I-1, or a pharmaceutically acceptable salt, solvate, isomer, or tautomer thereof, wherein $R^2$ is 5-7-membered heterocyclyl.

Embodiment I-6. The compound of Embodiment I-1, or a pharmaceutically acceptable salt, solvate, isomer, or tautomer thereof, wherein $R^2$ is 5-membered heteroaryl.

Embodiment I-7. The compound of Embodiment I-5, or a pharmaceutically acceptable salt, solvate, isomer, or tautomer thereof, wherein the 5-membered heteroaryl contains 2 nitrogens.

Embodiment I-8. The compound of Embodiment I-1, or a pharmaceutically acceptable salt, solvate, isomer, or tautomer thereof, wherein $R^2$ is 6-membered heteroaryl containing 6-11 annular atoms.

Embodiment I-9. The compound of Embodiment I-7, or a pharmaceutically acceptable salt, solvate, isomer, or tautomer thereof, wherein $R^2$ is the 6-membered heteroaryl containing 6-11 annular atoms contains 2 nitrogens.

Embodiment I-10. The compound of Embodiment I-1, or a pharmaceutically acceptable salt, solvate, isomer, or tautomer thereof, wherein $R^2$ is —$NR^{2g}R^{2h}$.

Embodiment I-11. The compound of any one of Embodiment I-1 to I-10, or a pharmaceutically acceptable salt, solvate, isomer, or tautomer thereof, wherein $R^1$ is

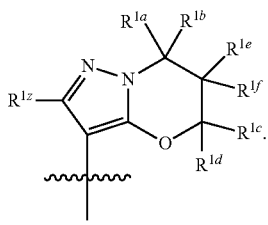

Embodiment I-12. The compound of any one of Embodiment I-1 to I-10, or a pharmaceutically acceptable salt, solvate, isomer, or tautomer thereof, wherein $R^1$ is

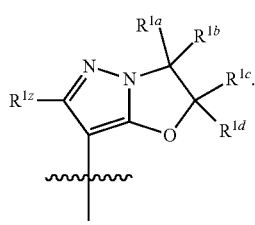

Embodiment I-13. The compound of any one of Embodiment I-1 to I-10, or a pharmaceutically acceptable salt, solvate, isomer, or tautomer thereof, wherein $R^1$ is

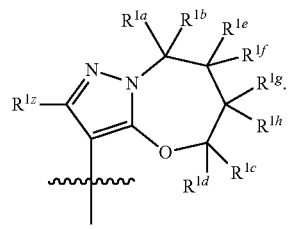

Embodiment I-14. The compound of any one of Embodiment I-1 to I-11, or a pharmaceutically acceptable salt, solvate, isomer, or tautomer thereof, wherein $R^1$ is

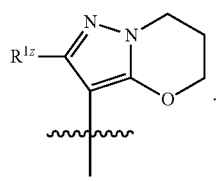

Embodiment I-15. The compound of any one of Embodiment I-1 to I-11, or a pharmaceutically acceptable salt, solvate, isomer, or tautomer thereof, wherein $R^1$ is

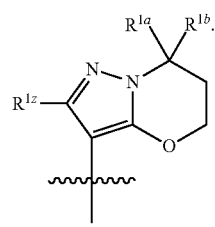

Embodiment I-16. The compound of any one of Embodiment I-1 to I-11, or a pharmaceutically acceptable salt, solvate, isomer, or tautomer thereof, wherein $R^1$ is

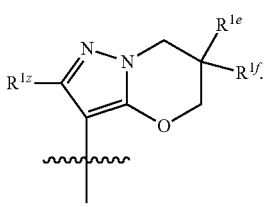

Embodiment I-17. The compound of any one of Embodiment I-1 to I-11, or a pharmaceutically acceptable salt, solvate, isomer, or tautomer thereof, wherein $R^1$ is

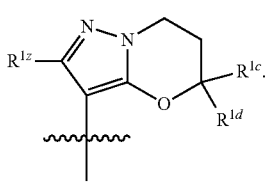

Embodiment I-18. The compound of any one of Embodiment I-1 to I-11, or a pharmaceutically acceptable salt, solvate, isomer, or tautomer thereof, wherein $R^1$ is selected from the group consisting of

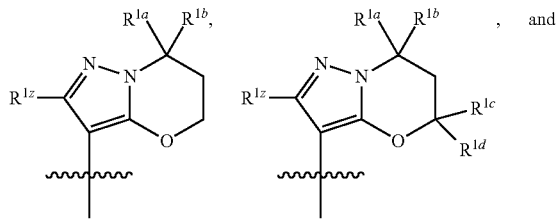

and

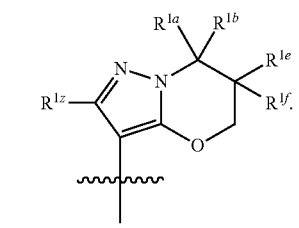

Embodiment I-19. The compound of any one of Embodiment I-1 to I-11, or a pharmaceutically acceptable salt, solvate, isomer, or tautomer thereof, wherein $R^1$ is selected from the group consisting of

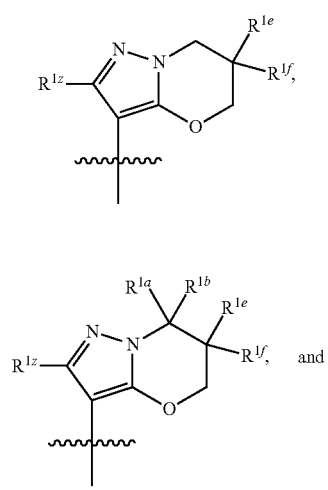

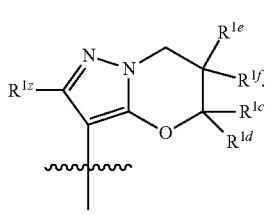

Embodiment I-20. The compound of any one of Embodiment I-1 to I-11, or a pharmaceutically acceptable salt, solvate, isomer, or tautomer thereof, wherein $R^1$ is selected from the group consisting of

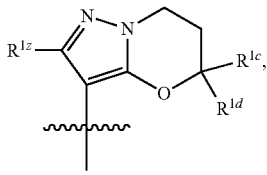

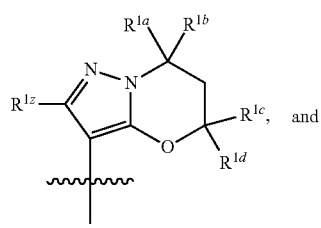

and

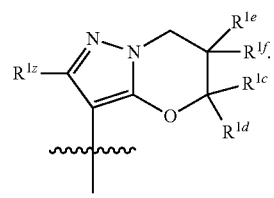

Embodiment I-21. The compound of any one of Embodiment I-1 to I-20, or a pharmaceutically acceptable salt, solvate, isomer, or tautomer thereof, wherein $R^{1z}$ is H.

Embodiment I-22. The compound of any one of Embodiment I-1 to I-11, or a pharmaceutically acceptable salt, solvate, isomer, or tautomer thereof, wherein $R^1$ is selected from the group consisting of

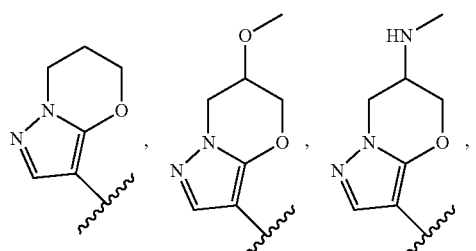

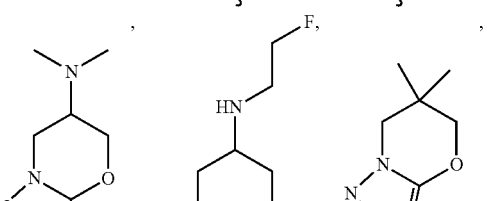

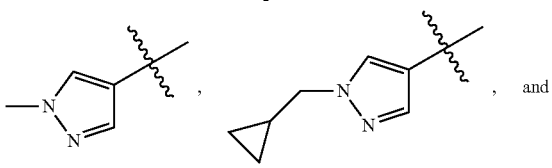

and

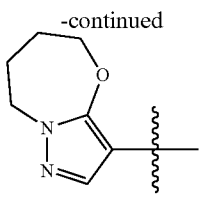

Embodiment I-23. The compound of any one of Embodiment I-1 to I-11, or a pharmaceutically acceptable salt, solvate, isomer, or tautomer thereof, wherein $R^1$ is selected from the group consisting of

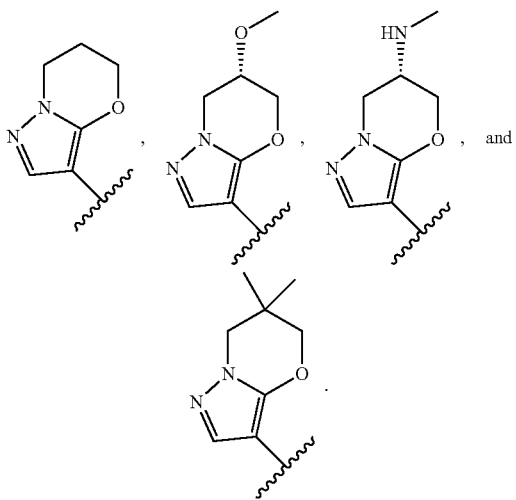

Embodiment I-24. The compound of any one of Embodiment I-1 to I-11, or a pharmaceutically acceptable salt, solvate, isomer, or tautomer thereof, wherein $R^1$ is selected from the group consisting of

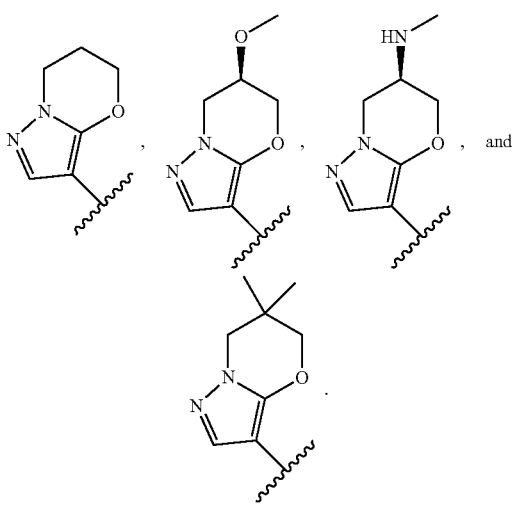

Embodiment I-25. The compound of any one of Embodiment I-1 to I-13, I-15 and I-18 to I-21, or a pharmaceutically acceptable salt, solvate, isomer, or tautomer thereof, wherein $R^{1a}$ and $R^{1b}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl.

Embodiment I-26. The compound of any one of Embodiment I-1 to I-13 and I-17 to I-21, or a pharmaceutically acceptable salt, solvate, isomer, or tautomer thereof, wherein $R^{1c}$ and $R^{1d}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl.

Embodiment I-27. The compound of any one of Embodiment I-1 to I-11, I-13, I-16, and I-18 to I-21, or a pharmaceutically acceptable salt, solvate, isomer, or tautomer thereof, wherein $R^{1e}$ and $R^{1f}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl.

Embodiment I-28. The compound of any one of Embodiment I-1 to I-10, I-13, and I-21, or a pharmaceutically acceptable salt, solvate, isomer, or tautomer thereof, wherein $R^{1g}$ and $R^{1h}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl.

Embodiment I-29. The compound of any one of Embodiment I-1 to I-13, I-15 and I-18 to I-21, or a pharmaceutically acceptable salt, solvate, isomer, or tautomer thereof, wherein $R^{1a}$ and $R^{1b}$ are independently H, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and |—$NR^{11a}S(O)_2R^{12a}$.

Embodiment I-30. The compound of any one of Embodiment I-1 to I-13, I-15 and I-18 to I-21, or a pharmaceutically acceptable salt, solvate, isomer, or tautomer thereof, wherein $R^{1a}$ and $R^{1b}$ are independently H, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$.

Embodiment I-31. The compound of any one of Embodiment I-1 to I-13 and I-17 to I-21, or a pharmaceutically acceptable salt, solvate, isomer, or tautomer thereof, wherein $R^{1c}$ and $R^{1d}$ are independently H, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)$ $NR^{12a}$, $-NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$; and wherein the 3-7-membered heterocyclyl is unsubstituted or substituted with one or more substituents selected from the group consisting of $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$.

Embodiment I-32. The compound of any one of Embodiment I-1 to I-13 and I-17 to I-21, or a pharmaceutically acceptable salt, solvate, isomer, or tautomer thereof, wherein $R^{1c}$ and $R^{1d}$ are independently independently H, $-NR^{11a}R^{12a}$, $-NR^{11a}C(O)R^{12a}$, $-NR^{11a}C(O)OR^{12a}$, $-NR^{11a}C(O)NR^{12a}$, $-NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$; and wherein the 3-7-membered heterocyclyl is unsubstituted or substituted with one or more substituents selected from the group consisting of $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$.

Embodiment I-33. The compound of any one of Embodiment I-1 to I-11, I-13, I-16, and I-18 to I-21, or a pharmaceutically acceptable salt, solvate, isomer, or tautomer thereof, wherein $R^{1e}$ and $R^{1f}$ are independently H, $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, $-NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$; and wherein the 3-7-membered heterocyclyl is unsubstituted or substituted with one or more substituents selected from the group consisting of $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$.

Embodiment I-34. The compound of any one of Embodiment I-1 to I-11, I-13, I-16, and I-18 to I-21, or a pharmaceutically acceptable salt, solvate, isomer, or tautomer thereof, wherein $R^{1e}$ and $R^{1f}$ are independently independently H, $-NR^{11a}R^{12a}$, $-NR^{11a}C(O)R^{12a}$, $-NR^{11a}C(O)OR^{12a}$, $-NR^{11a}C(O)NR^{12a}$, $-NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$; and wherein the 3-7-membered heterocyclyl is unsubstituted or substituted with one or more substituents selected from the group consisting of $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$.

Embodiment I-35. The compound of any one of Embodiment I-1 to I-10, I-13, and I-21, or a pharmaceutically acceptable salt, solvate, isomer, or tautomer thereof, wherein $R^{1g}$ and $R^{1h}$ are independently are independently H, $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, $-NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$; and wherein the 3-7-membered heterocyclyl is unsubstituted or substituted with one or more substituents selected from the group consisting of $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$.

Embodiment I-36. The compound of any one of Embodiment I-1 to I-10, I-13, and I-21, or a pharmaceutically acceptable salt, solvate, isomer, or tautomer thereof, wherein $R^{1g}$ and $R^{1h}$ are independently independently H, $-NR^{11a}R^{12a}$, $-NR^{11a}C(O)R^{12a}$, $-NR^{11a}C(O)OR^{12a}$, $-NR^{11a}C(O)NR^{12a}$, $-NR^{11a}S(O)_2R^{12a}$, $C_1$-$C_6$alkyl, or a 3-7-membered heterocyclyl; wherein the $C_1$-$C_6$alkyl is substituted with one or more substituents selected from the group consisting of $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$; and wherein the 3-7-membered heterocyclyl is unsubstituted or substituted with one or more substituents selected from the group consisting of $-NR^{11a}R^{12a}$, $-NR^{11a}C(O)R^{12a}$, $-NR^{11a}C(O)OR^{12a}$, $-NR^{11a}C(O)NR^{12a}$, and $-NR^{11a}S(O)_2R^{12a}$.

Embodiment I-37. The compound of any one of Embodiment I-29 to I-36, or a pharmaceutically acceptable salt, solvate, isomer, or tautomer thereof, wherein the 3-7-membered heterocyclyl contains a nitrogen.

Embodiment I-38. The compound of Embodiment I-1, or a pharmaceutically acceptable salt, solvate, isomer, or tautomer thereof, wherein the compound is selected from the group consisting of

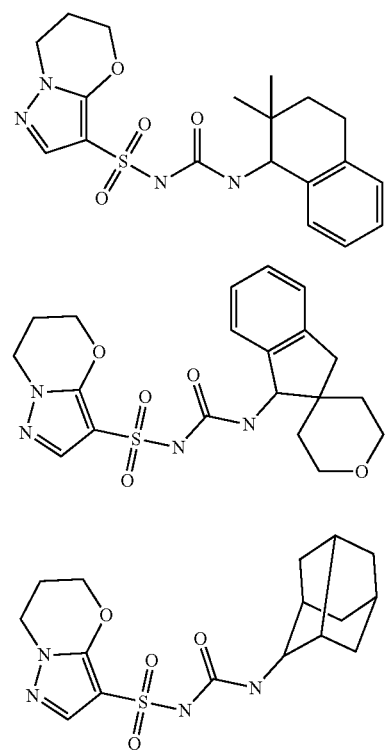

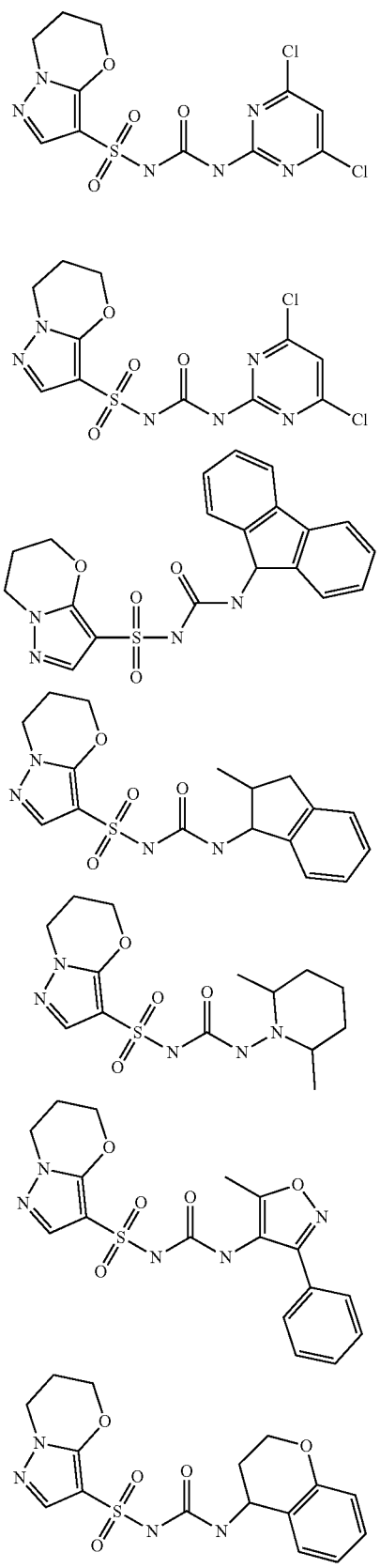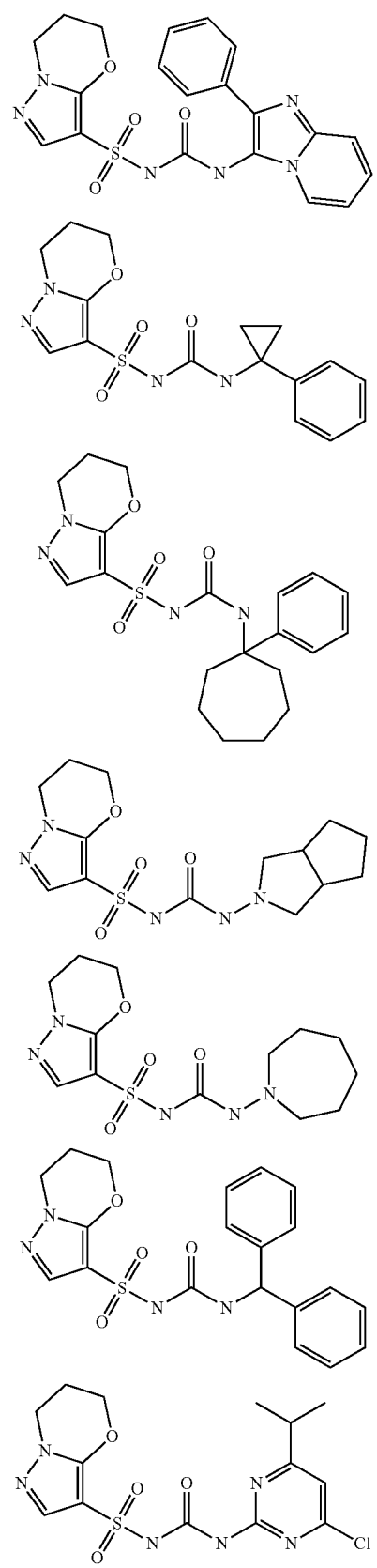

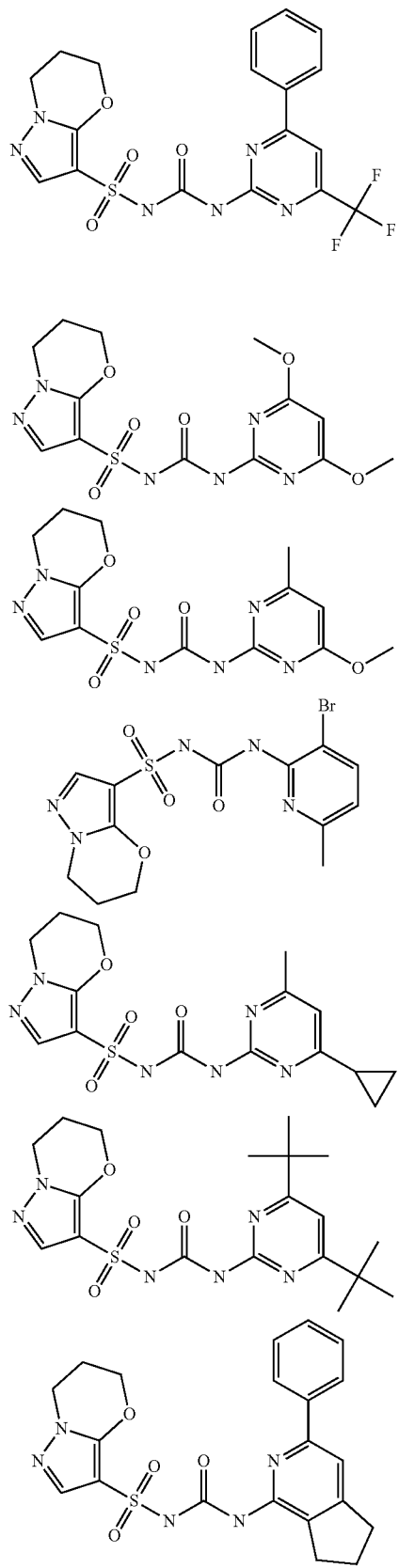
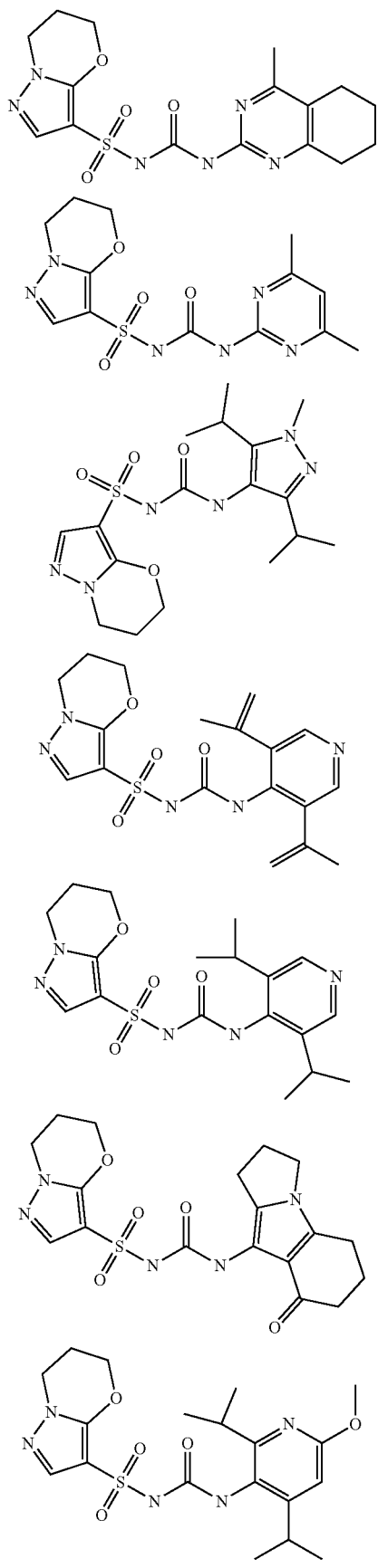

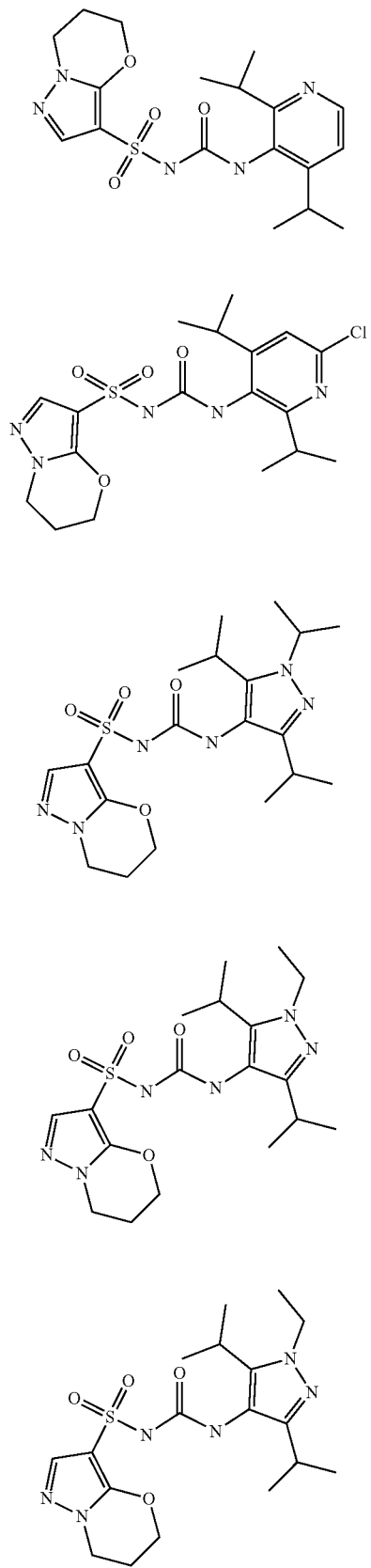
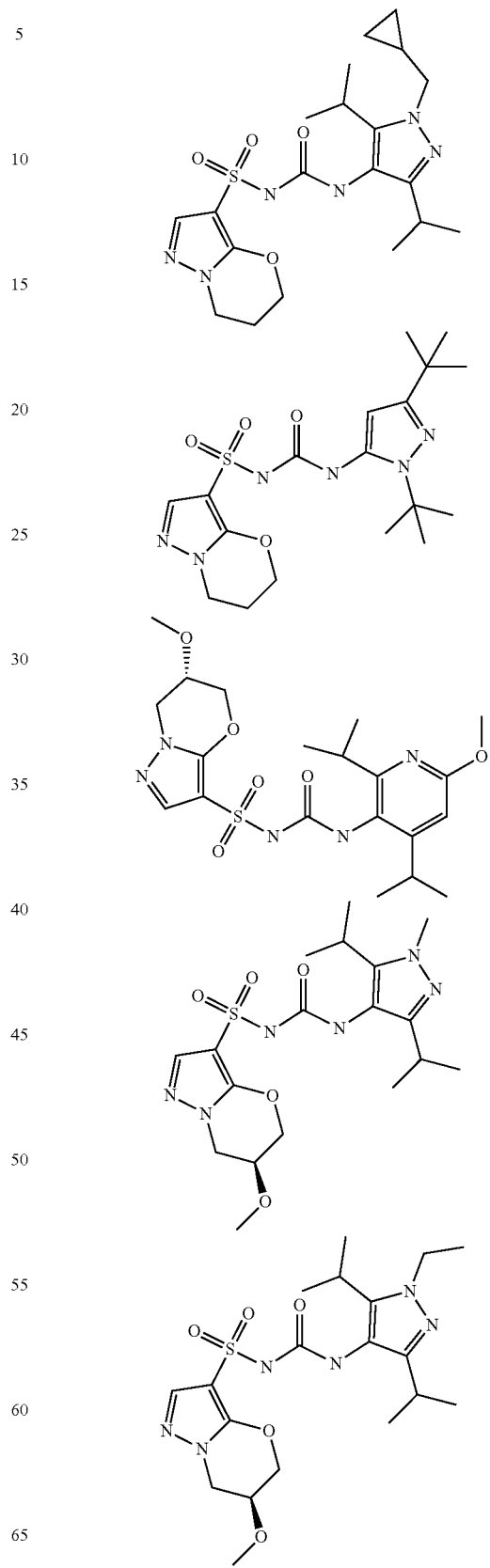

115
-continued
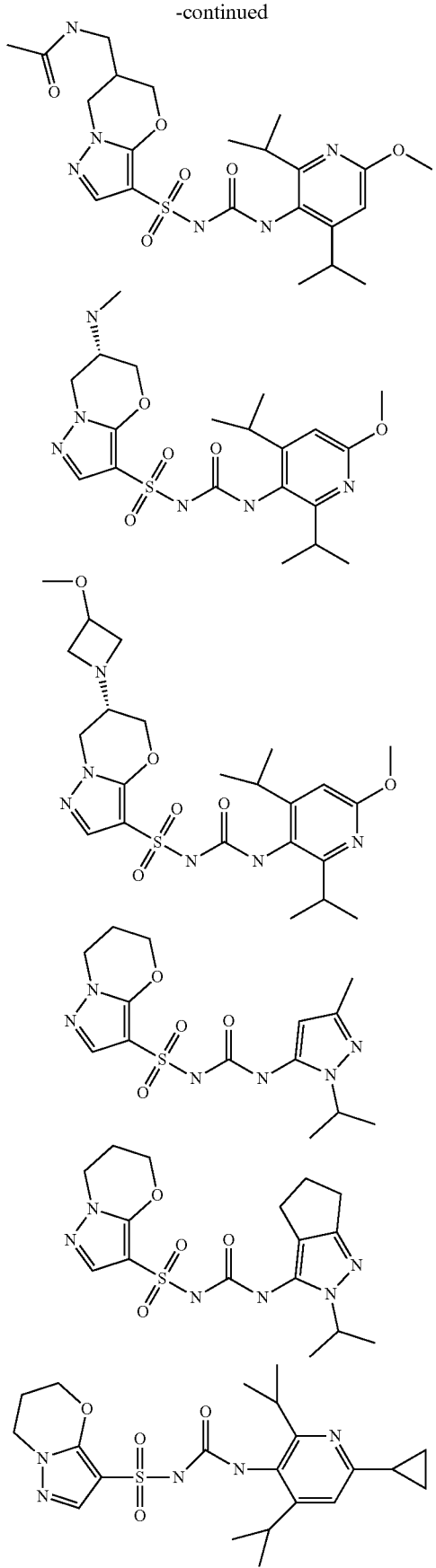
116
-continued
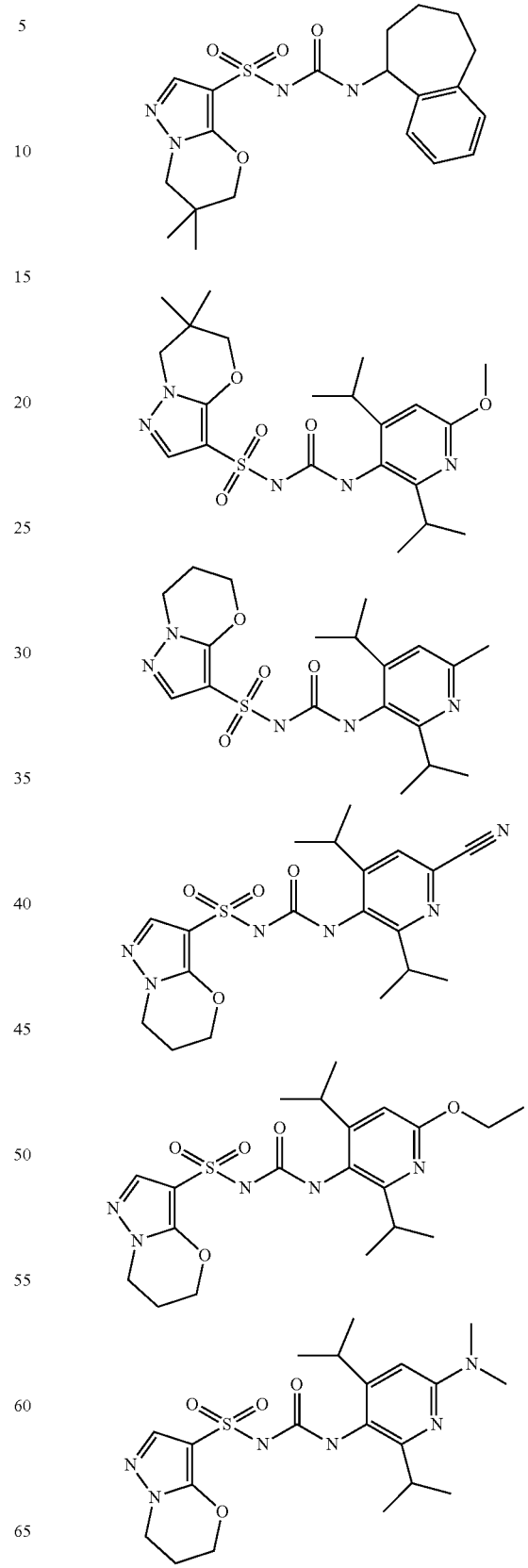

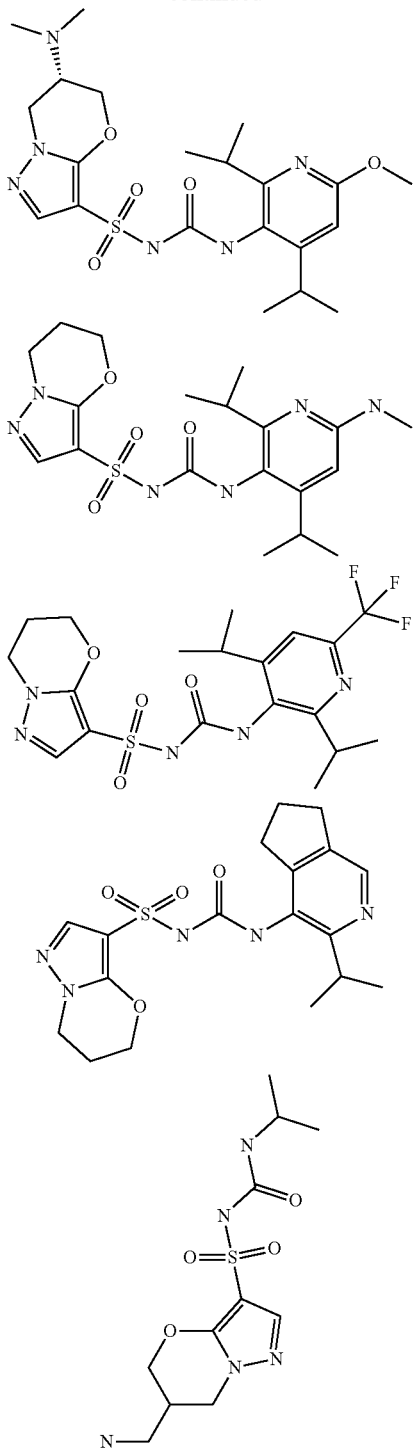

Embodiment I-39. A pharmaceutical composition comprising a compound of any one of Embodiment I-1 to I-38, or a pharmaceutically acceptable salt, solvate, isomer, or tautomer thereof, and a pharmaceutically acceptable carrier.

Embodiment I-40. A method of treatment of a disorder that is responsive to inhibition of inflammasome, comprising administering an effective amount of a compound of any one of Embodiment I-1 to I-38 to thereby treat the disorder in a subject in need thereof.

Embodiment I-41. The method of Embodiment I-40, wherein the disorder is one which is responsive to inhibition of activation of the NLRP3 inflammasome.

Embodiment I-42. The method of Embodiment I-40 or I-41, wherein the disorder is responsive to modulation of one or more of IL-6, IL-1β, IL-17, IL-18, IL-1α, IL-37, IL-22, IL-33 and Th17 cells.

Embodiment I-43. The method of Embodiment I-40 or I-41, wherein the disorder is responsive to modulation of one or more of IL-1β and IL-18.

Embodiment I-44. The method of any one of Embodiment I-40 to I-43, wherein the disorder is disorder of the immune system.

Embodiment I-45. The method of any one of Embodiment I-40 to I-43, wherein the disorder is an inflammatory disorder or an autoimmune disorder.

Embodiment I-46. The method of any one of Embodiment I-40 to I-43, wherein the disorder is disorder of the liver.

Embodiment I-47. The method of any one of Embodiment I-40 to I-43, wherein the disorder is a disorder of the lung.

Embodiment I-48. The method of any one of Embodiment I-40 to I-43, wherein the disorder is a disorder of the skin.

Embodiment I-49. The method of any one of Embodiment I-40 to I-43, wherein the disorder is a disorder of the cardiovascular system.

Embodiment I-50. The method of any one of Embodiment I-40 to I-43, wherein the disorder is a cancer, tumor or other malignancy.

Embodiment I-51. The method of any one of Embodiment I-40 to I-43, wherein the disorder is a disorder of the renal system.

Embodiment I-52. The method of any one of Embodiment I-40 to I-43, wherein the disorder is a disorder of the gastro-intestinal tract.

Embodiment I-53. The method of any one of Embodiment I-40 to I-43, wherein the disorder is a disorder of the respiratory system.

Embodiment I-54. The method of any one of Embodiment I-40 to I-43, wherein the disorder is a disorder of the endocrine system.

Embodiment I-55. The method of any one of Embodiment I-40 to I-43, wherein the disorder is a disorder of the central nervous system (CNS).

Embodiment I-56. The method of any one of Embodiment I-40 to I-43, wherein the disorder is selected from the group consisting of constitutive inflammation, the cryopyrin-associated periodic syndromes (CAPS), Muckle-Wells syndrome (MWS), familial cold autoinflammatory syndrome (FCAS), neonatal-onset multisystem inflammatory disease (NOMID), autoinflammatory diseases, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO), autoimmune diseases including multiple sclerosis (MS), type-1 diabetes, psoriasis, rheumatoid arthritis, Behcet's disease, Sjogren's syndrome, Schnitzler syndrome, respiratory diseases, idiopathic pulmonary fibrosis (IPF), chronic obstructive pulmonary disorder (COPD), steroid-resistant asthma, asbestosis, silicosis, cystic fibrosis, central nervous system diseases, Parkinson's disease, Alzheimer's disease, motor neuron disease, Huntington's disease, cerebral malaria, brain injury from pneumococcal meningitis, metabolic diseases, Type 2 diabetes, atherosclerosis, obesity, gout, pseudo-gout, ocular disease, disease of the ocular epithelium, age-related macular degeneration (AMD), corneal infection, uveitis, dry eye, kidney disease, chronic kidney disease, oxalate nephropathy, diabetic nephropathy, liver disease, non-alcoholic steatohepatitis, alcoholic liver disease, inflammatory reactions in skin, contact hypersensitivity, sunburn, inflammatory reactions in the joints, osteoarthritis, systemic juvenile idiopathic arthritis, adult-onset Still's disease, relapsing polychondritis, viral infections, alpha virus infection, Chikungunya virus infection, Ross River virus infection, flavivirus infection, Dengue virus infection, Zika virus infection, flu, HIV infection, hidradenitis suppurativa (HS), cyst-causing skin diseases, cancers, lung cancer metastasis, pancreatic cancers, gastric cancers, myelodisplastic syndrome, leukemia, polymyositis, stroke, myocardial infarction, Graft versus Host Disease, hypertension, colitis, helminth infection, bacterial infection, abdominal aortic aneurism, wound healing, depression, psychological stress, pericarditis, Dressler's syndrome, ischaemia reperfusion injury, and any disease where an individual has been determined to carry a germ line or somatic non-silent mutation in NLRP3.

Embodiment I-57. The method of any one of Embodiment I-40 to I-43, wherein the disorder is selected from the group consisting of a bacterial infection, a viral infection, a fungal infection, inflammatory bowel disease, celiac disease, colitis, intestinal hyperplasia, cancer, metabolic syndrome, obesity, rheumatoid arthritis, liver disease, hepatic steatosis, fatty liver disease, liver fibrosis, non-alcoholic fatty liver disease (NAFLD), and non-alcoholic steatohepatitis (NASH).

Embodiment I-58. The method of Embodiment I-57, wherein the disorder is non-alcoholic steatohepatitis (NASH).

Embodiment I-59. The method of any one of Embodiment I-40 to I-43, wherein the disorder is selected from the group consisting of lupus, lupus nephritis, cryopyrin-associated periodic syndromes (CAPS), myelodysplastic syndromes (MDS), gout, myeloproliferative neoplasms (MPN), atherosclerosis, Crohn's disease, and inflammatory bowel disease (IBD).

Embodiment I-60. A compound of any one of Embodiment I-1 to I-38, or a pharmaceutically acceptable salt, solvate, isomer, or tautomer thereof, for use as a medicament.

Embodiment I-61. A compound any one of Embodiment I-1 to I-38, or a pharmaceutically acceptable salt, solvate, isomer, or tautomer thereof, for use in treating a disorder that is responsive to inhibition of inflammasome.

Embodiment I-62. Use of a compound of any one of Embodiment I-1 to I-38, or a pharmaceutically acceptable salt, solvate, isomer, or tautomer thereof, in the manufacture of a medicament for treating a disorder that is responsive to inhibition of inflammasome.

Embodiment I-63. A pharmaceutical composition of Embodiment I-39 for use as a medicament.

Embodiment I-64. A pharmaceutical composition of Embodiment I-39 for use in treating a disorder that is responsive to inhibition of inflammasome.

Embodiment I-65. Use of pharmaceutical composition of Embodiment I-39 in the manufacture of a medicament for treating a disorder that is responsive to inhibition of inflammasome.

EXAMPLES

The following examples are provided to illustrate the present disclosure, and should not be construed as limiting thereof. In these examples, all parts and percentages are by weight, unless otherwise noted. Abbreviations in the examples are noted below.

Abbreviations aq. aqueous

EtOAc ethyl acetate h hour

HPLC high performance liquid chromatography min minutes mL milliliter mmol millimole MeOH methanol NMR nuclear magnetic resonance sat. saturated THF tetrahydrofuran TLC thin layer chromatography

SYNTHETIC EXAMPLES

Example 1

N-((2,2-dimethyl-1,2,3,4-tetrahydronaphthalen-1-yl)carbamoyl)-6,7-dihydro-5H-pyrazolo[5,1-b][1,3]oxazine-3-sulfonamide

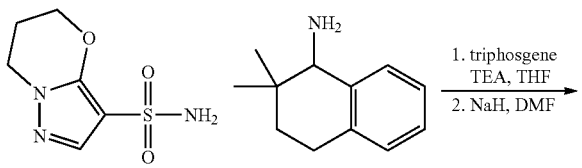

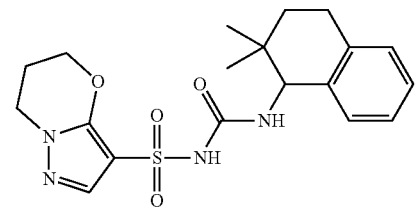

121

Step 1—Synthesis of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1)

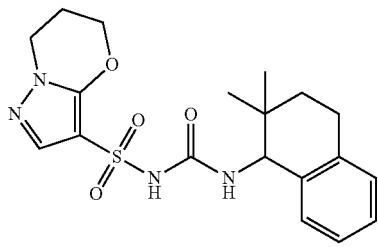 [SMILES: CC1(C)CCc2ccccc2C1NC(=O)NS(=O)(=O)c1cnn2c1OCCC2]

Triphosgene (60 mg, 0.35 Eq, 0.20 mmol) was added in one portion to a stirring solution of 2,2-dimethyl-1,2,3,4-tetrahydronaphthalen-1-amine (100 mg, 1 Eq, 0.57 mmol) in anhydrous THF (5 mL) under $N_2$. The mixture was then heated to 60° C. for 4 h before cooled to room temperature. Solvent was then removed under reduced pressure, and the residue was taken up in hexanes (50 mL). The white precipitates were filtered off and the filtrate was concentrated under reduced pressure to afford isocyanato-2,2-dimethyl-1,2,3,4-tetrahydronaphthalene as white solids, and used without additional purification.

Isocyanato-2,2-dimethyl-1,2,3,4-tetrahydronaphthalene obtained was then dissolved in anhydrous DMF (1 mL). To this solution was added 6,7-dihydro-5H-pyrazolo[5,1-b][1,3]oxazine-3-sulfonamide (80 mg, 0.39 mmol) followed by sodium hydride (16 mg, 09 mmol, 60% in mineral oil) at room temperature. The reaction was stirred for 2 h before 1 mL MeOH was added. The mixture was then concentrated and purified by silica gel chromatography (MeOH/DCM, 0 to 10%) to afford N-((2,2-dimethyl-1,2,3,4-tetrahydronaphthalen-1-yl)carbamoyl)-6,7-dihydro-5H-pyrazolo[5,1-b][1,3]oxazine-3-sulfonamide (13.6 mg, 9%) as white solids. LCMS: m/z=405 [M+1].

Example 2

N-((1,2',3,3',5',6'-hexahydrospiro[indene-2,4'-pyran]-1-yl)carbamoyl)-6,7-dihydro-5H-pyrazolo[5,1-b][1,3]oxazine-3-sulfonamide

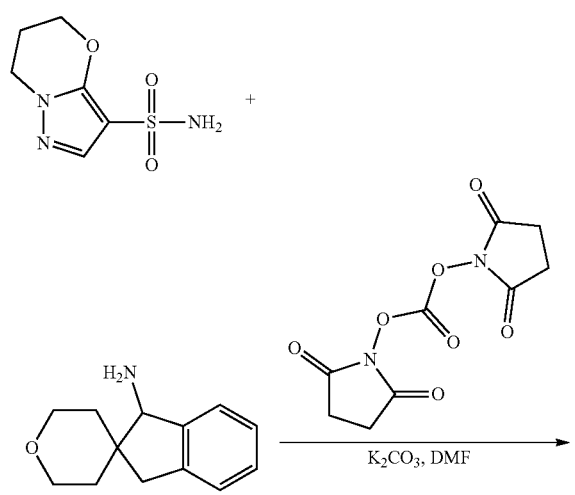

122

-continued

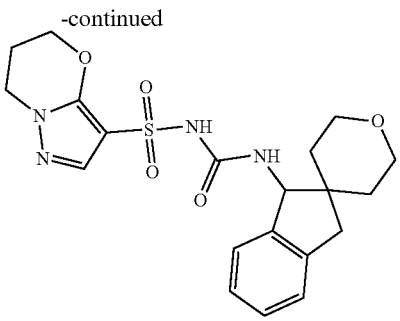

Step 1—Synthesis of N-((1,2',3,3',5',6'-hexahydrospiro[indene-2,4'-pyran]-1-yl)carbamoyl)-6,7-dihydro-5H-pyrazolo[5,1-b][1,3]oxazine-3-sulfonamide (Example 2)

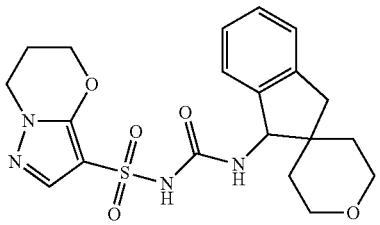 [SMILES: O=C(NC1c2ccccc2CC12CCOCC2)NS(=O)(=O)c1cnn2c1OCCC2]

1,2',3,3',5',6'-hexahydrospiro[indene-2,4'-pyran]-1-amine (0.025 g, 0.123 mmol) was mixed with bis(2,5-dioxopyrrolidin-1-yl) carbonate (0.031 g, 0.123 mmol) and K2CO3 (0.017 g, 0.123 mmol) in DMF (1 mL) for 3 h. 6,7-dihydro-5H-pyrazolo[5,1-b][1,3]oxazine-3-sulfonamide (25 mg, 0.123 mmol) was then added and the mixture left to stir overnight. The mixture was then diluted with water and a fine white precipitate filtered off and dried. The residue was then purified by flash or prep chromatography (in this case 0-100% EtOAc:hexanes; then 5-20% MeOH:DCM) to yield N-((1,2',3,3',5',6'-hexahydrospiro[indene-2,4'-pyran]-1-yl)carbamoyl)-6,7-dihydro-5H-pyrazolo[5,1-b][1,3]oxazine-3-sulfonamide (1.7 mg, 3.195%) as a white solid. MS: m/z 432 (M+H⁺).

Example 3

N-(((1r,3r,5r,7r)-adamantan-2-yl)carbamoyl)-6,7-dihydro-5H-pyrazolo[5,1-b][1,3]oxazine-3-sulfonamide

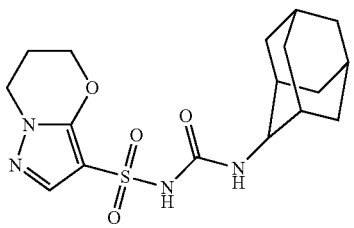 [SMILES: O=C(NC1C2CC3CC(C2)CC1C3)NS(=O)(=O)c1cnn2c1OCCC2]

N-(((1r,3r,5r,7r)-adamantan-2-yl)carbamoyl)-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 2,2-dimethyl-1,2,3,4-tetrahydronaphthalen-1-amine with (1r,3r,5r,7r)-adamantan-2-amine in Step 1. LCMS: m/z=381 [M+1].

Example 4

N-((4,6-dichloropyrimidin-2-yl)carbamoyl)-6,7-dihydro-5H-pyrazolo[5,1-b][1,3]oxazine-3-sulfonamide

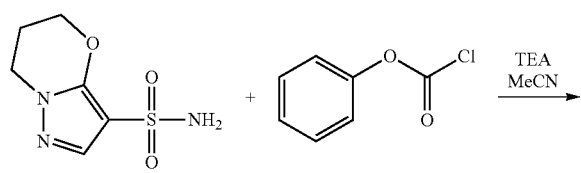

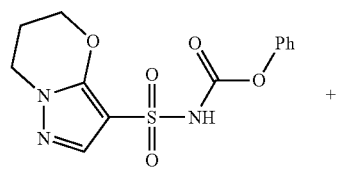

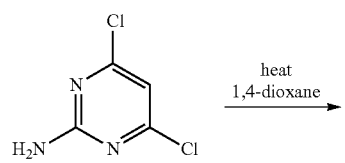

Step 1—Synthesis of phenyl ((6,7-dihydro-5H-pyrazolo[5,1-b][1,3]oxazin-3-yl)sulfonyl)carbamate

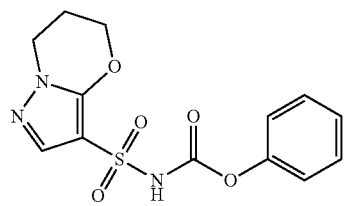 [SMILES: O=C(NS(=O)(=O)c1cnn2c1OCCC2)Oc1ccccc1]

To a solution of 6,7-dihydro-5H-pyrazolo[5,1-b][1,3]oxazine-3-sulfonamide (500 mg, 1 Eq, 2.460 mmol) in anhydrous MeCN (10 mL) was added TEA (0.50 g, 0.69 mL, 2 Eq, 4.92 mmol) flowed by phenyl chloroformate (0.46 g, 0.37 mL, 1.2 Eq, 2.95 mmol) dropwise at 0° C. The reaction was then warmed up to room temperature and stirred for 2 h before diluted with EtOAc (30 mL). The mixture was washed with water, brine, dried over Na$_2$SO$_4$ and concentrated under reduced pressure. The obtained residue was purified by silica gel chromatography (EtOAc/Hexanes, 0 to 100%) to afford phenyl ((6,7-dihydro-5H-pyrazolo[5,1-b][1,3]oxazin-3-yl)sulfonyl)carbamate (280 mg, 35%) as white solids. LCMS: m/z=324 [M+1].

Step 2—Synthesis of N-((4,6-dichloropyrimidin-2-yl)carbamoyl)-6,7-dihydro-5H-pyrazolo[5,1-b][1,3]oxazine-3-sulfonamide (Example 4)

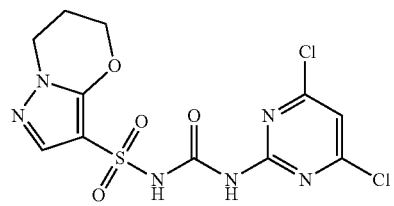 [SMILES: O=C(Nc1nc(Cl)cc(Cl)n1)NS(=O)(=O)c1cnn2c1OCCC2]

Phenyl ((6,7-dihydro-5H-pyrazolo[5,1-b][1,3]oxazin-3-yl)sulfonyl)carbamate (50 mg, 1 Eq, 0.15 mmol) and 4,6-dichloropyrimidin-2-amine (32 mg, 1.3 Eq, 0.201 mmol) were dissolved in anhydrous 1,4-dioxane (1 mL) and the reaction was heated at 100° C. overnight before cooled to room temperature. The solvent was removed under reduced pressure and the obtained residue was purified by silica gel chromatography (MeOH/DCM, 0 to 10%) to afford N-((4,6-dichloropyrimidin-2-yl)carbamoyl)-6,7-dihydro-5H-pyrazolo[5,1-b][1,3]oxazine-3-sulfonamide (15 mg, 23%) as white form. LCMS: m/z=393 [M+1].

Example 5

N-((9H-fluoren-9-yl)carbamoyl)-6,7-dihydro-5H-pyrazolo[5,1-b][1,3]oxazine-3-sulfonamide

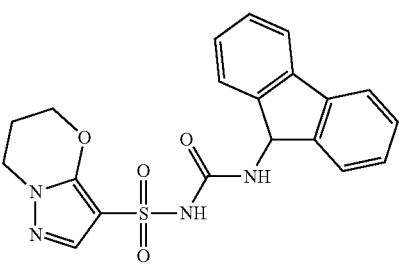 [SMILES: O=C(NC1c2ccccc2-c2ccccc21)NS(=O)(=O)c1cnn2c1OCCC2]

N-((9H-fluoren-9-yl)carbamoyl)-6,7-dihydro-5H-pyrazolo[5,1-b][1,3]oxazine-3-sulfonamide was prepared by using the general procedure described for the preparation of N-((1,2',3,3',5',6'-hexahydrospiro[indene-2,4'-pyran]-1-yl)carbamoyl)-6,7-dihydro-5H-pyrazolo[5,1-b][1,3]oxazine-3-sulfonamide (Example 2) by replacing 1,2',3,3',5',6'-hexahydrospiro[indene-2,4'-pyran]-1-amine with 9H-fluoren-9-amine in Step 1. LCMS: m/z=411 [M+1].

Example 6

N-((2-methyl-2,3-dihydro-1H-inden-1-yl)carbamoyl)-6,7-dihydro-5H-pyrazolo[5,1-b][1,3]oxazine-3-sulfonamide

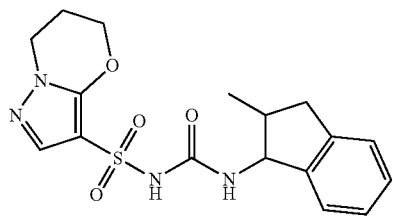 [SMILES: CC1Cc2ccccc2C1NC(=O)NS(=O)(=O)c1cnn2c1OCCC2]

N-((2-methyl-2,3-dihydro-1H-inden-1-yl)carbamoyl)-6,7-dihydro-5H-pyrazolo[5,1-b][1,3]oxazine-3-sulfonamide was prepared by using the general procedure described for the preparation of N-((1,2',3,3',5',6'-hexahydrospiro[indene-2,4'-pyran]-1-yl)carbamoyl)-6,7-dihydro-5H-pyrazolo[5,1-b][1,3]oxazine-3-sulfonamide (Example 2) by replacing 1,2',3,3',5',6'-hexahydrospiro[indene-2,4'-pyran]-1-amine with 2-methyl-2,3-dihydro-1H-inden-1-amine in Step 1. Mixture of enantiomers obtained. LCMS: m/z=377 [M+1].

Example 7

N-((2,6-dimethylpiperidin-1-yl)carbamoyl)-6,7-dihydro-5H-pyrazolo[5,1-b][1,3]oxazine-3-sulfonamide

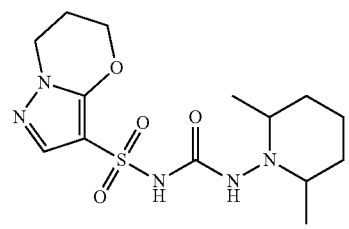 [SMILES: CC1CCCC(C)N1NC(=O)NS(=O)(=O)c1cnn2c1OCCC2]

N-((2,6-dimethylpiperidin-1-yl)carbamoyl)-6,7-dihydro-5H-pyrazolo[5,1-b][1,3]oxazine-3-sulfonamide was prepared by using the general procedure described for the preparation of N-((1,2',3,3',5',6'-hexahydrospiro[indene-2,4'-pyran]-1-yl)carbamoyl)-6,7-dihydro-5H-pyrazolo[5,1-b][1,3]oxazine-3-sulfonamide (Example 2) by replacing 1,2',3,3',5',6'-hexahydrospiro[indene-2,4'-pyran]-1-amine with 2,6-dimethylpiperidin-1-amine in Step 1. Mixture of diastereomers obtained. LCMS: m/z=358 [M+1].

Example 8

N-((5-methyl-3-phenylisoxazol-4-yl)carbamoyl)-6,7-dihydro-5H-pyrazolo[5,1-b][1,3]oxazine-3-sulfonamide

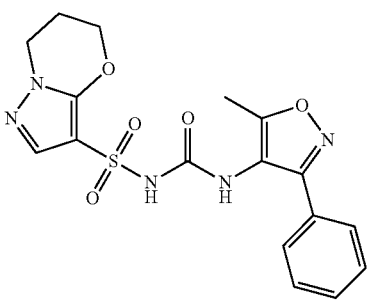 [SMILES: Cc1onc(-c2ccccc2)c1NC(=O)NS(=O)(=O)c1cnn2c1OCCC2]

N-((5-methyl-3-phenylisoxazol-4-yl)carbamoyl)-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 2,2-dimethyl-1,2,3,4-tetrahydronaphthalen-1-amine with (5-methyl-3-phenylisoxazol-4-amine in Step 1. LCMS: m/z=404 [M+1].

Example 9

N-(chroman-4-ylcarbamoyl)-6,7-dihydro-5H-pyrazolo[5,1-b][1,3]oxazine-3-sulfonamide

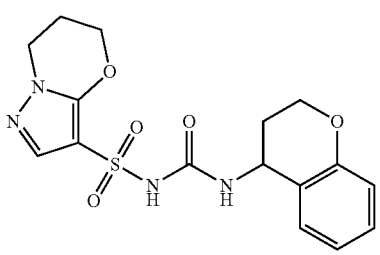 [SMILES: O=C(NC1CCOc2ccccc21)NS(=O)(=O)c1cnn2c1OCCC2]

N-(chroman-4-ylcarbamoyl)-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 2,2-dimethyl-1,2,3,4-tetrahydronaphthalen-1-amine with chroman-4-amine in Step 1. Mixture of enantiomers obtained. LCMS: m/z=379 [M+1].

Example 10

N-((2-phenylimidazo[1,2-a]pyridin-3-yl)carbamoyl)-6,7-dihydro-5H-pyrazolo[5,1-b][1,3]oxazine-3-sulfonamide

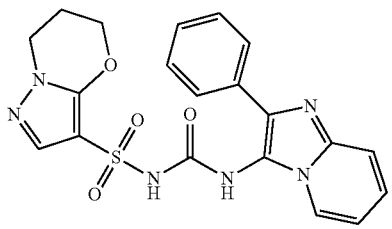 [SMILES: O=C(Nc1c(-c2ccccc2)nc2ccccn12)NS(=O)(=O)c1cnn2c1OCCC2]

N-((2-phenylimidazo[1,2-a]pyridin-3-yl)carbamoyl)-6,7-dihydro-5H-pyrazolo[5,1-b][1,3]oxazine-3-sulfonamide was prepared by using the general procedure described for the preparation of N-((4,6-dichloropyrimidin-2-yl)carbamoyl)-6,7-dihydro-5H-pyrazolo[5,1-b][1,3]oxazine-3-sulfonamide (Example 4) by replacing 4,6-dichloropyrimidin-2-amine with 2-phenylimidazo[1,2-a]pyridin-3-amine in Step 2. LCMS: m/z=439 [M+1].

Example 11

N-((1-phenylcyclopropyl)carbamoyl)-6,7-dihydro-5H-pyrazolo[5,1-b][1,3]oxazine-3-sulfonamide

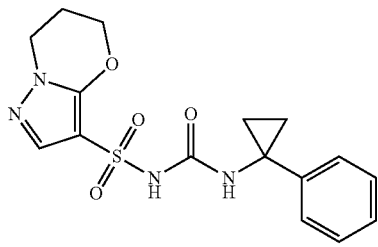 [SMILES: O=C(NC1(c2ccccc2)CC1)NS(=O)(=O)c1cnn2c1OCCC2]

N-((1-phenylcyclopropyl)carbamoyl)-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 2,2-dimethyl-1,2,3,4-tetrahydronaphthalen-1-amine with 1-phenylcyclopropan-1-amine in Step 1. LCMS: m/z=363 [M+1].

Example 12

N-((1-phenylcycloheptyl)carbamoyl)-6,7-dihydro-5H-pyrazolo[5,1-b][1,3]oxazine-3-sulfonamide

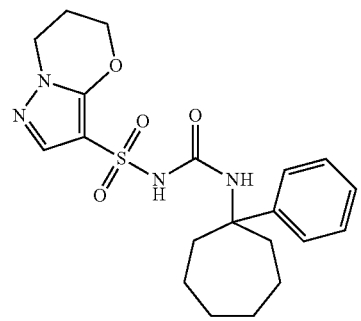 [SMILES: O=C(NC1(c2ccccc2)CCCCCC1)NS(=O)(=O)c1cnn2c1OCCC2]

N-((1-phenylcycloheptyl)carbamoyl)-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 2,2-dimethyl-1,2,3,4-tetrahydronaphthalen-1-amine with 1-phenylcycloheptan-1-amine in Step 1. LCMS: m/z=419 [M+1].

Example 13

N-((hexahydrocyclopenta[c]pyrrol-2(1H)-yl)carbamoyl)-6,7-dihydro-5H-pyrazolo[5,1-b][1,3]oxazine-3-sulfonamide Step 1—Synthesis of N-((hexahydrocyclopenta[c]pyrrol-2(1H)-yl)carbamoyl)-6,7-dihydro-5H-pyrazolo[5,1-b][1,3]oxazine-3-sulfonamide (Example 13a)

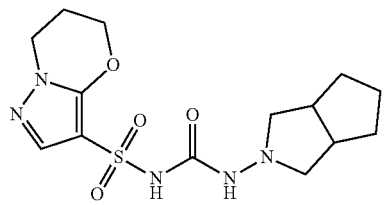 [SMILES: O=C(NN1CC2CCCC2C1)NS(=O)(=O)c1cnn2c1OCCC2]

To a solution of hexahydrocyclopenta[c]pyrrol-2(1H)-amine hydrochloride (200 mg, 5 Eq, 1.23 mmol) in anhydrous DCM (5 mL) was added TEA (0.19 g, 0.26 mL, 7.5 Eq, 1.85 mmol) followed by phenyl chloroformate (0.23 g, 0.19 mL, 6 Eq, 1.48 mmol) dropwise at 0° C. The reaction was then warmed up to room temperature and stirred for 3 h before diluted with DCM (30 mL). The mixture was washed with water, brine, dried over $Na_2SO_4$ and concentrated under reduced pressure to afford carbamate intermediate as white solids. The solids obtained was then dissolved in anhydrous DMF (1 mL). To this solution was added 6,7-dihydro-5H-pyrazolo[5,1-b][1,3]oxazine-3-sulfonamide (50 mg, 1 Eq, 0.25 mmol) followed by NaH (24 mg, 2.5 Eq, 0.62 mmol, 60% in mineral oil). The mixture was stirred at room temperature overnight before MeOH (1 mL) was added. The solvent was removed under reduced pressure and the residue was purified by silica gel chromatography (MeOH/DCM, 0 to 10%) to afford N-((hexahydrocyclopenta[c]pyrrol-2(1H)-yl)carbamoyl)-6,7-dihydro-5H-pyrazolo[5,1-b][1,3]oxazine-3-sulfonamide (22.2 mg, 25%) as white solids. Single unknown stereoisomer obtained. LCMS: m/z=356 [M+1].

Example 14

N-(azepan-1-ylcarbamoyl)-6,7-dihydro-5H-pyrazolo[5,1-b][1,3]oxazine-3-sulfonamide

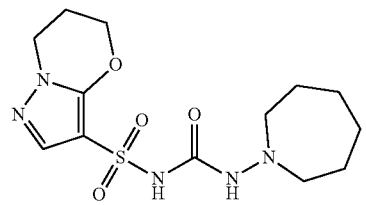 [SMILES: O=C(NN1CCCCCC1)NS(=O)(=O)c1cnn2c1OCCC2]

N-(azepan-1-ylcarbamoyl)-6,7-dihydro-5H-pyrazolo[5,1-b][1,3]oxazine-3-sulfonamide was prepared by using the general procedure described for the preparation of N-((hexahydrocyclopenta[c]pyrrol-2(1H)-yl)carbamoyl)-6,7-dihydro-5H-pyrazolo[5,1-b][1,3]oxazine-3-sulfonamide (Example 13) by replacing hexahydrocyclopenta[c]pyrrol-2(1H)-amine hydrochloride with azepan-1-amine in Step 1. LCMS: m/z=344 [M+1].

Example 15

N-(benzhydrylcarbamoyl)-6,7-dihydro-5H-pyrazolo[5,1-b][1,3]oxazine-3-sulfonamide

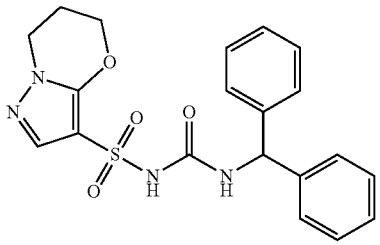 [SMILES: O=C(NC(c1ccccc1)c1ccccc1)NS(=O)(=O)c1cnn2c1OCCC2]

N-(benzhydrylcarbamoyl)-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 2,2-dimethyl-1,2,3,4-tetrahydronaphthalen-1-amine with diphenylmethanamine in Step 1. LCMS: m/z=413 [M+1].

Example 16

N-((4-chloro-6-isopropylpyrimidin-2-yl)carbamoyl)-6,7-dihydro-5H-pyrazolo[5,1-b][1,3]oxazine-3-sulfonamide

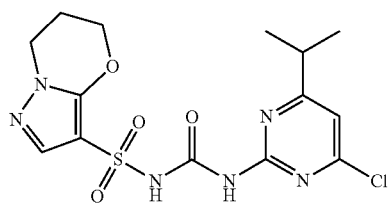

N-((4-chloro-6-isopropylpyrimidin-2-yl)carbamoyl)-6,7-dihydro-5H-pyrazolo[5,1-b][1,3]oxazine-3-sulfonamide was prepared by using the general procedure described for the preparation of N-((hexahydrocyclopenta[c]pyrrol-2(1H)-yl)carbamoyl)-6,7-dihydro-5H-pyrazolo[5,1-b][1,3]oxazine-3-sulfonamide (Example 13) by replacing hexahydrocyclopenta[c]pyrrol-2(1H)-amine hydrochloride with 4-chloro-6-isopropylpyrimidin-2-amine in Step 1. LCMS: m/z=401 [M+1].

Example 17

N-((4-phenyl-6-(trifluoromethyl)pyrimidin-2-yl)carbamoyl)-6,7-dihydro-5H-pyrazolo[5,1-b][1,3]oxazine-3-sulfonamide

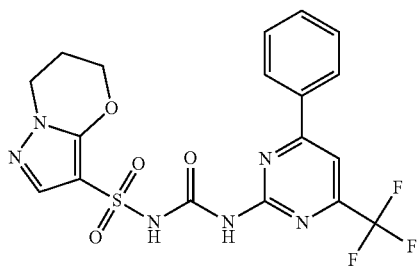 [SMILES: O=C(Nc1nc(-c2ccccc2)cc(C(F)(F)F)n1)NS(=O)(=O)c1cnn2c1OCCC2]

N-((4-phenyl-6-(trifluoromethyl)pyrimidin-2-yl)carbamoyl)-6,7-dihydro-5H-pyrazolo[5,1-b][1,3]oxazine-3-sulfonamide was prepared by using the general procedure described for the preparation of N-((hexahydrocyclopenta[c]pyrrol-2(1H)-yl)carbamoyl)-6,7-dihydro-5H-pyrazolo[5,1-b][1,3]oxazine-3-sulfonamide (Example 13) by replacing hexahydrocyclopenta[c]pyrrol-2(1H)-amine hydrochloride with 4-phenyl-6-(trifluoromethyl)pyrimidin-2-amine in Step 1. LCMS: m/z=469 [M+1].

Example 18

N-((4,6-dimethoxypyrimidin-2-yl)carbamoyl)-6,7-dihydro-5H-pyrazolo[5,1-b][1,3]oxazine-3-sulfonamide

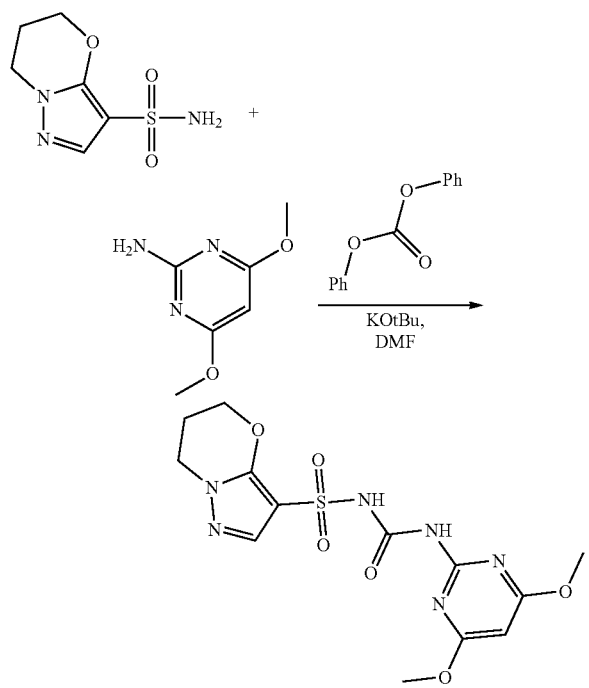

Step 1—Synthesis of N-((4,6-dimethoxypyrimidin-2-yl)carbamoyl)-6,7-dihydro-5H-pyrazolo[5,1-b][1,3]oxazine-3-sulfonamide (Example 18)

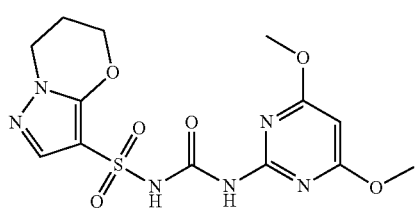 [SMILES: COc1cc(OC)nc(NC(=O)NS(=O)(=O)c2cnn3c2OCCC3)n1]

4,6-dimethoxypyrimidin-2-amine (31 mg, 0.199 mmol) was dissolved in DMF (1 mL) and treated with potassium tert-butoxide (0.022 g, 0.199 mmol) at 0 C. The mixture was added to a stirring solution of diphenyl carbonate (0.085 g, 0.399 mmol) slowly and the mixture was left to stir for 15 min. At this time 6,7-dihydro-5H-pyrazolo[5,1-b][1,3]oxazine-3-sulfonamide (0.081 g, 0.399 mmol) was added and the reaction was allowed to warm to r.t. and stir over the weekend. The reaction was then diluted with water (25 mL) and some urea impurity filtered off. The aq. layer was then washed with EtOAc (30 mL) and this layer discarded. The aq. layer was then acidified with HCl and extracted with EtOAc (2×25 mL). The combined organic extracts were then concentrated and purified by flash (0-100% EtOAc:hexane, then 5-20% MeOH:DCM) to yield N-((4,6-dimethoxypyrimidin-2-yl)carbamoyl)-6,7-dihydro-5H-pyrazolo[5,1-b][1,3]oxazine-3-sulfonamide (15.9 mg, 20.70%) as a white solid.

Example 19

N-((4-methoxy-6-methylpyrimidin-2-yl)carbamoyl)-6,7-dihydro-5H-pyrazolo[5,1-b][1,3]oxazine-3-sulfonamide

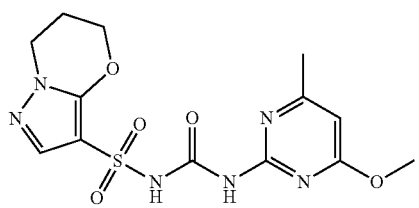 [SMILES: COc1cc(C)nc(NC(=O)NS(=O)(=O)c2cnn3c2OCCC3)n1]

N-((4-methoxy-6-methylpyrimidin-2-yl)carbamoyl)-6,7-dihydro-5H-pyrazolo[5,1-b][1,3]oxazine-3-sulfonamide was prepared by using the general procedure described for the preparation of N-((4,6-dimethoxypyrimidin-2-yl)carbamoyl)-6,7-dihydro-5H-pyrazolo[5,1-b][1,3]oxazine-3-sulfonamide (Example 18) by replacing 4,6-dimethoxypyrimidin-2-amine with 4-methoxy-6-methylpyrimidin-2-amine in Step 1. LCMS: m/z=369 [M+1].

Example 20

N-((3-bromo-6-methylpyridin-2-yl)carbamoyl)-6,7-dihydro-5H-pyrazolo[5,1-b][1,3]oxazine-3-sulfonamide

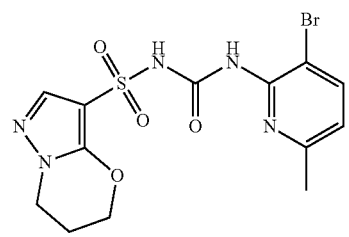

N-((3-bromo-6-methylpyridin-2-yl)carbamoyl)-6,7-dihydro-5H-pyrazolo[5,1-b][1,3]oxazine-3-sulfonamide was prepared by using the general procedure described for the preparation of N-((4,6-dimethoxypyrimidin-2-yl)carbamoyl)-6,7-dihydro-5H-pyrazolo[5,1-b][1,3]oxazine-3-sulfonamide (Example 18) by replacing 4,6-dimethoxypyrimidin-2-amine with 3-bromo-6-methylpyridin-2-amine in Step 1. LCMS: m/z=417 [M+1].

Example 21

N-((4-cyclopropyl-6-methylpyrimidin-2-yl)carbamoyl)-6,7-dihydro-5H-pyrazolo[5,1-b][1,3]oxazine-3-sulfonamide

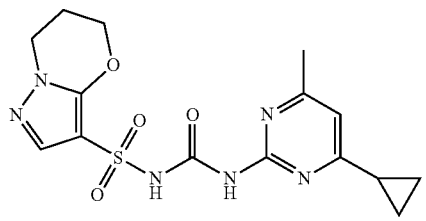 [SMILES: Cc1cc(C2CC2)nc(NC(=O)NS(=O)(=O)c2cnn3c2OCCC3)n1]

N-((4-cyclopropyl-6-methylpyrimidin-2-yl)carbamoyl)-6,7-dihydro-5H-pyrazolo[5,1-b][1,3]oxazine-3-sulfonamide was prepared by using the general procedure described for the preparation of N-((4,6-dimethylpyrimidin-2-yl)carbamoyl)-6,7-dihydro-5H-pyrazolo[5,1-b][1,3]oxazine-3-sulfonamide (Example 25) by replacing 4,6-dimethylpyrimidin-2-amine with 4-cyclopropyl-6-methylpyrimidin-2-amine in Step 1. LCMS: m/z=379 [M+1].

Example 22

N-((4,6-di-tert-butylpyrimidin-2-yl)carbamoyl)-6,7-dihydro-5H-pyrazolo[5,1-b][1,3]oxazine-3-sulfonamide

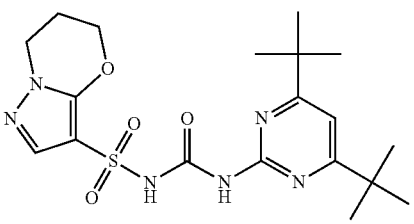 [SMILES: CC(C)(C)c1cc(C(C)(C)C)nc(NC(=O)NS(=O)(=O)c2cnn3c2OCCC3)n1]

N-((4,6-di-tert-butylpyrimidin-2-yl)carbamoyl)-6,7-dihydro-5H-pyrazolo[5,1-b][1,3]oxazine-3-sulfonamide was prepared by using the general procedure described for the preparation of N-((4,6-dimethylpyrimidin-2-yl)carbamoyl)-6,7-dihydro-5H-pyrazolo[5,1-b][1,3]oxazine-3-sulfonamide (Example 25) by replacing 4,6-dimethylpyrimidin-2-amine with 4,6-di-tert-butylpyrimidin-2-amine in Step 1. LCMS: m/z=437 [M+1].

Example 23

N-((3-phenyl-6,7-dihydro-5H-cyclopenta[c]pyridin-1-yl)carbamoyl)-6,7-dihydro-5H-pyrazolo[5,1-b][1,3]oxazine-3-sulfonamide

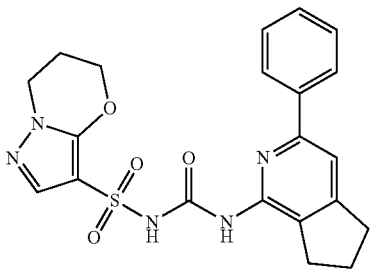 [SMILES: O=C(Nc1nc(-c2ccccc2)cc2c1CCC2)NS(=O)(=O)c1cnn2c1OCCC2]

N-((3-phenyl-6,7-dihydro-5H-cyclopenta[c]pyridin-1-yl)carbamoyl)-6,7-dihydro-5H-pyrazolo[5,1-b][1,3]oxazine-3-sulfonamide was prepared by using the general procedure described for the preparation of N-((4,6-dimethylpyrimidin-2-yl)carbamoyl)-6,7-dihydro-5H-pyrazolo[5,1-b][1,3]oxazine-3-sulfonamide (Example 25) by replacing 4,6-dimethylpyrimidin-2-amine with 3-phenyl-6,7-dihydro-5H-cyclopenta[c]pyridin-1-amine in Step 1. LCMS: m/z=440 [M+1].

Example 24

N-((4-methyl-5,6,7,8-tetrahydroquinazolin-2-yl)carbamoyl)-6,7-dihydro-5H-pyrazolo[5,1-b][1,3]oxazine-3-sulfonamide

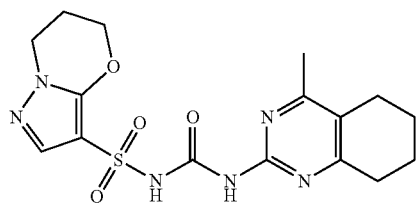

N-((4-methyl-5,6,7,8-tetrahydroquinazolin-2-yl)carbamoyl)-6,7-dihydro-5H-pyrazolo[5,1-b][1,3]oxazine-3-sulfonamide was prepared by using the general procedure described for the preparation of N-((4,6-dimethylpyrimidin-2-yl)carbamoyl)-6,7-dihydro-5H-pyrazolo[5,1-b][1,3]oxazine-3-sulfonamide (Example 25) by replacing 4,6-dimethylpyrimidin-2-amine with 4-methyl-5,6,7,8-tetrahydroquinazolin-2-amine in Step 1. LCMS: m/z=393 [M+1].

Example 25

N-((4,6-dimethylpyrimidin-2-yl)carbamoyl)-6,7-dihydro-5H-pyrazolo[5,1-b][1,3]oxazine-3-sulfonamide

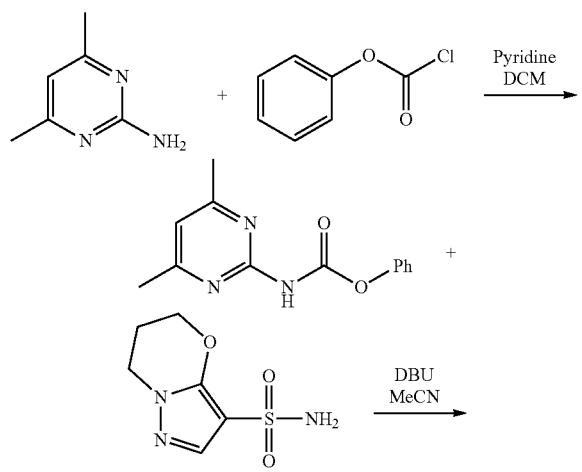

Step 1—Synthesis of N-((4,6-dimethylpyrimidin-2-yl)carbamoyl)-6,7-dihydro-5H-pyrazolo[5,1-b][1,3]oxazine-3-sulfonamide (Example 25)

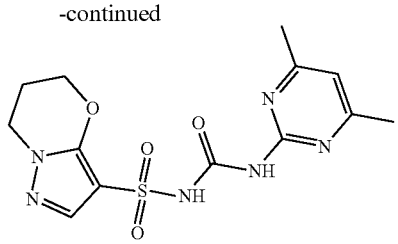

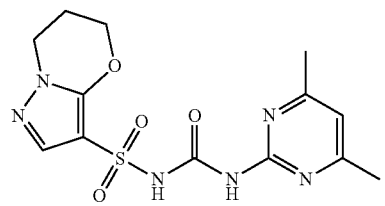 [SMILES: Cc1cc(C)nc(NC(=O)NS(=O)(=O)c2cnn3c2OCCC3)n1]

To a solution of phenyl chloroformate (82 mg, 66 μL, 1.3 Eq, 0.53 mmol) and pyridine (51 mg, 52 μL, 1.6 Eq, 0.65 mmol) in anhydrous DCM (1 mL) was added 4,6-dimethylpyrimidin-2-amine (50 mg, 1 Eq, 0.41 mmol) at room temperature under $N_2$. The reaction was stirred at room temperature for 30 min before quenched with saturated $NaHCO_3$ solution (10 mL). The mixture was extracted with DCM (3×10 mL), combined organic extracts were washed with water, brine, dried over $Na_2SO_4$, and concentrated under reduced pressure to afford carbamate intermediate as white solids. The carbamate obtained was then dissolved in anhydrous MeCN (1 mL). To this solution was added 6,7-dihydro-5H-pyrazolo[5,1-b][1,3]oxazine-3-sulfonamide (60 mg, 1 Eq, 0.31 mmol) followed by DBU (61 mg, 60 DL, 1 Eq. 0.41 mmol). The reaction was stirred at room temperature overnight before solvent was removed under reduced pressure. The residue was purified by silica gel chromatography (EtOAc/Hexanes, 0 to 100% followed by MeOH/DCM 0 to 10%) to afford N-((4,6-dimethylpyrimidin-2-yl)carbamoyl)-6,7-dihydro-5H-pyrazolo[5,1-b][1,3]oxazine-3-sulfonamide (76.2 mg, 53%) as white solids. LCMS: m/z=353 [M+1].

Example 26

N-((3,5-diisopropyl-1-methyl-1H-pyrazol-4-yl)carbamoyl)-6,7-dihydro-5H-pyrazolo[5,1-b][1,3]oxazine-3-sulfonamide

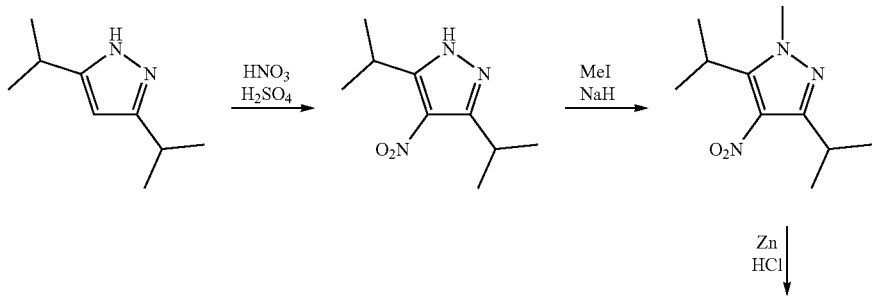

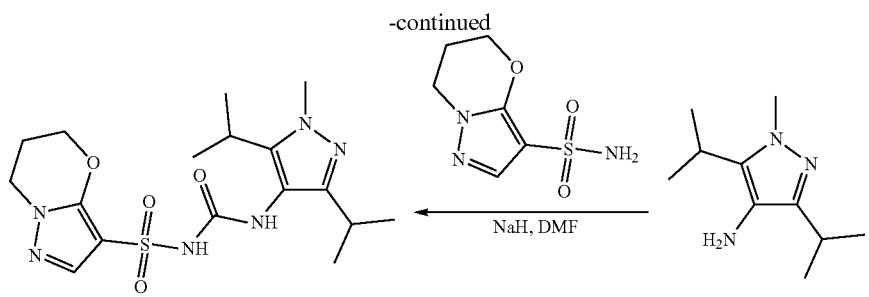

Step 1—Synthesis of 3,5-diisopropyl-4-nitro-1H-pyrazole

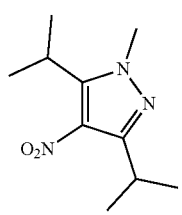

To 3,5-diisopropyl-1H-pyrazole (100 mg, 1 Eq, 657 µmol) was added concentrated nitric acid (0.59 g, 0.42 mL, 10 Eq, 6.57 mmol) followed by concentrated sulfuric acid (644 mg, 0.35 mL, 10 Eq, 6.57 mmol) at 0° C. The reaction was heated to 100° C. overnight before cooled to room temperature. EtOAc (30 mL) was added and the mixture was washed with water, saturated NaHCO$_3$ solution, brine, dried over Na$_2$SO$_4$ and concentrated under reduced pressure. The obtained residue was purified by silica gel chromatography (EtOAc/Hexanes, 0 to 50%) to afford 3,5-diisopropyl-4-nitro-1H-pyrazole (103 mg, 79.5%) as clear crystals. LCMS: m/z=198 [M+1].

Step 2—Synthesis of 3,5-diisopropyl-1-methyl-4-nitro-1H-pyrazole

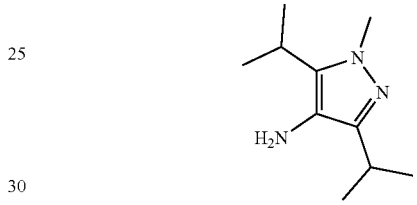

To a solution of 3,5-diisopropyl-4-nitro-1H-pyrazole (500 mg, 1 Eq, 2.53 mmol) in anhydrous DMF (5 mL) was added sodium hydride (0.30 g, 3 Eq, 7.60 mmol, 60% in mineral oil). The reaction was stirred at room temperature for 30 min before iodomethane (1.08 g, 476 µL, 3 Eq, 7.60 mmol) was added dropwise. The reaction was stirred for an additional 3 h before water (20 mL) was added. The mixture was extracted with EtOAc (3×20 mL), combined organic extracts were washed with water, brine, dried over Na$_2$SO$_4$ and concentrated under reduced pressure. The obtained residue was purified by silica gel chromatography (EtOAc/Hexanes, 0 to 100%) to afford 3,5-diisopropyl-1-methyl-4-nitro-1H-pyrazole (480 mg, 90%) as white solids. LCMS: m/z=212 [M+1].

Step 3—Synthesis of 3,5-diisopropyl-methyl-1H-pyrazol-4-amine 3,5-Diisopropyl-1-methyl-4-nitro-1H-pyrazole (95 mg, 1 Eq, 0.45 mmol) was dissolved in acetic acid (3 mL), to this mixture was added concentrated hydrochloric acid (0.13 g, 0.11 mL, 3 Eq, 1.3 mmol) dropwise followed by zinc (88 mg, 3 Eq, 1.3 mmol) at room temperature. The reaction was then heated to 60° C. for 2 h before cooled to room temperature. Zinc was filtered off through Celite and acetic acid was removed under reduced pressure. The obtained residue was dissolved in EtOAc (50 mL) and washed with saturated NaHCO$_3$, water, brine, concentrated and purified by silica gel chromatography (EtOAc/Hexanes, 0 to 100%) to afford,5-diisopropyl-1-methyl-1H-pyrazol-4-amine (76 mg, 93%) as white solids. LCMS: m/z=182 [M+1].

Step 4—Synthesis of N-((3,5-diisopropyl-1-methyl-1H-pyrazol-4-yl)carbamoyl)-6,7-dihydro-5H-pyrazolo[5,1-b][1,3]oxazine-3-sulfonamide (Example 26)

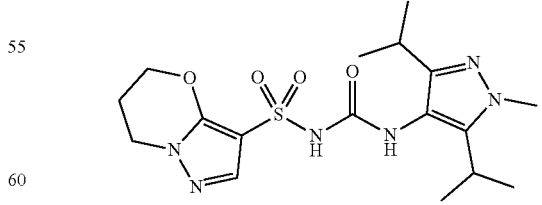

N-((3,5-diisopropyl-1-methyl-1H-pyrazol-4-yl)carbamoyl)-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H- pyrazolo[5,1-b][1,3]oxazine-3-sulfonamide (Example 1) by replacing 2,2-dimethyl-1,2,3,4-tetrahydronaphthalen-1-amine with 3,5-diisopropyl-1-methyl-1H-pyrazol-4-amine in Step 1. LCMS: m/z=411 [M+1].

Example 27

N-((3,5-di(prop-1-en-2-yl)pyridin-4-yl)carbamoyl)-6,7-dihydro-5H-pyrazolo[5,1-b][1,3]oxazine-3-sulfonamide

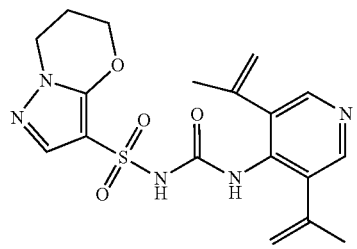

N-((3,5-di (prop-1-en-2-yl)pyridin-4-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 3,5-di(prop-1-en-2-yl)pyridin-4-amine in Step 10. ¹H NMR (400 MHz, DMSO-d₆): δ=8.26 (s, 2H), 7.88 (s, 1H), 7.51 (s, 1H), 5.12 (s, 2H), 4.89 (s, 2H), 4.41 (t, J=4.8 Hz, 2H), 4.11 (t, J=5.6 Hz, 2H), 2.21-2.15 (m, 2H), 1.92 (s, 6H). LCMS: m/z=403.8 [M+1].

Example 28

N-((3,5-diisopropylpyridin-4-yl)carbamoyl)-6,7-dihydro-5H-pyrazolo[5,1-b][1,3]oxazine-3-sulfonamide

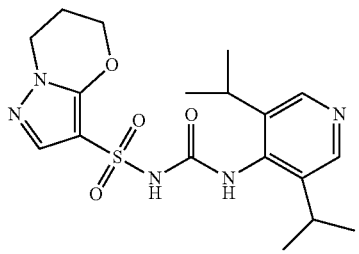 [SMILES: CC(C)c1cncc(C(C)C)c1NC(=O)NS(=O)(=O)c1cnn2c1OCCC2]

N-((3,5-diisopropylpyridin-4-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 3,5-diisopropylpyridin-4-amine in Step 10. ¹H NMR (400 MHz, DMSO-d6): δ=8.33 (s, 2H), 7.83 (s, 1H), 7.50 (s, 1H), 4.39 (t, J=4.0 Hz, 2H), 4.09 (t, J (400 MHz, DMSO-d₆): δ=8.33 (s, 2H), 7.83 (s, 1H), 7.50 (s, 1H), 4.39 (t, J=4.0 Hz, 2H), 4.09 (t, J=6.0 Hz, 2H), 2.97-2.94 (m, 2H), 2.19-2.15 (m, 2H), 1.12 (d, J=6.8 Hz, 12H). J=6.8 Hz, 12H). LCMS: m/z=408.1 [M+1].

Example 29

N-((8-oxo-2,3,5,6,7,8-hexahydro-1H-pyrrolo[1,2-a]indol-9-yl)carbamoyl)-6,7-dihydro-5H-pyrazolo[5,1-b][1,3]oxazine-3-sulfonamide

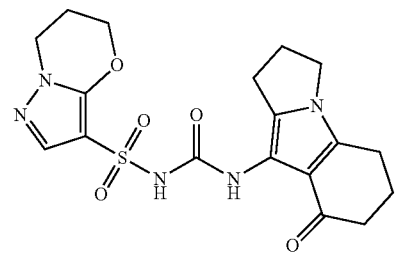 [SMILES: O=C(Nc1c2c(n3c1CCC3)CCCC2=O)NS(=O)(=O)c1cnn2c1OCCC2]

N-((8-oxo-2,3,5,6,7,8-hexahydro-1H-pyrrolo[1,2-a]indol-9-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 9-amino-1,2,3,5,6,7-hexahydro-8H-pyrrolo[1,2-a]indol-8-one in Step 10. ¹H NMR (400 MHz, DMSO-d₆): δ=11.17 (brs, 1H), 8.56 (s, 1H), 7.62 (s, 1H), 4.43 (t, J=5.2 Hz, 2H), 4.09 (t, J=5.6 Hz, 2H), 3.82 (t, J=6.8 Hz, 2H), 2.84 (t, J=7.6 Hz, 2H), 2.67 (t, J=6.0 Hz, 2H), 2.34-2.26 (m, 4H), 2.21-2.18 (m, 2H), 1.99-1.95 (m, 2H). LCMS: m/z=419.8 [M+1].

Example 30

N-((2,4-diisopropyl-6-methoxypyridin-3-yl)carbamoyl)-6,7-dihydro-5H-pyrazolo[5,1-b][1,3]oxazine-3-sulfonamide

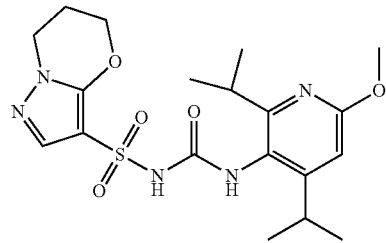 [SMILES: COc1cc(C(C)C)c(NC(=O)NS(=O)(=O)c2cnn3c2OCCC3)c(C(C)C)n1]

N-((2,4-diisopropyl-6-methoxypyridin-3-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide in Step 10. $^1$H (400 MHz, DMSO-d$_6$): δ=10.71 (brs, 1H), 7.70 (brs, 1H), 7.59 (s, 1H), 6.51 (s, 1H), 4.45 (t, J=4.8 Hz, 2H), 4.11 (t, J=5.6 Hz, 2H), 3.81 (s, 3H), 3.01-2.94 (m, 1H), 2.85-2.78 (m, 1H), 2.22-2.18 (m, 2H), 1.22-0.94 (m, 12H). LCMS: m/z=438.1 [M+1].

Example 31

N-((2,4-diisopropylpyridin-3-yl)carbamoyl)-6,7-dihydro-5H-pyrazolo[5,1-b][1,3]oxazine-3-sulfonamide

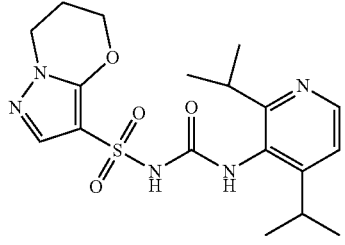 [SMILES: CC(C)c1ccnc(C(C)C)c1NC(=O)NS(=O)(=O)c1cnn2c1OCCC2]

N-((2,4-diisopropylpyridin-3-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 2,4-diisopropylpyridin-3-amine in Step 10. $^1$H NMR (400 MHz, DMSO-d$_6$): δ=10.81 (brs, 1H), 8.35 (d, J=4.8 Hz, 1H), 7.88 (s, 1H), 7.58 (s, 1H), 7.14 (d, J=4.8 Hz, 1H), 4.44 (t, J=4.8 Hz, 2H), 4.11 (t, J=6.0 Hz, 2H), 3.11-3.04 (m, 1H), 2.94-2.88 (m, 1H), 2.23-2.18 (m, 2H), 1.06 (d, J=6.0 Hz, 12H). LCMS: m/z=407.9 [M+1].

Example 32

N-((6-chloro-2,4-diisopropylpyridin-3-yl)carbamoyl)-6,7-dihydro-5H-pyrazolo[5,1-b][1,3]oxazine-3-sulfonamide

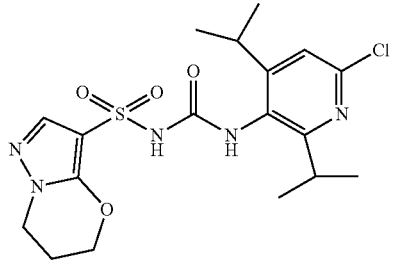 [SMILES: CC(C)c1cc(Cl)nc(C(C)C)c1NC(=O)NS(=O)(=O)c1cnn2c1OCCC2]

N-((6-chloro-2,4-diisopropylpyridin-3-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 6-chloro-2,4-diisopropylpyridin-3-amine in Step 10. $^1$H NMR (400 MHz, DMSO-d$_6$): δ=7.94 (s, 1H), 7.55 (s, 1H), 7.23 (s, 1H), 4.42 (t, J=4.8 Hz, 2H), 4.10 (t, J=6.0 Hz, 2H), 3.08-3.04 (m, 1H), 2.92-2.89 (m, 1H), 2.20-2.17 (m, 2H), 1.15-1.00 (m, 12H). LCMS: m/z=441.8 [M+1].

Example 33

N-((1,3,5-triisopropyl-1H-pyrazol-4-yl)carbamoyl)-6,7-dihydro-5H-pyrazolo[5,1-b][1,3]oxazine-3-sulfonamide

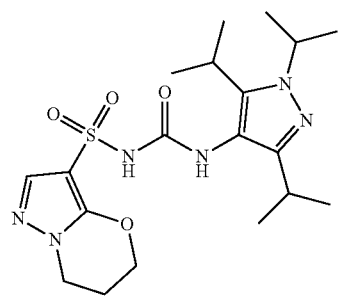 [SMILES: CC(C)c1nn(C(C)C)c(C(C)C)c1NC(=O)NS(=O)(=O)c1cnn2c1OCCC2]

N-((1,3,5-triisopropyl-1H-pyrazol-4-yl)carbamoyl)-6,7-dihydro-5H-pyrazolo[5,1-b][1,3]oxazine-3-sulfonamide was prepared by using the general procedure described for the preparation of N-((3,5-diisopropyl-1-methyl-1H-pyrazol-4-yl)carbamoyl)-6,7-dihydro-5H-pyrazolo[5,1-b][1,3]oxazine-3-sulfonamide (Example 26) by replacing iodomethane with 2-iodopropane in Step 2. LCMS: m/z=439 [M+1].

Example 34

N-((1-ethyl-3,5-diisopropyl-1H-pyrazol-4-yl)carbamoyl)-6,7-dihydro-5H-pyrazolo[5,1-b][1,3]oxazine-3-sulfonamide

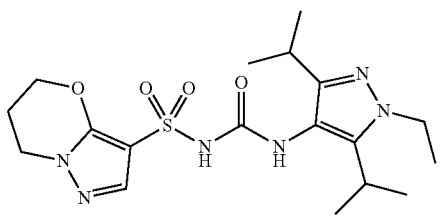 [SMILES: CCn1nc(C(C)C)c(NC(=O)NS(=O)(=O)c2cnn3c2OCCC3)c1C(C)C]

N-((1-ethyl-3,5-diisopropyl-1H-pyrazol-4-yl)carbamoyl)-6,7-dihydro-5H-pyrazolo[5,1-b][1,3]oxazine-3-sulfonamide was prepared by using the general procedure described for the preparation of N-((3,5-diisopropyl-1- methyl-1H-pyrazol-4-yl)carbamoyl)-6,7-dihydro-5H-pyrazolo[5,1-b][1,3]oxazine-3-sulfonamide (Example 26) by replacing iodomethane with iodoethane in Step 2. LCMS: m/z=425 [M+1].

Example 35

N-((1-(cyclopropylmethyl)-3,5-diisopropyl-1H-pyrazol-4-yl)carbamoyl)-6,7-dihydro-5H-pyrazolo[5,1-b][1,3]oxazine-3-sulfonamide

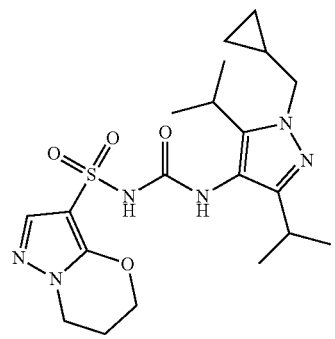 [SMILES: CC(C)c1nn(CC2CC2)c(C(C)C)c1NC(=O)NS(=O)(=O)c1cnn2c1OCCC2]

N-((1-(cyclopropylmethyl)-3,5-diisopropyl-1H-pyrazol-4-yl)carbamoyl)-6,7-dihydro-5H-pyrazolo[5,1-b][1,3]oxazine-3-sulfonamide was prepared by using the general procedure described for the preparation of N-((3,5-diisopropyl-1-methyl-1H-pyrazol-4-yl)carbamoyl)-6,7-dihydro-5H-pyrazolo[5,1-b][1,3]oxazine-3-sulfonamide (Example 26) by replacing iodomethane with (bromomethyl)cyclopropane in Step 2. LCMS: m/z=451 [M+1].

Example 36

N-((1,3-di-tert-butyl-1H-pyrazol-5-yl)carbamoyl)-6,7-dihydro-5H-pyrazolo[5,1-b][1,3]oxazine-3-sulfonamide, ammonia

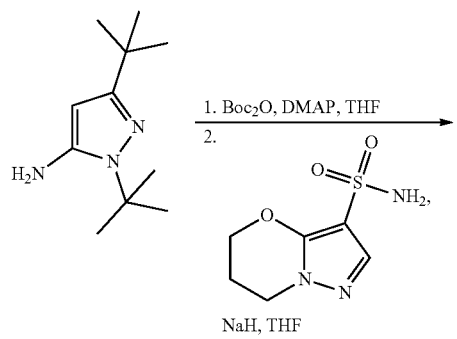

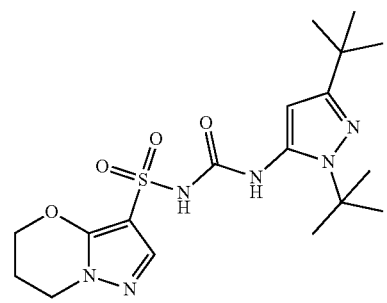

Step 1—Synthesis of N-((1,3-di-tert-butyl-1H-pyrazol-5-yl)carbamoyl)-6,7-dihydro-5H-pyrazolo[5,1-b][1,3]oxazine-3-sulfonamide, ammonia (Example 36)

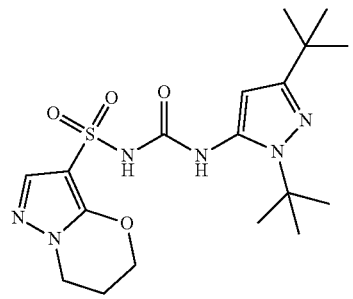 [SMILES: CC(C)(C)c1cc(NC(=O)NS(=O)(=O)c2cnn3c2OCCC3)n(C(C)(C)C)n1]

A solution of DMAP (9.4 mg, 77 µmol) in THF (0.4 mL) was added slowly to a solution of di-tert-butyl dicarbonate (34 mg, 0.15 mmol) in THF (0.4 mL) stirred under a $N_2$ atmosphere. After stirring for 5 min, a solution of 1,3-di-tert-butyl-1H-pyrazol-5-amine (30 mg, 0.15 mmol) in THF (0.25 mL) was added and the reaction mixture was left to stir at room temperature for 30 min. At the same time, 6,7-dihydro-5H-pyrazolo[5,1-b][1,3]oxazine-3-sulfonamide (31 mg, 0.15 mmol) in THF (0.25 mL) stirred under a $N_2$ atmosphere was treated with sodium hydride (60%, 6.1 mg, 0.15 mmol), and the reaction mixture was left to stir at room temperature for 20 min. At this time two reaction mixtures were combined and left to stir under a $N_2$ atmosphere for 24 h. Then, the reaction mixture was quenched with MeOH, filtered and the filtrate was purified by prep-HPLC ($CH_3CN/H_2O$/10 mM aq. $NH_3$) to afford N-((1,3-di-tert-butyl-1H-pyrazol-5-yl)carbamoyl)-6,7-dihydro-5H-pyrazolo[5,1-b][1,3]oxazine-3-sulfonamide (3 mg, yield: 5%) as a white solid (as an ammonium salt). MS: m/z 425 (M+H$^+$).

Example 37

Sodium (S)—N-((2,4-diisopropyl-6-methoxypyridin-3-yl)carbamoyl)-6-methoxy-6,7-dihydro-5H-pyrazolo[5,1-b][1,3]oxazine-3-sulfonamide (Example 37a)

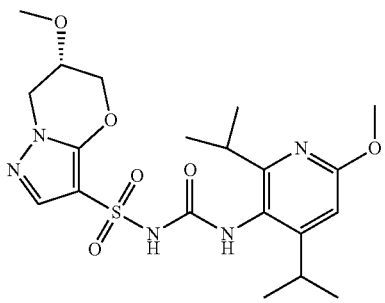 [SMILES: COc1cc(C(C)C)c(NC(=O)NS(=O)(=O)c2cnn3c2OC[C@@H](OC)C3)c(C(C)C)n1]

Sodium (S)—N-((2,4-diisopropyl-6-methoxypyridin-3-yl)carbamoyl)-6-methoxy-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (5)-6-(3-methoxyazetidin-1-yl)-6,7-dihydro-5H-pyrazolo[5,1-b][1,3]oxazine-3-sulfonamide with (S)-6-methoxy-6,7-dihydro-5H-pyrazolo[5,1-b][1,3]oxazine-3-sulfonamide in Step 10. Single known stereoisomer obtained. $^1$H NMR (400 MHz, DMSO-$d_6$): δ=7.33 (s, 1H), 7.29 (s, 1H), 6.38 (s, 1H), 4.47 (d, J=11.2 Hz, 1H), 4.17-4.10 (m, 3H), 3.95 (s, 1H), 3.78 (s, 3H), 3.34 (overlap, 3H), 3.22-3.16 (m, 1H), 3.04-2.98 (m, 1H), 1.05-1.01 (m, 12H). LCMS: m/z=467.8 [M+1].

Example 38

(S)—N-((3,5-diisopropyl-1-methyl-1H-pyrazol-4-yl)carbamoyl)-6-methoxy-6,7-dihydro-5H-pyrazolo[5,1-][1,3]oxazine-3-sulfonamide (Example 38a)

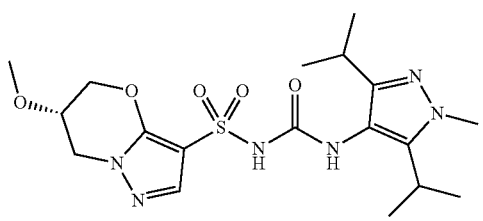

(S)—N-((3,5-diisopropyl-1-methyl-1H-pyrazol-4-yl)carbamoyl)-6-methoxy-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 6,7-dihydro-5H-pyrazolo[5,1-b][1,3]oxazine-3-sulfonamide with (S)-6-methoxy-6,7-dihydro-5H-pyrazolo[5,1-b][1,3]oxazine-3-sulfonamide and 2,2-dimethyl-1,2,3,4-tetrahydronaphthalen-1-amine with 3,5-diisopropyl-1-methyl-1H-pyrazol-4-amine in Step 1. Single known stereoisomer obtained. LCMS: m/z=441 [M+1].

Example 39

(S)—N-((1-ethyl-3,5-diisopropyl-1H-pyrazol-4-yl)carbamoyl)-6-methoxy-6,7-dihydro-5H-pyrazolo[5,1-b][1,3]oxazine-3-sulfonamide (Example 39a)

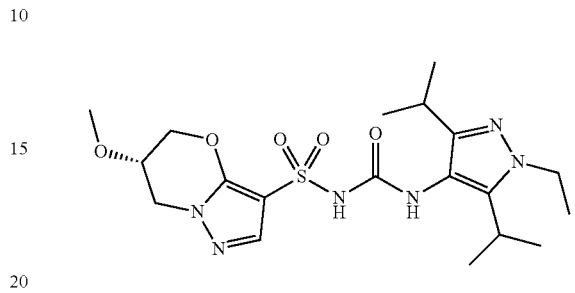

(S)—N-((1-ethyl-3,5-diisopropyl-1H-pyrazol-4-yl)carbamoyl)-6-methoxy-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 6,7-dihydro-5H-pyrazolo[5,1-b][1,3]oxazine-3-sulfonamide with (S)-6-methoxy-6,7-dihydro-5H-pyrazolo[5,1-b][1,3]oxazine-3-sulfonamide and 2,2-dimethyl-1,2,3,4-tetrahydronaphthalen-1-amine with 1-ethyl-3,5-diisopropyl-1H-pyrazol-4-amine in Step 1. Single known stereoisomer obtained. LCMS: m/z=455 [M+1].

Example 40

N-((3-(N-((2,4-diisopropyl-6-methoxypyridin-3-yl)carbamoyl)sulfamoyl)-6,7-dihydro-5H-pyrazolo[5,1-b][1,3]oxazin-6-yl)methyl)acetamide

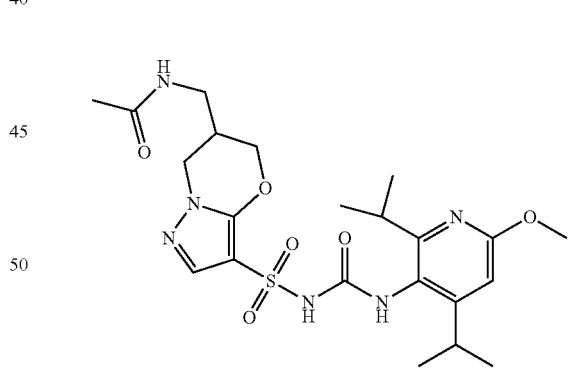

N-((3-(N-((2,4-diisopropyl-6-methoxypyridin-3-yl)carbamoyl)sulfamoyl)-6,7-dihydro-5H-pyrazolo[5,1-b][1,3]oxazin-6-yl)methyl)acetamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with N-((3-sulfamoyl-6,7-dihydro-5H-pyrazolo[5,1-b][1,3]oxazin-6-yl)methyl)acetamide in Step 10. Mixture of enantiomers obtained. $^1$H NMR (400 MHz, DMSO-$d_6$): δ=8.11 (t, J=4.8 Hz, 1H), 7.32

(s, 1H), 7.25 (s, 1H), 6.38 (s, 1H), 4.31 (d, J=10.0 Hz, 1H), 4.10 (dd, J=12.4, 5.2 Hz, 1H), 4.00 (t, J=10.0 Hz, 1H), 3.82-3.74 (m, 4H), 3.20-3.10 (m, 3H), 3.04-2.94 (m, 1H), 2.40-2.30 (m, 1H), 1.83 (s, 3H), 1.10-0.96 (m, 12H). LCMS: m/z=509.2 [M+1].

Example 41

(S)—N-((2,4-diisopropyl-6-methoxypyridin-3-yl)carbamoyl)-6-(methylamino)-6,7-dihydro-5H-pyrazolo[5,1-b][1,3]oxazine-3-sulfonamide (Example 41a)

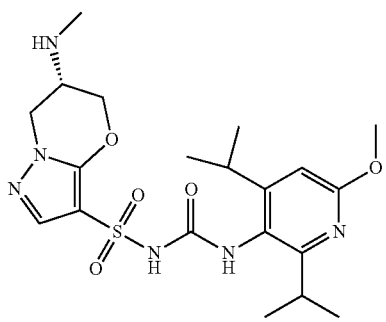 [SMILES: CN[C@@H]1COc2c(S(=O)(=O)NC(=O)Nc3c(C(C)C)cc(OC)nc3C(C)C)cnn2C1]

(S)—N-((2,4-diisopropyl-6-methoxypyridin-3-yl)carbamoyl)-6-(methylamino)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (5)-6-(3-methoxyazetidin-1-yl)-6,7-dihydro-5H-pyrazolo[5,1-b][1,3]oxazine-3-sulfonamide with (S)-6-(methylamino)-6,7-dihydro-5H-pyrazolo[5,1-b][1,3]oxazine-3-sulfonamide in Step 10. Single known stereoisomer obtained. $^1$H NMR (400 MHz, DMSO-d$_6$): δ=7.33 (s, 1H), 7.31 (s, 1H), 6.39 (s, 1H), 4.26 (dd, J=10.8, 2.0 Hz, 1H), 4.15 (dd, J=12.4, 4.8 Hz, 1H), 4.05 (dd, J=10.8, 5.2 Hz, 1H), 3.83-3.77 (m, 4H), 3.21-3.15 (m, 1H), 3.10-2.98 (m, 2H), 2.33 (d, J=6.0 Hz, 3H), 2.02-1.99 (m, 1H), 1.10-0.90 (m, 12H). LCMS: m/z=465.2 [M+1].

Example 42

Sodium (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide

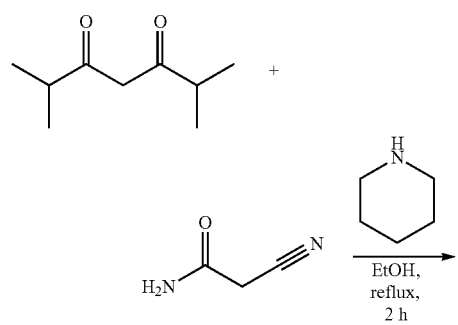

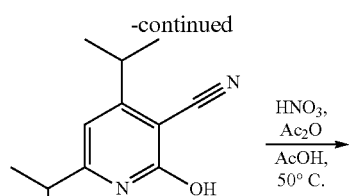
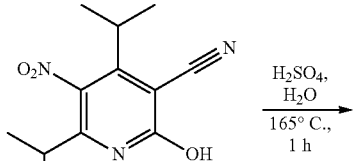
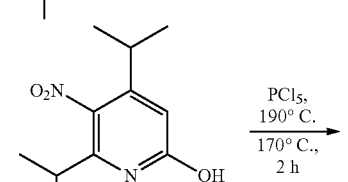
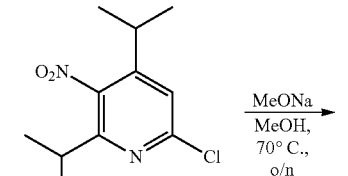
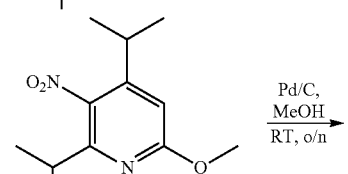
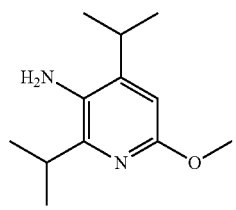

Intermediate 1

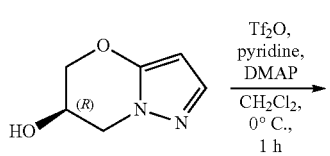
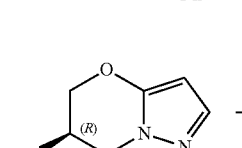
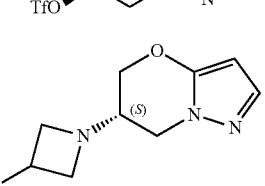

-continued

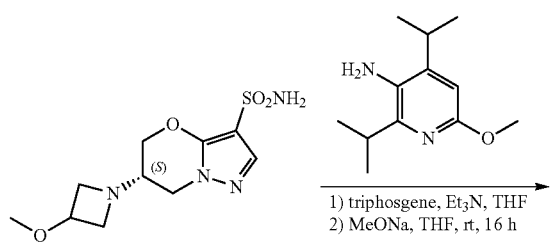

1) triphosgene, Et₃N, THF
2) MeONa, THF, rt, 16 h

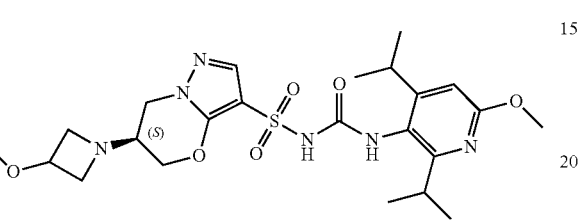

Step 1—Synthesis of
2-hydroxy-4,6-diisopropylnicotinonitrile

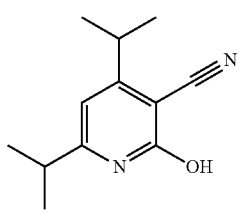

To a solution of 2,6-dimethylheptane-3,5-dione (20 g, 128.2 mmol) in EtOH (75 mL) was added 2-cyanoacetamide (10.8 g, 128.2 mmol) and piperidine (1.5 mL). The resulting mixture was stirred at 90° C. for 2 days. The reaction mixture was cooled to room temperature and filtered. The filter cake was rinsed with EtOH (5 mL) and dried to afford 2-hydroxy-4,6-diisopropylnicotinonitrile (13.6 g, yield: 52%) as a white solid. ¹H NMR (400 MHz, DMSO-d₆): δ=12.31 (brs, 1H), 6.27 (s, 1H), 3.06-3.03 (m, 1H), 2.84-2.81 (m, 1H), 1.22-1.21 (m, 12H). MS: m/z 205.1 (M+H⁺).

Step 2—Synthesis of
2-hydroxy-4,6-diisopropyl-5-nitronicotinonitrile

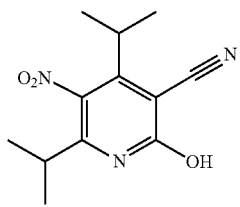 [SMILES: CC(C)c1nc(O)c(C#N)c(C(C)C)c1[N+](=O)[O-]]

To a suspension of 2-hydroxy-4,6-diisopropylnicotinonitrile (1 g, 4.9 mmol) in acetic anhydride (3.2 mL) was added a mixture of 0.4 mL of HNO₃ and 0.4 mL of acetic acid slowly at 50° C. The resulting mixture was stirred at 50° C. for 2 hrs. Then the reaction solution was cooled to room temperature and poured into ice-water (20 mL) slowly. The precipitate was collected by filtration. The filter cake was rinsed with H₂O (5 mL) and dried to afford 2-hydroxy-4,6-diisopropyl-5-nitronicotinonitrile (1.0 g, yield: 87%) as a white solid. ¹H NMR (400 MHz, DMSO-d₆): δ=13.07 (brs, 1H), 2.88-2.77 (m, 2H), 1.36-1.34 (m, 12H). MS: m/z 250.1 (M+H⁺).

Step 3—Synthesis of
4,6-diisopropyl-5-nitropyridin-2-ol

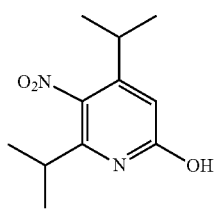 [SMILES: CC(C)c1cc(O)nc(C(C)C)c1[N+](=O)[O-]]

H₂SO₄ (20 mL) was added to H₂O (10 mL) at 0° C. After reaching room temperature, 2-hydroxy-4,6-diisopropyl-5-nitronicotinonitrile (3.4 g, 13.6 mmol) was added in portions. The resulting mixture was stirred at 165° C. for 4 hrs. The reaction mixture was cooled to room temperature and poured into ice-water (100 mL). The precipitate was collected by filtration. The filter cake was rinsed with H₂O (10 mL) and dried to afford 4,6-diisopropyl-5-nitropyridin-2-ol (2.0 g, yield: 67%) as a yellow solid. ¹H NMR (400 MHz, DMSO-d₆): δ=6.38 (s, 1H), 2.85-2.80 (m, 1H), 2.68-2.65 (m, 1H), 1.25-1.22 (m, 12H). MS: m/z 225.3 (M+H⁺).

Step 4—Synthesis of
6-chloro-2,4-diisopropyl-3-nitropyridine

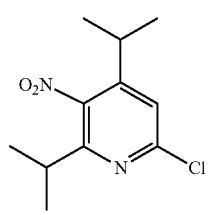 [SMILES: CC(C)c1cc(Cl)nc(C(C)C)c1[N+](=O)[O-]]

A mixture of 4,6-diisopropyl-5-nitropyridin-2-ol (1.2 g, 5.3 mmol) and PCl₅ (1.78 g, 8.57 mmol) was stirred at 190° C. After the solid was all melted, the reaction was cooled to 170° C. and stirred for 2 hrs. The reaction was then poured into saturated NaHCO₃ solution (75 mL) and extracted with EA (50 mL×2). The combined organic layer was washed with brine (50 mL), dried over Na₂SO₄ and concentrated. The residue was purified by silica gel column (PE) to afford 6-chloro-2,4-diisopropyl-3-nitropyridine (620 mg, yield: 48%) as a yellow oil. ¹H NMR (400 MHz, DMSO-d₆): δ=7.72 (s, 1H), 2.93-2.86 (m, 1H), 2.76-2.73 (m, 1H), 1.24-1.18 (m, 12H).

Step 5—Synthesis of 2,4-diisopropyl-6-methoxy-3-nitro-pyridine

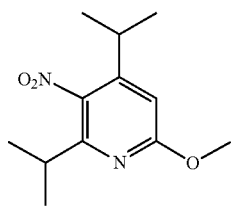

A mixture of 6-chloro-2,4-diisopropyl-3-nitropyridine (700 mg, 2.9 mmol) and MeONa (2.3 g, 43.4 mmol) in MeOH (10 mL) was stirred at 70° C. overnight. The reaction was poured into water (60 mL) and extracted with EA (60 mL). The organic layer was washed with water (50 mL) and brine (40 mL), dried over $Na_2SO_4$ and concentrated to give 2,4-diisopropyl-6-methoxy-3-nitro-pyridine (500 mg, yield: 72%) as a white solid. MS: m/z 239.1 (M+H$^+$).

Other compounds may be prepared where NaOMe is replaced with an appropriate reactant and solvent to furnish the described substitution. For example, $H_2NMe\cdot HCl$ may be used in place of NaOMe to give the —NHMe analog.

Step 6—Synthesis of 2,4-diisopropyl-6-methoxypyridin-3-amine

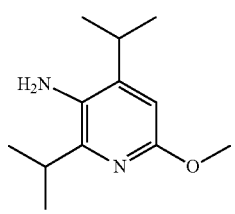 [SMILES: COc1cc(C(C)C)c([N+](=O)[O-])c(C(C)C)n1]

To a solution of 2,4-diisopropyl-6-methoxy-3-nitropyridine (530 mg, 2.2 mmol) in MeOH (6 mL) was added Pd/C (106 mg). The reaction was stirred at room temperature under $H_2$ for 16 hrs. The reaction was filtered and the filtrate was concentrated in vacuum to dryness. The residue was purified by gel silica column (PE/EA=10/1) to afford 2,4-diisopropyl-6-methoxypyridin-3-amine (426 mg, yield: 92%) as a colorless oil. $^1$H NMR (300 MHz, CDCl$_3$): δ=6.43 (s, 1H), 3.88 (s, 3H), 3.32 (brs, 2H), 3.06-3.02 (m, 1H), 2.94-2.89 (m, 1H), 1.30-1.24 (m, 12H).

Step 7—Synthesis of (R)-6,7-dihydro-5H-pyrazolo[5,1-b][1,3]oxazin-6-yl trifluoromethanesulfonate

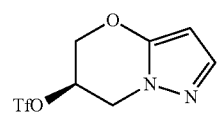 [SMILES: O=S(=O)(O[C@H]1COc2ccnn2C1)C(F)(F)F]

To a stirred solution of (R)-6,7-dihydro-5H-pyrazolo[5,1-b][1,3]oxazin-6-ol (400 mg, 2.9 mmol) in DCM (4 mL) was added DMAP (35 mg, 0.3 mmol) and pyridine (4 mL) at 0° C. under an atmosphere of $N_2$. Then trifluoromethanesulfonic anhydride (1.2 g, 4.3 mmol) was added to the mixture at 0° C. The reaction was stirred at 0° C. for 1 hr, then the reaction mixture was purified by silica gel column (PE/EA=3/1) to give (R)-6,7-dihydro-5H-pyrazolo[5,1-b][1,3]oxazin-6-yl trifluoromethanesulfonate (400 mg, yield: 51%) as a yellow solid. MS: m/z 273.0 (M+H$^+$).

Step 8—Synthesis of (S)-6-(3-methoxyazetidin-1-yl)-6,7-dihydro-5H-pyrazolo[5,1-b][1,3]oxazine

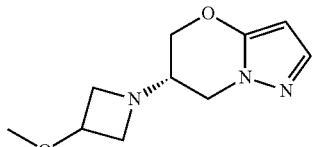

3-Methoxyazetidine hydrochloride (372 mg, 3.0 mmol) was added dropwise to a stirred solution of (R)-6,7-dihydro-5H-pyrazolo[5,1-b][1,3]oxazin-6-yl trifluoromethanesulfonate (400 mg, 1.5 mmol) and TEA (610 mg, 6.0 mmol) in THF (10 mL) at 0° C. under an atmosphere of $N_2$. The reaction was allowed to warm to room temperature within 1 hr and stirred at this temperature for another 16 hrs. Then the mixture was purified by C18 reverse phase column (5% 90% MeCN in $H_2O$) to give (S)-6-(3-methoxyazetidin-1-yl)-6,7-dihydro-5H-pyrazolo[5,1-b][1,3]oxazine (125 mg, yield: 31%) as a yellow oil. MS: m/z 210.1 (M+H$^+$).

Step 9—Synthesis of (S)-6-(3-methoxyazetidin-1-yl)-6,7-dihydro-5H-pyrazolo[5,1-b][1,3]oxazine-3-sulfonamide

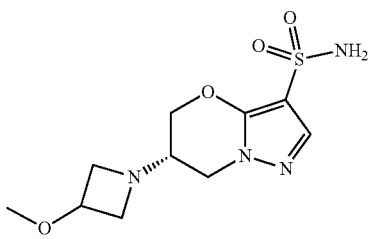 [SMILES: COC1CN([C@@H]2COc3c(S(N)(=O)=O)cnn3C2)C1]

To a solution of (S)-6-(3-methoxyazetidin-1-yl)-6,7-dihydro-5H-pyrazolo[5,1-b][1,3]oxazine (428 mg, 2.1 mmol) in DCM (5 mL) was added $ClSO_3H$ (1.2 mL, 9.0 mmol) dropwise at 0° C. The mixture was refluxed at 45° C. for 2 hrs. Then pyridine (0.5 mL, 9.0 mmol) was added dropwise at 0° C. and PCl$_5$ (1.3 g, 6.3 mmol) was added portion wise at 0° C. The reaction mixture was refluxed at 45° C. for 1 hr, and stirred at room temperature for 2 hrs. After cooled to room temperature, the reaction solution was added to $NH_3\cdot H_2O$ (25%, 50 mL, excessive) at 0° C. The mixture was stirred at 0° C. for 2 hrs. Then the mixture was concentrated and the residue was purified by C18 reverse phase column (5% 60% MeCN in $H_2O$) to give (S)-6-(3-methoxyazetidin-1-yl)-6,7-dihydro-5H-pyrazolo[5,1-b][1,3]oxazine-3-sulfonamide (473 mg, yield: 78%) as a yellow solid. $^1$H NMR (400 MHz, DMSO-A): δ=7.46 (s, 1H), 7.12 (s, 2H), 4.29-4.25 (m, 2H), 4.14 (dd, J=12.8 Hz, 3.6 Hz, 1H), 3.94 (t, J=5.6 Hz, 1H), 3.85 (d, J=12.4 Hz, 1H), 3.55-3.52 (m, 2H), 3.15 (s, 3H), 3.01-2.97 (m, 3H). MS: m/z 289.0 (M+H$^+$).

Step 10—Synthesis of sodium (S)—N-((2,4-diiso-propyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42a)

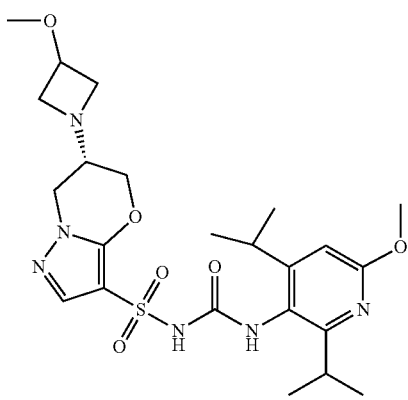

To a solution of (S)-6-(3-methoxyazetidin-1-yl)-6,7-dihydro-5H-pyrazolo[5,1-b][1,3]oxazine-3-sulfonamide (58 mg, 0.2 mmol) in THF (5 mL) was added MeONa (32 mg, 0.6 mmol) and the solution was stirred at room temperature for 20 mins to give a sodium salt suspension.

In another flask, to a solution of 2,4-diisopropyl-6-methoxypyridin-3-amine (42 mg, 0.2 mmol) and TEA (22 mg, 0.2 mmol) in THF (3 mL) was added triphosgene (24 mg, 0.08 mmol) in one portion and the solution was stirred at room temperature under $N_2$ for 20 mins. The reaction mixture was then filtered. The filtrate was added to the sodium salt suspension above and the resulting solution was stirred at room temperature for 16 hrs. The reaction mixture was concentrated to dryness and the residue was purified by C18 reverse phase column (5% 40% MeCN in $H_2O$) to give sodium (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (58 mg, yield: 55%) as a white solid (single known stereoisomer). $^1$H NMR (400 MHz, DMSO-$d_6$): δ=7.49 (brs, 1H), 7.43 (s, 1H), 6.44 (s, 1H), 4.22-4.15 (m, 2H), 4.14 (dd, J=12.8 Hz, 4.0 Hz, 1H), 3.96-3.91 (m, 1H), 3.84-3.79 (m, 4H), 3.58-3.52 (m, 2H), 3.14 (s, 3H), 3.13-3.10 (m, 1H), 2.51-2.49 (m, 4H), 1.07-1.03 (m, 12H). MS: m/z 523.2 (M+H$^+$).

Example 43

N-((1-isopropyl-3-methyl-1H-pyrazol-5-yl)carbamoyl)-6,7-dihydro-5H-pyrazolo[5,1-b][1,3]oxazine-3-sulfonamide

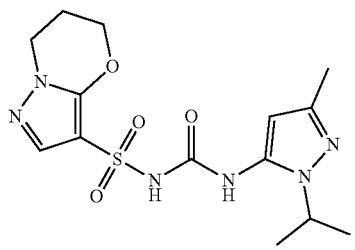 [SMILES: Cc1cc(NC(=O)NS(=O)(=O)c2cnn3c2OCCC3)n(C(C)C)n1]

N-((1-isopropyl-3-methyl-1H-pyrazol-5-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 1-isopropyl-3-methyl-1H-pyrazol-5-amine in Step 10. $^1$H NMR (400 MHz, DMSO-$d_6$): δ=7.99 (s, 1H), 7.34 (s, 1H), 5.76 (s, 1H), 4.40-4.34 (m, 1H), 4.29 (t, J=4.8 Hz, 2H), 4.03 (t, J=6.4 Hz, 2H), 2.15-2.09 (m, 2H), 2.03 (s, 3H), 1.22 (d, J=6.4 Hz, 6H). LCMS: m/z=368.8 [M+1].

Example 44

N-((2-isopropyl-2,4,5,6-tetrahydrocyclopenta[c]pyrazol-3-yl)carbamoyl)-6,7-dihydro-5H-pyrazolo[5,1-b][1,3]oxazine-3-sulfonamide

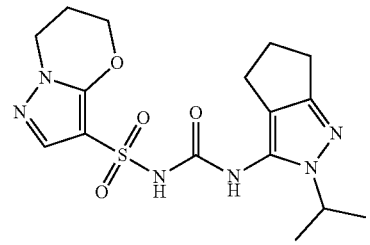 [SMILES: CC(C)n1nc2c(c1NC(=O)NS(=O)(=O)c1cnn3c1OCCC3)CCC2]

N-((2-isopropyl-2,4,5,6-tetrahydrocyclopenta[c]pyrazol-3-yl)carbamoyl)-6,7-dihydro-5H-pyrazolo[5,1-b][1,3]oxazine-3-sulfonamide was prepared by using the general procedure described for the preparation of N-((4,6-dimethylpyrimidin-2-yl)carbamoyl)-6,7-dihydro-5H-pyrazolo[5,1-b][1,3]oxazine-3-sulfonamide (Example 25) by replacing 4,6-dimethylpyrimidin-2-amine with 2-isopropyl-2,4,5,6-tetrahydrocyclopenta[c]pyrazol-3-amine in Step 1. LCMS: m/z=395 [M+1].

Example 45

N-((6-cyclopropyl-2,4-diisopropylpyridin-3-yl)carbamoyl)-6,7-dihydro-5H-pyrazolo[5,1-b][1,3]oxazine-3-sulfonamide

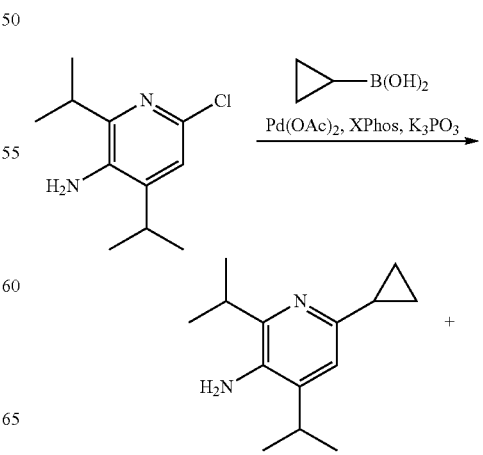

155

-continued

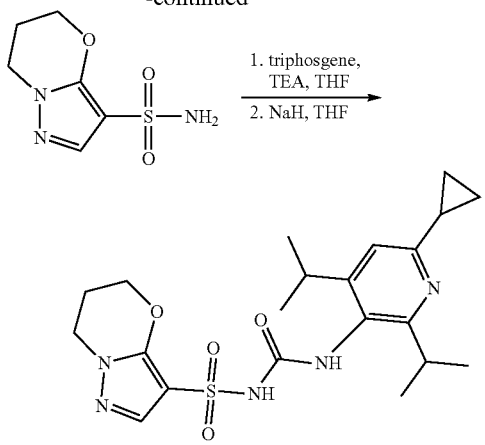

Step 1—Synthesis of 6-cyclopropyl-2,4-diisopropylpyridin-3-amine

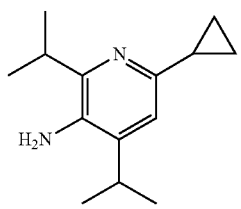 [SMILES: CC(C)c1cc(C2CC2)nc(C(C)C)c1N]

A mixture of 6-chloro-2,4-diisopropylpyridin-3-amine (215 mg, 1 mmol), cyclopropylboronic acid (260 mg, 3 mmol), palladium(II) acetate (23 mg), XPhos (96 mg, 0.20 mmol), potassium phosphate (429 mg, 2 mmol) in 1,4-Dioxane (6.6 mL) and Water (0.66 mL) was purged with nitrogen for 5 min before being heated to 100° C. After 3 h, LCMS analysis showed evidence of the desired product. The mixture was cooled to rt and filtered through celite. The filtrate was diluted with water and EtOAc and separated. After the aqueous phase was washed with EtOAc (2×), the combined organic layers were washed with brine, dried over sodium sulfate, filtered and concentrated under reduced pressure. The resulting residue was purified by silica gel using a gradient of EtOAC (0-50%) in hexanes. The fractions were concentrated to afford 6-cyclopropyl-2,4-diisopropylpyridin-3-amine (40 mg, 18%) as a white solid. MS: m/z=219 [M+1].

Step 2—Synthesis of N-((6-cyclopropyl-2,4-diisopropylpyridin-3-yl)carbamoyl)-6,7-dihydro-5H-pyrazolo[5,1-b][1,3]oxazine-3-sulfonamide (Example 45)

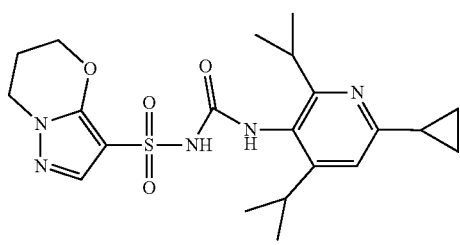 [SMILES: CC(C)c1cc(C2CC2)nc(C(C)C)c1NC(=O)NS(=O)(=O)c1cnn2c1OCCC2]

156

N-((6-cyclopropyl-2,4-diisopropylpyridin-3-yl)carbamoyl)-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 2,2-dimethyl-1,2,3,4-tetrahydronaphthalen-1-amine with 6-cyclopropyl-2,4-diisopropylpyridin-3-amine in Step 1. LCMS: m/z=448 [M+1].

Example 46

6,6-dimethyl-N-((6,7,8,9-tetrahydro-5H-benzo[7]annulen-5-yl)carbamoyl)-6,7-dihydro-5H-pyrazolo[5,1-b][1,3]oxazine-3-sulfonamide

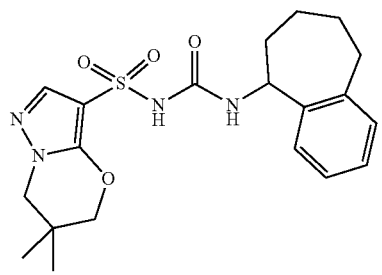 [SMILES: CC1(C)COc2c(S(=O)(=O)NC(=O)NC3CCCCc4ccccc43)cnn2C1]

6,6-dimethyl-N-((6,7,8,9-tetrahydro-5H-benzo[7]annulen-5-yl)carbamoyl)-6,7-dihydro-5H-pyrazolo[5,1-b][1,3]oxazine-3-sulfonamide was prepared by using the general procedure described for the preparation of N-((1,3-di-tert-butyl-1H-pyrazol-5-yl)carbamoyl)-6,7-dihydro-5H-pyrazolo[5,1-b][1,3]oxazine-3-sulfonamide (Example 36) by replacing 6,7-dihydro-5H-pyrazolo[5,1-b][1,3]oxazine-3-sulfonamide with 6,6-dimethyl-6,7-dihydro-5H-pyrazolo[5,1-b][1,3]oxazine-3-sulfonamide and 1,3-di-tert-butyl-1H-pyrazol-5-amine with 6,7,8,9-tetrahydro-5H-benzo[7]annulen-5-amine in Step 1. ¹H NMR (500 MHz, DMSO-d6): δ=7.52 (br.s, 1H), 7.51 (s, 1H), 7.14-7.10 (m, 4H), 6.75-6.70 (m, 1H), 4.09 (s, 2H), 4.08-4.02 (m, 1H), 3.87 (s, 2H), 2.83-2.73 (m, 2H), 1.84-1.59 (m, 5H), 1.48-1.38 (m, 1H), 1.05 (s, 6H). MS: m/z 419 (M+H+). LCMS: m/z=419 [M+1].

Example 47

N-((2,4-diisopropyl-6-methoxypyridin-3-yl)carbamoyl)-6,6-dimethyl-6,7-dihydro-5H-pyrazolo[5,1-b][1,3]oxazine-3-sulfonamide

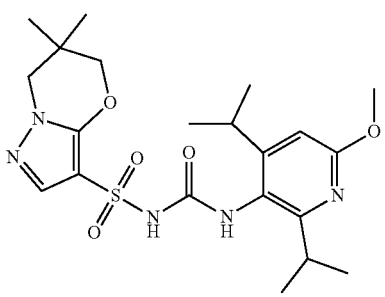

N-((2,4-diisopropyl-6-methoxypyridin-3-yl)carbamoyl)-6,6-dimethyl-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,6-dimethyl-6,7-dihydro-5H-pyrazolo[5,1-b][1,3]oxazine-3-sulfonamide in Step 10. $^1$H NMR (400 MHz, DMSO-d$_6$): δ=7.39 (s, 1H), 7.34 (s, 1H), 6.39 (s, 1H), 3.94 (s, 2H), 3.78 (s, 5H), 3.16-3.13 (m, 1H), 2.98-2.97 (m, 1H), 1.10-0.90 (m, 18H). LCMS: m/z=466 [M+1].

Example 48

N-((2,4-diisopropyl-6-methylpyridin-3-yl)carbamoyl)-6,7-dihydro-5H-pyrazolo[5,1-b][1,3]oxazine-3-sulfonamide

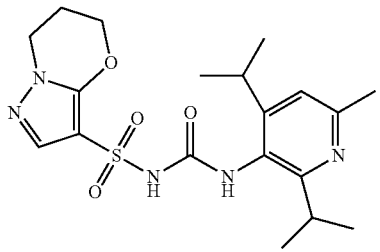 [SMILES: Cc1cc(C(C)C)c(NC(=O)NS(=O)(=O)c2cnn3c2OCCC3)c(C(C)C)n1]

N-((2,4-diisopropyl-6-methylpyridin-3-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 2,4-diisopropyl-6-methylpyridin-3-amine in Step 10. $^1$H NMR (400 MHz, DMSO-d$_6$): δ=7.54 (s, 1H), 7.41 (s, 1H), 6.90 (s, 1H), 4.31-4.26 (m, 2H), 4.06 (t, J=6.0 Hz, 2H), 3.15-3.10 (m, 1H), 3.01-2.90 (m, 1H), 2.37 (s, 3H), 2.12-2.09 (m, 2H), 1.12 (d, J=6.4 Hz, 12H). LCMS: m/z=422.2 [M+1].

Example 49

N-((6-cyano-2,4-diisopropylpyridin-3-yl)carbamoyl)-6,7-dihydro-5H-pyrazolo[5,1-b][1,3]oxazine-3-sulfonamide

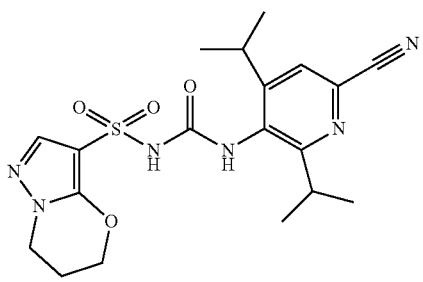 [SMILES: CC(C)c1cc(C#N)nc(C(C)C)c1NC(=O)NS(=O)(=O)c1cnn2c1OCCC2]

N-((6-cyano-2,4-diisopropylpyridin-3-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 5-amino-4,6-diisopropylpicolinonitrile in Step 10. $^1$H NMR (400 MHz, DMSO-d$_6$): δ=7.71 (s, 2H), 7.30 (s, 1H), 4.26 (t, J=4.8 Hz, 2H), 4.03 (t, J=6.0 Hz, 2H), 3.32 (overlap, 1H), 3.21-3.09 (m, 1H), 2.12-2.09 (m, 2H), 1.10-1.05 (m, 12H). LCMS: m/z=433.2 [M+1].

Example 50

N-((6-ethoxy-2,4-diisopropylpyridin-3-yl)carbamoyl)-6,7-dihydro-5H-pyrazolo[5,1-b][1,3]oxazine-3-sulfonamide

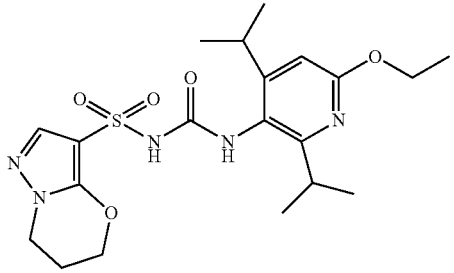 [SMILES: CCOc1cc(C(C)C)c(NC(=O)NS(=O)(=O)c2cnn3c2OCCC3)c(C(C)C)n1]

N-((6-ethoxy-2,4-diisopropylpyridin-3-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 6-ethoxy-2,4-diisopropylpyridin-3-amine in Step 10. $^1$H NMR (400 MHz, DMSO-d$_6$): δ=7.53 (s, 1H), 7.49 (s, 1H), 6.43 (s, 1H), 4.38 (t, J=4.8 Hz, 2H), 4.27 (q, J=6.8 Hz, 2H), 4.08 (t, J=6.0 Hz, 2H), 3.05-3.02 (m, 1H), 2.89-2.84 (m, 1H), 2.19-2.17 (m, 2H), 1.29 (t, J=6.8 Hz, 3H), 1.10-0.90 (m, 12H). LCMS: m/z=452.2 [M+1].

Example 51

Sodium N-((6-(dimethylamino)-2,4-diisopropylpyridin-3-yl)carbamoyl)-6,7-dihydro-5H-pyrazolo[5,1-b][1,3]oxazine-3-sulfonamide

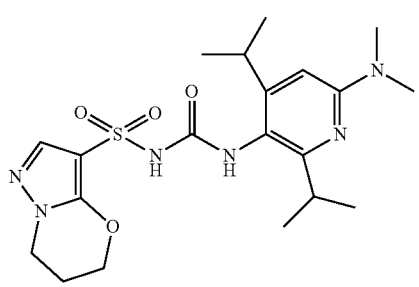 [SMILES: CC(C)c1cc(N(C)C)nc(C(C)C)c1NC(=O)NS(=O)(=O)c1cnn2c1OCCC2]

Sodium N-((6-(dimethylamino)-2,4-diisopropylpyridin-3-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 4,6-diisopropyl-N²,N²-dimethylpyridine-2,5-diamine in Step 10. ¹H NMR (400 MHz, DMSO-d₆): δ=7.56 (s, 1H), 7.45 (s, 1H), 6.26 (s, 1H), 4.42 (t, J=4.8 Hz, 2H), 4.10 (t, J=6.0 Hz, 2H), 2.99 (s, 6H), 2.96-2.91 (m, 1H), 2.81-2.77 (m, 1H), 2.22-2.18 (m, 2H), 1.05-0.95 (m, 12H). LCMS: m/z=451.2 [M+1].

Example 52

(S)—N-((2,4-diisopropyl-6-methoxypyridin-3-yl)carbamoyl)-6-(dimethylamino)-6,7-dihydro-5H-pyrazolo[5,1-b][1,3]oxazine-3-sulfonamide (Example 52a)

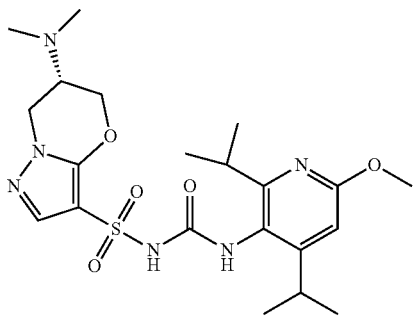

(S)—N-((2,4-diisopropyl-6-methoxypyridin-3-yl)carbamoyl)-6-(dimethylamino)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (5)-6-(3-methoxyazetidin-1-yl)-6,7-dihydro-5H-pyrazolo[5,1-b][1,3]oxazine-3-sulfonamide with (S)-6-(dimethylamino)-6,7-dihydro-5H-pyrazolo[5,1-b][1,3]oxazine-3-sulfonamide in Step 10. Single known stereoisomer obtained. ¹H NMR (400 MHz, DMSO-d₆): δ=7.40 (s, 1H), 7.32 (s, 1H), 6.45 (s, 1H), 4.40 (d, J=10.0 Hz, 1H), 4.32-4.26 (m, 1H), 4.21 (dd, J=12.4, 4.8 Hz, 1H), 4.10 (dd, J=12.4, 6.0 Hz, 1H), 3.84 (s, 3H), 3.28-3.18 (m, 1H), 3.12-3.02 (m, 1H), 2.94-2.86 (m, 1H), 2.32 (s, 6H), 1.20-1.00 (m, 12H). LCMS: m/z=481.2 [M+1].

Example 53

N-((2,4-diisopropyl-6-(methylamino)pyridin-3-yl)carbamoyl)-6,7-dihydro-5H-pyrazolo[5,1-b][1,3]oxazine-3-sulfonamide

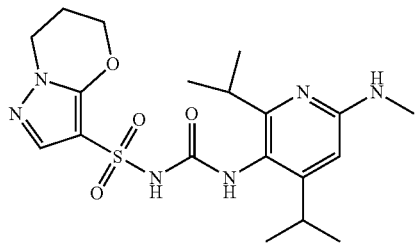 [SMILES: CNc1cc(C(C)C)c(NC(=O)NS(=O)(=O)c2cnn3c2OCCC3)c(C(C)C)n1]

N-((2,4-diisopropyl-6-(methylamino)pyridin-3-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 4,6-diisopropyl-N²-methylpyridine-2,5-diamine in Step 10. ¹H NMR (400 MHz, DMSO-d₆): δ=10.48 (s, 1H), 7.57 (s, 1H), 7.43 (s, 1H), 6.20-6.18 (m, 1H), 6.11 (s, 1H), 4.43 (t, J=5.2 Hz, 2H), 4.11 (t, J=6.0 Hz, 2H), 2.94-2.82 (m, 1H), 2.77-2.70 (m, 4H), 2.24-2.17 (m, 2H), 1.10-0.90 (m, 12H). LCMS: m/z=437.2 [M+1].

Example 54

N-((2,4-diisopropyl-6-(trifluoromethyl)pyridin-3-yl)carbamoyl)-6,7-dihydro-5H-pyrazolo[5,1-b][1,3]oxazine-3-sulfonamide

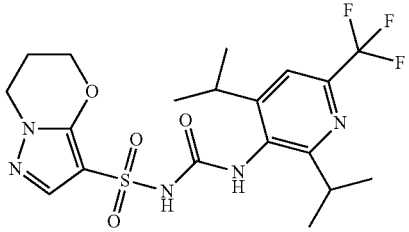 [SMILES: CC(C)c1cc(C(F)(F)F)nc(C(C)C)c1NC(=O)NS(=O)(=O)c1cnn2c1OCCC2]

N-((2,4-diisopropyl-6-(trifluoromethyl)pyridin-3-yl)carbamoyl)-6,7-dihydro-5H-pyrazolo[5,1-b][1,3]oxazine-3-sulfonamide was prepared by using the general procedure described for the preparation of (S)—N-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonamide (Example 42) by replacing (S)-6-(3-methoxyazetidin-1-yl)-6,7-dihydro-5H-pyrazolo[5,1-b][1,3]oxazine-3-sulfonamide with 6,7-dihydro-5H-pyrazolo[5,1-b][1,3]oxazine-3-sulfonamide and 2,4-diisopropyl-6-methoxypyridin-3-amine with 2,4-diisopropyl-6-(trifluoromethyl)pyridin-3-amine in Step 10. ¹H NMR (400 MHz, DMSO-d₆): δ=10.98 (brs, 1H), 8.13 (s, 1H), 7.60 (s, 1H), 7.58 (s, 1H), 4.43 (t, J=4.8 Hz, 2H), 4.10 (t, J=6.0 Hz, 2H), 3.16-3.13 (m, 1H), 3.02-2.98 (m, 1H), 2.23-2.17 (m, 2H), 1.16-1.03 (m, 12H). LCMS: m/z=476.1 [M+1].

Example 55

N-((3-isopropyl-6,7-dihydro-5H-cyclopenta[c]pyridin-4-yl)carbamoyl)-6,7-dihydro-5H-pyrazolo[5,1-b][1,3]oxazine-3-sulfonamide

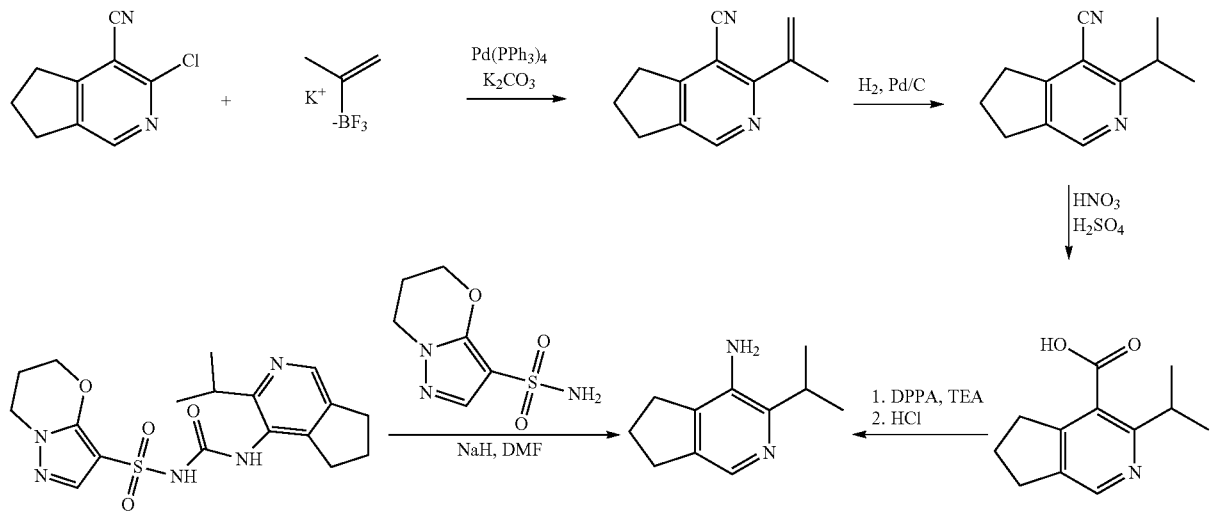

Step 1—Synthesis of 3-(prop-1-en-2-yl)-6,7-dihydro-5H-cyclopenta[c]pyridine-4-carbonitrile

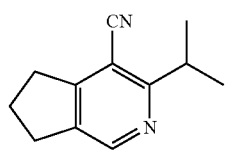

3-chloro-6,7-dihydro-5H-cyclopenta[c]pyridine-4-carbonitrile (900 mg, 1 Eq, 5.04 mmol) and potassium trifluoro(prop-1-en-2-yl)borate (2.24 g, 3 Eq, 15.1 mmol) were dissolved in anhydrous Ethanol (25 mL) and toluene (50 mL). To this solution was added potassium carbonate (2.09 g, 3 Eq, 15.1 mmol) and Pd(PPh₃)₄ (582 mg, 0.1 Eq, 504 μmol). The reaction was heated to 100° C. overnight before cooled to room temperature. The mixture was filtered through Celite and washed thoroughly with DCM. Solvent was then removed under reduced pressure and the resulting residue was purified by silica gel chromatography (EtOAc/Hexanes, 0 to 100%) to afford 3-(prop-1-en-2-yl)-6,7-dihydro-5H-cyclopenta[c]pyridine-4-carbonitrile (800 mg, 86%) as clear oil.

Step 2—Synthesis of 3-isopropyl-6,7-dihydro-5H-cyclopenta[c]pyridine-4-carbonitrile To a solution of 3-(prop-1-en-2-yl)-6,7-dihydro-5H-cyclopenta[c]pyridine-4-carbonitrile (800 mg, 1 Eq, 4.34 mmol) in MeOH (10 mL) was added Pd/C (92 mg, 0.1 Eq, 434 μmol). The reaction was purged with hydrogen for 5 min and then stirred at room temperature for 1 h. Upon completion, the reaction was filtered through Celite and concentrated to afford 3-isopropyl-6,7-dihydro-5H-cyclopenta[c]pyridine-4-carbonitrile (800 mg, 99%) as clear oil.

Step 3- Synthesis of 3-isopropyl-6,7-dihydro-5H-cyclopenta[c]pyridine-4-carboxylic acid

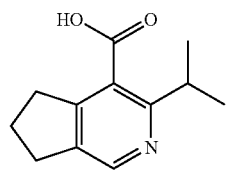

To a solution of 3-isopropyl-6,7-dihydro-5H-cyclopenta[c]pyridine-4-carbonitrile (700 mg, 1 Eq, 3.76 mmol) in concentrated sulfuric acid (7.37 g, 4.01 mL, 20 Eq, 72.5 mmol) was added nitric acid (4.74 g, 3.36 mL, 20 Eq, 75.2 mmol). The reaction was heated to 100° C. for 72 h before cooled to room temperature. EtOAc and MeOH (100:180 mL) was added. The solution was dried over Na₂SO₄, filtered and concentrated to afford 3-isopropyl-6,7-dihydro-5H-cyclopenta[c]pyridine-4-carboxylic acid (550 mg, 71%) as white solids. The crude product was used without additional purification.

Step 4—Synthesis of tert-butyl (3-isopropyl-6,7-dihydro-5H-cyclopenta[c]pyridin-4-yl)carbamate

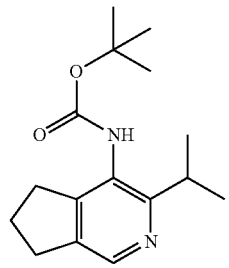 [SMILES: CC(C)c1ncc2c(c1NC(=O)OC(C)(C)C)CCC2]

To a solution of 3-isopropyl-6,7-dihydro-5H-cyclopenta[c]pyridine-4-carboxylic acid (550 mg, 1 Eq, 2.68 mmol) in tBuOH (20 mL) was added triethylamine (813 mg, 1.12 mL, 3 Eq, 8.04 mmol) followed by diphenyl phosphorazidate (1.47 g, 2 Eq, 5.36 mmol). The mixture was heated to 80° C. overnight before cooled to room temperature. The solvent was removed under reduced pressure and resulting residue was purified by silica gel chromatography (EtOAc/Hexanes, 0 to 30%) to afford tert-butyl (3-isopropyl-6,7-dihydro-5H-cyclopenta[c]pyridin-4-yl)carbamate (340 mg, 45.9%) as white solids.

Step 5—Synthesis of 3-isopropyl-6,7-dihydro-5H-cyclopenta[c]pyridin-4-amine

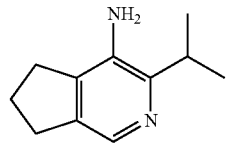

Tert-butyl (3-isopropyl-6,7-dihydro-5H-cyclopenta[c]pyridin-4-yl)carbamate obtained as described above was dissolved in a solution of HCl in dioxane (488 mg, 3 mL, 5 Eq, 13.4 mmol). The reaction was stirred at room temperature for 4 h before ether (20 mL) was added. The precipitate was collected by filtration to afford 3-isopropyl-6,7-dihydro-5H-cyclopenta[c]pyridin-4-amine (60 mg, 13%) as white solids.

Step 6—Synthesis of N-((3-isopropyl-6,7-dihydro-5H-cyclopenta[c]pyridin-4-yl)carbamoyl)-6,7-dihydro-5H-pyrazolo[5,1-b][1,3]oxazine-3-sulfonamide (Example 55)

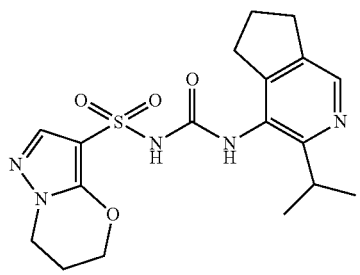 [SMILES: CC(C)c1ncc2c(c1NC(=O)NS(=O)(=O)c1cnn3c1OCCC3)CCC2]

N-((3-isopropyl-6,7-dihydro-5H-cyclopenta[c]pyridin-4-yl)carbamoyl)-6,7-dihydro-5H-pyrazolo[5,1-b][1,3]oxazine-3-sulfonamide was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing 2,2-dimethyl-1,2,3,4-tetrahydronaphthalen-1-amine with 3-isopropyl-6,7-dihydro-5H-cyclopenta[c]pyridin-4-amine in Step 1. LCMS: m/z=406 [M+1].

Example 56

6-(aminomethyl)-N-(isopropylcarbamoyl)-6,7-dihydro-5H-pyrazolo[5,1-b][1,3]oxazine-3-sulfonamide

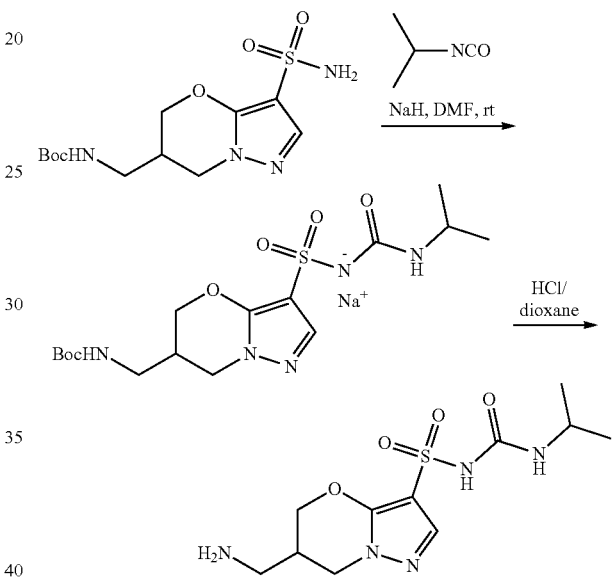

Step 1—Synthesis of tert-butyl ((3-(N-(isopropylcarbamoyl)sulfamoyl)-6,7-dihydro-5H-pyrazolo[5,1-b][1,3]oxazin-6-yl)methyl)carbamate

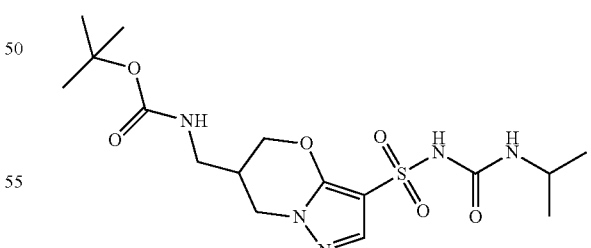

tert-Butyl ((3-(N-(isopropylcarbamoyl)sulfamoyl)-6,7-dihydro-5H-pyrazolo[5,1-b][1,3]oxazin-6-yl)methyl)carbamate was prepared by using the general procedure described for the preparation of N-((2,2-dimethyl-1,2,3,4-tetrahydronaphthalen-1-yl)carbamoyl)-6,7-dihydro-5H-pyrazolo[5,1-b][1,3]oxazine-3-sulfonamide (Example 1) by replacing isocyanato-2,2-dimethyl-1,2,3,4-tetrahydronaphthalene with 2-isocyanatopropane and 6,7-dihydro-5H-pyrazolo[5, 1-b][1,3]oxazine-3-sulfonamide with tert-butyl ((3-sulfamoyl-6,7-dihydro-5H-pyrazolo[5,1-b][1,3]oxazin-6-yl)methyl)carbamate in Step 1. MS: m/z 418 (M+H⁺).

Step 2—Synthesis of 6-(aminomethyl)-N-(isopropylcarbamoyl)-6,7-dihydro-5H-pyrazolo[5,1-b][1,3]oxazine-3-sulfonamide (Example 56)

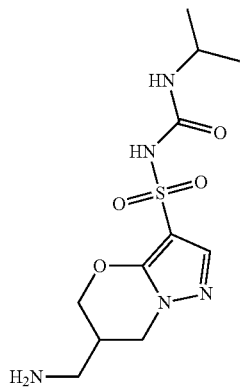 [SMILES: CC(C)NC(=O)NS(=O)(=O)c1cnn2c1OCC(CN)C2]

HCl (4N in dioxane, 0.6 mL, 2.3 mmol) was added dropwise to a solution of sodium ((6-(((tert-butoxycarbonyl)amino)methyl)-6,7-dihydro-5H-pyrazolo[5,1-b][1,3]oxazin-3-yl)sulfonyl)(isopropylcarbamoyl)amide (34 mg, 77 µmol) in 1,4-dioxane (0.5 mL) at 10° C. The reaction mixture was warmed to room temperature over 2 hours, at which point it was concentrated to dryness and the crude residue was purified by prep-HPLC (CH₃CN/H₂O/10 mM aqueous NH₃) to afford 6-(aminomethyl)-N-(isopropylcarbamoyl)-6,7-dihydro-5H-pyrazolo[5,1-b][1,3]oxazine-3-sulfonamide (11.8 mg, purity 80%, yield: 38%) as a white solid (mixture of enantiomers). $^1$H NMR (500 MHz, DMSO-d₆): δ=7.72 (brs, 3H), 7.59 (s, 1H), 6.35 (s, 1H), 4.61 (dd, J=11.0, 2.9 Hz, 1H), 4.31-4.27 (m, 2H), 4.02 (dd, J=12.4, 7.8 Hz, 1H), 3.66-3.59 (m, 1H), 2.91-2.84 (m, 2H), 2.69-2.62 (m, 1H), 1.03 (d, J=6.5 Hz, 6H). MS: m/z 318 (M+H⁺).

Example 57

N-((1-(2,2-difluoroethyl)-3,5-diisopropyl-1H-pyrazol-4-yl)carbamoyl)-6,6-dimethyl-6,7-dihydro-5H-pyrazolo[5,1-b][1,3]oxazine-3-sulfonamide, ammonia

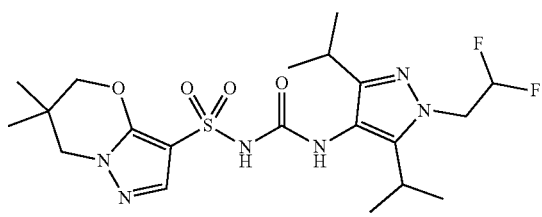 [SMILES: CC(C)c1nn(CC(F)F)c(C(C)C)c1NC(=O)NS(=O)(=O)c1cnn2c1OCC(C)(C)C2]

1,1-Difluoro-2-iodoethane (2.0 m, 22.8 mmol) was added to a solution of potassium carbonate (2.10 g, 15.2 mmol) and 3,5-diisopropyl-4-nitro-1H-pyrazole (1.50 g, 7.61 mmol) in DMF (15.2 mL) and the reaction was heated at 50° C. for 4 hours. After cooling to room temperature, the reaction was diluted with water and isopropyl acetate. The aqueous layer was extracted with isopropyl acetate. The combined organic layers were dried with sodium sulfate, concentrated and the crude residue was submitted to the next step without further purification.

Hydrochloric acid (11.6 mol/L, 2 mL) was added to a mixture of the crude residue and zinc (1.49 g, 22.8 mmol) in acetic acid (15.2 mL) at room temperature. After 20 minutes, the reaction was concentrated under reduced pressure. The crude residue was diluted with water and isopropyl acetate. The aqueous layer was extracted with isopropyl acetate. The combined organic layers were washed with saturated aqueous sodium bicarbonate, dried with sodium sulfate, concentrated, and the crude residue was submitted to the next step without further purification.

Triphosgene (220 mg, 0.72 mmol) was added in one portion to a stirred solution of the crude 1-(2,2-difluoroethyl)-3,5-diisopropyl-pyrazol-4-amine (0.50 g, 2.2 mmol) and triethylamine (0.32 mL, 2.3 mmol) in THF (7.2 mL). The mixture was heated to reflux for 30 minutes, then cooled to room temperature. The reaction was diluted with heptane and the triethylammonium salts were filtered off. The filtrate was concentrated under reduced pressure and the crude residue was used in the next reaction without further purification.

Sodium hydride (60% in mineral oil, 23 mg, 0.583 mmol) was added to a solution of 6,6-dimethyl-5,7-dihydropyrazolo[5,1-b][1,3]oxazine-3-sulfonamide (90 mg, 0.389 mmol) and 1-(2,2-difluoroethyl)-4-isocyanato-3,5-diisopropyl-pyrazole (100 mg, 0.389 mmol) in THF (3.9 mL) at room temperature. After 30 minutes, the reaction was quenched with 3 drops of water. The reaction was concentrated under reduced pressure and the crude residue was purified by reverse phase HPLC (2-30% MeCN/0.1% ammonium hydroxide in water) to give N-((1-(2,2-difluoroethyl)-3,5-diisopropyl-1H-pyrazol-4-yl)carbamoyl)-6,6-di methyl-6,7-dihydro-5H-pyrazolo[5,1-b][1,3]oxazine-3-sulfonamide (149 mg, 78%) as an ammonium salt. $^1$H NMR (400 MHz, DMSO-d₆): δ=7.29 (s, 1H), 6.76 (bs, 1H), 6.42-6.05 (m, 1H), 4.35 (td, J=14.6, 4.1 Hz, 2H), 3.91 (s, 2H), 3.75 (s, 2H), 3.00-2.85 (m, 1H), 2.81-2.65 (m, 1H), 1.14 (d, J=7.0 Hz, 6H), 1.06 (d, J=6.9 Hz, 6H), 1.02 (s, 6H). MS: m/z 489.2 (M+H⁺).

Example 58

N-((3,5-diisopropyl-1-(2,2,2-trifluoroethyl)-1H-pyrazol-4-yl)carbamoyl)-6,7-dihydro-5H-pyrazolo[5,1-b][1,3]oxazine-3-sulfonamide, ammonia Step 1—Synthesis of 3,5-diisopropyl-4-nitro-1-(2,2,2-trifluoroethyl)-1H-pyrazole

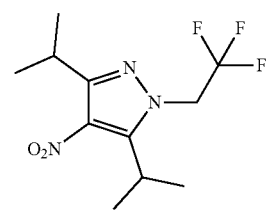 [SMILES: CC(C)c1nn(CC(F)(F)F)c(C(C)C)c1[N+](=O)[O-]]

2-Iodo-1,1,1-trifluoroethane (4.5 mL 45.6 mmol) was added to a solution of potassium carbonate (2.10 g, 15.2 mmol) and 3,5-diisopropyl-4-nitro-1H-pyrazole (1.50 g, 7.61 mmol) in DMF (15.2 mL) and the reaction was heated at 80° C. for 4 days. After cooling to room temperature, the reaction was diluted with water and isopropyl acetate. The aqueous layer was extracted with isopropyl acetate. The combined organic layers were dried with sodium sulfate, concentrated and the crude residue was purified by flash column chromatography (silica, 0% to 50% isopropyl acetate-heptane) to give 3,5-diisopropyl-4-nitro-1-(2,2,2-trifluoroethyl)pyrazole (0.90 g, 42%).

Step 2—Synthesis of N-((3,5-diisopropyl-1-(2,2,2-trifluoroethyl)-1H-pyrazol-4-yl)carbamoyl)-6,7-dihydro-5H-pyrazolo[5,1-b][1,3]oxazine-3-sulfonamide, ammonia (Example 58)

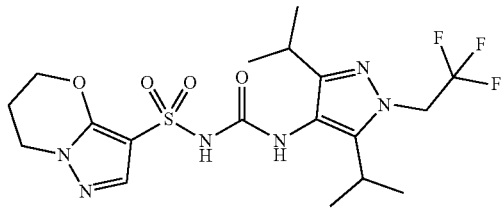 [SMILES: CC(C)c1nn(CC(F)(F)F)c(C(C)C)c1NC(=O)NS(=O)(=O)c1cnn2c1OCCC2]

Hydrochloric acid (11.6 mol/L, 0.83 mL) was added to a mixture of 3,5-diisopropyl-4-nitro-1-(2,2,2-trifluoroethyl) pyrazole (0.90 g, 3.2 mmol) and zinc (0.63 g, 9.7 mmol) in acetic acid (6.4 mL) at room temperature. After 20 minutes, the reaction was concentrated under reduced pressure. The crude residue was diluted with water and isopropyl acetate. The aqueous layer was extracted with isopropyl acetate. The combined organic layers were washed with saturated aqueous sodium bicarbonate, dried with sodium sulfate, concentrated and the crude residue was submitted to the next step without further purification.

Triphosgene (163 mg, 0.534 mmol) was added in one portion to a stirred solution of crude 3,5-diisopropyl-1-(2,2,2-trifluoroethyl)pyrazol-4-amine (400 mg, 1.60 mmol) and triethylamine (0.24 mL, 1.68 mmol) in THF (5.3 mL). The mixture was heated to reflux for 30 minutes, then cooled to room temperature. The reaction was diluted with heptane and the triethylammonium salts were filtered off. The filtrate was concentrated under reduced pressure and the crude residue was used in the next reaction without further purification.

Sodium hydride (60% in mineral oil, 22 mg, 0.545 mmol) was added to a solution of 6,7-dihydro-5H-pyrazolo[5,1-b][1,3]oxazine-3-sulfonamide (74 mg, 0.363 mmol) and 4-isocyanato-3,5-diisopropyl-1-(2,2,2-trifluoroethyl)pyrazole (100 mg, 0.363 mmol) in THF (3.6 mL) at room temperature. After 30 minutes, the reaction was quenched with 3 drops of water. The reaction was concentrated under reduced pressure and the crude residue was purified by reverse phase HPLC (2-30% MeCN/0.1% ammonium hydroxide in water) to give N-((3,5-diisopropyl-1-(2,2,2-trifluoroethyl)-1H-pyrazol-4-yl)carbamoyl)-6,7-dihydro-5H-pyrazolo[5,1-b][1,3]oxazine-3-sulfonamide (93 mg, 54%) as an ammonium salt. $^1$H NMR (400 MHz, DMSO-d$_6$): δ=7.35 (s, 1H), 6.98 (s, 1H), 4.88 (q, J=9.1 Hz, 2H), 4.34-4.25 (m, 2H), 4.04 (t, J=6.0 Hz, 2H), 3.03-2.90 (m, 1H), 2.78-2.64 (m, 1H), 2.18-2.07 (m, 2H), 1.12 (d, J=6.9 Hz, 6H), 1.06 (d, J=6.9 Hz, 6H). MS: m/z 479.2 (M+H$^+$).

Example 59

(S)—N-((3,5-diisopropyl-1-(2,2,2-trifluoroethyl)-1H-pyrazol-4-yl)carbamoyl)-6-methoxy-6,7-dihydro-5H-pyrazolo[5,1-b][1,3]oxazine-3-sulfonamide, ammonia (Example 59a)

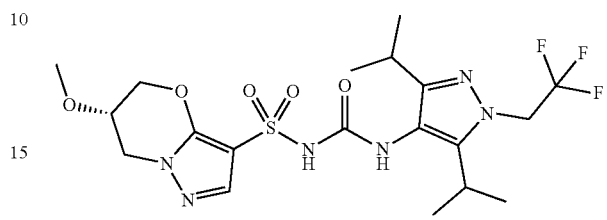

(S)—N-((3,5-diisopropyl-1-(2,2,2-trifluoroethyl)-1H-pyrazol-4-yl)carbamoyl)-6-methoxy-6,7-dihydro-5H-pyrazolo[5,1-b][1,3]oxazine-3-sulfonamide, ammonia (purified by reverse phase HPLC (2-30% MeCN/0.1% ammonium hydroxide in water; 125 mg, 67%) was prepared by using the general procedure described for the preparation of N-((3,5-diisopropyl-1-(2,2,2-trifluoroethyl)-1H-pyrazol-4-yl)carbamoyl)-6,7-dihydro-5H-pyrazolo[5,1-b][1,3]oxazine-3-sulfonamide (Example 58) by replacing 6,7-dihydro-5H-pyrazolo[5,1-b][1,3]oxazine-3-sulfonamide with (6S)-6-methoxy-6,7-dihydro-5H-pyrazolo[5,1-b][1,3]oxazine-3-sulfonamide in Step 2. Obtained as an ammonium salt and a single known stereoisomer. $^1$H NMR (400 MHz, DMSO-d$_6$): δ=7.42 (bs, 1H), 7.06 (bs, 1H), 4.89 (q, J=9.0 Hz, 2H), 4.53 (d, J=12.0 Hz, 1H), 4.25-4.09 (m, 3H), 4.00 (bs, 1H), 3.35 (s, 3H), 3.05-2.92 (m, 1H), 2.75-2.66 (m, 1H), 1.12 (d, J=6.9 Hz, 6H), 1.06 (d, J=7.0, 6H). MS: m/z 509.2 (M+H$^+$).

Example 60

Sodium (S)—N-((2-isopropyl-2,4,5,6-tetrahydrocyclopenta[c]pyrazol-3-yl)carbamoyl)-6-methoxy-6,7-dihydro-5H-pyrazolo[5,1-b][1,3]oxazine-3-sulfonamide (Example 60a)

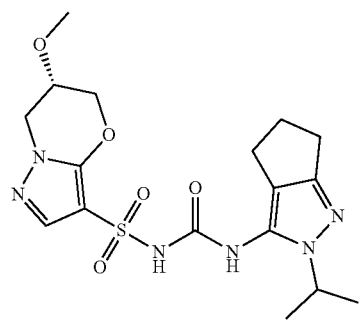 [SMILES: CO[C@@H]1COc2c(S(=O)(=O)NC(=O)Nc3c4c(nn3C(C)C)CCC4)cnn2C1]

To a solution of (S)-6-methoxy-6,7-dihydro-5H-pyrazolo[5,1-b][1,3]oxazine-3-sulfonamide (250 mg, 1.07 mmol) in THF (4 mL) was added NaH (60% in mineral oil, 50 mg, 1.26 mmol) at 0° C. under nitrogen atmosphere. After 20 minutes, 3-isocyanato-2-isopropyl-2,4,5,6-tetrahydrocyclopenta[c]pyrazole (200 mg, 1.05 mmol) was added. The reaction mixture was warmed to room temperature and was allowed to stir for an additional 12 hours. The mixture was concentrated and the crude residue was purified by reverse phase chromatography HPLC (0-30% MeCN/10 mM NH₄HCO₃ in water) to give (S)—N-((2-isopropyl-2,4,5,6-tetrahydrocyclopenta[c]pyrazol-3-yl)carbamoyl)-6-methoxy-6,7-dihydro-5H-pyrazolo[5,1-b][1,3]oxazine-3-sulfonamide (83.2 mg, yield: 18%) as a sodium salt. Single known stereoisomer obtained. ¹H NMR (400 MHz, DMSO-d₆): δ=7.99 (s, 1H), 7.48 (s, 1H), 4.56-4.53 (m, 1H), 4.28-4.20 (m, 4H), 4.17-4.01 (m, 1H), 3.34 (s, 3H), 2.47-2.42 (m, 4H), 2.24-2.11 (m, 2H), 1.25 (d, J=6.4 Hz, 6H). MS: m/z 425.1 (M+H⁺).

Example 61

N-((2-isopropyl-2,4,5,6-tetrahydrocyclopenta[c]pyrazol-3-yl)carbamoyl)-6,6-dimethyl-6,7-dihydro-5H-pyrazolo[5,1-b][1,3]oxazine-3-sulfonamide

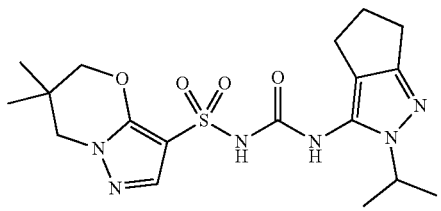 [SMILES: CC(C)n1nc2c(c1NC(=O)NS(=O)(=O)c1cnn3c1OCC(C)(C)C3)CCC2]

N-((2-isopropyl-2,4,5,6-tetrahydrocyclopenta[c]pyrazol-3-yl)carbamoyl)-6,6-dimethyl-6,7-dihydro-5H-pyrazolo[5,1-b][1,3]oxazine-3-sulfonamide (purified by reverse phase HPLC (0-40% MeCN/0.05% NH₄HCO₃ in water), 12.1 mg, yield: 4%) was prepared by using the general procedure described for the preparation of (S)—N-((2-isopropyl-2,4,5,6-tetrahydrocyclopenta[c]pyrazol-3-yl)carbamoyl)-6-methoxy-6,7-dihydro-5H-pyrazolo[5,1-b][1,3]oxazine-3-sulfonamide (Example 83) by replacing (S)-6-methoxy-6,7-dihydro-5H-pyrazolo[5,1-b][1,3]oxazine-3-sulfonamide with 6,6-dimethyl-6,7-dihydro-5H-pyrazolo[5,1-b][1,3]oxazine-3-sulfonamide in Step 1. ¹H NMR (400 MHz, DMSO-d₆): δ=7.82 (s, 1H), 7.41 (s, 1H), 7.03 (s, 1H), 4.25-4.23 (m, 1H), 3.99 (s, 2H), 3.80 (s, 2H), 2.43-2.40 (m, 4H), 2.21-2.17 (m, 2H), 1.22 (d, J=6.4 Hz, 6H), 1.01 (s, 6H). MS: m/z 423.0 (M+H⁺).

Example 62

(S)—N-((1-(2,2-difluoroethyl)-3,5-diisopropyl-1H-pyrazol-4-yl)carbamoyl)-6-methoxy-6,7-dihydro-5H-pyrazolo[5,1-b][1,3]oxazine-3-sulfonamide, ammonia (Example 62a)

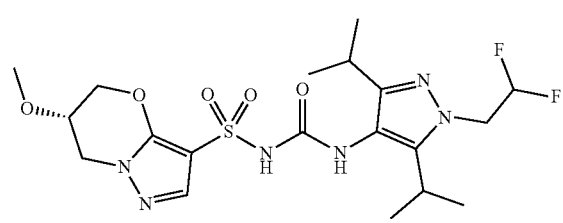 [SMILES: CO[C@@H]1COc2c(S(=O)(=O)NC(=O)Nc3c(C(C)C)nn(CC(F)F)c3C(C)C)cnn2C1]

(S)—N-((1-(2,2-difluoroethyl)-3,5-diisopropyl-1H-pyrazol-4-yl)carbamoyl)-6-methoxy-6,7-dihydro-5H-pyrazolo[5,1-b][1,3]oxazine-3-sulfonamide, ammonia (purified by reverse phase HPLC (2-30% MeCN/0.1% ammonium hydroxide in water; 86.4 mg, 45%) was prepared by using the general procedure described for the preparation of N-((1-(2,2-difluoroethyl)-3,5-diisopropyl-1H-pyrazol-4-yl)carbamoyl)-6,6-dimethyl-6,7-dihydro-5H-pyrazolo[5,1-b][1,3]oxazine-3-sulfonamide (Example 57) by replacing 6,6-dimethyl-5,7-dihydropyrazolo[5,1-b][1,3]oxazine-3-sulfonamide with (6S)-6-methoxy-6,7-dihydro-5H-pyrazolo[5,1-b][1,3]oxazine-3-sulfonamide in Step 1. Obtained as an ammonium salt and as a single known stereoisomer. ¹H NMR (400 MHz, DMSO-d₆): δ=7.31 (s, 1H), 6.87 (s, 1H), 6.24 (tt, J=55.4, 4.1 Hz, 1H), 4.51-4.30 (m, 3H), 4.21-4.05 (m, 3H), 3.98-3.92 (m, 1H), 3.35 (s, 3H), 2.99-2.86 (m, 1H), 2.81-2.66 (m, 1H), 1.14 (d, J=7.0 Hz, 6H), 1.07 (d, J=6.9 Hz, 6H). MS: m/z 491.2 (M+H⁺).

Example 63

N-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonamide, ammonia

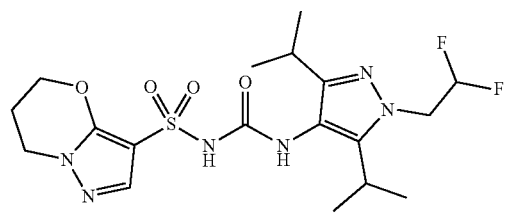 [SMILES: CC(C)c1nn(CC(F)F)c(C(C)C)c1NC(=O)NS(=O)(=O)c1cnn2c1OCCC2]

N-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonamide, ammonia (purified by reverse phase HPLC (2-30% MeCN/0.1% ammonium hydroxide in water; 58.7 mg, 33%) was prepared by using the general procedure described for the preparation of N-((1-(2,2-difluoroethyl)-3,5-diisopropyl-1H-pyrazol-4-yl)carbamoyl)-6,6-dimethyl-6,7-dihydro-5H-pyrazolo[5,1-b][1,3]oxazine-3-sulfonamide (Example 57) by replacing 6,6-dimethyl-5,7-dihydropyrazolo[5,1-b][1,3]oxazine-3-sulfonamide with 6,7-dihydro-5H-pyrazolo[5,1-b][1,3]oxazine-3-sulfonamide in Step 1. Obtained as an ammonium salt. ¹H NMR (400 MHz, DMSO-d₆): δ=7.28 (s, 1H), 6.85 (s, 1H), 6.24 (tt, J=55.4, 4.1 Hz, 1H), 4.44-4.30 (m, 2H), 4.29-4.21 (m, 2H), 4.02 (t, J=6.1 Hz, 2H), 2.93 (p, J=7.0 Hz, 1H), 2.80-2.65 (m, 1H), 2.17-2.05 (m, 2H), 1.13 (d, J=7.0 Hz, 6H), 1.06 (d, J=7.0 Hz, 6H). MS: m/z 461.2 (M+H⁺).

Example 64

(S)—N-((3,5-diisopropyl-1-(trifluoromethyl)-1H-pyrazol-4-yl)carbamoyl)-6-(methylamino)-6,7-dihydro-5H-pyrazolo[5,1-b][1,3]oxazine-3-sulfonamide, ammonia Step 1—Synthesis of 4-isocyanato-3,5-diisopropyl-1-(trifluoromethyl)pyrazole

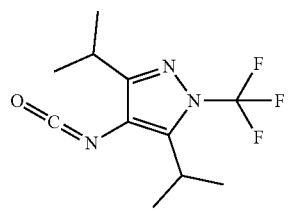 [SMILES: CC(C)c1nn(C(F)(F)F)c(C(C)C)c1N=C=O]

Cesium carbonate (5.0 g, 15 mmol) and dibromodifluoromethane (0.93 mL, 10 mmol) were added to a solution of 3,5-diisopropyl-4-nitro-1H-pyrazole (1.0 g, 5.1 mmol) in acetonitrile (17 mL). The reaction was sealed and heated at 55° C. for 36 hours. The reaction was diluted with water and isopropyl acetate. The aqueous layer was extracted with isopropyl acetate. The combined organic layers were dried with sodium sulfate, concentrated and the crude residue was submitted to the next reaction without further purification.

Silver tetrafluoroborate (1.5 g, 7.6 mmol) was added to a solution of the crude residue in dichloromethane (51 mL) at −78° C. The reaction was warmed to room temperature slowly and continued to stir for an additional 1 hour. The reaction was diluted with DCM/MeOH, filtered through a pad of Celite, concentrated, and the crude residue was submitted to the next reaction without further purification.

Hydrochloric acid (11.6 mol/L, 1.3 mL) was added to a mixture of the crude residue and zinc (990 mg, 15 mmol) in acetic acid (10 mL) at room temperature. After 20 minutes, the reaction was concentrated under reduced pressure. The crude residue was diluted with water and isopropyl acetate. The aqueous layer was extracted with isopropyl acetate. The combined organic layers were washed with saturated aqueous sodium bicarbonate, dried with sodium sulfate, concentrated and the crude residue was submitted to the next step without further purification.

Triphosgene (173 mg, 0.57 mmol) was added in one portion to a stirred solution of 3,5-diisopropyl-1-(trifluoromethyl)pyrazol-4-amine (0.400 g, 1.70 mmol) and triethylamine (0.25 mL, 1.79 mmol) in THF (5.7 mL). The mixture was heated to reflux for 30 minutes, then cooled to room temperature. The reaction was diluted with heptane and the triethylammonium salts were filtered off. The filtrate was concentrated under reduced pressure and the crude residue was used in the next reaction without further purification.

Step 2—Synthesis of (S)—N-((3,5-diisopropyl-1-(trifluoromethyl)-1H-pyrazol-4-yl)carbamoyl)-6-(methylamino)-6,7-dihydro-5H-pyrazolo[5,1-b][1,3]oxazine-3-sulfonamide, ammonia (Example 64a)

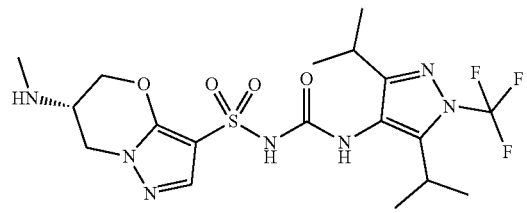 [SMILES: CN[C@@H]1COc2c(S(=O)(=O)NC(=O)Nc3c(C(C)C)nn(C(F)(F)F)c3C(C)C)cnn2C1]

Sodium hydride (60% in mineral oil, 23 mg, 0.574 mmol) was added to a solution of 2,2,2-trifluoro-N-methyl-N-[(6S)-3-sulfamoyl-6,7-dihydro-5H-pyrazolo[5,1-b][1,3]oxazin-6-yl]acetamide (126 mg, 0.383 mmol) and 4-isocyanato-3,5-diisopropyl-1-(trifluoromethyl)pyrazole (100 mg, 0.383 mmol) in THF (2.1 mL) at room temperature. After 30 minutes, the reaction was quenched with 3 drops of 10% sodium hydroxide and the reaction was allowed to stir for an additional 10 minutes. The reaction was concentrated under reduced pressure and the crude residue was purified by reverse phase HPLC (2-20% MeCN/0.1% ammonium hydroxide in water) to give (S)—N-((3,5-diisopropyl-1-(trifluoromethyl)-1H-pyrazol-4-yl)carbamoyl)-6-(methylamino)-6,7-dihydro-5H-pyrazolo[5,1-b][1,3]oxazine-3-sulfonamide (86.9 mg, 46%) as an ammonium salt. Single known stereoisomer obtained. $^1$H NMR (400 MHz, DMSO-$d_6$): δ=7.37 (s, 1H), 7.30 (bs, 1H), 4.28 (dd, J=11.0, 2.6 Hz, 1H), 4.22-4.05 (m, 2H), 3.84 (dd, J=12.2, 5.2 Hz, 1H), 3.16-3.02 (m, 2H), 2.89-2.69 (m, 1H), 2.34 (s, 3H), 1.19 (d, J=7.1 Hz, 6H), 1.09 (d, J=7.0 Hz, 6H). MS: m/z 494.2 (M+H$^+$).

Example 65

N-((1-ethyl-3,5-diisopropyl-1H-pyrazol-4-yl)carbamoyl)-6,6-dimethyl-6,7-dihydro-5H-pyrazolo[5,1-b][1,3]oxazine-3-sulfonamide, ammonia

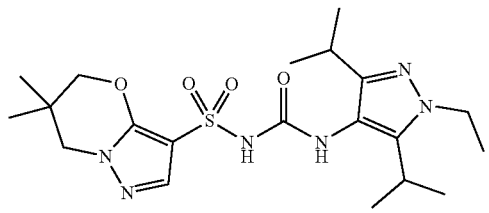 [SMILES: CCn1nc(C(C)C)c(NC(=O)NS(=O)(=O)c2cnn3c2OCC(C)(C)C3)c1C(C)C]

Triphosgene (261 mg, 0.853 mmol) was added in one portion to a stirred solution of 1-ethyl-3,5-diisopropyl-pyrazol-4-amine (0.500 g, 2.56 mmol) and triethylamine (0.380 mL, 2.69 mmol) in THF (8.5 mL). The mixture was heated to reflux for 30 minutes, then cooled to room temperature. The reaction was diluted with heptane and the triethylammonium salts were filtered off. The filtrate was concentrated under reduced pressure and the crude residue was used in the next reaction without further purification.

Sodium hydride (60% in mineral oil, 27 mg, 0.678 mmol) was added to a solution of 6,6-dimethyl-5,7-dihydropyrazolo[5,1-b][1,3]oxazine-3-sulfonamide (104.5 mg, 0.452 mmol) and 1-ethyl-4-isocyanato-3,5-diisopropyl-pyrazole (100 mg, 0.452 mmol) in THF (4.5 mL) at room temperature. After 30 minutes, the reaction was quenched with 3 drops of water. The reaction was concentrated under reduced pressure and the crude residue was purified by reverse phase HPLC (2-30% MeCN/0.1% ammonium hydroxide in water) to give N-((1-ethyl-3,5-diisopropyl-1H-pyrazol-4-yl)carbamoyl)-6,6-dimethyl-6,7-dihydro-5H-pyrazolo[5,1-b][1,3]oxazine-3-sulfonamide (162 mg, 79%) as an ammonium salt. $^1$H NMR (400 MHz, DMSO-d$_6$): δ=7.34 (s, 1H), 6.80 (bs, 1H), 3.98-3.85 (m, 4H), 3.77 (s, 2H), 2.90 (p, J=7.0 Hz, 1H), 2.76-2.62 (m, 1H), 1.24 (t, J=7.1 Hz, 3H), 1.14 (d, J=7.0 Hz, 6H), 1.09-0.96 (m, 12H). MS: m/z 453.3 (M+H$^+$).

Example 66

(S)—N-((1-ethyl-3,5-diisopropyl-1H-pyrazol-4-yl)carbamoyl)-6-(methylamino)-6,7-dihydro-5H-pyrazolo[5,1-b][1,3]oxazine-3-sulfonamide, ammonia (Example 66a)

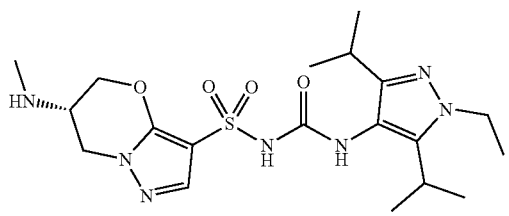 [SMILES: CCn1nc(C(C)C)c(NC(=O)NS(=O)(=O)c2cnn3c2OC[C@@H](NC)C3)c1C(C)C]

Sodium hydride (60% in mineral oil, 27 mg, 0.678 mmol) was added to a solution of 2,2,2-trifluoro-N-methyl-N-[(6S)-3-sulfamoyl-6,7-dihydro-5H-pyrazolo[5,1-b][1,3]oxazin-6-yl]acetamide (148 mg, 0.452 mmol) and 1-ethyl-4-isocyanato-3,5-diisopropyl-pyrazole (100 mg, 0.452 mmol) in THF (2.5 mL) at room temperature. After 30 minutes, the reaction was quenched with 3 drops of 10% sodium hydroxide and the reaction was allowed to stir for an additional 10 minutes. The reaction was concentrated under reduced pressure and the crude residue was purified by reverse phase HPLC (2-20% MeCN/0.1% ammonium hydroxide in water) to give (S)—N-((1-ethyl-3,5-diisopropyl-1H-pyrazol-4-yl)carbamoyl)-6-(methylamino)-6,7-dihydro-5H-pyrazolo[5,1-b][1,3]oxazine-3-sulfonamide (50.9 mg, 23%) as an ammonium salt. Single known stereoisomer obtained. $^1$H NMR (400 MHz, DMSO-d$_6$): δ=7.28 (s, 1H), 6.71 (bs, 1H), 4.25 (dd, J=10.9, 2.7 Hz, 1H), 4.14 (dd, J=12.1, 4.9 Hz, 1H), 4.09-3.99 (m, 1H), 3.90 (q, J=7.1 Hz, 2H), 3.79 (dd, J=12.0, 5.8 Hz, 1H), 3.08 (bs, 1H), 2.90 (p, J=7.0, 6.5 Hz, 1H), 2.34 (d, J=5.6 Hz, 3H), 1.96 (s, 1H), 1.24 (t, J=7.1 Hz, 3H), 1.15 (d, J=7.1 Hz, 6H), 1.06 (d, J=6.9 Hz, 6H). MS: m/z 454.2 (M+H$^+$).

Example 67

N-((3,5-diisopropyl-1-(trifluoromethyl)-1H-pyrazol-4-yl)carbamoyl)-6,7-dihydro-5H-pyrazolo[5,1-b][1,3]oxazine-3-sulfonamide, ammonia

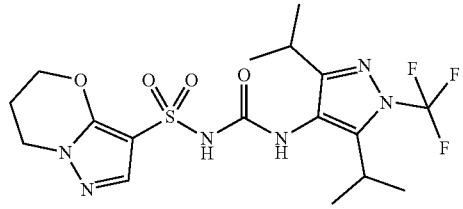 [SMILES: CC(C)c1nn(C(F)(F)F)c(C(C)C)c1NC(=O)NS(=O)(=O)c1cnn2c1OCCC2]

Sodium hydride (60% in mineral oil, 23 mg, 0.574 mmol) was added to a solution of 6,7-dihydro-5H-pyrazolo[5,1-b][1,3]oxazine-3-sulfonamide, ammonia (78 mg, 0.383 mmol) and 4-isocyanato-3,5-diisopropyl-1-(trifluoromethyl)pyrazole (100 mg, 0.383 mmol) in THF (3.8 mL) at room temperature. After 30 minutes, the reaction was quenched with 3 drops of water. The reaction was concentrated under reduced pressure and the crude residue was purified by reverse phase HPLC (2-30% MeCN/0.1% ammonium hydroxide in water) to give N-((3,5-diisopropyl-1-(trifluoromethyl)-1H-pyrazol-4-yl)carbamoyl)-6,7-dihydro-5H-pyrazolo[5,1-b][1,3]oxazine-3-sulfonamide (71.9 mg, 40%). Obtained as an ammonium salt. $^1$H NMR (400 MHz, DMSO-d$_6$): δ=7.70-7.30 (m, 2H), 4.36 (bs, 2H), 4.07 (t, J=6.0 Hz, 2H), 3.15-3.04 (m, 1H), 2.84-2.66 (m, 1H), 2.24-2.07 (m, 2H), 1.17 (d, J=7.0 Hz, 6H), 1.09 (d, J=6.9 Hz, 6H). MS: m/z 465.2 (M+H$^+$).

Example 68

N-((3,5-diisopropyl-1-methyl-1H-pyrazol-4-yl)carbamoyl)-6,6-dimethyl-6,7-dihydro-5H-pyrazolo[5,1-b][1,3]oxazine-3-sulfonamide, ammonia

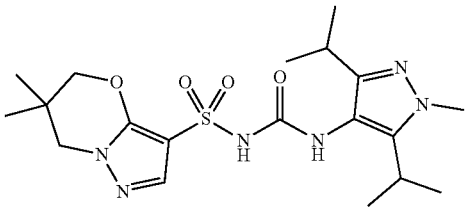

Sodium hydride (60% in mineral oil, 29 mg, 0.72 mmol) was added to a solution of 6,6-dimethyl-5,7-dihydropyrazolo[5,1-b][1,3]oxazine-3-sulfonamide (112 mg, 0.482 mmol) and 4-isocyanato-3,5-diisopropyl-1-methyl-pyrazole (100 mg, 0.482 mmol) in THF (4.8 mL) at room temperature. After 30 minutes, the reaction was quenched with 3 drops of water. The reaction was concentrated under reduced pressure and the crude residue was purified by reverse phase HPLC (2-30% MeCN/0.1% ammonium hydroxide in water) to give N-((3,5-diisopropyl-1-methyl-1H-pyrazol-4-yl)carbamoyl)-6,6-dimethyl-6,7-dihydro-5H-pyrazolo[5,1-b][1,3]oxazine-3-sulfonamide (87 mg, 41%) as an ammonium salt. $^1$H NMR (400 MHz, DMSO-d$_6$): δ=7.40 (s, 1H), 6.93 (bs, 1H), 3.98 (s, 2H), 3.79 (s, 2H), 3.62 (s, 3H), 2.90 (p, J=7.1

Hz, 1H), 2.73-2.60 (m, 1H), 1.12 (d, J=7.1 Hz, 6H), 1.08-0.96 (m, 12H). MS: m/z 439.2 (M+H$^+$).

Example 69

Sodium N-((2-isopropyl-2'-methoxy-6-(trifluoromethyl)-[4,4'-bipyridin]-3-yl)carbamoyl)-6,7-dihydro-5H-pyrazolo[5,1-b][1,3]oxazine-3-sulfonamide

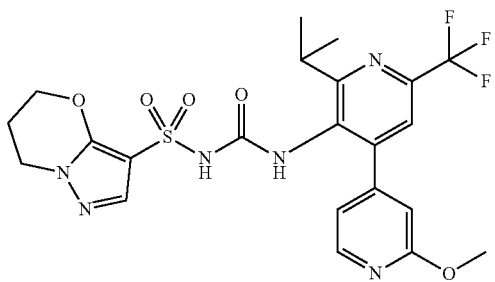 [SMILES: COc1cc(-c2cc(C(F)(F)F)nc(C(C)C)c2NC(=O)NS(=O)(=O)c2cnn3c2OCCC3)ccn1]

Step 1—Synthesis of 3-nitro-2-(prop-1-en-2-yl)-6-(trifluoromethyl)pyridine

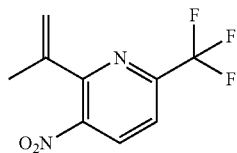

A mixture of 2-chloro-6-(trifluoromethyl)pyridin-3-amine (5.0 g, 25.44 mmol), 4,4,5,5-tetramethyl-2-(prop-1-en-2-yl)-1,3,2-dioxaborolane (4.7 g, 27.98 mmol), Pd(dppf)Cl$_2$ (1.86 g, 2.54 mmol) and K$_2$CO$_3$ (8.79 g, 63.59 mmol) in 1,4-dioxane (50 mL) and H$_2$O (10 mL) was stirred at 80° C. for 7 hours under a nitrogen atmosphere. After cooling to room temperature, the reaction mixture was concentrated. The crude residue was purified by silica gel column chromatography (0-10% EtOAc in petroleum ether) to give 3-nitro-2-(prop-1-en-2-yl)-6-(trifluoromethyl)pyridine (4.68 g, yield: 91%) as a light yellow solid. $^1$H NMR (400 MHz, CDCl$_3$) δ=7.34, (d, J=8.4 Hz, 1H), 7.03 (d, J=8.4 Hz, 1H), 5.54-5.53 (m, 1H), 5.36-5.34 (m, 1H), 4.22 (s, 2H), 2.18 (s, 3H)

Step 2—Synthesis of 2-isopropyl-6-(trifluoromethyl)pyridin-3-amine

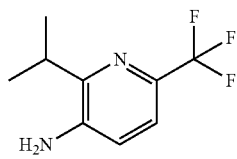

A mixture of 3-nitro-2-(prop-1-en-2-yl)-6-(trifluoromethyl)pyridine (4.68 g, 23.15 mmol) and 10% Pd (2.46 g, 23.15 mmol) on carbon in EtOH (50 mL) was stirred at room temperature under a hydrogen atmosphere for 3 hours. The reaction mixture was filtered over a short pad of celite. The filtrate was concentrated to give 2-isopropyl-6-(trifluoromethyl)pyridin-3-amine (4.45 g, yield: 94%) as a colorless oil. MS: m/z 205.1 (M+H$^+$).

Step 3—Synthesis of 4-bromo-2-isopropyl-6-(trifluoromethyl)pyridin-3-amine

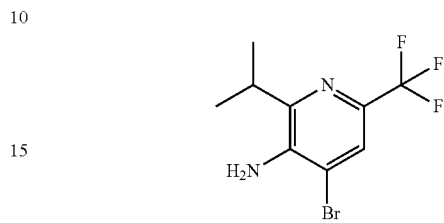

To a solution of 2-isopropyl-6-(trifluoromethyl)pyridin-3-amine (500 mg, 2.45 mmol) in MeCN (8 mL) was added NBS (0.44 g, 2.45 mmol) at room temperature. The reaction mixture was stirred at room temperature for 1 hour under a nitrogen atmosphere. The mixture was concentrated and the crude residue was purified by silica gel column (0-10% EtOAc in petroleum ether) to give 4-bromo-2-isopropyl-6-(trifluoromethyl)pyridin-3-amine (680 mg, yield: 98%) as a light yellow solid. $^1$H NMR (400 MHz, CDCl$_3$) δ=7.58 (s, 1H), 4.47 (s, 2H), 3.07-3.01 (m, 1H), 1.32 (d, J=7.2 Hz, 6H).

Step 4—Synthesis of 2-isopropyl-2'-methoxy-6-(trifluoromethyl)-[4,4'-bipyridin]-3-amine

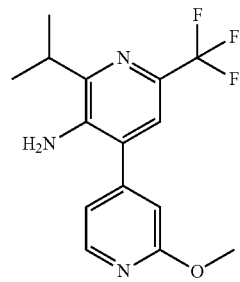 [SMILES: COc1cc(-c2cc(C(F)(F)F)nc(C(C)C)c2N)ccn1]

A mixture of 4-bromo-2-isopropyl-6-(trifluoromethyl)pyridin-3-amine (680 mg, 2.40 mmol), (2-methoxypyridin-4-yl)boronic acid (551 mg, 3.60 mmol), Pd(dppf)Cl$_2$ (176 mg, 0.24 mmol) and K$_2$CO$_3$ (830 mg, 6.01 mmol) in 1,4-dioxane (8 mL) was stirred at 80° C. for 3 hours under a nitrogen atmosphere. After cooling to room temperature, the reaction mixture was concentrated. The crude residue was purified by silica gel column (0-20% EtOAc in petroleum ether) to give 2-isopropyl-2'-methoxy-6-(trifluoromethyl)-[4,4'-bipyridin]-3-amine (700 mg, yield: 94%) as a light yellow solid. $^1$H NMR (400 MHz, CDCl$_3$) δ=8.30 (d, J=6.4 Hz, 1H), 7.24 (s, 1H), 6.96 (d, J=6.4 Hz, 1H), 6.82 (s, 1H), 4.14 (s, 2H), 4.00 (s, 3H), 3.07-3.02 (m, 1H), 1.35 (d, J=6.8 Hz, 6H).

Step 5—Synthesis of 3-isocyanato-2-isopropyl-2'-methoxy-6-(trifluoromethyl)-4,4'-bipyridine

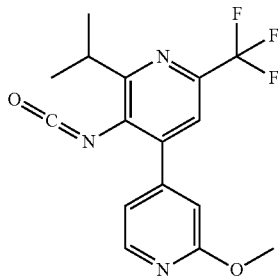 [SMILES: COc1cc(-c2cc(C(F)(F)F)nc(C(C)C)c2N=C=O)ccn1]

To a solution of 2-isopropyl-2'-methoxy-6-(trifluoromethyl)-[4,4'-bipyridin]-3-amine (200 mg, 0.64 mmol) and triethylamine (0.13 mL, 0.64 mmol) in THF (5 mL) was added triphosgene (76 mg, 0.26 mmol). The mixture was stirred at 70° C. for 2 hours. After cooling to room temperature, the mixture was filtered through a plug of silica gel to remove the triethylamine hydrochloride. The filtrate was concentrated under reduced pressure to give 3-isocyanato-2-isopropyl-2'-methoxy-6-(trifluoromethyl)-4,4'-bipyridine (180 mg, yield: 83%) as a brown oil, which was used in the next step directly.

Step 6—Synthesis of N-((2-isopropyl-2'-methoxy-6-(trifluoromethyl)-4,4'-bipyridin-3-yl)carbamoyl)-6,7-dihydro-5H-pyrazolo[5,1-b][1,3]oxazine-3-sulfonamide (Example 69)

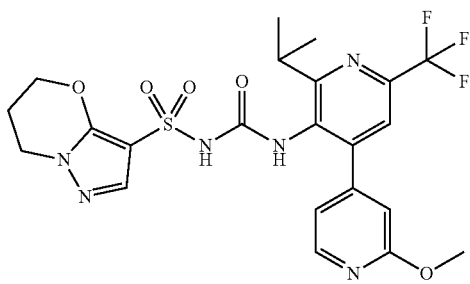 [SMILES: COc1cc(-c2cc(C(F)(F)F)nc(C(C)C)c2NC(=O)NS(=O)(=O)c2cnn3c2OCCC3)ccn1]

To a solution of 6,7-dihydro-5H-pyrazolo[5,1-b][1,3]oxazine-3-sulfonamide (180 mg, 0.89 mmol) in THF (5 mL) was added NaH (60% in mineral oil, 26 mg, 1.06 mmol) at 0° C. After 20 minutes, 3-isocyanato-2-isopropyl-2'-methoxy-6-(trifluoromethyl)-4,4'-bipyridine (300 mg, 0.89 mmol) was added. The reaction mixture was warmed to room temperature and was allowed to stir for an additional 12 hours. The mixture was concentrated and the crude residue was purified by reverse phase chromatography (MeCN 22-52%/10 mM NH$_4$HCO$_3$ in water) to give N-((2-isopropyl-2'-methoxy-6-(trifluoromethyl)-[4,4'-bipyridin]-3-yl)carbamoyl)-6,7-dihydro-5H-pyrazolo[5,1-b][1,3]oxazine-3-sulfonamide (155 mg, yield: 30%) as a sodium salt. $^1$H NMR (400 MHz, DMSO-A) δ=8.13-8.12 (m, 2H), 7.65 (s, 1H), 7.36 (s, 1H), 6.94 (d, J=4.8 Hz, 1H), 6.89 (s, 1H), 4.36-4.34 (m, 2H), 4.11-4.08 (m, 2H), 3.88 (s, 3H), 3.39-3.37 (m, 1H), 2.20-2.17 (m, 2H), 1.14 (d, J=6.4 Hz, 6H). MS: m/z 541.0 (M+H$^+$).

Example 70

(S)—N-((1-(2,2-difluoroethyl)-3,5-diisopropyl-1H-pyrazol-4-yl)carbamoyl)-6-(methylamino)-6,7-dihydro-5H-pyrazolo[5,1-b][1,3]oxazine-3-sulfonamide, ammonia (Example 70a)

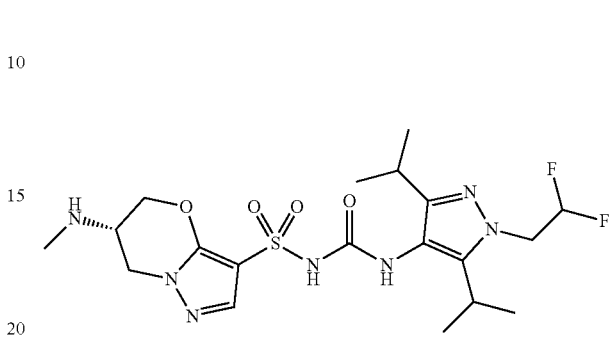

(S)—N-((1-(2,2-difluoroethyl)-3,5-diisopropyl-1H-pyrazol-4-yl)carbamoyl)-6-(methylamino)-6,7-dihydro-5H-pyrazolo[5,1-b][1,3]oxazine-3-sulfonamide, ammonia (purified by reverse phase HPLC (2-30% MeCN/0.1% ammonium hydroxide in water; 71.7 mg, 38%) was prepared by using the general procedure described for the preparation of (S)—N-((1-ethyl-3,5-diisopropyl-1H-pyrazol-4-yl)carbamoyl)-6-(methylamino)-6,7-dihydro-5H-pyrazolo[5,1-b][1,3]oxazine-3-sulfonamide (Example 66) by replacing 1-ethyl-4-isocyanato-3,5-diisopropyl-pyrazole with 1-(2,2-difluoroethyl)-4-isocyanato-3,5-diisopropyl-pyrazole in Step 1. Obtained as an ammonium salt and a single known stereoisomer. $^1$H NMR (400 MHz, DMSO-d$_6$): δ=7.28 (s, 1H), 6.79 (s, 1H), 6.51-5.97 (m, 1H), 4.36 (td, J=14.6, 4.1 Hz, 2H), 4.25 (dd, J=11.0, 2.7 Hz, 1H), 4.14 (dd, J=12.1, 4.9 Hz, 1H), 4.04 (dd, J=11.0, 6.3 Hz, 1H), 3.79 (dd, J=12.1, 5.7 Hz, 1H), 3.13-3.01 (m, 1H), 2.98-2.87 (m, 1H), 2.83-2.65 (m, 1H), 2.34 (d, J=5.0 Hz, 3H), 2.03-1.90 (m, 1H), 1.14 (d, J=7.0 Hz, 6H), 1.06 (d, J=6.9 Hz, 6H). MS: m/z 490.2 (M+H$^+$).

Example 71

Sodium N-((2,4-diisopropyl-6-(trifluoromethoxy)pyridin-3-yl)carbamoyl)-6,7-dihydro-5H-pyrazolo[5,1-b][1,3]oxazine-3-sulfonamide

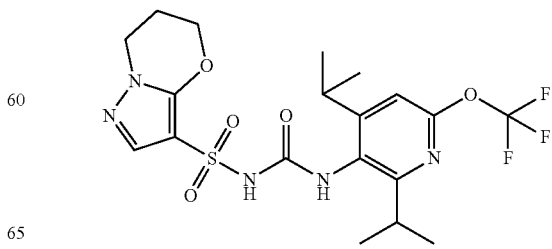

Step 1—Synthesis of 2,4-dibromo-6-(trifluoromethoxy)pyridin-3-amine

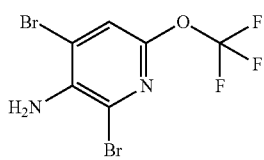 [SMILES: Nc1c(Br)cc(OC(F)(F)F)nc1Br]

A solution of Br$_2$ (0.25 mL, 4.87 mmol) in HOAc (3 mL) was added dropwise to a stirring solution of 6-(trifluoromethoxy)pyridin-3-amine (400 mg, 2.25 mmol) in EtOH (15 mL) and HOAc (1.5 mL) at 0° C. under a nitrogen atmosphere. After addition was complete, the reaction was warmed to room temperature and was allowed to stir for an additional 15 hours. The reaction mixture was concentrated. DCM (30 mL) and saturated aqueous NaHCO$_3$ (20 mL) were added to the crude residue. The aqueous layer was extracted with DCM (50 mL×3). The combined organic layers were dried over Na$_2$SO$_4$, filtered and concentrated. The crude residue was purified by column chromatography (0-10% EtOAc in petroleum ether) to give 2,4-dibromo-6-(trifluoromethoxy)pyridin-3-amine (670 mg, yield: 89%) as light yellow solid. $^1$H NMR (400 MHz, CDCl$_3$): δ=7.18 (s, 1H), 4.59 (s, 2H).

Step 2—Synthesis of 2,4-di(prop-1-en-2-yl)-6-(trifluoromethoxy)pyridin-3-amine

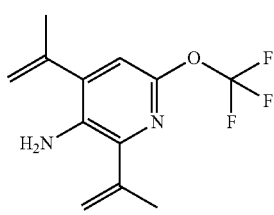 [SMILES: C=C(C)c1cc(OC(F)(F)F)nc(C(=C)C)c1N]

A mixture of 2,4-dibromo-6-(trifluoromethoxy)pyridin-3-amine (670 mg, 1.99 mmol), isopropenylboronicacidpinacolester (771 mg, 4.59 mmol), Pd(dppf)Cl$_2$ (146 mg, 0.2 mmol) and Cs$_2$CO$_3$ (2.28 g, 6.98 mmol) in 1,4-dioxane (15 mL) and water (1.5 mL) were stirred at 100° C. for 8 hours under a nitrogen atmosphere. After cooling to room temperature, the reaction mixture was concentrated. The crude residue was purified by silica gel column chromatography (0-10% EtOAc in petroleum ether) to give 2,4-di(prop-1-en-2-yl)-6-(trifluoromethoxy)pyridin-3-amine (450 mg, yield: 87%) as a light yellow solid. $^1$H NMR (400 MHz, CDCl$_3$) δ=6.64 (s, 1H), 5.52 (s, 1H), 5.43-5.33 (m, 2H), 5.16 (s, 1H), 4.12 (s, 2H), 2.15 (s, 3H), 2.08 (s, 3H).

Step 3—Synthesis of 2,4-diisopropyl-6-(trifluoromethoxy)pyridin-3-amine

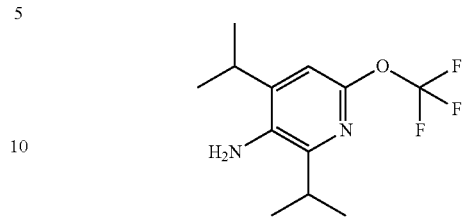

To a stirred solution of 2,4-di(prop-1-en-2-yl)-6-(trifluoromethoxy)pyridin-3-amine (450 mg, 1.74 mmol) in EtOH (8 mL) was added 10% palladium (19 mg, 0.17 mmol) on carbon and the mixture was allowed to stir at room temperature for 2 hours under a hydrogen atmosphere. The reaction mixture was filtered over a short pad of Celite. The filtrate was concentrated to give 2,4-diisopropyl-6-(trifluoromethoxy)pyridin-3-amine (390 mg, yield: 85%) as a light yellow oil. MS: m/z 263.2 (M+H$^+$).

Step 4—Synthesis of 3-isocyanato-2,4-diisopropyl-6-(trifluoromethoxy)pyridine

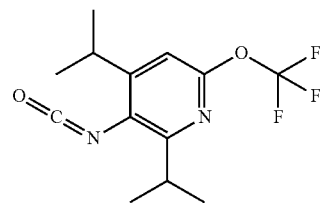 [SMILES: CC(C)c1cc(OC(F)(F)F)nc(C(C)C)c1N=C=O]

To a stirred solution of 2,4-diisopropyl-6-(trifluoromethoxy)pyridin-3-amine (150 mg, 0.57 mmol) and triethylamine (0.2 mL, 1.43 mmol) in THF (5 mL) was added triphosgene (85 mg, 0.29 mmol) at 0° C. under a nitrogen atmosphere. The reaction mixture was stirred at 70° C. for 1.5 hours. After cooling to room temperature, the reaction mixture was filtered. The filter was washed with EtOAc (5 mL). The filtrate was concentrated to afford 3-isocyanato-2,4-diisopropyl-6-(trifluoromethoxy)pyridine (160 mg, yield: 97%) as a yellow oil, which was used in the next step directly.

Step 5—Synthesis of N-((2,4-diisopropyl-6-(trifluoromethoxy)pyridin-3-yl)carbamoyl)-6,7-dihydro-5H-pyrazolo[5,1-b][1,3]oxazine-3-sulfonamide (Example 71)

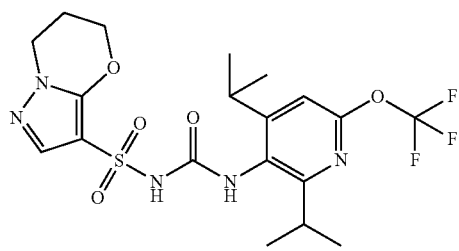 [SMILES: CC(C)c1cc(OC(F)(F)F)nc(C(C)C)c1NC(=O)NS(=O)(=O)c1cnn2c1OCCC2]

To a solution of 6,7-dihydro-5H-pyrazolo[5,1-b][1,3]oxazine-3-sulfonamide (100 mg, 0.49 mmol) in THF (5 mL) was added NaH (60% in mineral oil, 26 mg, 0.64 mmol) at 0° C. After 20 minutes, 3-isocyanato-2,4-diisopropyl-6-(trifluoromethoxy)pyridine (156 mg, 0.54 mmol) was added. The reaction mixture was warmed to room temperature and was allowed to stir for an additional 12 hours. The mixture was concentrated and the crude residue was purified by reverse phase chromatography (MeCN 0-60%/0.1% NH$_4$HCO$_3$ in water) to give N-((2,4-diisopropyl-6-(trifluoromethoxy)pyridin-3-yl)carbamoyl)-6,7-dihydro-5H-pyrazolo[5,1-b][1,3]oxazine-3-sulfonamide (147.3 mg, yield: 57%) as a sodium salt. $^1$H NMR (400 MHz, DMSO-d$_6$) δ=7.96 (s, 1H), 7.53 (s, 1H), 6.98 (s, 1H), 4.41-4.39 (m, 2H), 4.10-4.07 (m, 2H), 3.13-3.02 (m, 1H), 3.01-2.88 (m, 1H), 2.24-2.12 (m, 2H), 1.07-1.03 (m, 12H). MS: m/z 492.2 (M+H$^+$).

Example 72

(S)-N-((3,5-diisopropyl-1-(2,2,2-trifluoroethyl)-1H-pyrazol-4-yl)carbamoyl)-6-(methylamino)-6,7-dihydro-5H-pyrazolo[5,1-b][1,3]oxazine-3-sulfonamide, ammonia (Example 72a)

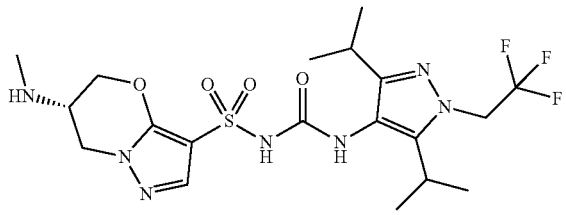 [SMILES: CN[C@@H]1COc2c(S(=O)(=O)NC(=O)Nc3c(C(C)C)nn(CC(F)(F)F)c3C(C)C)cnn2C1]

(S)-N-((3,5-diisopropl-1-(2,2,2-trifluoroethyl)-1H-pyrazol-4-yl)carbamoyl)-6-(methylamino)-6,7-dihydro-5H-pyrazolo[5,1-b][1,3]oxazine-3-sulfonamide, ammonia (purified by reverse phase HPLC (2-20% MeCN/0.1% ammonium hydroxide in water); 91.2 mg, 46%) was prepared by using the general procedure described for the preparation of (S)-N-((1-ethyl-3,5-diisopropyl-1H-pyrazol-4-yl)carbamoyl)-6-(methylamino)-6,7-dihydro-5H-pyrazolo[5,1-b][1,3]oxazine-3-sulfonamide (Example 66) by replacing 1-ethyl-4-isocyanato-3,5-diisopropyl-pyrazole with 4-isocyanato-3,5-diisopropyl-1-(2,2,2-trifluoroethyl) pyrazole in Step 1. Obtained as an ammonium salt and a single known enantiomer. $^1$H NMR (400 MHz, DMSO-d$_6$): δ=7.28 (s, 1H), 6.84 (s, 1H), 4.85 (q, J=9.0 Hz, 2H), 4.25 (dd, J=10.8, 2.7 Hz, 1H), 4.20-4.09 (m, 1H), 4.04 (dd, J=11.0, 6.3 Hz, 1H), 3.79 (dd, J=12.1, 5.8 Hz, 1H), 3.12-3.03 (m, 1H), 3.01-2.86 (m, 1H), 2.80-2.65 (m, 1H), 2.34 (d, J=5.8 Hz, 3H), 2.01-1.91 (m, 1H), 1.14 (d, J=6.9 Hz, 6H), 1.06 (d, J=6.9 Hz, 6H). MS: m/z 508.2 (M+H$^+$).

Example 73

(S)-N-((3,5-diisopropyl-1-methyl-1H-pyrazol-4-yl)carbamoyl)-6-(methylamino)-6,7-dihydro-5H-pyrazolo[5,1-b][1,3]oxazine-3-sulfonamide, ammonia (Example 73a)

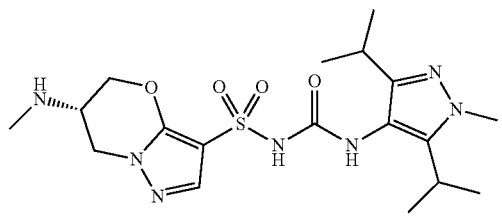

(S)-N-((3,5-diisopropyl-1-methyl-1H-pyrazol-4-yl)carbamoyl)-6-(methylamino)-6,7-dihydro-5H-pyrazolo[5,1-b][1,3]oxazine-3-sulfonamide, ammonia (purified by reverse phase HPLC (2-20% MeCN/0.1% ammonium hydroxide in water); 50.4 mg, 24%) was prepared by using the general procedure described for the preparation of (S)-N-((1-ethyl-3,5-diisopropyl-1H-pyrazol-4-yl)carbamoyl)-6-(methylamino)-6,7-dihydro-5H-pyrazolo[5,1-b][1,3]oxazine-3-sulfonamide (Example 66) by replacing 1-ethyl-4-isocyanato-3,5-diisopropyl-pyrazole with 4-isocyanato-3,5-diisopropyl-1-methyl-pyrazole in Step 1. Obtained as an ammonium salt and a single known enantiomer. $^1$H NMR (400 MHz, DMSO-d$_6$): δ=7.28 (s, 1H), 6.74 (s, 1H), 4.25 (dd, J=11.0, 2.7 Hz, 1H), 4.15 (dd, J=12.1, 4.9 Hz, 1H), 4.04 (dd, J=11.0, 6.3 Hz, 1H), 3.79 (dd, J=12.1, 5.7 Hz, 1H), 3.61 (s, 3H), 3.13-3.03 (m, 1H), 2.98-2.82 (m, 1H), 2.80-2.65 (m, 1H), 2.34 (s, 3H), 2.02-1.90 (m, 1H), 1.14 (d, J=7.1 Hz, 6H), 1.05 (d, J=6.9 Hz, 6H). MS: m/z 440.2 (M+H$^+$).

Example 74

Sodium N-((4-isopropyl-2'-methoxy-6-(trifluoromethyl)-[2,4'-bipyridin]-3-yl)carbamoyl)-6,7-dihydro-5H-pyrazolo[5,1-b][1,3]oxazine-3-sulfonamide

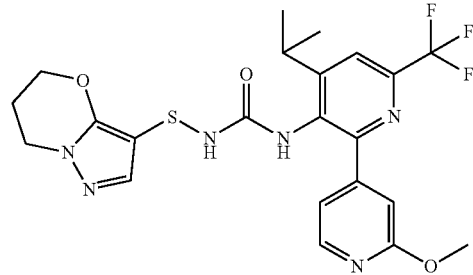 [SMILES: COc1cc(-c2nc(C(F)(F)F)cc(C(C)C)c2NC(=O)NSc2cnn3c2OCCC3)ccn1]

Step 1—Synthesis of 5-nitro-4-(prop-1-en-2-yl)-2-(trifluoromethyl)pyridine

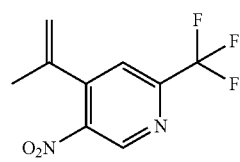

A mixture of 4-chloro-5-nitro-2-(trifluoromethyl)pyridine (500 mg, 2.21 mmol), 4,4,5,5-tetramethyl-2-(prop-1-en-2-yl)-1,3,2-dioxaborolane (0.41 g, 2.43 mmol), Pd(dppf)Cl$_2$ (0.16 g, 0.22 mmol) and K$_2$CO$_3$ (0.76 g, 5.52 mmol) in 1,4-dioxane (8 mL) and H$_2$O (2 mL) were stirred at 80° C. for 3 hours under a nitrogen atmosphere. After cooling to room temperature, the reaction mixture was concentrated. The crude residue was purified by silica gel column (0-10% EtOAc in petroleum ether) to give 5-nitro-4-(prop-1-en-2-yl)-2-(trifluoromethyl)pyridine (420 mg, yield: 82%) as a light yellow solid. $^1$H NMR (400 MHz, CDCl$_3$) δ=9.12 (s, 1H), 7.69 (s, 1H), 5.40 (s, 1H), 5.15 (s, 1H), 2.14 (s, 3H)

Step 2—Synthesis of 4-isopropyl-6-(trifluoromethyl)pyridin-3-amine

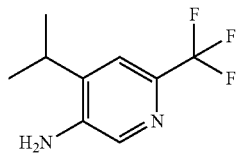

A mixture of 5-nitro-4-(prop-1-en-2-yl)-2-(trifluoromethyl)pyridine (420 mg, 1.81 mmol) and 10% Pd (190 mg, 1.81 mmol) on carbon in EtOH (8 mL) were stirred at room temperature under a hydrogen atmosphere for 3 hours. The reaction mixture was filtered over a short pad of Celite. The filtrate was concentrated to give 4-isopropyl-6-(trifluoromethyl)pyridin-3-amine (300 mg, yield: 81%) as a colorless oil, which was used in the next step directly. MS: m/z 205.2 (M+H$^+$).

Step 3—Synthesis of 2-bromo-4-isopropyl-6-(trifluoromethyl)pyridin-3-amine

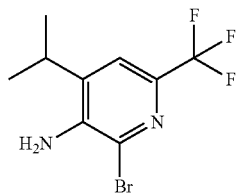

To a solution of 4-isopropyl-6-(trifluoromethyl)pyridin-3-amine (300 mg, 1.47 mmol) in MeCN (6 mL) was added NBS (261 mg, 1.47 mmol) at room temperature. After 3 hours, the reaction mixture was concentrated and the crude residue was purified by silica gel column (0-10% EtOAc in petroleum ether) to give 2-bromo-4-isopropyl-6-(trifluoromethyl)pyridin-3-amine (350 mg, yield: 84%) as a light yellow solid. $^1$H NMR (400 MHz, CDCl$_3$) δ=7.37 (s, 1H), 4.52 (s, 2H), 3.07-3.01 (m, 1H), 1.32 (d, J=12 Hz, 6H)

Step 4—Synthesis of 4-isopropyl-2'-methoxy-6-(trifluoromethyl)-[2,4'-bipyridin]-3-amine

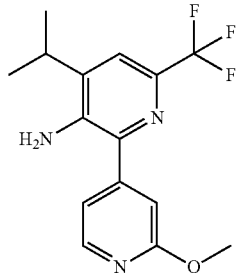 [SMILES: COc1cc(-c2nc(C(F)(F)F)cc(C(C)C)c2N)ccn1]

A mixture of 2-bromo-4-isopropyl-6-(trifluoromethyl) pyridin-3-amine (300 mg, 1.06 mmol), (2-methoxypyridin-4-yl)boronic acid (243 mg, 1.59 mmol), Pd(dppf)Cl$_2$ (78 mg, 0.11 mmol) and K$_2$CO$_3$ (366 mg, 2.65 mmol) in 1,4-dioxane (8 mL) was stirred at 80° C. for 3 hours under a nitrogen atmosphere. After cooling to room temperature, the reaction mixture was concentrated. The crude residue was purified by silica gel column (0-20% EtOAc in petroleum ether) to give 4-isopropyl-2'-methoxy-6-(trifluoromethyl)-[2,4'-bipyridin]-3-amine (290 mg, yield: 94%) as light yellow solid. $^1$H NMR (400 MHz, CDCl$_3$) δ=8.30 (d, J=5.2 Hz, 1H), 7.44 (s, 1H), 7.17 (d, J=5.2 Hz, 1H), 7.05 (s, 1H), 4.21 (s, 2H), 4.00 (s, 3H), 2.96-2.88 (m, 1H), 1.33 (d, J=6.8 Hz, 6H)

Step 5—Synthesis of 3-isocyanato-4-isopropyl-2'-methoxy-6-(trifluoromethyl)-2,4'-bipyridine

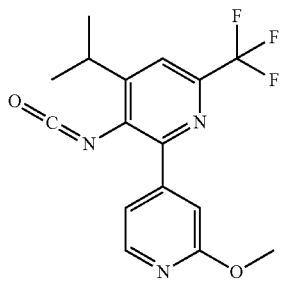 [SMILES: COc1cc(-c2nc(C(F)(F)F)cc(C(C)C)c2N=C=O)ccn1]

To a solution of 4-isopropyl-2'-methoxy-6-(trifluoromethyl)-[2,4'-bipyridin]-3-amine (100 mg, 0.32 mmol) and triethylamine (0.13 mL, 0.32 mmol) in THF (4 mL) was added triphosgene (38 mg, 0.13 mmol) at 0° C. under a nitrogen atmosphere. The reaction mixture was stirred at 70° C. for 2 hours. After cooling to room temperature, the mixture was filtered through a plug of silica gel to remove the triethylamine hydrochloride. The filtrate was concentrated under reduced pressure to afford 3-isocyanato-4-isopropyl-2'-methoxy-6-(trifluoromethyl)-2,4'-bipyridine (180 mg, yield: 92%) as a brown oil, which was used in the next step directly.

Step 6—Synthesis of N-((4-isopropyl-2'-methoxy-6-(trifluoromethyl)-[2,4'-bipyridin]-3-yl)carbamoyl)-6,7-dihydro-5H-pyrazolo[5,1-b][1,3]oxazine-3-sulfonamide (Example 74)

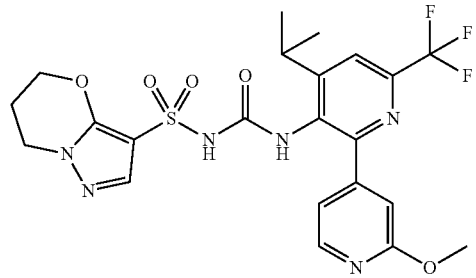 [SMILES: COc1cc(-c2nc(C(F)(F)F)cc(C(C)C)c2NC(=O)NS(=O)(=O)c2cnn3c2OCCC3)ccn1]

To a solution of 6,7-dihydro-5H-pyrazolo[5,1-b][1,3] oxazine-3-sulfonamide (180 mg, 0.89 mmol) in THF (5 mL) was added NaH (60% in mineral oil, 26 mg, 1.06 mmol) at 0° C. After 20 minutes, 3-isocyanato-4-isopropyl-2'-methoxy-6-(trifluoromethyl)-2,4'-bipyridine (300 mg, 0.89 mmol) was added. The reaction mixture was allowed warm to room temperature and was allowed to stir for an additional 12 hours. The reaction mixture was concentrated and the crude residue was purified by reverse phase chromatography (MeCN 24-54%/10 mM NH₄HCO₃ in water) to give N-((4-isopropyl-2'-methoxy-6-(trifluoromethyl)-[2,4'-bipyridin]-3-yl)carbamoyl)-6,7-dihydro-5H-pyrazolo[5,1-b][1,3]oxazine-3-sulfonamide (9.2 mg, yield: 2%) as a sodium salt. ¹H NMR (400 MHz, DMSO-d₆) β=8.13-8.12 (m, 2H), 7.84 (s, 1H), 7.33 (s, 1H), 6.94 (d, J=4.8 Hz, 1H), 6.95 (s, 1H), 4.35-4.32 (m, 2H), 4.11-4.08 (m, 2H), 3.88 (s, 3H), 3.19-3.16 (m, 1H), 2.19-2.16 (m, 2H), 1.15 (d, J=6.4 Hz, 6H). MS: m/z 541.1 (M+H⁺).

Example 75

N-((3,5-diisopropyl-1-(2,2,2-trifluoroethyl)-1H-pyrazol-4-yl)carbamoyl)-6,6-dimethyl-6,7-dihydro-5H-pyrazolo[5,1-b][1,3]oxazine-3-sulfonamide, ammonia

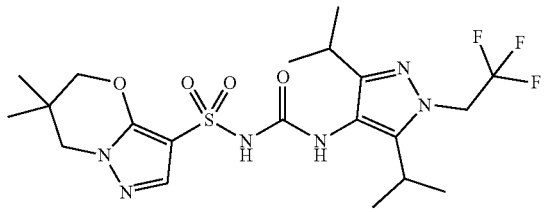 [SMILES: CC(C)c1nn(CC(F)(F)F)c(C(C)C)c1NC(=O)NS(=O)(=O)c1cnn2c1OCC(C)(C)C2]

N-((3,5-diisopropyl-1-(2,2,2-trifluoroethyl)-1H-pyrazol-4-yl)carbamoyl)-6,6-dimethyl-6,7-dihydro-5H-pyrazolo[5,1-b][1,3]oxazine-3-sulfonamide, ammonia (purified by reverse phase HPLC (2-20% MeCN/0.1% ammonium hydroxide in water); 115 mg, 62%) was prepared by using the general procedure described for the preparation of N-((3,5-diisopropyl-1-(2,2,2-trifluoroethyl)-1H-pyrazol-4-yl)carbamoyl)-6,7-dihydro-5H-pyrazolo[5,1-b][1,3]oxazine-3-sulfonamide (Example 58) by replacing of 6,7-dihydro-5H-pyrazolo[5,1-b][1,3]oxazine-3-sulfonamide with 6,6-dimethyl-5,7-dihydropyrazolo[5,1-b][1,3]oxazine-3-sulfonamide in Step 2. Obtained as an ammonium salt. ¹H NMR (400 MHz, DMSO-d₆): δ=7.45 (bs, 1H), 7.07 (bs, 1H), 4.90 (q, J=9.0 Hz, 2H), 4.02 (s, 2H), 3.81 (s, 2H), 2.98 (p, J=7.0 Hz, 1H), 2.76-2.59 (m, 1H), 1.11 (d, J=6.9 Hz, 6H), 1.08-0.97 (m, 12H). MS: m/z 507.2 (M+H⁺).

Example 76

(S)—N-((2,4-diisopropyl-6-(trifluoromethyl)pyridin-3-yl)carbamoyl)-6-(dimethylamino)-6,7-dihydro-5H-pyrazolo[5,1-b][1,3]oxazine-3-sulfonamide (Example 76a)

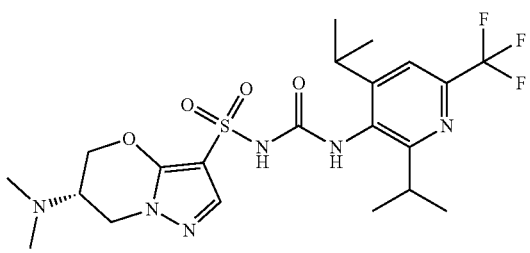 [SMILES: CC(C)c1cc(C(F)(F)F)nc(C(C)C)c1NC(=O)NS(=O)(=O)c1cnn2c1OC[C@@H](N(C)C)C2]

(S)—N-((2,4-diisopropyl-6-(trifluoromethyl)pyridin-3-yl)carbamoyl)-6-(dimethylamino)-6,7-dihydro-5H-pyrazolo[5,1-b][1,3]oxazine-3-sulfonamide (purified by reverse phase HPLC (21-51% MeCN/0.1% NH₄HCO₃ in water), 27.8 mg, yield: 16%) was prepared by using the general procedure described for the preparation of (S)—N-((2,4-diisopropyl-6-(trifluoromethyl)pyridin-3-yl)carbamoyl)-6-methoxy-6,7-dihydro-5H-pyrazolo[5,1-b][1,3]oxazine-3-sulfonamide (Example 80) by replacing (S)-6-methoxy-6,7-dihydro-5H-pyrazolo[5,1-b][1,3]oxazine-3-sulfonamide with (6S)-6-(dimethylamino)-6,7-dihydro-5H-pyrazolo[5,1-][1,3]oxazine-3-sulfonamide in Step 5. Single known stereoisomer obtained. ¹H NMR (400 MHz, DMSO-d₆): δ=11.06 (s, 1H), 8.15 (s, 1H), 7.61-7.60 (m, 2H), 4.49-4.47 (m, 2H), 4.25-4.18 (m, 2H), 3.17-3.15 (m, 1H), 3.03-3.01 (m, 1H), 2.93-2.91 (m, 1H), 2.28 (s, 6H), 1.20-0.97 (m, 12H). MS: m/z 519.1 (M+H⁺).

Example 77

(S)-6-(dimethylamino)-N-((2-isopropyl-2,4,5,6-tetrahydrocyclopenta[c]pyrazol-3-yl)carbamoyl)-6,7-dihydro-5H-pyrazolo[5,1-b][1,3]oxazine-3-sulfonamide (Example 77a)

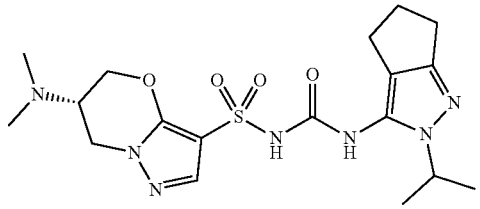 [SMILES: CC(C)n1nc2c(c1NC(=O)NS(=O)(=O)c1cnn3c1OC[C@@H](N(C)C)C3)CCC2]

(S)-6-(dimethylamino)-N-((2-isopropyl-2,4,5,6-tetrahydrocyclopenta[c]pyrazol-3-yl)carbamoyl)-6,7-dihydro-5H-pyrazolo[5,1-b][1,3]oxazine-3-sulfonamide (purified by reverse phase HPLC (67-77% MeCN/10 mM NH₄HCO₃ in water), 12.1 mg, yield: 4%) was prepared by using the general procedure described for the preparation of (S)—N-((2-isopropyl-2,4,5,6-tetrahydrocyclopenta[c]pyrazol-3-yl)carbamoyl)-6-methoxy-6,7-dihydro-5H-pyrazolo[5,1-b][1,3]oxazine-3-sulfonamide (Example 83) by replacing (S)-6-methoxy-6,7-dihydro-5H-pyrazolo[5,1-b][1,3]oxazine-3-sulfonamide with (S)-6-(dimethylamino)-6,7-dihydro-5H-pyrazolo[5,1-b][1,3]oxazine-3-sulfonamide in Step 1. Single known stereoisomer obtained. ¹H NMR (400 MHz, DMSO-d₆): δ=7.99 (s, 1H), 7.48 (s, 1H), 4.41-4.39 (m, 2H), 4.25-4.20 (m, 2H), 4.18-4.14 (m, 1H), 2.92-2.88 (m, 1H), 2.50-2.42 (m, 4H), 2.26 (s, 6H), 2.24-2.21 (m, 2H), 1.25 (d, J=6.8 Hz, 6H). MS: m/z 438.1 (M+H⁺).

Example 78

(S)—N-((3,5-diisopropyl-1-(trifluoromethyl)-1H-pyrazol-4-yl)carbamoyl)-6-methoxy-6,7-dihydro-5H-pyrazolo[5,1-b][1,3]oxazine-3-sulfonamide (Example 78a)

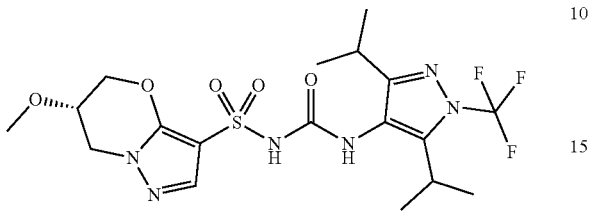

(S)—N-((3,5-diisopropyl-1-(trifluoromethyl)-1H-pyrazol-4-yl)carbamoyl)-6-methoxy-6,7-dihydro-5H-pyrazolo[5,1-b][1,3]oxazine-3-sulfonamide (purified by reverse phase HPLC (2-30% MeCN/in water); 78.4 mg, 41%) was prepared by using the general procedure described for the preparation of N-((3,5-diisopropyl-1-(trifluoromethyl)-1H-pyrazol-4-yl)carbamoyl)-6,7-dihydro-5H-pyrazolo[5,1-b][1,3]oxazine-3-sulfonamide (Example 67) by replacing 6,7-dihydro-5H-pyrazolo[5,1-b][1,3]oxazine-3-sulfonamide with (6S)-6-methoxy-6,7-dihydro-5H-pyrazolo[5,1-b][1,3]oxazine-3-sulfonamide in Step 1. Single known stereoisomer obtained. $^1$H NMR (400 MHz, DMSO-$d_6$): δ=7.55-7.27 (m, 2H), 4.53 (d, J=12.0 Hz, 1H), 4.26-4.10 (m, 3H), 4.00 (bs, 1H), 3.35 (s, 3H), 3.15-3.05 (m, 1H), 2.86-2.69 (m, 1H), 1.19 (d, J=7.0 Hz, 6H), 1.09 (d, J=7.1 Hz, 6H). MS: m/z 495.2 (M+H$^+$).

Example 79

N-((3,5-diisopropyl-1-(trifluoromethyl)-1H-pyrazol-4-yl)carbamoyl)-6,6-dimethyl-6,7-dihydro-5H-pyrazolo[5,1-b][1,3]oxazine-3-sulfonamide

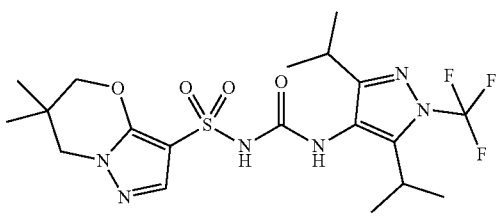 [SMILES: CC(C)c1nn(C(F)(F)F)c(C(C)C)c1NC(=O)NS(=O)(=O)c1cnn2c1OCC(C)(C)C2]

N-((3,5-diisopropyl-1-(trifluoromethyl)-1H-pyrazol-4-yl (carbamoyl)-6,6-dimethyl-6,7-dihydro-5H-pyrazolo[5,1-b][1,3]oxazine-3-sulfonamide (purified by reverse phase HPLC (2-30% MeCN/in water); 53.3 mg, 28%) was prepared by using the general procedure described for the preparation of N-((3,5-diisopropyl-1-(trifluoromethyl)-1H-pyrazol-4-yl (carbamoyl)-6,7-dihydro-5H-pyrazolo[5,1-b][1,3]oxazine-3-sulfonamide (Example 67) by replacing 6,7-dihydro-5H-pyrazolo[5,1-b][1,3]oxazine-3-sulfonamide with 6,6-dimethyl-5,7-dihydropyrazolo[5,1-b][1,3]oxazine-3-sulfonamide in Step 1. Single known stereoisomer obtained. $^1$H NMR (400 MHz, DMSO-$d_6$): δ=10.77 (s, 1H), 7.76-7.49 (m, 2H), 4.10 (s, 2H), 3.86 (s, 2H), 3.15-3.06 (m, 1H), 2.76-2.66 (m, 1H), 1.16 (d, J=7.0 Hz, 6H), 1.08 (d, J=6.9 Hz, 6H), 1.03 (s, 6H). MS: m/z 493.2 (M+H$^+$).

Example 80

(S)—N-((2,4-diisopropyl-6-(trifluoromethyl)pyridin-3-yl)carbamoyl)-6-methoxy-6,7-dihydro-5H-pyrazolo[5,1-b][1,3]oxazine-3-sulfonamide, ammonia (Example 80a)

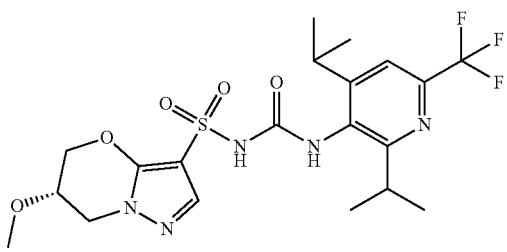 [SMILES: CO[C@@H]1COc2c(S(=O)(=O)NC(=O)Nc3c(C(C)C)cc(C(F)(F)F)nc3C(C)C)cnn2C1]

Step 1—Synthesis of 6-iodo-2,4-diisopropyl-3-nitropyridine

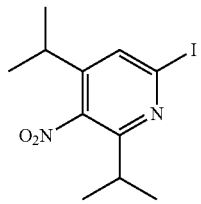 [SMILES: CC(C)c1cc(I)nc(C(C)C)c1[N+](=O)[O-]]

To a solution of 6-chloro-2,4-diisopropyl-3-nitropyridine (1 g, 4.12 mmol) and NaI (1.85 g, 12.36 mmol) in MeCN (10 mL) was added TMSCl (716 mg, 6.59 mmol) dropwise at room temperature under nitrogen atmosphere. The mixture was stirred at 80° C. for 2 hours. After cooling to room temperature, the reaction was quenched with water (50 mL) and extracted with EtOAc (20 mL×2). The combined organic phases were washed with brine (20 mL), dried over anhydrous Na$_2$SO$_4$, filtered and concentrated. The crude residue was purified by silica gel column (petroleum ether) to give 6-iodo-2,4-diisopropyl-3-nitropyridine (370 mg, yield: 27%) as a yellow solid. MS: m/z 334.9 (M+H$^+$).

Step 2—Synthesis of 2,4-diisopropyl-3-nitro-6-(trifluoromethyl)pyridine

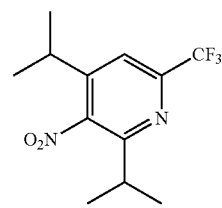 [SMILES: CC(C)c1cc(C(F)(F)F)nc(C(C)C)c1N]

To a solution of 6-iodo-2,4-diisopropyl-3-nitropyridine (880 mg, 2.63 mmol) in DMF (50 mL) was added methyl 2,2-difluoro-2-(fluorosulfonyl)acetate (3.54 g, 18.43 mmol), CuI (3.51 g, 18.43 mmol) at room temperature under a nitrogen atmosphere. The mixture was stirred at 70° C. for 16 hours. After cooling to room temperature, the reaction was quenched with water (50 mL). The resulting mixture was filtered and the filtrate was extracted with EtOAc (50 mL×2). The combined organic layers were washed with brine (20 mL), dried over anhydrous Na$_2$SO$_4$ and concentrated. The crude residue was purified by silica gel column (petroleum ether) to give 2,4-diisopropyl-3-nitro-6-(trifluoromethyl)pyridine (540 mg, yield: 74%) as a yellow solid. $^1$H NMR (400 MHz, CDCl$_3$): δ=7.57 (s, 1H), 2.95-2.84 (m, 1H), 2.82-2.70 (m, 1H), 1.28 (d, J=6.8, 6H), 1.25 (d, J=6.8, 6H). MS: m/z 276.9 (M+H$^+$).

Step 3—Synthesis of
2,4-diisopropyl-6-(trifluoromethyl)pyridin-3-amine

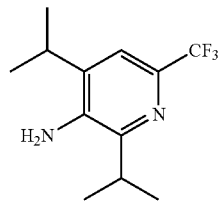

To a solution of 2,4-diisopropyl-3-nitro-6-(trifluoromethyl)pyridine (540 mg, 1.95 mmol) in EtOH (34 mL) was added 10% palladium (228 mg, 2.15 mmol) on carbon. The mixture was stirred at room temperature for 16 hours under hydrogen atmosphere (15 psi). The reaction was filtered through a plug of Celite. The filtrate was concentrated to give 2,4-diisopropyl-6-(trifluoromethyl)pyridin-3-amine (418 mg, yield: 87%) as a colorless liquid. $^1$H NMR (400 MHz, CDCl$_3$): δ=7.27 (s, 1H), 3.97 (s, 2H), 3.11-2.99 (m, 1H), 2.94-2.84 (m, 1H), 1.32 (d, J=6.8, 6H), 1.28 (d, J=6.8, 6H). MS: m/z 247.0 (M+H$^+$).

Step 4—Synthesis of 3-isocyanato-2,4-diisopropyl-6-(trifluoromethyl)pyridine

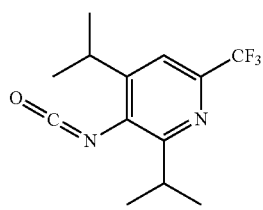 [SMILES: CC(C)c1cc(C(F)(F)F)nc(C(C)C)c1N=C=O]

To a solution of 2,4-diisopropyl-6-(trifluoromethyl)pyridin-3-amine (100 mg, 0.41 mmol) and triethylamine (0.08 mL, 0.61 mmol) in anhydrous THF (2 mL) was added triphosgene (60 mg, 0.20 mmol). The mixture was stirred at 70° C. for 1 hour. After cooling to room temperature, the mixture was filtered and concentrated to give 3-isocyanato-2,4-diisopropyl-6-(trifluoromethyl)pyridine (111 mg crude, purity: 82%) as a white solid.

Step 5—Synthesis of (S)—N-((2,4-diisopropyl-6-(trifluoromethyl)pyridin-3-yl)carbamoyl)-6-methoxy-6,7-dihydro-5H-pyrazolo[5,1-b][1,3]oxazine-3-sulfonamide, ammonia (Example 80)

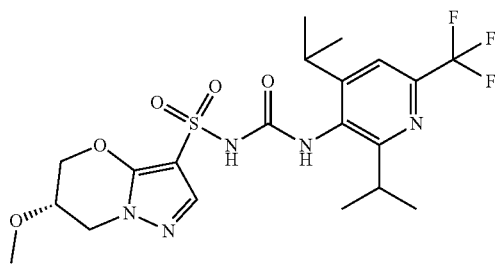 [SMILES: CO[C@@H]1COc2c(S(=O)(=O)NC(=O)Nc3c(C(C)C)cc(C(F)(F)F)nc3C(C)C)cnn2C1]

To a solution of (S)-6-methoxy-6,7-dihydro-5H-pyrazolo[5,1-b][1,3]oxazine-3-sulfonamide (78 mg, 0.33 mmol) in anhydrous THF (5 mL) and DMF (1 mL) was added NaH (60% in mineral oil, 16 mg, 0.40 mmol) at 0° C. under a nitrogen atmosphere. After 15 minutes, a solution of 3-isocyanato-2,4-diisopropyl-6-(trifluoromethyl)pyridine (109 mg, 0.40 mmol) in THF (2.5 mL) was added. The reaction mixture was warmed to room temperature and stirred for an additional 16 hours. The mixture was concentrated and the crude residue was purified by reverse phase chromatography (MeCN 22-52%/0.1% NH$_4$HCO$_3$ in water) to give (S)—N-((2,4-diisopropyl-6-(trifluoromethyl)pyridin-3-yl)carbamoyl)-6-methoxy-6,7-dihydro-5H-pyrazolo[5,1-b][1,3]oxazine-3-sulfonamide (98.6 mg, yield: 57%) as an ammonium salt. Single known stereoisomer obtained. $^1$H NMR (400 MHz, DMSO-d$_6$): δ=11.04 (s, 1H), 8.16 (s, 1H), 7.63-7.59 (m, 2H), 4.65 (d, J=11.6 Hz, 1H), 4.34 (d, J=11.6 Hz, 1H), 4.26-4.20 (m, 2H), 4.10-4.05 (m, 1H), 3.36 (s, 3H), 3.19-3.10 (m, 1H), 3.05-2.94 (m, 1H), 1.15-1.01 (m, 12H). MS: m/z 506.1 (M+H$^+$).

Example 81

Sodium N-((6-cyclopropoxy-2,4-diisopropylpyridin-3-yl)carbamoyl)-6,7-dihydro-5H-pyrazolo[5,1-b][1,3]oxazine-3-sulfonamide

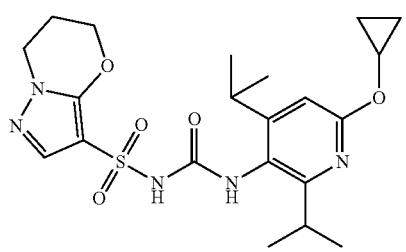 [SMILES: CC(C)c1cc(OC2CC2)nc(C(C)C)c1NC(=O)NS(=O)(=O)c1cnn2c1OCCC2]

Step 1—Synthesis of 6-cyclopropoxy-2,4-diisopropyl-3-nitropyridine

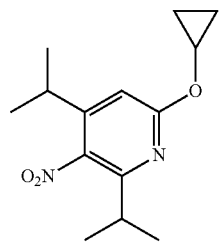

A mixture of 6-chloro-2,4-diisopropyl-3-nitropyridine (518 mg, 2.13 mmol) and Cs$_2$CO$_3$ (2.1 g, 6.4 mmol) in DMSO (26 mL) was added cyclopropanol (1.24 g, 21.34 mmol). The reaction mixture was stirred at 40° C. for 16 hours under a nitrogen atmosphere. After cooling to room temperature, the reaction mixture was diluted in water (50 mL). The aqueous layer was extracted with EtOAc (50 mL×3). The combined organic layers were washed with brine (100 mL×2), dried over Na$_2$SO$_4$, filtered and concentrated. The crude residue was purified by silica gel column (10% EtOAc in petroleum ether) to give 6-cyclopropoxy-2,4-diisopropyl-3-nitropyridine (116 mg, yield: 21%) as a yellow oil. MS: m/z 265.2 (M+H$^+$).

Step 2—Synthesis of 6-cyclopropoxy-2,4-diisopropylpyridin-3-amine

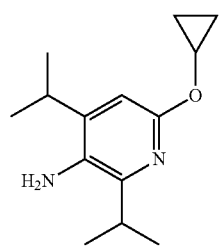 [SMILES: CC(C)c1cc(OC2CC2)nc(C(C)C)c1[N+](=O)[O-]]

A mixture of 6-cyclopropoxy-2,4-diisopropyl-3-nitropyridine (178 mg, 0.67 mmol), NH$_4$Cl (180 mg, 3.37 mmol) and Fe powder (188 mg, 3.37 mmol) in EtOH (10 mL) and water (2 mL) were stirred at 80° C. under a nitrogen atmosphere for 5 hours. After cooling to room temperature, the reaction mixture was filtered over a short pad of Celite. The Celite pad was washed with EtOAc (5 mL×3). The filtrate was concentrated under reduced pressure. The crude residue was purified by silica gel column (10-20% EtOAc/ petroleum ether) to give 6-cyclopropoxy-2,4-diisopropylpyridin-3-amine (110 mg, yield: 51%) as a white solid. $^1$H NMR (400 MHz, CDCl$_3$): δ=6.54 (s, 1H), 4.06-4.01 (m, 1H), 3.35 (s, 2H), 3.05-3.00 (m, 1H), 2.94-2.89 (m, 1H), 1.29 (d, J=6.8 Hz, 6H), 1.25 (d, J=6.8 Hz, 6H), 0.79-0.69 (m, 4H)

Step 3—Synthesis of 6-cyclopropoxy-3-isocyanato-2,4-diisopropylpyridine

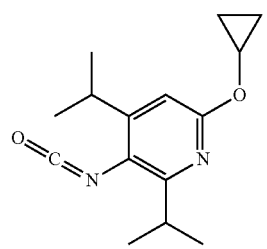 [SMILES: CC(C)c1cc(OC2CC2)nc(C(C)C)c1N=C=O]

To a solution of 6-cyclopropoxy-2,4-diisopropylpyridin-3-amine (110 mg, 0.47 mmol) and triethylamine (0.18 mL, 1.26 mmol) in THF (10 mL) was added triphosgene (56 mg, 0.19 mmol). The reaction mixture was stirred at 70° C. for 2 hours under a nitrogen atmosphere. After cooling to room temperature, the reaction mixture was filtered to remove the triethylammonium salts. The filtrate, containing 6-cyclopropoxy-3-isocyanato-2,4-diisopropylpyridine, was used directly as a THF solution in the next step.

Step 4—Synthesis of N-(((6-cyclopropoxy-2,4-diisopropylpyridin-3-yl)carbamoyl)-6,7-dihydro-5H-pyrazolo[5,1-b][1,3]oxazine-3-sulfonamide (Example 81)

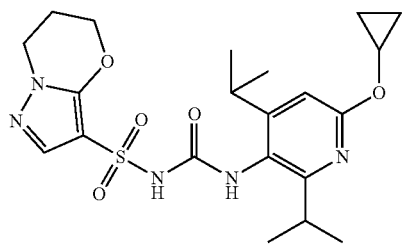 [SMILES: CC(C)c1cc(OC2CC2)nc(C(C)C)c1NC(=O)NS(=O)(=O)c1cnn2c1OCCC2]

To a solution of 6-cyclopropoxy-3-isocyanato-2,4-diisopropylpyridine (109 mg, 0.42 mmol) in THF (10 mL) and DMF (2 mL) was added NaH (60% in mineral oil, 25 mg, 0.63 mmol) at 0° C. under an atmosphere of nitrogen. After 30 minutes, a solution of 6,7-dihydro-5H-pyrazolo[5,1-b][1,3]oxazine-3-sulfonamide (85 mg, 0.42 mmol) in THF was added. The reaction mixture was allowed warm to room temperature stirred for 16 hours. The reaction mixture was concentrated and the crude residue was purified by reverse phase chromatography (MeCN 23-53/10 mM NH$_4$HCO$_3$ in water) to give N-(((6-cyclopropoxy-2,4-diisopropylpyridin-3-yl)carbamoyl)-6,7-dihydro-5H-pyrazolo[5,1-b][1,3]oxazine-3-sulfonamide (110 mg, yield: 54%) as a sodium salt. $^1$H NMR (400 MHz, DMSO-d$_6$) δ=7.67 (s, 1H), 7.54 (s, 1H), 6.55 (s, 1H), 4.42-4.40 (m, 2H), 4.16-4.14 (m, 1H), 4.11-4.08 (m, 2H), 3.04-2.98 (m, 1H), 2.87-2.84 (m, 1H), 2.20-2.18 (m, 2H), 1.05 (d, J=5.2 Hz, 12H), 0.76-0.71 (m, 2H), 0.64-0.60 (m, 2H). MS: m/z 464.1 (M+H$^+$).

Example 82

N-((2,4-diisopropyl-6-(trifluoromethyl)pyridin-3-yl)carbamoyl)-6,6-dimethyl-6,7-dihydro-5H-pyrazolo[5,1-b][1,3]oxazine-3-sulfonamide

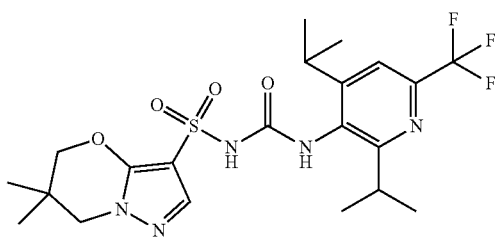 [SMILES: CC(C)c1cc(C(F)(F)F)nc(C(C)C)c1NC(=O)NS(=O)(=O)c1cnn2c1OCC(C)(C)C2]

N-((2,4-diisopropyl-6-(trifluoromethyl)pyridin-3-yl)carbamoyl)-6,6-dimethyl-6,7-dihydro-5H-pyrazolo[5,1-b][1,3]oxazine-3-sulfonamide (purified by reverse phase chromatography HPLC (22-52% MeCN/0.1% NH$_4$HCO$_3$ in water), 59.6 mg, yield: 33%) was prepared by using the general procedure described for the preparation of (S)—N-((2,4-diisopropyl-6-(trifluoromethyl)pyridin-3-yl)carbamoyl)-6-methoxy-6,7-dihydro-5H-pyrazolo[5,1-b][1,3]oxazine-3-sulfonamide (Example 80) by replacing (S)-6-methoxy-6,7-dihydro-5H-pyrazolo[5,1-b][1,3]oxazine-3-sulfonamide with 6,6-dimethyl-5,7-dihydropyrazolo[5,1-b][1,3]oxazine-3-sulfonamide in Step 5. $^1$H NMR (400 MHz, DMSO-d$_6$): δ=11.02 (s, 1H), 8.15 (s, 1H), 7.63-7.61 (m, 2H), 4.13 (s, 2H), 3.88 (s, 2H), 3.23-3.07 (m, 1H), 3.04-2.90 (m, 1H), 1.20-1.05 (m, 12H), 1.04 (s, 6H). MS: m/z 504.1 (M+H$^+$).

Exemplary compounds and chemical data are also provided in Table A1.

TABLE A1

| Compound | Name | m/z [M + 1] | $^1$H NMR data |
|---|---|---|---|
|  | N-(((1R,3S,5r)-adamantan-2-yl)carbamoyl)-6,7-dihydro-5H-pyrazolo[5,1-b][1,3]oxazine-3-sulfonamide | 381 |  |
|  | N-((9H-fluoren-9-yl)carbamoyl)-6,7-dihydro-5H-pyrazolo[5,1-b][1,3]oxazine-3-sulfonamide | 411 |  |
|  | N-((2-methyl-2,3-dihydro-1H-inden-1-yl)carbamoyl)-6,7-dihydro-5H-pyrazolo[5,1-b][1,3]oxazine-3-sulfonamide | 377 |  |
|  | N-((2,6-dimethylpiperidin-1-yl)carbamoyl)-6,7-dihydro-5H-pyrazolo[5,1-b][1,3]oxazine-3-sulfonamide | 358 |  |

TABLE A1-continued

| Compound | Name | m/z [M + 1] | ¹H NMR data |
|---|---|---|---|
| | N-((5-methyl-3-phenylisoxazol-4-yl)carbamoyl)-6,7-dihydro-5H-pyrazolo[5,1-b][1,3]oxazine-3-sulfonamide | 404 | |
| | N-(chroman-4-ylcarbamoyl)-6,7-dihydro-5H-pyrazolo[5,1-b][1,3]oxazine-3-sulfonamide | 379 | |
| | N-((2-phenylimidazo[1,2-a]pyridin-3-yl)carbamoyl)-6,7-dihydro-5H-pyrazolo[5,1-b][1,3]oxazine-3-sulfonamide | 439 | |
| | N-((1-phenylcyclopropyl)carbamoyl)-6,7-dihydro-5H-pyrazolo[5,1-b][1,3]oxazine-3-sulfonamide | 363 | |
| | N-((1-phenylcycloheptyl)carbamoyl)-6,7-dihydro-5H-pyrazolo[5,1-b][1,3]oxazine-3-sulfonamide | 419 | |
| | N-(azepan-1-ylcarbamoyl)-6,7N-(azepan-1-ylcarbamoyl)-6,7-dihydro-5H-pyrazolo[5,1-b][1,3]oxazine-3-sulfonamide | 344 | |

TABLE A1-continued

| Compound | Name | m/z [M + 1] | ¹H NMR data |
|---|---|---|---|
| | N-(benzhydrylcarbamoyl)-6,7-dihydro-5H-pyrazolo[5,1-b][1,3]oxazine-3-sulfonamide | 413 | |
| | N-((4-chloro-6-isopropylpyrimidin-2-yl)carbamoyl)-6,7-dihydro-5H-pyrazolo[5,1-b][1,3]oxazine-3-sulfonamide | 401 | |
| | N-((4-phenyl-6-(trifluoromethyl)pyrimidin-2-yl)carbamoyl)-6,7-dihydro-5H-pyrazolo[5,1-b][1,3]oxazine-3-sulfonamide | 469 | |
| | N-((4-methoxy-6-methylpyrimidin-2-yl)carbamoyl)-6,7-dihydro-5H-pyrazolo[5,1-b][1,3]oxazine-3-sulfonamide | 369 | |
| | N-((3-bromo-6-methylpyridin-2-yl)carbamoyl)-6,7-dihydro-5H-pyrazolo[5,1-b][1,3]oxazine-3-sulfonamide | 417 | |
| | N-((4-cyclopropyl-6-methylpyrimidin-2-yl)carbamoyl)-6,7-dihydro-5H-pyrazolo[5,1-b][1,3]oxazine-3-sulfonamide | 379 | |

TABLE A1-continued

| Compound | Name | m/z [M + 1] | ¹H NMR data |
|---|---|---|---|
| | N-((4,6-di-tert-butylpyrimidin-2-yl)carbamoyl)-6,7-dihydro-5H-pyrazolo[5,1-b][1,3]oxazine-3-sulfonamide | 437 | |
| | N-((3-phenyl-6,7-dihydro-5H-cyclopenta[c]pyridin-1-yl)carbamoyl)-6,7-dihydro-5H-pyrazolo[5,1-b][1,3]oxazine-3-sulfonamide | 440 | |
| | N-((4-methyl-5,6,7,8-tetrahydroquinazolin-2-yl)carbamoyl)-6,7-dihydro-5H-pyrazolo[5,1-b][1,3]oxazine-3-sulfonamide | 393 | |
| | N-((4,6-dimethylpyrimidin-2-yl)carbamoyl)-6,7-dihydro-5H-pyrazolo[5,1-b][1,3]oxazine-3-sulfonamide | 353 | |
| | N-((3,5-diisopropyl-1-methyl-1H-pyrazol-4-yl)carbamoyl)-6,7-dihydro-5H-pyrazolo[5,1-b][1,3]oxazine-3-sulfonamide | 411 | |
| | N-((3,5-di(prop-1-en-2-yl)pyridin-4-yl)carbamoyl)-6,7-dihydro-5H-pyrazolo[5,1-b][1,3]oxazine-3-sulfonamide | 403.8 | (400 MHz, DMSO-$d_6$): δ = 8.26 (s, 2H), 7.88 (s, 1H), 7.51 (s, 1H), 5.12 (s, 2H), 4.89 (s, 2H), 4.41 (t, J = 4.8 Hz, 2H), 4.11 (t, J = 5.6 Hz, 2H), 2.21-2.15 (m, 2H), 1.92 (s, 6H). |

TABLE A1-continued

| Compound | Name | m/z [M + 1] | ¹H NMR data |
|---|---|---|---|
| | N-((3,5-diisopropylpyridin-4-yl)carbamoyl)-6,7-dihydro-5H-pyrazolo[5,1-b][1,3]oxazine-3-sulfonamide | 408.1 | (400 MHz, DMSO-d₆): δ = 8.33 (s, 2H), 7.83 (s, 1H), 7.50 (s, 1H), 4.39 (t, J = 4.0 Hz, 2H), 4.09 (t, J = 6.0 Hz, 2H), 2.97-2.94 (m, 2H), 2.19-2.15 (m, 2H), 1.12 (d, J = 6.8 Hz, 12H). |
| | N-((8-oxo-2,3,5,6,7,8-hexahydro-1H-pyrrolo[1,2-a]indol-9-yl)carbamoyl)-6,7-dihydro-5H-pyrazolo[5,1-b][1,3]oxazine-3-sulfonamide | 419.8 | (400 MHz, DMSO-d₆): δ = 11.17 (brs, 1H), 8.56 (s, 1H), 7.62 (s, 1H), 4.43 (t, J = 5.2 Hz, 2H), 4.09 (t, J = 5.6 Hz, 2H), 3.82 (t, J = 6.8 Hz, 2H), 2.84 (t, J = 7.6 Hz, 2H), 2.67 (t, J = 6.0 Hz, 2H), 2.34-2.26 (m, 4H), 2.21-2.18 (m, 2H), 1.99-1.95 (m, 2H). |
| | N-((2,4-diisopropyl-6-methoxypyridin-3-yl)carbamoyl)-6,7-dihydro-5H-pyrazolo[5,1-b][1,3]oxazine-3-sulfonamide | 438.1 | (400 MHz, DMSO-d₆): δ = 10.71 (brs, 1H), 7.70 (brs, 1H), 7.59 (s, 1H), 6.51 (s, 1H), 4.45 (t, J = 4.8 Hz, 2H), 4.11 (t, J = 5.6 Hz, 2H), 3.81 (s, 3H), 3.01-2.94 (m, 1H), 2.85-2.78 (m, 1H), 2.22-2.18 (m, 2H), 1.22-0.94 (m, 12H). |
| | N-((2,4-diisopropylpyridin-3-yl)carbamoyl)-6,7-dihydro-5H-pyrazolo[5,1-b][1,3]oxazine-3-sulfonamide | 407.9 | (400 MHz, DMSO-d₆): δ = 10.81 (brs, 1H), 8.35 (d, J = 4.8 Hz, 1H), 7.88 (s, 1H), 7.58 (s, 1H), 7.14 (d, J = 4.8 Hz, 1H), 4.44 (t, J = 4.8 Hz, 2H), 4.11 (t, J = 6.0 Hz, 2H), 3.11-3.04 (m, 1H), 2.94-2.88 (m, 1H), 2.23-2.18 (m, 2H), 1.06 (d, J = 6.0 Hz, 12H). |
| | N-((6-chloro-2,4-diisopropylpyridin-3-yl)carbamoyl)-6,7-dihydro-5H-pyrazolo[5,1-b][1,3]oxazine-3-sulfonamide | 441.8 | (400 MHz, DMSO-d₆): δ = 7.94 (s, 1H), 7.55 (s, 1H), 7.23 (s, 1H), 4.42 (t, J = 4.8 Hz, 2H), 4.10 (t, J = 6.0 Hz, 2H), 3.08-3.04 (m, 1H), 2.92-2.89 (m, 1H), 2.20-2.17 (m, 2H), 1.15-1.00 (m, 12H). |

TABLE A1-continued

| Compound | Name | m/z [M + 1] | ¹H NMR data |
|---|---|---|---|
| | N-((1,3,5-triisopropyl-1H-pyrazol-4-yl)carbamoyl)-6,7-dihydro-5H-pyrazolo[5,1-b][1,3]oxazine-3-sulfonamide | 439 | |
| | N-((1-ethyl-3,5-diisopropyl-1H-pyrazol-4-yl)carbamoyl)-6,7-dihydro-5H-pyrazolo[5,1-b][1,3]oxazine-3-sulfonamide | 425 | |
| | N-((1-(cyclopropylmethyl)-3,5-diisopropyl-1H-pyrazol-4-yl)carbamoyl)-6,7-dihydro-5H-pyrazolo[5,1-b][1,3]oxazine-3-sulfonamide | 451 | |
| | N-((1,3-di-tert-butyl-1H-pyrazol-5-yl)carbamoyl)-6,7-dihydro-5H-pyrazolo[5,1-b][1,3]oxazine-3-sulfonamide | 425 | |
| | sodium (S)-((2,4-diisopropyl-6-methoxypyridin-3-yl)carbamoyl)((6-methoxy-6,7-dihydro-5H-pyrazolo[5,1-b][1,3]oxazin-3-yl)sulfonyl)amide | 467.8 | (400 MHz, DMSO-d$_6$): δ = 7.33 (s, 1H), 7.29 (s, 1H), 6.38 (s, 1H), 4.47 (d, J = 11.2 Hz, 1H), 4.17-4.10 (m, 3H), 3.95 (s, 1H), 3.78 (s, 3H), 3.34 (overlap, 3H), 3.22-3.16 (m, 1H), 3.04-2.98 (m, 1H), 1.05-1.01 (m, 12H). |

TABLE A1-continued

| Compound | Name | m/z [M + 1] | ¹H NMR data |
|---|---|---|---|
| | N-((3,5-diisopropyl-1-methyl-1H-pyrazol-4-yl)carbamoyl)-6-methoxy-6,7-dihydro-5H-pyrazolo[5,1-b][1,3]oxazine-3-sulfonamide | 441 | |
| | (R)-N-((1-ethyl-3,5-diisopropyl-1H-pyrazol-4-yl)carbamoyl)-6-methoxy-6,7-dihydro-5H-pyrazolo[5,1-b][1,3]oxazine-3-sulfonamide | 455 | |
| | N-((3-(N-((2,4-diisopropyl-6-methoxypyridin-3-yl)carbamoyl)sulfamoyl)-6,7-dihydro-5H-pyrazolo[5,1-b][1,3]oxazin-6-yl)methyl)acetamide | 509.2 | (400 MHz, DMSO-d₆): δ = 8.11 (t, J = 4.8 Hz, 1H), 7.32 (s, 1H), 7.25 (s, 1H), 6.38 (s, 1H), 4.31 (d, J = 10.0 Hz, 1H), 4.10 (dd, J = 12.4, 5.2 Hz, 1H), 4.00 (t, J = 10.0 Hz, 1H), 3.82-3.74 (m, 4H), 3.20-3.10 (m, 3H), 3.04-2.94 (m, 1H), 2.40-2.30 (m, 1H), 1.83 (s, 3H), 1.10-0.96 (m, 12H). |
| | (S)-N-((2,4-diisopropyl-6-methoxypyridin-3-yl)carbamoyl)-6-(methylamino)-6,7-dihydro-5H-pyrazolo[5,1-b][1,3]oxazine-3-sulfonamide | 465.2 | (400 MHz, DMSO-d₆): δ = 7.33 (s, 1H), 7.31 (s, 1H), 6.39 (s, 1H), 4.26 (dd, J = 10.8, 2.0 Hz, 1H), 4.15 (dd, J = 12.4, 4.8 Hz, 1H), 4.05 (dd, J = 10.8, 5.2 Hz, 1H), 3.83-3.77 (m, 4H), 3.21-3.15 (m, 1H), 3.10-2.98 (m, 2H), 2.33 (d, J = 6.0 Hz, 3H), 2.02-1.99 (m, 1H), 1.10-0.90 (m, 12H). |
| | N-((1-isopropyl-3-methyl-1H-pyrazol-5-yl)carbamoyl)-6,7-dihydro-5H-pyrazolo[5,1-b][1,3]oxazine-3-sulfonamide | 368.8 | (400 MHz, DMSO-d₆): δ = 7.99 (s, 1H), 7.34 (s, 1H), 5.76 (s, 1H), 4.40-4.34 (m, 1H), 4.29 (t, J = 4.8 Hz, 2H), 4.03 (t, J = 6.4 Hz, 2H), 2.15-2.09 (m, 2H), 2.03 (s, 3H), 1.22 (d, J = 6.4 Hz, 6H). |

TABLE A1-continued

| Compound | Name | m/z [M + 1] | ¹H NMR data |
|---|---|---|---|
| | N-((2-isopropyl-2,4,5,6-tetrahydrocyclopenta[c]pyrazol-3-yl)carbamoyl)-6,7-dihydro-5H-pyrazolo[5,1-b][1,3]oxazine-3-sulfonamide | 395 | |
| | N-((6-cyclopropyl-2,4-diisopropylpyridin-3-yl)carbamoyl)-6,7-dihydro-5H-pyrazolo[5,1-b][1,3]oxazine-3-sulfonamide | 448 | |
| | 6,6-dimethyl-N-((6,7,8,9-tetrahydro-5H-benzo[7]annulen-5-yl)carbamoyl)-6,7-dihydro-5H-pyrazolo[5,1-b][1,3]oxazine-3-sulfonamide | 419 | (500 MHz, DMSO-$d_6$): δ = 7.52 (br.s, 1H), 7.51 (s, 1H), 7.14-7.10 (m, 4H), 6.75-6.70 (m, 1H), 4.09 (s, 2H), 4.08-4.02 (m, 1H), 3.87 (s, 2H), 2.83-2.73 (m, 2H), 1.84-1.59 (m, 5H), 1.48-1.38 (m, 1H), 1.05 (s, 6H). MS: m/z (M + H+). |
| | N-((2,4-diisopropyl-6-methoxypyridin-3-yl)carbamoyl)-6,6-dimethyl-6,7-dihydro-5H-pyrazolo[5,1-b][1,3]oxazine-3-sulfonamide | 466 | (400 MHz, DMSO-$d_6$): δ =7.39 (s, 1H), 7.34 (s, 1H), 6.39 (s, 1H), 3.94 (s, 2H), 3.78 (s, 5H), 3.16-3.13 (m, 1H), 2.98-2.97 (m, 1H), 1.10-0.90 (m, 18H) |
| | N-((2,4-diisopropyl-6-methylpyridin-3-yl)carbamoyl)-6,7-dihydro-5H-pyrazolo[5,1-b][1,3]oxazine-3-sulfonamide | 422.2 | (400 MHz, DMSO-$d_6$): δ =7.54 (s, 1H), 7.41 (s, 1H), 6.90 (s, 1H), 4.31-4.26 (m, 2H), 4.06 (t, J = 6.0 Hz, 2H), 3.15-3.10 (m, 1H), 3.01-2.90 (m, 1H), 2.37 (s, 3H), 2.12-2.09 (m, 2H), 1.12 (d, J = 6.4 Hz, 12H). |

TABLE A1-continued

| Compound | Name | m/z [M + 1] | ¹H NMR data |
|---|---|---|---|
|  | N-((6-cyano-2,4-diisopropylpyridin-3-yl)carbamoyl)-6,7-dihydro-5H-pyrazolo[5,1-b][1,3]oxazine-3-sulfonamide | 433.2 | (400 MHz, DMSO-$d_6$): δ =7.71 (s, 2H), 7.30 (s, 1H), 4.26 (t, J = 4.8 Hz, 2H), 4.03 (t, J = 6.0 Hz, 2H), 3.32 (overlap, 1H), 3.21-3.09 (m, 1H), 2.12-2.09 (m, 2H), 1.10-1.05 (m, 12H). |
|  | Sodium ((6,7-dihydro-5H-pyrazolo[5,1-b][1,3]oxazin-3-yl)sulfonyl)((6-ethoxy-2,4-diisopropylpyridin-3-yl)carbamoyl)amide | 452.2 | (400 MHz, DMSO-$d_6$): δ = 7.53 (s, 1H), 7.49 (s, 1H), 6.43 (s, 1H), 4.38 (t, J = 4.8 Hz, 2H), 4.27 (q, J = 6.8 Hz, 2H), 4.08 (t, J = 6.0 Hz, 2H), 3.05-3.02 (m, 1H), 2.89-2.84 (m, 1H), 2.19-2.17 (m, 2H), 1.29 (t, J = 6.8 Hz, 3H), 1.10-0.90 (m, 12H). |
|  | Sodium ((6,7-dihydro-5H-pyrazolo[5,1-b][1,3]oxazin-3-yl)sulfonyl)((6-(dimethylamino)-2,4-diisopropylpyridin-3-yl)carbamoyl)amide | 451.2 | (400 MHz, DMSO-$d_6$): δ = 7.56 (s, 1H), 7.45 (s, 1H), 6.26 (s, 1H), 4.42 (t, J = 4.8 Hz, 2H), 4.10 (t, J = 6.0 Hz, 2H), 2.99 (s, 6H), 2.96-2.91 (m, 1H), 2.81-2.77 (m, 1H), 2.22-2.18 (m, 2H), 1.05-0.95 (m, 12H). |
|  | (S)-N-((2,4-diisopropyl-6-methoxypyridin-3-yl)carbamoyl)-6-(dimethylamino)-6,7-dihydro-5H-pyrazolo[5,1-b][1,3]oxazine-3-sulfonamide | 481.2 | (400 MHz, DMSO-$d_6$): δ = 7.40 (s, 1H), 7.32 (s, 1H), 6.45 (s, 1H), 4.40 (d, J = 10.0 Hz, 1H), 4.32-4.26 (m, 1H), 4.21 (dd, J = 12.4, 4.8 Hz, 1H), 4.10 (dd, J = 12.4, 6.0 Hz, 1H), 3.84 (s, 3H), 3.28-3.18 (m, 1H), 3.12-3.02 (m, 1H), 2.94-2.86 (m, 1H), 2.32 (s, 6H), 1.20-1.00 (m, 12H). |
|  | N-((2,4-diisopropyl-6-(methylamino)pyridin-3-yl)carbamoyl)-6,7-dihydro-5H-pyrazolo[5,1-b][1,3]oxazine-3-sulfonamide | 437.2 | (400 MHz, DMSO-$d_6$): δ = 10.48 (s, 1H), 7.57 (s, 1H), 7.43 (s, 1H), 6.20-6.18 (m, 1H), 6.11 (s, 1H), 4.43 (t, J = 5.2 Hz, 2H), 4.11 (t, J = 6.0 Hz, 2H), 2.94-2.82 (m, 1H), 2.77-2.70 (m, 4H), 2.24-2.17 (m, 2H), 1.10-0.90 (m, 12H). |

TABLE A1-continued

| Compound | Name | m/z [M + 1] | ¹H NMR data |
|---|---|---|---|
| 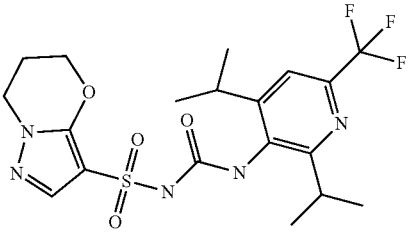 [SMILES: CC(C)c1cc(C(F)(F)F)nc(C(C)C)c1NC(=O)NS(=O)(=O)c1cnn2c1OCCC2] | N-((2,4-diisopropyl-6-(trifluoromethyl)pyridin-3-yl)carbamoyl)-6,7-dihydro-5H-pyrazolo[5,1-b][1,3]oxazine-3-sulfonamide | 476.1 | (400 MHz, DMSO-$d_6$): δ = 10.98 (brs, 1H), 8.13 (s, 1H), 7.60 (s, 1H), 7.58 (s, 1H), 4.43 (t, J = 4.8 Hz, 2H), 4.10 (t, J = 6.0 Hz, 2H), 3.16-3.13 (m, 1H), 3.02-2.98 (m, 1H), 2.23-2.17 (m, 2H), 1.16-1.03 (m, 12H). |
| 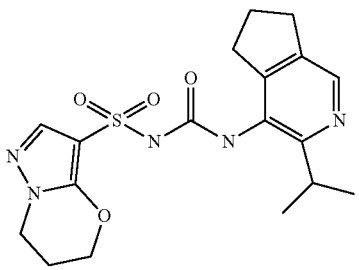 [SMILES: CC(C)c1ncc2c(c1NC(=O)NS(=O)(=O)c1cnn3c1OCCC3)CCC2] | N-((3-isopropyl-6,7-dihydro-5H-cycloenta[c]pyridin-4-yl)carbamoyl)-6,7-dihydro-5H-pyrazolo[5,1-b][1,3]oxazine-3-sulfonamide | 406 | |
| 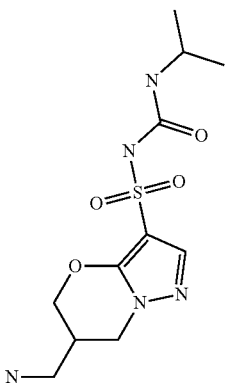 [SMILES: CC(C)NC(=O)NS(=O)(=O)c1cnn2c1OCC(CN)C2] | 6-(aminomethyl)-N-(isopropylcarbamoyl)-6,7-dihydro-5H-pyrazolo[5,1-b][1,3]oxazine-3-sulfonamide | 318 | (500 MHz, DMSO d6): δ = 7.72 (br.s, 3H), 7.59 (s, 1H), 6.35 (s, 1H), 4.61 (dd, J = 11.0, 2.9 Hz, 1H), 4.31-4.27 (m, 2H), 4.02 (dd, J = 12.4, 7.8 Hz, 1H), 3.66-3.59 (m, 1H), 2.91-2.84 (m, 2H), 2.69-2.62 (m, 1H), 1.03 (d, J = 6.5 Hz, 6H). |

Biological Testing Methods

Abbreviations

PBMCs: peripheral blood mononuclear cells
KCs: Kupffer cells
FBS: fetal bovine serum
LPS: lipopolysaccharides
NLRP3 Activation and Inhibitory Assays Some of the following assays were used to determine the inhibitory activity of the compounds on the NLRP3 inflammasome using a common inflammasome activation stimuli-nigericin.

Example B1: Cell Culture

Human peripheral blood mononuclear cells (PBMCs), consisting of lymphocytes (T, B and NK cells), monocytes and dendritic cells, are freshly isolated from human peripheral blood from healthy donors. Cells are obtained through an IRB approved donor program by iXCells Biotechnologies where all the donors are tested for bacterial and viral infections. Cells are purified from peripheral blood using ficoll gradient centrifugation.

Human Kupffer cells (KCs), specialized liver macrophages residing in the space of Disse, are obtained by gradient isolation from liver specimens harvested postmortem by Samsara Sciences. Cells are obtained through an IRB approved donor program by Samsara Sciences and all donors tested negative for bacterial and viral infections.

Example B2: NLRP3 Inflammasome Activation Assays

Fresh or cryopreserved PMBCs are seeded in V-bottom 96-well plate at 0.5-1×10⁵ cells per well and incubated overnight at 37° C. with 5% $CO_2$ in RPMI 1640 medium with GlutaMAX supplement, 4.5 g/L D-glucose, 10% Fetal Bovine Serum (FBS), 100 mM Sodium Pyruvate, 1% Penicillin/Streptomycin, 10 mM HEPES and 0.05 mM of P-mercaptoethanol. Freshly isolated or cryopreserved KCs cells are seeded in flat-bottom 96-well plates at 0.6-1.5×10⁵ cells/well and incubated overnight at 37° C., 5% $CO_2$ in RPMI 1640 Medium with GlutaMAX supplement, FBS, 1% Penicillin/Streptomycin and 10 mM HEPES. The following day, the cells are primed with 100 ng/mL of lipopolysaccharides (LPS; Sigma Aldrich) in FBS-free RPMI 1640 for 3 h. After the priming step, the media is removed and PBMCs are pre-incubated with serial concentrations of test compounds (0.00017-10 uM) or vehicle (DMSO) for 30 min in FBS-free media prior to addition of the NLRP3 activator. Cells are then stimulated with 10 μM Nigericin (Sigma Aldrich; InvivoGen) for 1.5 h. Plates were centrifuged at 1,500 rpm for 3 minutes to pellet cells and supernatant was transferred into new plates for subsequent experiments.
Measurement of Cytokines/Assessment of NLRP3 Inflammasome Activity For ELISA assays cells are seeded into 96-well plates. Post study, supernatants are removed and the levels of mature IL-1β, IL18 and TNFα (Quantikine ELISA, R&D systems) are measured in cell conditioned media by ELISA according to manufacturer's instructions.

Example B3: CTG (CellTitre-Glo) Assay

Viability of compound treated cells is measured using CellTiter-Glo® assay (Promega, Madison, Wis.) that measures the ATP content of cells which is proportional to the number of live cells within a well. This is a counter-screen to establish that the reduction of IL-1β levels in LPS and nigericin stimulated and compound treated cells is not due to cytotoxicity, but rather through the inhibition of the inflammasome pathway. Compounds inhibiting NRLP3 inflammasome activation ultimately increase the viability of LPS and nigericin stimulated cells by blocking NLRP3 mediated pyroptosis that would otherwise lead to cell lysis.

Example B4: TNF-α

TNFα levels of LPS and nigericin stimulated cells are measured by HTRF assay (Cisbio, Bedford, Mass.). Inflammasome pathway selective compounds do not inhibit TNFα production that is solely dependent on LPS stimulation and proceeds through the TLR4/NFκB pathway. Measuring TNFalpha production also serves as a technical counter-screen to eliminate compounds that interfere with the HTRF reagents. Thus compounds that inhibit both IL-1β and TNFα levels are triaged for either being non-selective for inflammasome or interfering with the HTRF readout.

Assay Results

Results of certain compounds are shown below. For the table below,
A: <100 nM; B: 100 nM-1 μM; C: 1-10 μM; D: >10 μM

| Compound | IL-1B pIC50 (μM) | CTG pIC50 | TNFa pIC50 |
|---|---|---|---|
|  | D |  |  |
|  | D |  |  |
|  | C | D |  |
|  | D |  |  |

| Compound | IL-1B pIC50 (μM) | CTG pIC50 | TNFa pIC50 |
|---|---|---|---|
| | D | | |
| | D | | |
| | D | | |
| | D | D | |
| | D | | |
| | D | | |

-continued

| Compound | IL-1B pIC50 (μM) | CTG pIC50 | TNFa pIC50 |
|---|---|---|---|
| (structure) | D | D | |
| (structure) | D | | |
| (structure) | D | | |
| (structure) | D | | |
| (structure) | D | | |
| (structure) | D | | |

-continued
| Compound | IL-1B pIC50 (μM) | CTG pIC50 | TNFa pIC50 |
|---|---|---|---|
| 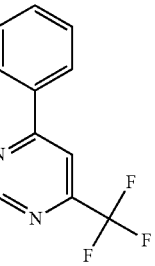 | D | | |
| 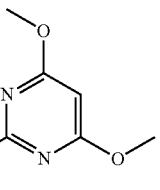 | D | | |
| 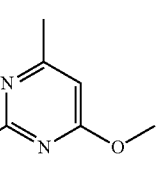 | D | | |
| 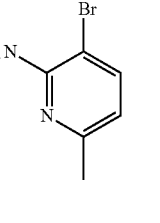 | D | | |
| 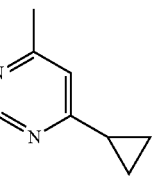 | D | | |
| 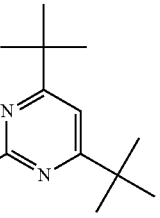 | D | | |

| Compound | IL-1B pIC50 (μM) | CTG pIC50 | TNFa pIC50 |
|---|---|---|---|
| [structure] | D | | |
| [structure] | D | | |
| [structure] | D | | |
| [structure] | C | | |
| [structure] | D | | |
| [structure] | B | B | |

-continued
| Compound | IL-1B pIC50 (μM) | CTG pIC50 | TNFa pIC50 |
|---|---|---|---|
| 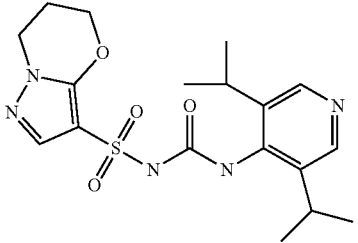 [SMILES: CC(C)c1cncc(C(C)C)c1NC(=O)NS(=O)(=O)c1cnn2c1OCCC2] | C | A | |
| 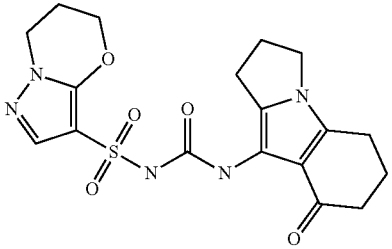 [SMILES: O=C(Nc1c2c(n3c1CCC3)CCCC2=O)NS(=O)(=O)c1cnn2c1OCCC2] | D | | |
| 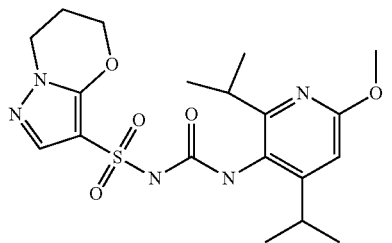 [SMILES: COc1cc(C(C)C)c(NC(=O)NS(=O)(=O)c2cnn3c2OCCC3)c(C(C)C)n1] | B | B | |
| 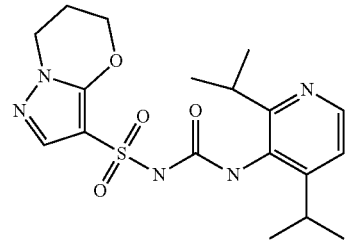 [SMILES: CC(C)c1ccnc(C(C)C)c1NC(=O)NS(=O)(=O)c1cnn2c1OCCC2] | C | C | |
| 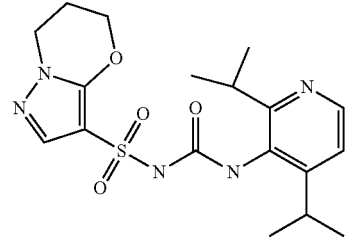 [SMILES: CC(C)c1ccnc(C(C)C)c1NC(=O)NS(=O)(=O)c1cnn2c1OCCC2] | C | B | |
| 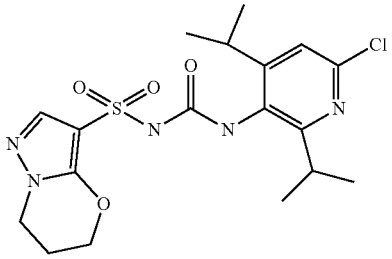 [SMILES: CC(C)c1cc(Cl)nc(C(C)C)c1NC(=O)NS(=O)(=O)c1cnn2c1OCCC2] | B | B | |

-continued

| Compound | IL-1B pIC50 (μM) | CTG pIC50 | TNFa pIC50 |
|---|---|---|---|
| [structure] | C | C | |
| [structure] | C | B | |
| [structure] | B | B | |
| [structure] | D | | |
| [structure] | B | B | |

| Compound | IL-1B pIC50 (μM) | CTG pIC50 | TNFa pIC50 |
|---|---|---|---|
| 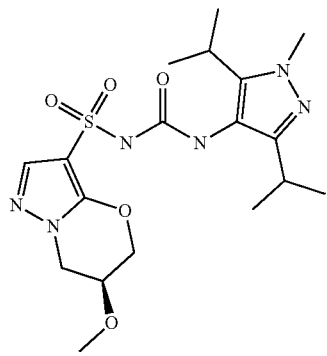 [SMILES: CO[C@@H]1COc2c(S(=O)(=O)NC(=O)Nc3c(C(C)C)nn(C)c3C(C)C)cnn2C1] | | C | B |
| 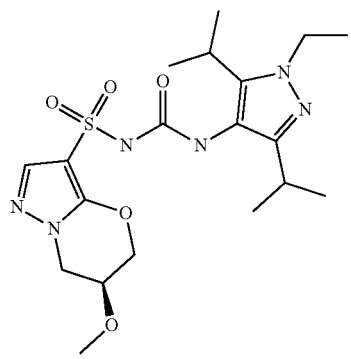 [SMILES: CCn1nc(C(C)C)c(NC(=O)NS(=O)(=O)c2cnn3c2OC[C@@H](OC)C3)c1C(C)C] | | C | B |
| 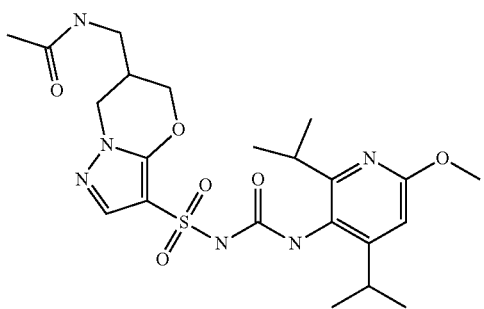 [SMILES: COc1cc(C(C)C)c(NC(=O)NS(=O)(=O)c2cnn3c2OCC(CNC(C)=O)C3)c(C(C)C)n1] | | C | C |
| 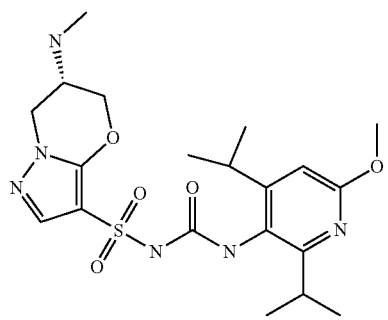 [SMILES: CN[C@@H]1COc2c(S(=O)(=O)NC(=O)Nc3c(C(C)C)cc(OC)nc3C(C)C)cnn2C1] | | B | A |

-continued
| Compound | IL-1B pIC50 (μM) | CTG pIC50 | TNFa pIC50 |
|---|---|---|---|
| 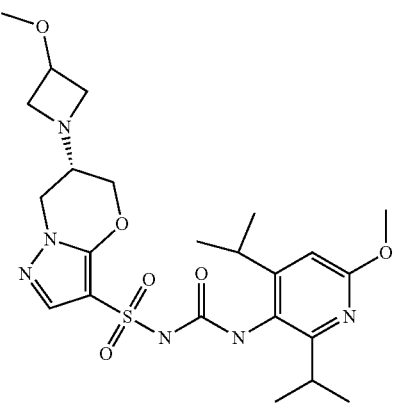 | A | B | |
| 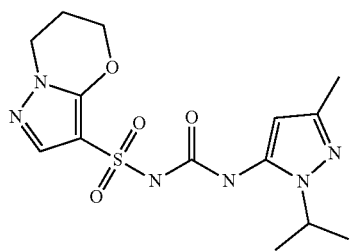 [SMILES: Cc1cc(NC(=O)NS(=O)(=O)c2cnn3c2OCCC3)n(C(C)C)n1] | | D | |
| 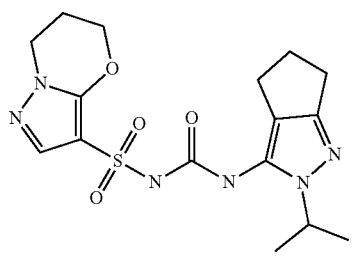 [SMILES: CC(C)n1nc2c(c1NC(=O)NS(=O)(=O)c1cnn3c1OCCC3)CCC2] | C | D | |
| 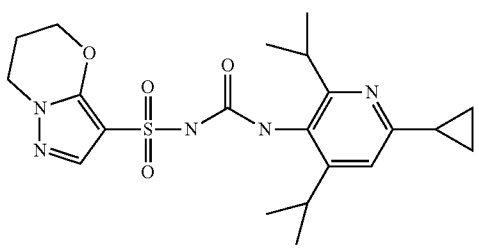 [SMILES: CC(C)c1cc(C2CC2)nc(C(C)C)c1NC(=O)NS(=O)(=O)c1cnn2c1OCCC2] | B | B | |
| 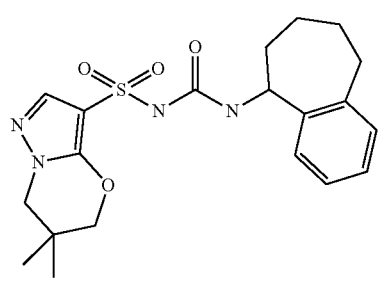 [SMILES: CC1(C)COc2c(S(=O)(=O)NC(=O)NC3CCCCc4ccccc43)cnn2C1] | | D | |

-continued
| Compound | IL-1B pIC50 (μM) | CTG pIC50 | TNFa pIC50 |
|---|---|---|---|
| 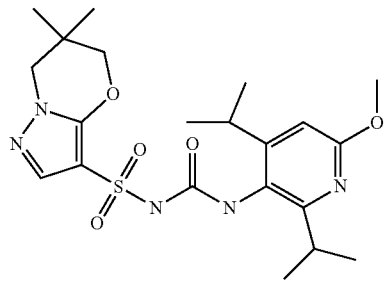 [SMILES: COc1cc(C(C)C)c(NC(=O)NS(=O)(=O)c2cnn3c2OCC(C)(C)C3)c(C(C)C)n1] | C | C | D |
| 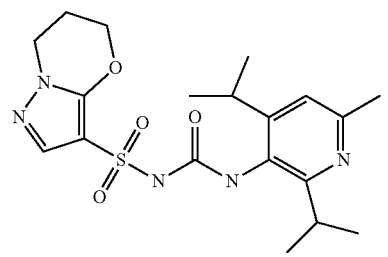 [SMILES: Cc1cc(C(C)C)c(NC(=O)NS(=O)(=O)c2cnn3c2OCCC3)c(C(C)C)n1] | C | C | D |
| 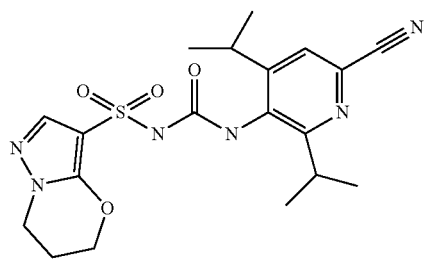 [SMILES: CC(C)c1cc(C#N)nc(C(C)C)c1NC(=O)NS(=O)(=O)c1cnn2c1OCCC2] | C | B | |
| 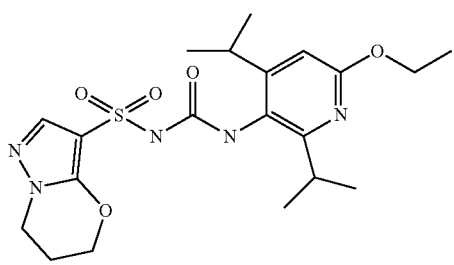 [SMILES: CCOc1cc(C(C)C)c(NC(=O)NS(=O)(=O)c2cnn3c2OCCC3)c(C(C)C)n1] | C | C | |
| 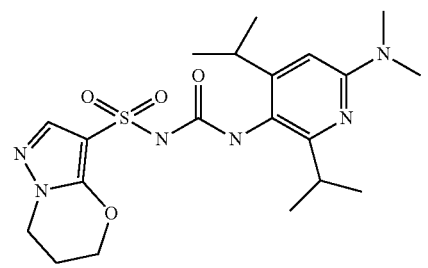 [SMILES: CC(C)c1cc(N(C)C)nc(C(C)C)c1NC(=O)NS(=O)(=O)c1cnn2c1OCCC2] | C | B | |

-continued

| Compound | IL-1B pIC50 (μM) | CTG pIC50 | TNFa pIC50 |
|---|---|---|---|
| | B | B | D |
| | C | B | D |
| | B | A | D |
| | D | D | D |
| | D | D | D |

Example B5: PMBC IL-1β HTRF Assay

Cell Culture and NLRP3 Infammasome Activation Assay:

Human frozen PBMCs were purchased from StemCells Technologies. Cells were rapidly thawed in 37° C. water bath and resuspended in fresh assay media consisting of RPMI 1640 Medium containing 1% sodium pyruvate, 10 mM HEPES, 2.5 g/L glucose and 55 μM 2-Mercaptoethanol. Cell density was adjusted to $8.1 \times 10^5$ cells/mL. Cells were primed by adding lipopolysaccharide (Invivogen Ultrapure lipopolysaccharide from *E. coli*, tlrl-3pelps) at a final concentration of 100 ng/mL in cell suspension. 37 μL of cell suspension with LPS was seeded per well of a 384 well plate and incubated for 3 hours at 37° C. and 5% $CO_2$. After priming, PBMCs were preincubated with serially diluted test compounds with starting concentration of 40 μM followed by 2-fold dilution for a 20-point curve or vehicle (DMSO) for 30 min in assay media at 37° C. and 5% $CO_2$. Cells were then stimulated with 10 μM nigericin (Invivogen, tlrl-nig-5) for 90 min at 37° C. and 5% $CO_2$ to activate NLRP3 dependent inflammasome pathway and IL-1β release in cell culture supernatant. Cells were centrifuged at 1200 RPM for 1 min and 40 μL of supernatant was transferred into fresh plates and stored at −80° C. until IL-1β analysis.

IL-1β HTRF Assay:

16 μL of supernatant was added to white 384 well HTRF plates, followed by addition of 4 μL of HTRF cocktail in each well. Plates were quickly centrifuged, sealed and incubated overnight at room temperature. Next day, HTRF signal was read on a Pherastar and ratio of 665/620 was calculated based on manufacturer's protocol to obtain concentration of IL-1β in cell culture supernatant.

Example B6: THP-1 ASC-GFP Speck Assay

Cell Culture:

THP-1 ASC-GFP cell line was purchased from Invivogen, San Diego, for infammasome activation assay. THP-1 ASC-GFP cells stably express a 37.6 kDa ASC::GFP fusion protein that enables monitoring of spec formation by microscopy after activation of NLRP3 dependent inflammasome pathway. Cells were maintained at a density of 600,000 cells/mL in growth media consisting of RPMI 1640, 2 mM L-glutamine, 25 mM HEPES and 10% heat inactivated fetal bovine serum at 37° C. and 5% $CO_2$. Cells were passaged every 3-4 days and used for assays for up to 20 passages.

NLRP3 Infammasome Activation Assay:

THP-1 ASC-GFP cells were collected by centrifuging cells at 800 RPM for 5 minutes. Cell culture supernatant was removed and cells were re-suspended in fresh media at density of $1 \times 10^6$ cells/mL in assay media consisting of RPMI 1640, 2 mM L-glutamine, 25 mM HEPES and 10% heat inactivated fetal bovine serum. Phorbol 12-myristate 13-acetate (PMA) (Invivogen,tlrl-pma) was added to the cell suspension at a final concentration of 500 ng/ml and mixed thoroughly. 40,000 cells were added per well of a 384 well plate and differentiated into macrophages overnight at 37° C. and 5% $CO_2$. Cells were primed with 1 μg/mL of lipopolysaccharide (Invivogen Ultrapure lipopolysaccharide from *E. coli*, tlrl-3pelps) in assay media for 3 hours at 37° C. and 5% $CO_2$. After priming, media was removed and THP-1 ASC-GFP cells were preincubated with serially diluted test compounds with starting concentration of 40 μM followed by 2-fold dilution for a 20-point curve or vehicle (DMSO) for 30 min in assay media at 37° C. and 5% $CO_2$. Cells were then stimulated with 10 μM nigericin (Invivogen, tlrl-nig-5) for 90 min at 37° C. and 5% $CO_2$ to activate NLRP3 dependent inflammasome pathway and spec formation. After stimulation, cells were fixed with 4.8% paraformaldehyde (Electron Microscopy Sciences #15710-S) and incubated at room temperature for 15 min. Cells were then washed 3-times with 100 μL of phosphate buffered saline and permeabilized in the presence of premeablization/block buffer for 20 min at room temperature. Cells were then washed 3-times with 100 μL phosphate buffered saline and incubated for 1 hr at room temperature in the presence of hoechst. After staining with Hoechst, cells were washed 3-times with 100 μL phosphate buffered saline and imaged for ASC spec formation.

Imaging ASC-GFP Specks:

THP-1 ASC-GFP cells were imaged in 488 and Hoechst channels. Hoechst channel was used for cell count and 488 channel was used to identify number of GFP ASC specks in imaged fields. Percentage of cells with a spec was calculated by dividing the number of GFP positive spots by total number of cells.

Additional assay results are provided in Table B1.

TABLE B1

| Ex. No. | PMBC IL-1β $IC_{50}$ (μM) | PMBC CTG $IC_{50}$ (μM) | PMBC TNFα $IC_{50}$ (μM) | THP-1 ASC Speck $IC_{50}$ (μM) |
|---|---|---|---|---|
| 1 | >10 | | | |
| 2 | >10 | | | |
| 3 | 2.08 | >10 | | |
| 4 | >10 | | | >20 |
| 5 | >10 | | | |
| 6 | >10 | | | |
| 7 | >10 | | | |
| 8 | >10 | >10 | | >20 |
| 9 | >10 | | | |
| 10 | >10 | | | |
| 11 | >10 | >10 | | |
| 12 | >10 | | | |
| 13a | >10 | | | |
| 14 | >10 | | | |
| 15 | >10 | | | |
| 16 | >10 | | | >20 |
| 17 | >10 | | | >9.8 |
| 18 | >10 | | | >20 |
| 19 | >10 | | | >20 |
| 20 | >10 | | | |
| 21 | >10 | | | 12 |
| 22 | >10 | | | >20 |
| 23 | >10 | | | >20 |
| 24 | >10 | | | >20 |
| 25 | >10 | | | >20 |
| 26 | >10 | | | |
| 27 | >10 | | | |
| 28 | 1.79 | 0.069 | | |
| 29 | >10 | | | |
| 30 | 0.85 | 0.73 | | 1.8 |
| 31 | 4.38 | 0.89 | | |
| 32 | 0.59 | 0.92 | | |
| 33 | 4.96 | 4.51 | | 4.0 |
| 34 | 3.19 | 1.98 | | 3.7 |
| 35 | 0.95 | 0.12 | | 1.4 |
| 36 | >10 | | | |
| 37a | 0.55 | 0.60 | | |
| 38a | 1.14 | 0.68 | | 2.5 |
| 39a | 1.24 | 0.97 | | 0.4 |
| 40 | 1.50 | 1.25 | | 0.72 |
| 41a | 0.37 | 0.013 | | 0.68 |
| 42a | 0.12 | 0.24 | | 1.1 |
| 43 | >10 | | | |
| 44 | 1.22 | >10 | | |
| 45 | 0.91 | 0.37 | | |
| 46 | >10 | | | |
| 47 | 2.01 | 1.16 | >10 | 8.3 |
| 48 | 2.47 | 2.43 | >10 | 2.0 |
| 49 | 1.25 | 0.56 | | 2.5 |
| 50 | 2.81 | 1.18 | | 4.7 |
| 51 | 2.07 | 1.12 | | |

TABLE B1-continued

| Ex. No. | PMBC IL-1β IC$_{50}$ (μM) | PMBC CTG IC$_{50}$ (μM) | PMBC TNFα IC$_{50}$ (μM) | THP-1 ASC Speck IC$_{50}$ (μM) |
|---|---|---|---|---|
| 52a | 0.79 | 0.39 | >10 | 0.50 |
| 53 | 3.40 | 0.88 | >10 | 3.3 |
| 54 | 0.32 | 0.016 | >10 | 0.62 |
| 55 | >10 | >10 | >10 | |
| 56 | >10 | >10 | >10 | |
| 57 | | | | 0.56 |
| 58 | | | | 0.20 |
| 59a | | | | 0.17 |
| 60a | | | | 0.57 |
| 61 | | | | 0.90 |
| 62a | | | | 0.64 |
| 63 | | | | 0.35 |
| 64a | | | | 0.24 |
| 65 | | | | 1.40 |
| 66a | | | | 3.60 |
| 67 | | | | 0.17 |
| 68 | | | | 1.50 |
| 69 | | | | 0.52 |
| 70a | | | | 4.10 |
| 71 | | | | 1.9 |
| 72a | | | | 2.50 |
| 73a | | | | 8.70 |
| 74 | | | | 0.34 |
| 75 | | | | 0.42 |
| 76a | | | | 0.56 |
| 77a | | | | 1.9 |
| 78a | | | | 0.071 |
| 79 | | | | 0.74 |
| 80a | | | | 0.15 |
| 81 | | | | 8.2 |
| 82 | | | | 1.4 |

EQUIVALENTS

While the present disclosure has been described in conjunction with the specific embodiments set forth herein, many alternatives, modifications and other variations thereof will be apparent to those of ordinary skill in the art. All such alternatives, modifications and variations are intended to fall within the spirit and scope of the present disclosure.

The invention claimed is:

1. A compound having the structure of Formula (I),

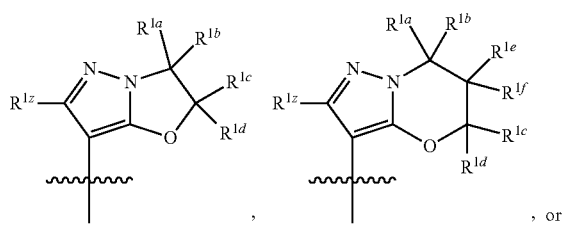

or a pharmaceutically acceptable salt, solvate, isomer, or tautomer thereof, wherein:

$R^1$ is

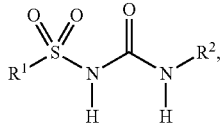

,

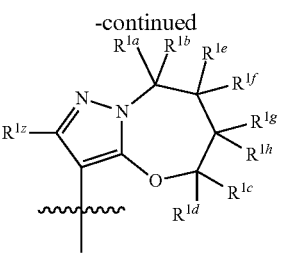

, or

-continued

[structure]

$R^{1z}$ is H, D, or halogen;

each $R^{1a}$, $R^{1b}$, $R^{1c}$, $R^{1e}$, $R^{1f}$, $R^{1g}$, is independently selected from the group consisting of H, D, halogen, —CN, —NO$_2$, —SR$^{11a}$, —OR$^{11a}$, —C(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, $C_1$-$C_6$alkyl, $C_2$-$C_6$alkenyl, $C_2$-$C_6$alkynyl, $C_3$-$C_{10}$cycloalkyl, and 3-7-membered heterocyclyl; wherein the $C_1$-$C_6$alkyl, $C_2$-$C_6$alkenyl, $C_2$-$C_6$alkynyl, $C_3$-$C_{10}$cycloalkyl, and 3-7-membered heterocyclyl are independently unsubstituted or substituted with one or more substituents selected from the group consisting of D, —CN, halogen, $C_1$-$C_6$alkyl, —OR$^{11a}$, —C(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, $C_3$-$C_{10}$cycloalkyl, and 3-7-membered heterocyclyl; or two of the following groups, $R^{1a}$, $R^{1b}$ $R^{1c}$, $R^{1d}$, $R^{1e}$, $R^{1f}$, $R^{1g}$, $R^{1h}$, when present, together with the atoms to which they are attached can form a C3-C10cycloalkyl or a 3-7-membered heterocyclyl; wherein the C3-C10cycloalkyl and 3-7-membered heterocyclyl are independently unsubstituted or substituted with one or more substituents selected from the group consisting of D, —CN, halogen, $C_1$-$C_6$alkyl, —OR$^{13a}$, —C(O)R$^{13b}$, —NR$^{13a}$R$^{14a}$, —NR$^{13a}$C(O)OR$^{14a}$, and —NR$^{13a}$C(O)NR$^{14a}$; or two geminal groups $R^{1a}$ and $R^{1b}$; $R^{1c}$ and $R^{1d}$; $R^{1e}$ and $R^{1f}$; or $R^{1g}$ and $R^{1h}$, when present, can form an oxo group;

$R^2$ is $C_1$-$C_6$alkyl, $C_3$-$C_{10}$cycloalkyl, 5-7-membered heterocyclyl, 5-membered heteroaryl, or 6-membered heteroaryl containing 6-11 annular atoms; wherein the $C_1$-$C_6$ alkyl, $C_3$-$C_{10}$cycloalkyl, 5-7-membered heterocyclyl, 5-membered heteroaryl, and 6-membered heteroaryl containing 6-11 annular atoms are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{23a}$, —C(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —(CH$_2$)$_{1-4}$C$_3$-$C_{10}$cycloalkyl, $C_6$aryl, 3-7-membered heterocyclyl, and 5-6 membered heteroaryl; or optionally two of the substituents when present, together with the atoms to which they are attached can form a ring;

$R^{11a}$, $R^{12a}$, $R^{13a}$, $R^{14a}$, $R^{23a}$, and $R^{24a}$ are independently, at each occurrence, H, D, $C_1$-$C_8$ alkyl, $C_2$-$C_8$ alkenyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$ alkyl, $C_2$-$C_8$alkenyl, $C_2$-$C_8$ alkynyl, $C_3$-$C_{10}$cycloalkyl, $C_4$—$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$ alkyl, —OH, —O—$C_1$-$C_6$alkyl, —$NH_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl; and $R^{11b}$, $R^{13b}$, and $R^{23b}$ are independently, at each occurrence, H, D, —OH, —O($C_1$-$C_6$alkyl), —$NH_2$, —NH($C_1$-$C_6$ alkyl), —N($C_1$-$C_6$alkyl)$_2$, —NHS(O)$_2$CH$_3$, $C_1$-$C_8$alkyl, $C_2$-$C_8$ alkenyl, $C_2$-$C_8$ alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$ alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl.

2. The compound of claim 1, or a pharmaceutically acceptable salt, solvate, isomer, or tautomer thereof, wherein $R^2$ is $C_1$-$C_6$alkyl, which is unsubstituted or substituted with one or more $C_6$aryl.

3. The compound of claim 1, or a pharmaceutically acceptable salt, solvate, isomer, or tautomer thereof, wherein $R^2$ is $C_3$-$C_{10}$cycloalkyl, which is unsubstituted or substituted with one or more substituents selected from the group consisting of $C_1$-$C_6$alkyl and $C_6$aryl.

4. The compound of claim 3, or a pharmaceutically acceptable salt, solvate, isomer, or tautomer thereof, wherein the $C_3$-$C_{10}$cycloalkyl of $R^2$ is cyclohexyl, cycloheptyl, 2-adamantyl, 2,3-dihydro-1H-inden-2-yl, or 9-fluorenyl, each of which is independently unsubstituted or substituted with one or more substituents selected from the group consisting of $C_1$-$C_6$alkyl and $C_6$aryl.

5. The compound of claim 1, or a pharmaceutically acceptable salt, solvate, isomer, or tautomer thereof, wherein $R^2$ is 5-7-membered heterocyclyl, which is unsubstituted or substituted with one or more $C_1$-$C_6$alkyl.

6. The compound of claim 1, or a pharmaceutically acceptable salt, solvate, isomer, or tautomer thereof, wherein $R^2$ is 5-membered heteroaryl, which is unsubstituted or substituted with one or more substituents selected from the group consisting of $C_1$-$C_6$alkyl, $C_1$-$C_6$haloalkyl, $C_6$aryl, oxo, and —(CH$_2$)$_{1-4}$$C_3$-$C_{10}$cycloalkyl.

7. The compound of claim 6, or a pharmaceutically acceptable salt, solvate, isomer, or tautomer thereof, wherein the 5-membered heteroaryl of $R^2$ contains 2 nitrogen atoms, and is unsubstituted or substituted with one or more substituents selected from the group consisting of $C_1$-$C_6$alkyl, $C_1$-$C_6$haloalkyl, $C_6$aryl, oxo, and —(CH$_2$)$_{1-4}$$C_3$-$C_1$cycloalkyl.

8. The compound of claim 1, or a pharmaceutically acceptable salt, solvate, isomer, or tautomer thereof, wherein $R^2$ is 6-membered heteroaryl containing 6-11 annular atoms, which is unsubstituted or substituted with one or more substituents selected from the group consisting of halogen, $C_1$-$C_6$alkyl, $C_1$-$C_6$haloalkyl, $C_6$aryl, 5-6-membered heteroaryl, —OR$^{23}$a, $C_3$-$C_{10}$cycloalkyl, $C_2$-$C_6$alkenyl, —CN, and —NR$^{23a}$R$^{24a}$.

9. The compound of claim 8, or a pharmaceutically acceptable salt, solvate, isomer, or tautomer thereof, wherein the 6-membered heteroaryl containing 6-11 annular atoms of $R^2$ contains 2 nitrogen atoms, and is unsubstituted or substituted with one or more substituents selected from the group consisting of halogen, $C_1$-$C_6$alkyl, $C_1$-$C_6$haloalkyl, $C_6$aryl, 5-6-membered heteroaryl, —OR$^{23a}$, $C_3$-$C_{10}$cycloalkyl, $C_2$-$C_6$alkenyl, —CN, and —NR$^{23a}$R$^{24a}$.

10. The compound of claim 1, or a pharmaceutically acceptable salt, solvate, isomer, or tautomer thereof, wherein $R^2$ is selected from the group consisting of:

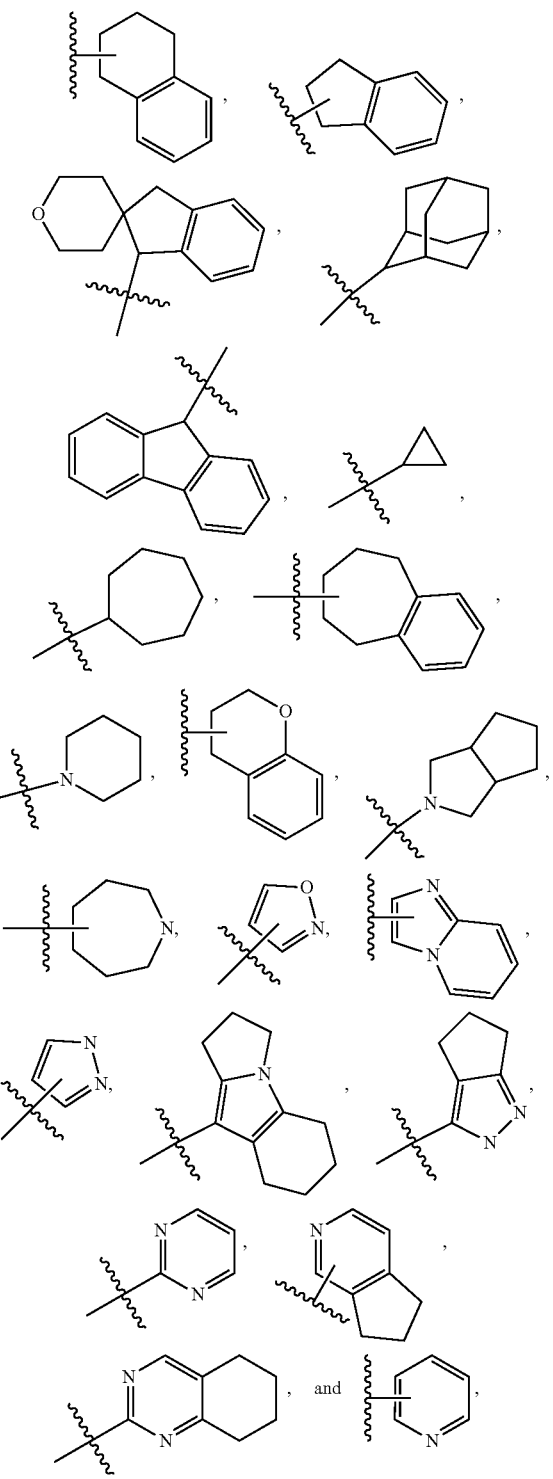

and wherein the selected $R^2$ is further unsubstituted or substituted.

11. The compound of claim 1, or a pharmaceutically acceptable salt, solvate, isomer, or tautomer thereof, wherein $R^1$ is

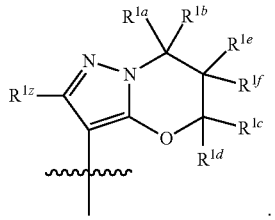

12. The compound of claim 11, or a pharmaceutically acceptable salt, solvate, isomer, or tautomer thereof, wherein:

$R^{1z}$ is H, and each $R^{1a}$, $R^{1b}$, $R^{1c}$, $R^{1d}$, $R^{1e}$, and $R^{1f}$ is independently selected from the group consisting of H, halogen, $-OR^{11a}$, $-NR^{11a}R^{12a}$, $C_1$-$C_6$alkyl, $C_3$-$C_{10}$cycloalkyl, and 3-7-membered heterocyclyl; wherein the $C_1$-$C_6$alkyl, $C_3$-$C_{10}$cycloalkyl, and 3-7-membered heterocyclyl; are independently unsubstituted or substituted with one or more substituents selected from the group consisting of D, —CN, halogen, $C_1$-$C_6$alkyl, $-OR^{11a}$, $-NR^{11a}R^{12a}$, $C_3$-$C_{10}$cycloalkyl, and 3-7-membered heterocyclyl.

13. The compound of claim 12, or a pharmaceutically acceptable salt, solvate, isomer, or tautomer thereof, wherein:

$R^2$ is selected from the group consisting of $C_1$-$C_6$alkyl, $C_3$-$C_{10}$cycloalkyl, 5-7-membered heterocyclyl, 5-membered heteroaryl, and 6-membered heteroaryl containing 6-11 annular atoms; wherein the $C_1$-$C_6$alkyl, $C_3$-$C_{10}$cycloalkyl, 5-7-membered heterocyclyl, 5-membered heteroaryl, or 6-membered heteroaryl containing 6-11 annular atoms is unsubstituted or substituted with one or more substituents independently selected from the group consisting of D, —CN, halogen, $C_1$-$C_6$alkyl, $C_1$-$C_6$haloalkyl, $C_2$-$C_6$alkenyl, oxo, $OR^{23a}$, $-(CH_2)_{1-4}C_3$-$C_{10}$cycloalkyl, $C_3$-$C_{10}$cycloalkyl, $-NR^{23a}R^{24a}$ $C_6$aryl, and 5-6-membered heteroaryl, wherein $R^{23a}$ and $R^{24a}$ are independently, at each occurrence, H, D, $C_1$-$C_8$alkyl, or $C_3$-$C_{10}$cycloalkyl; wherein the $C_1$-$C_8$ alkyl and $C_3$-$C_{10}$cycloalkyl are independently unsubstituted or substituted with one or more halogen.

14. The compound of claim 1, or a pharmaceutically acceptable salt, solvate, isomer, or tautomer thereof, wherein $R^1$ is

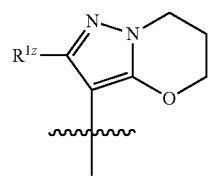

and $R^{1z}$ is H.

15. The compound of claim 1, or a pharmaceutically acceptable salt, solvate, isomer, or tautomer thereof, wherein $R^1$ is

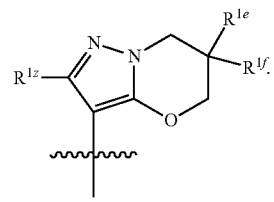

16. The compound of claim 1, or a pharmaceutically acceptable salt, solvate, isomer, or tautomer thereof, wherein $R^1$ is selected from the group consisting of:

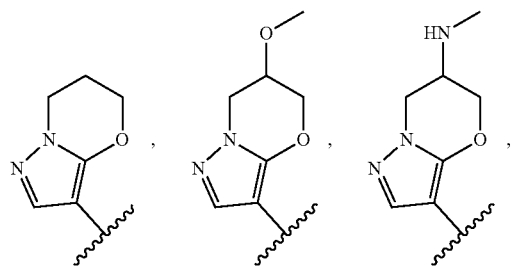

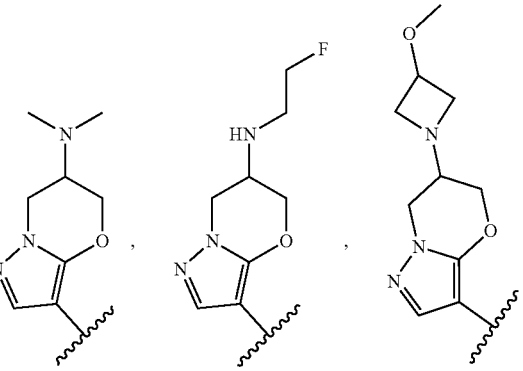

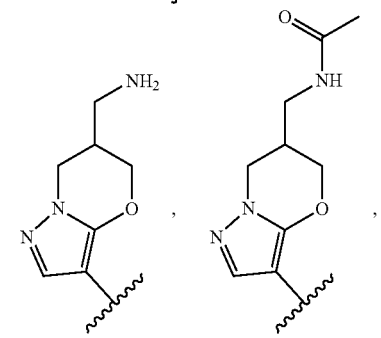

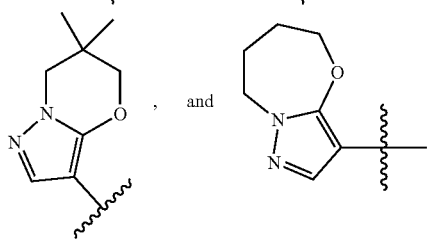

17. The compound of claim 1, wherein the compound is:
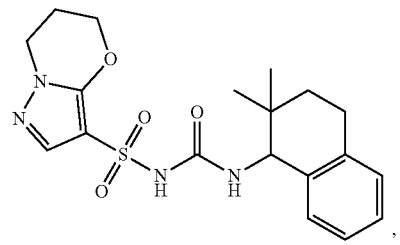
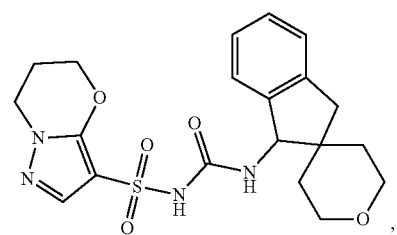
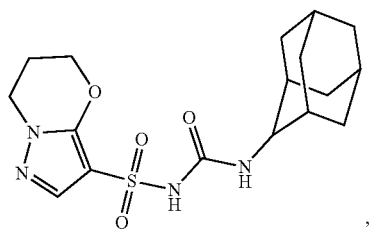
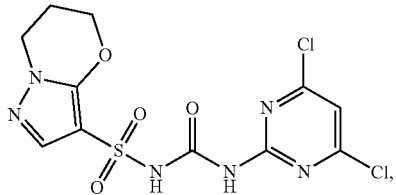
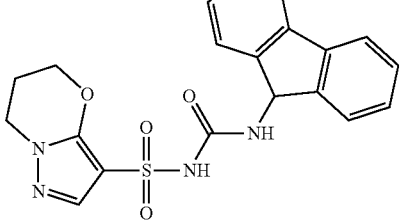
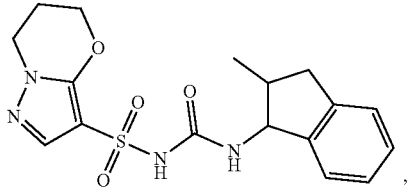
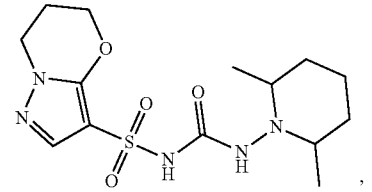
-continued
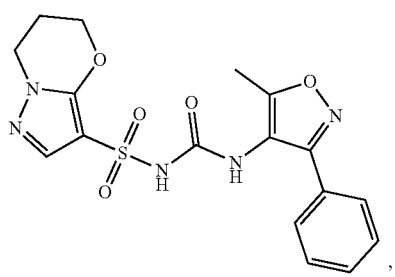
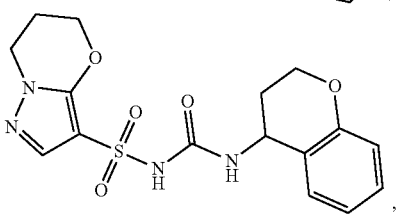
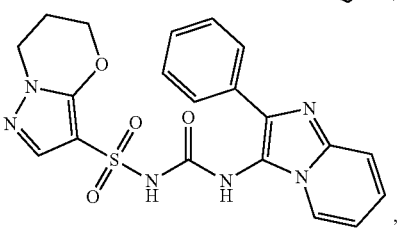
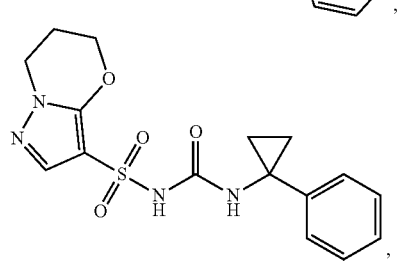
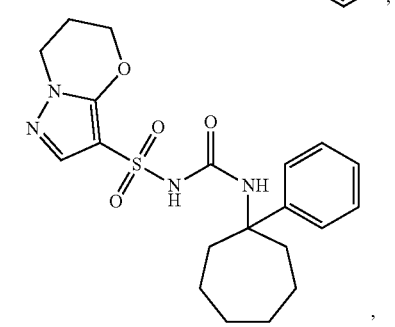
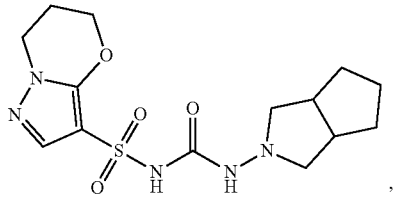
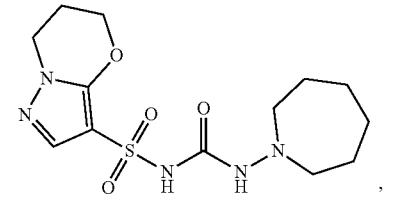

245
-continued
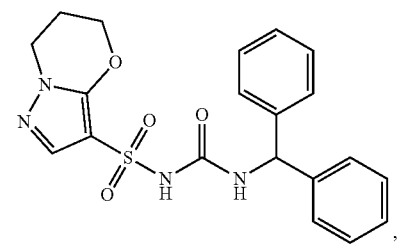 [SMILES: O=C(NC(c1ccccc1)c1ccccc1)NS(=O)(=O)c1cnn2c1OCCC2]
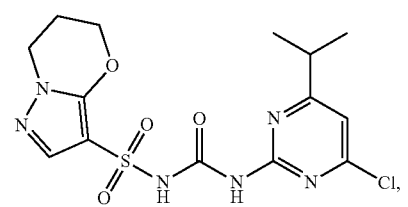
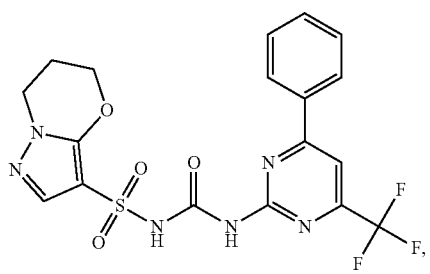
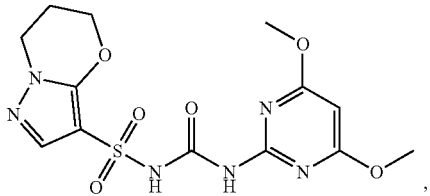
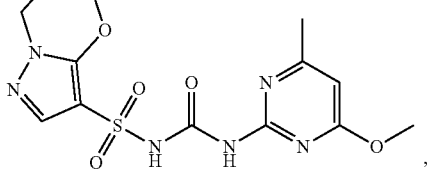
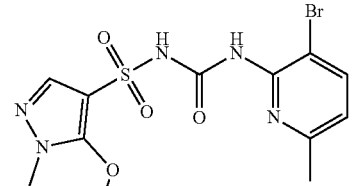
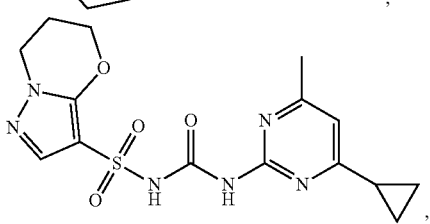
246
-continued
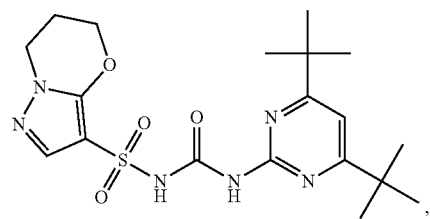
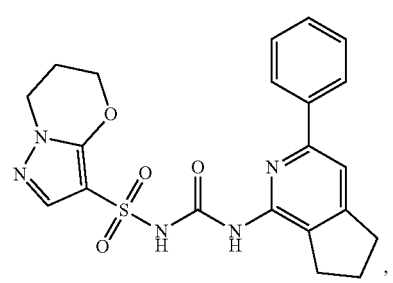
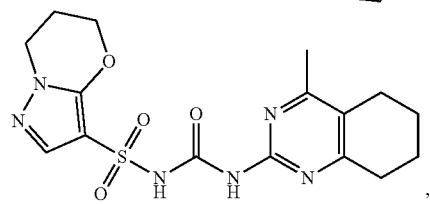
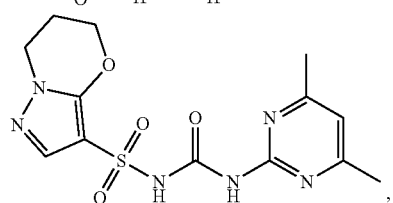
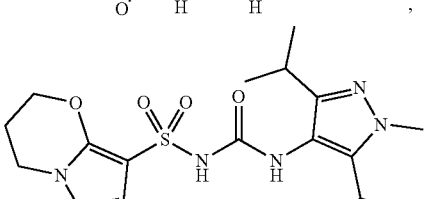
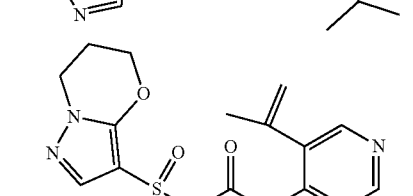
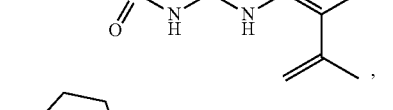
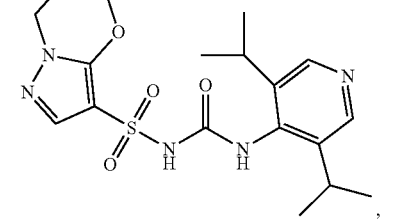

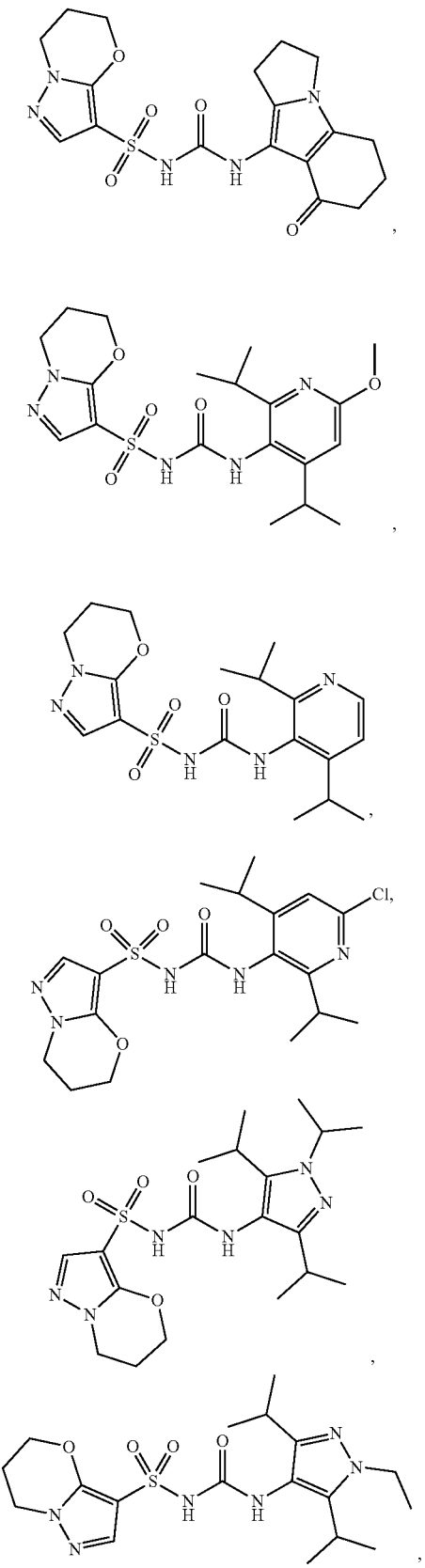
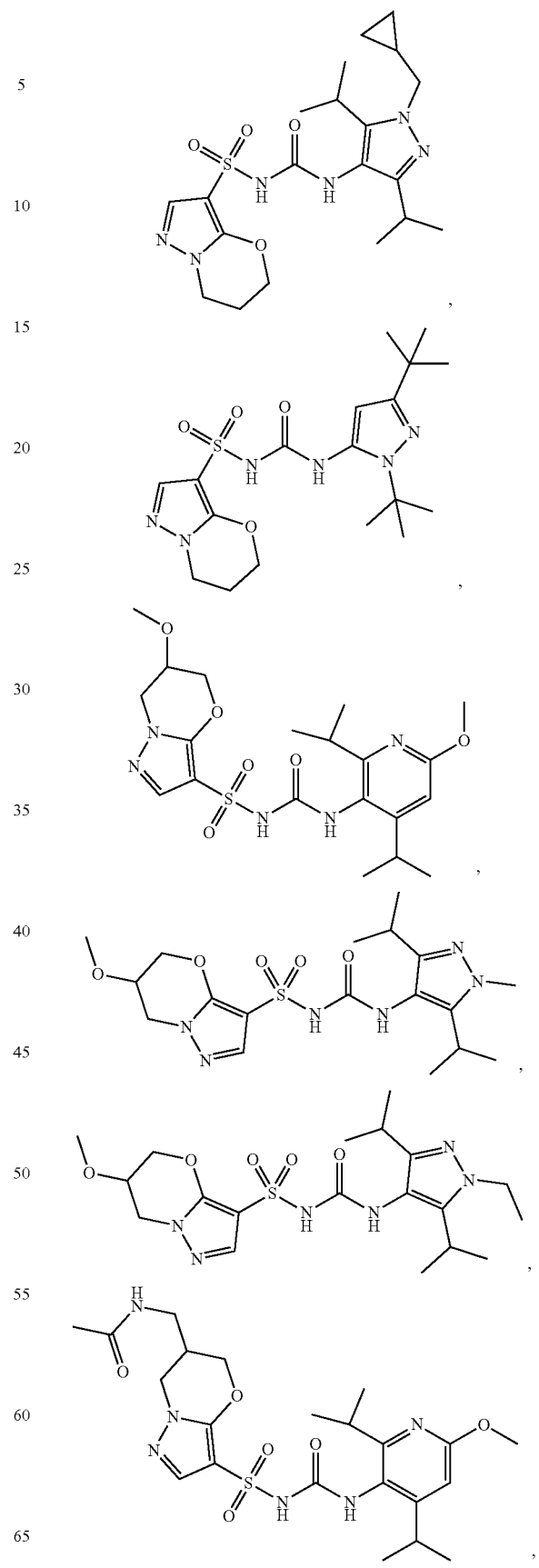

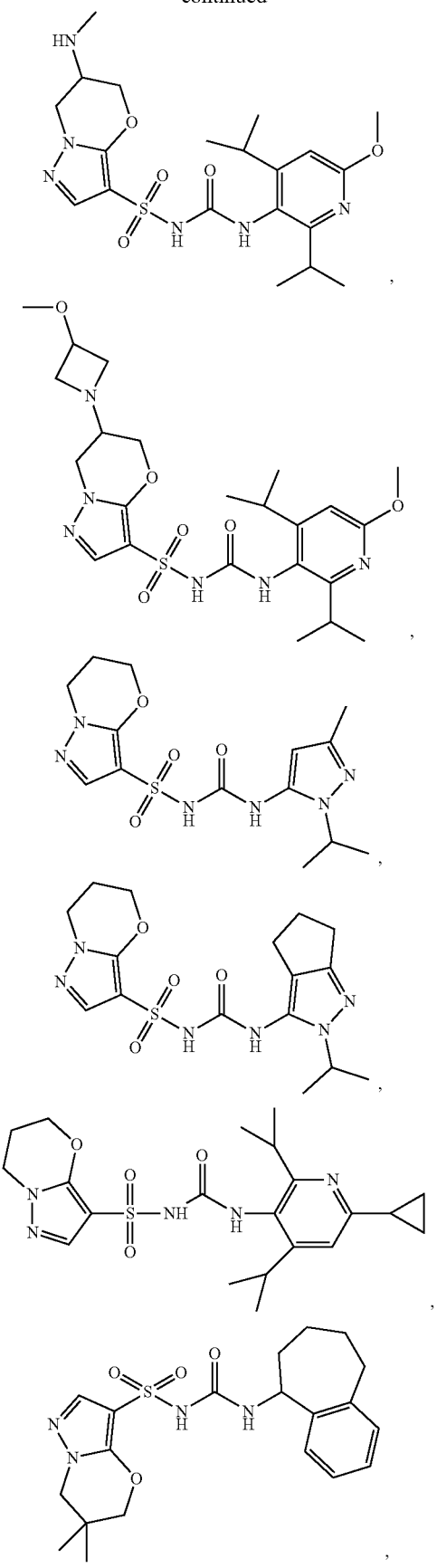
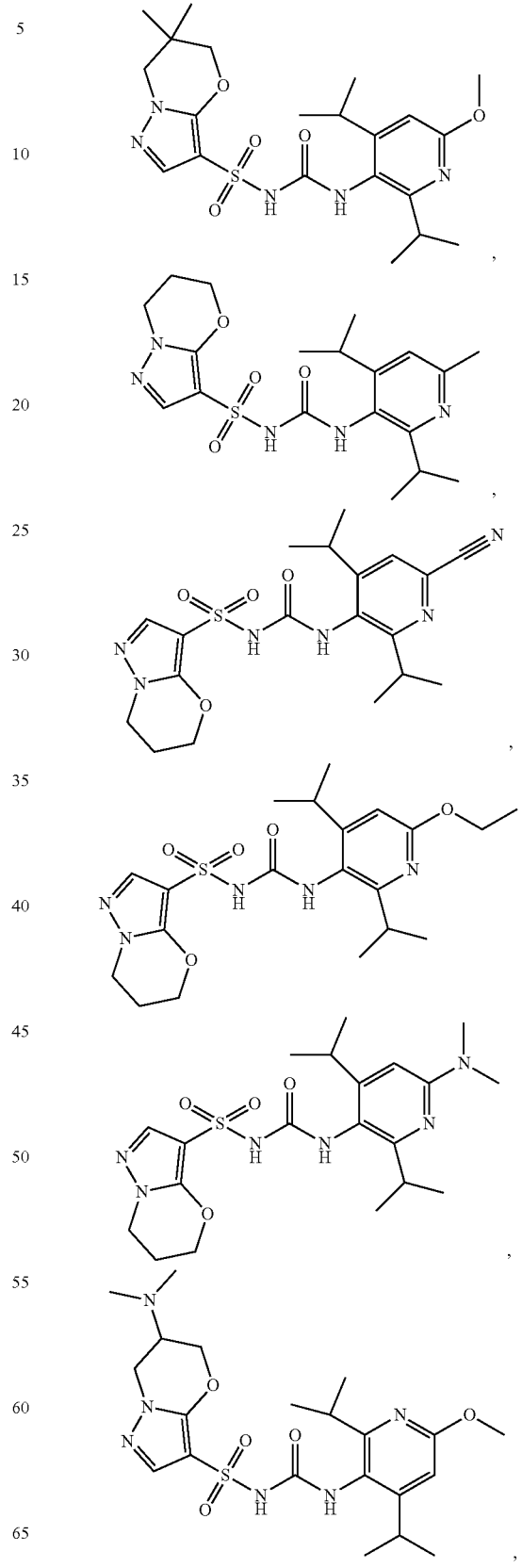

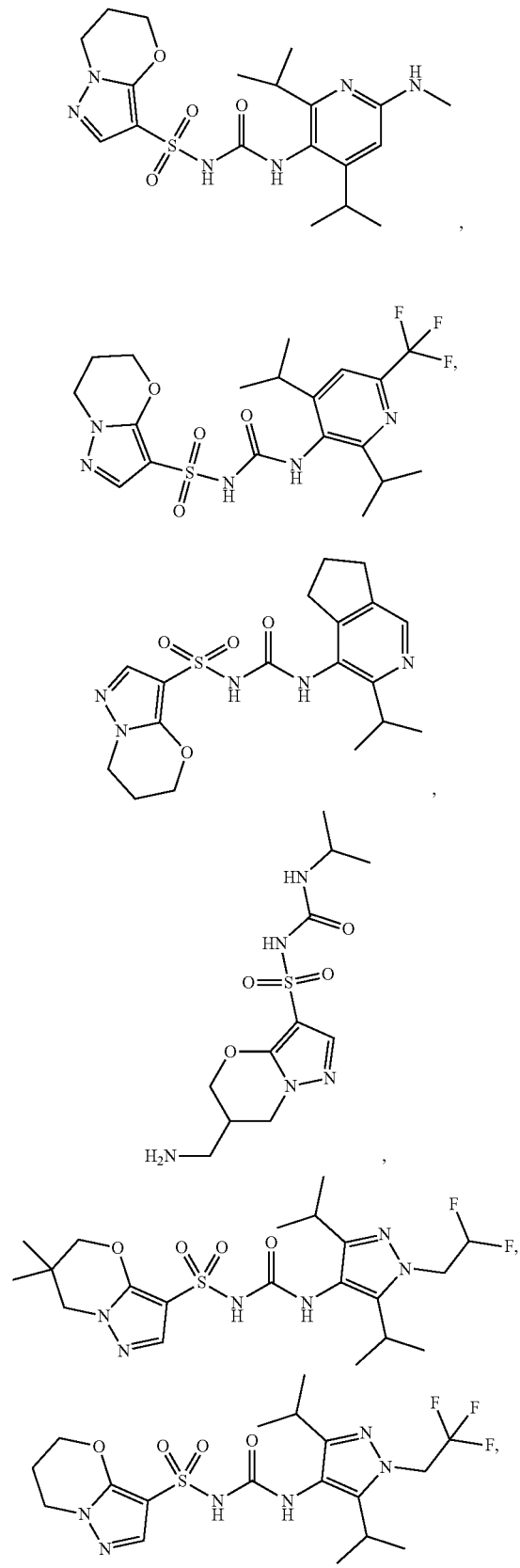
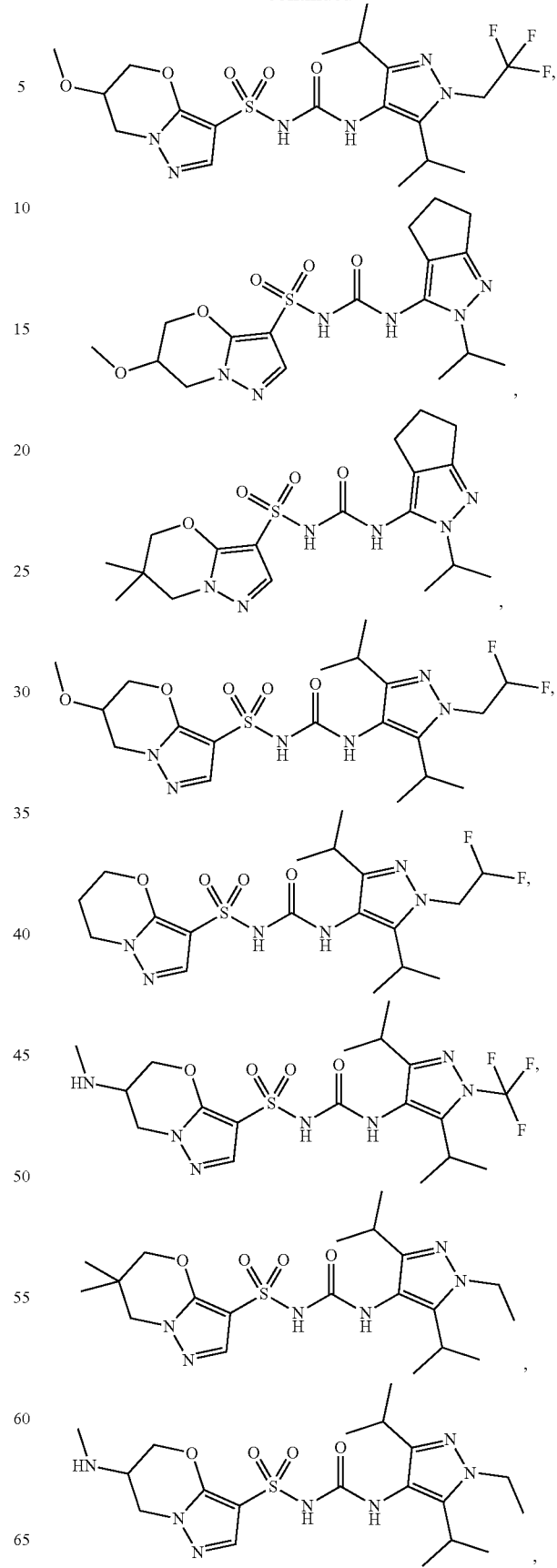

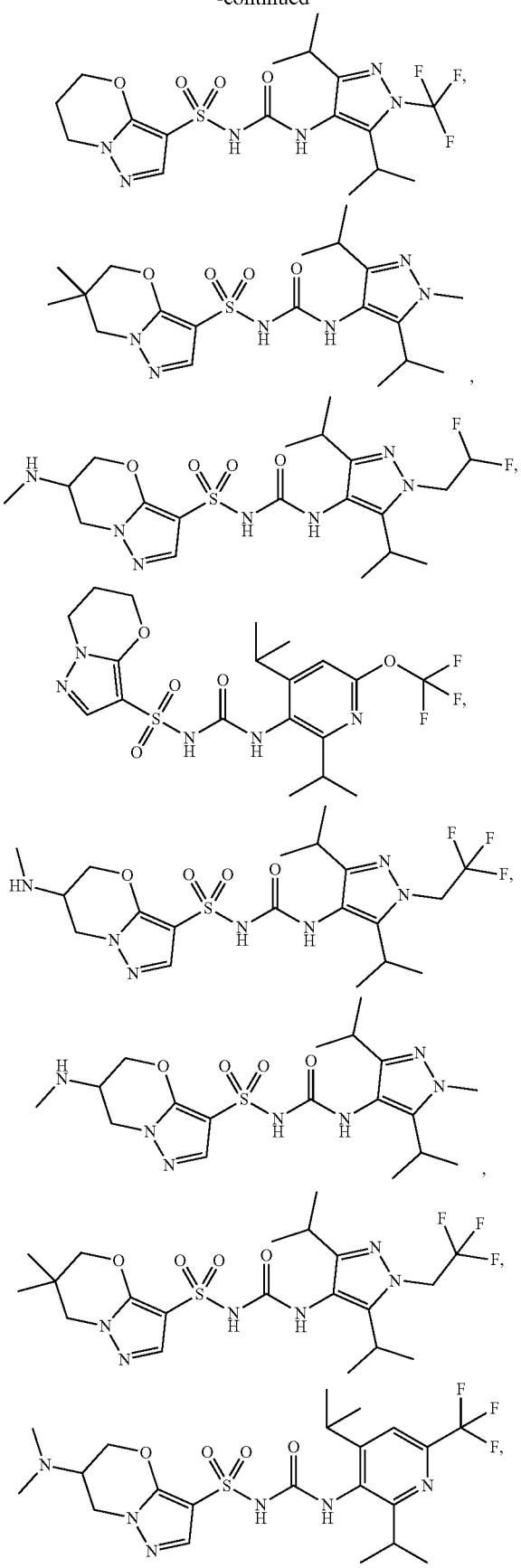
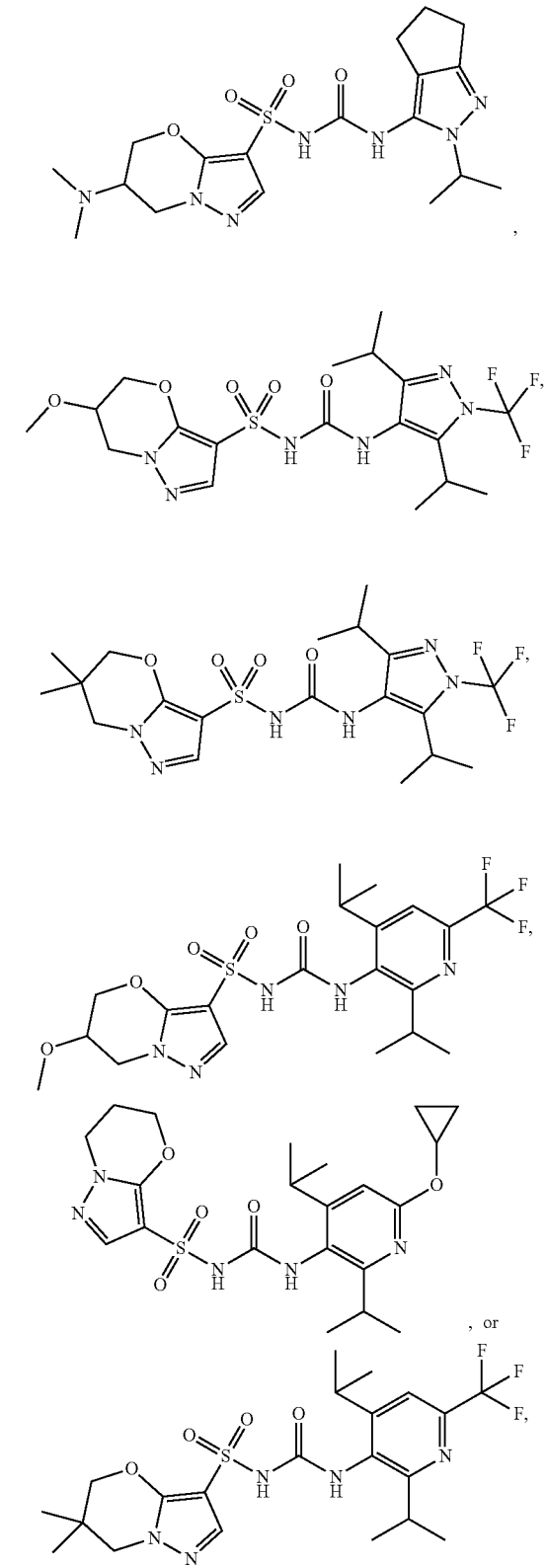
or a pharmaceutically acceptable salt, solvate, isomer, or tautomer thereof.

18. The compound of claim 17, wherein the compound is:
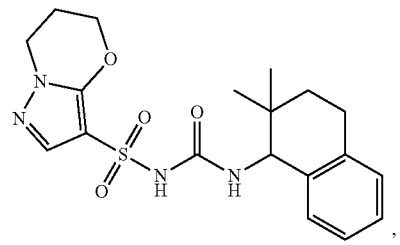
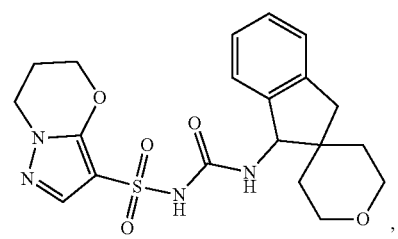
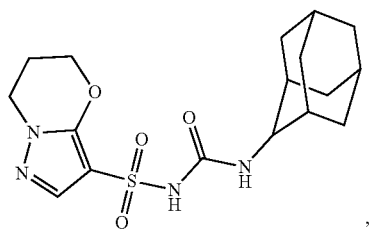
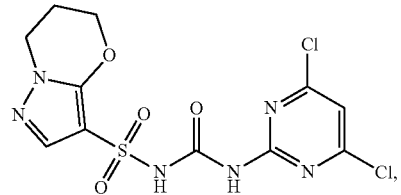
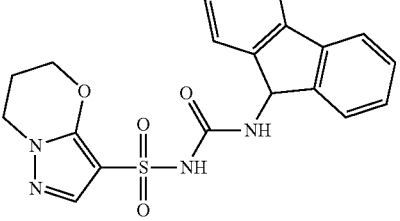
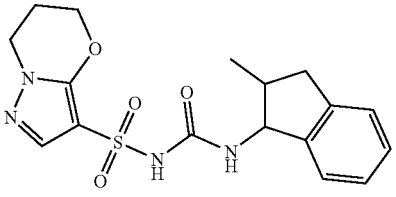
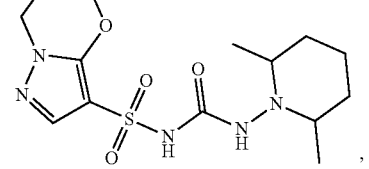
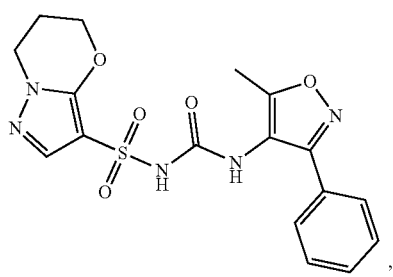
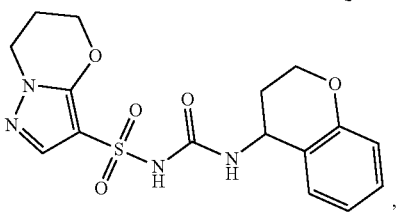
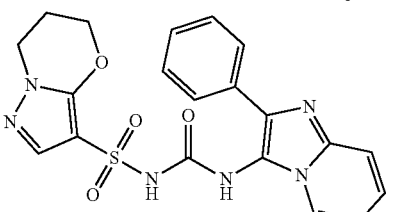
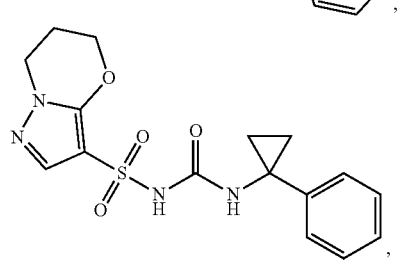
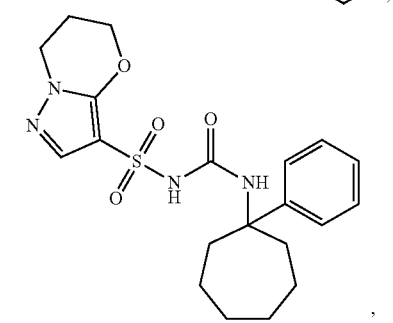
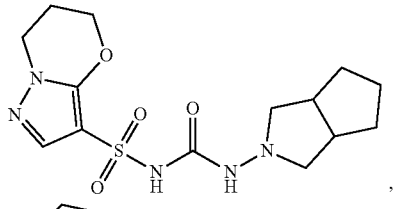
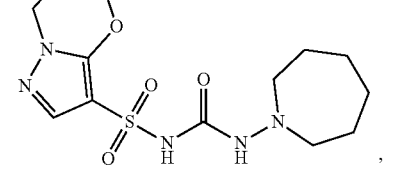

257
-continued
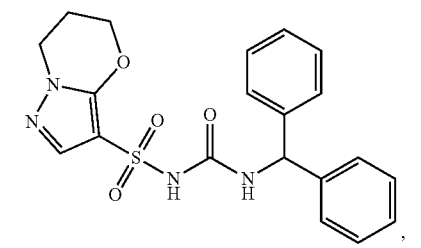 [SMILES: O=C(NC(c1ccccc1)c1ccccc1)NS(=O)(=O)c1cnn2c1OCCC2]
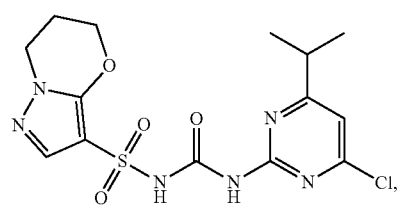
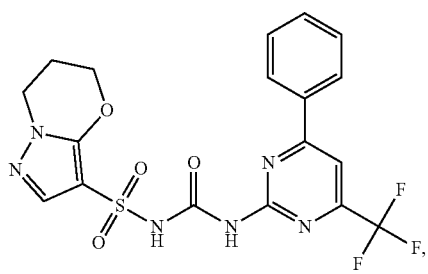
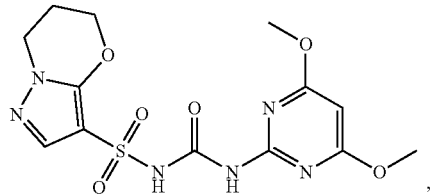
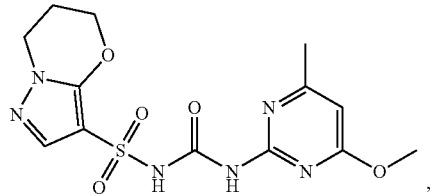
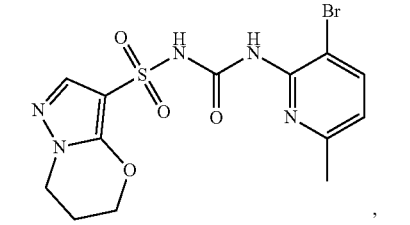
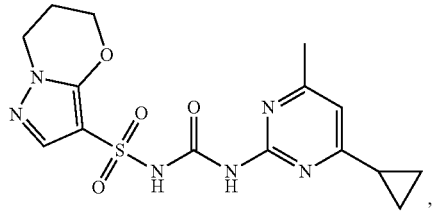
258
-continued
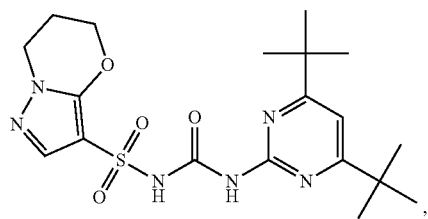
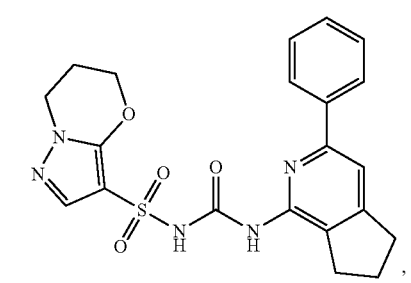
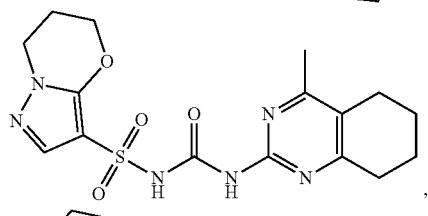
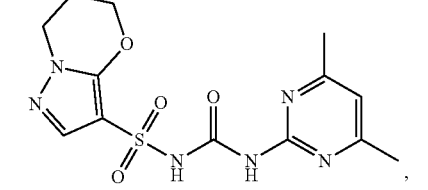
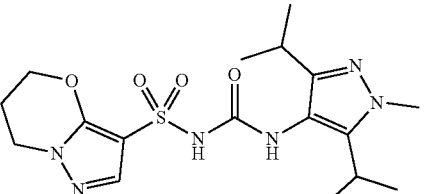
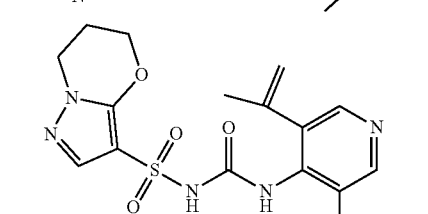
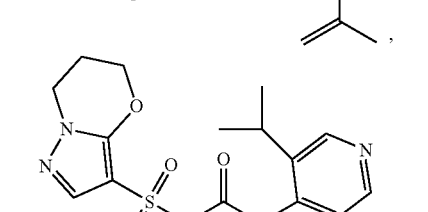

-continued
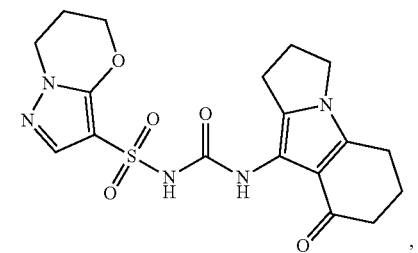
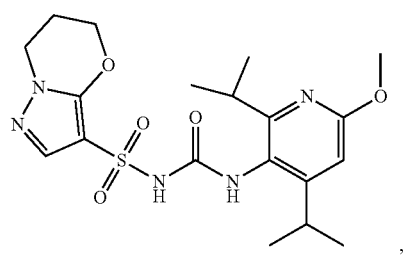
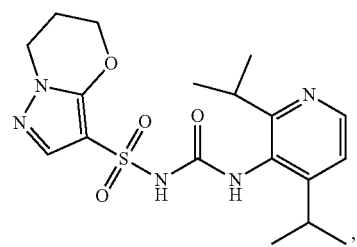
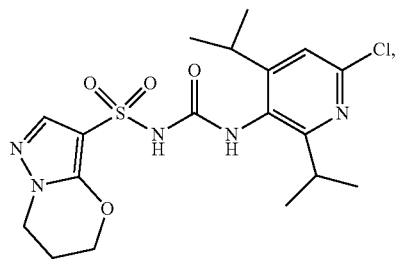
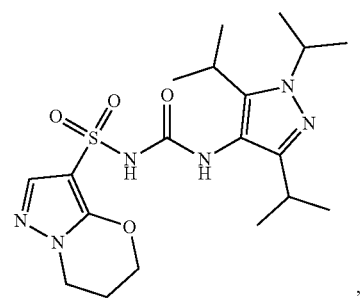
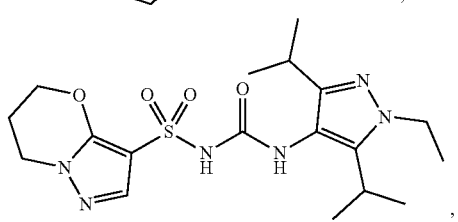
-continued
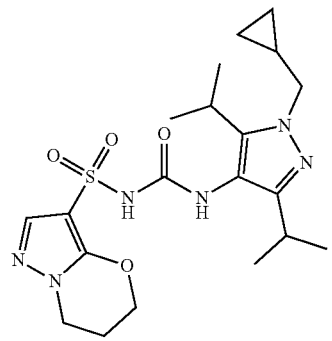
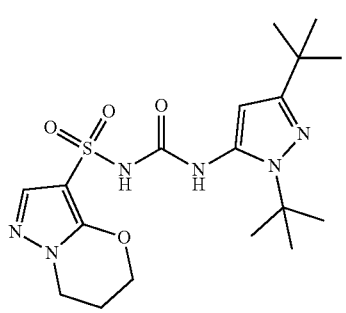
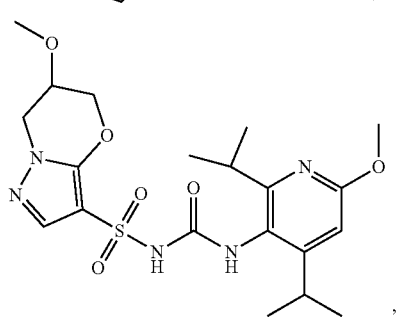
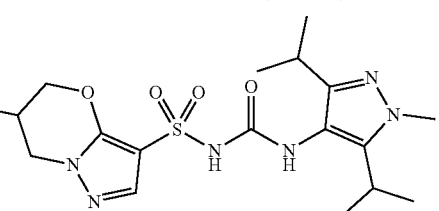
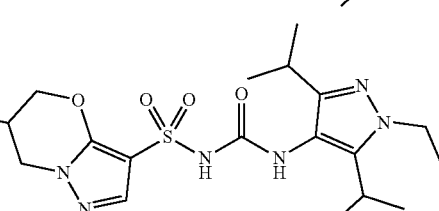
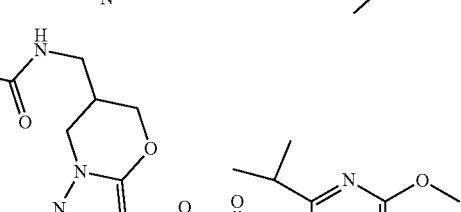

261
-continued
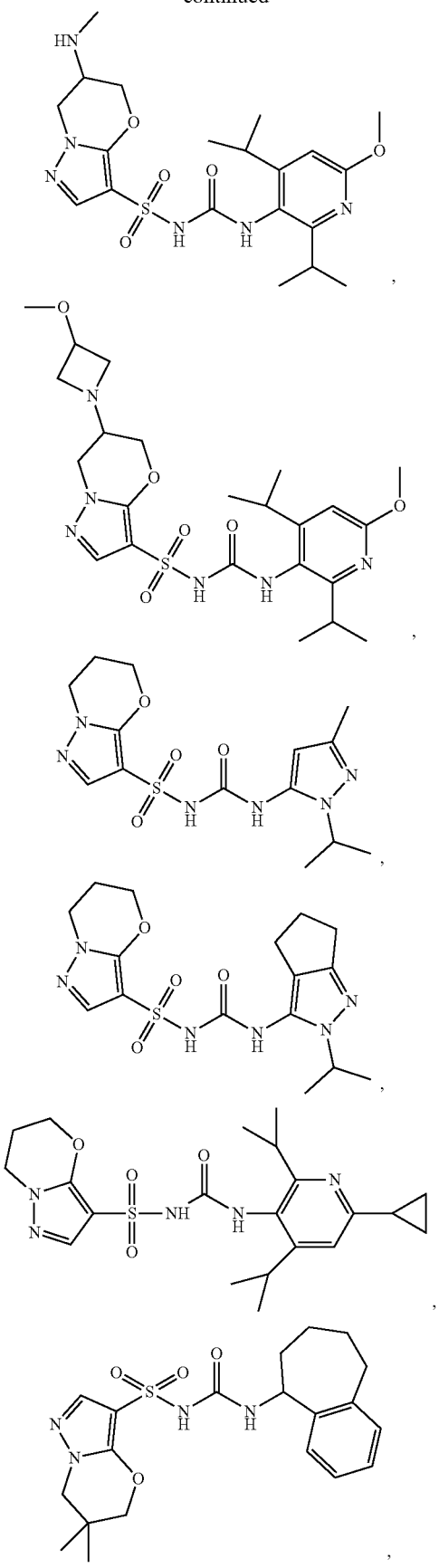
262
-continued
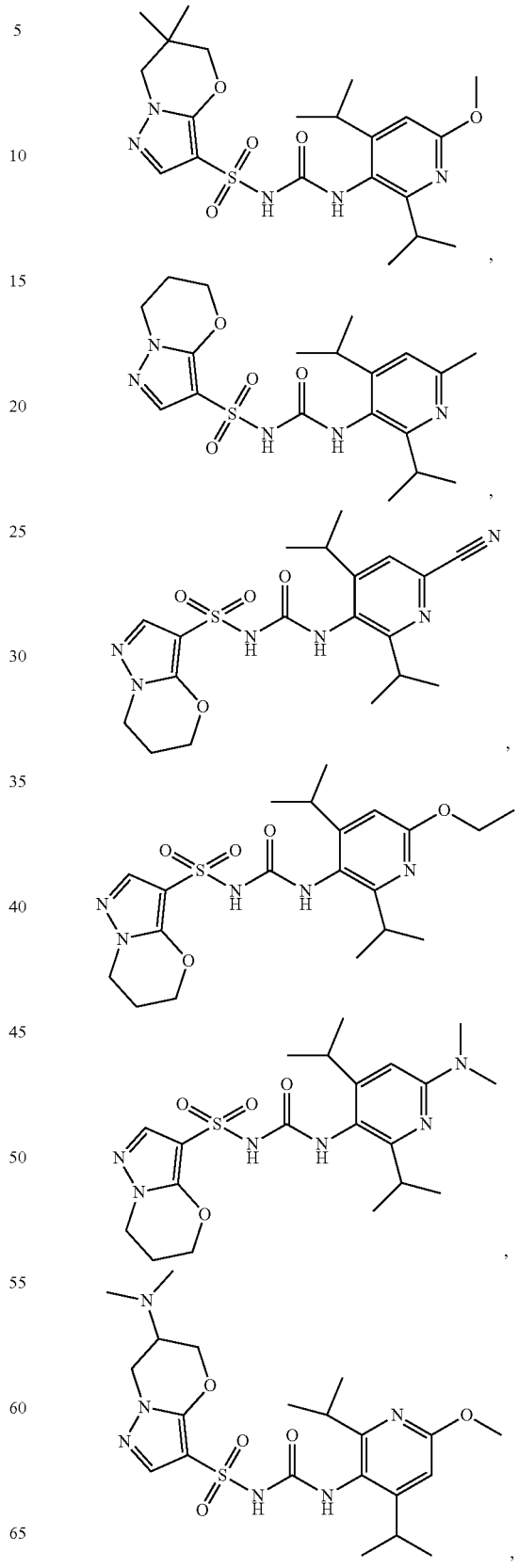

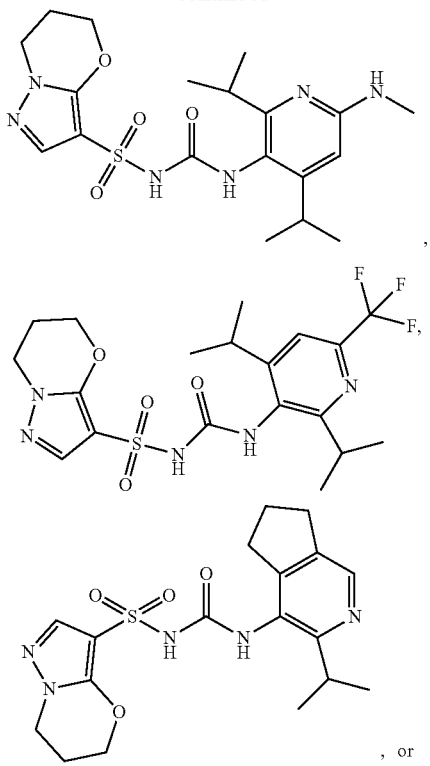

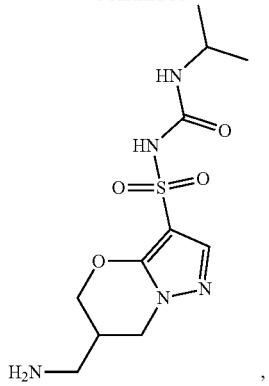

or a pharmaceutically acceptable salt, solvate, isomer, or tautomer thereof.

19. A pharmaceutical composition, comprising a compound of claim 1, or a pharmaceutically acceptable salt, solvate, isomer, or tautomer thereof, and a pharmaceutically acceptable carrier.

20. A pharmaceutical composition, comprising a compound of claim 17, or a pharmaceutically acceptable salt, solvate, isomer, or tautomer thereof, and a pharmaceutically acceptable carrier.

21. A pharmaceutical composition, comprising a compound of claim 18, or a pharmaceutically acceptable salt, solvate, isomer, or tautomer thereof, and a pharmaceutically acceptable carrier.

* * * * *